US012774287B2

(12) United States Patent
Tominari et al.

(10) Patent No.: US 12,774,287 B2
(45) Date of Patent: Oct. 27, 2026

(54) HETEROCYCLIC COMPOUND

(71) Applicant: FIMECS, INC., Fujisawa (JP)

(72) Inventors: Yusuke Tominari, Sagamihara (JP); Yoshihide Tomata, Tsukuba (JP); Kanae Gamo, Yokohama (JP); Naomi Kitamoto, Amagasaki (JP)

(73) Assignee: FIMECS, Inc., Fujisawa (JP)

( * ) Notice: Subject to any disclaimer, the term of this patent is extended or adjusted under 35 U.S.C. 154(b) by 1307 days.

(21) Appl. No.: 17/630,203

(22) PCT Filed: Jul. 31, 2020

(86) PCT No.: PCT/JP2020/029589
§ 371 (c)(1),
(2) Date: Jul. 29, 2022

(87) PCT Pub. No.: WO2021/020585
PCT Pub. Date: Feb. 4, 2021

(65) Prior Publication Data
US 2022/0402935 A1 Dec. 22, 2022

(30) Foreign Application Priority Data
Jul. 31, 2019 (JP) ................................ 2019-141699

(51) Int. Cl.
*C07D 495/04* (2006.01)
*A61P 11/00* (2006.01)
(Continued)

(52) U.S. Cl.
CPC ............ *C07D 495/04* (2013.01); *A61P 11/00* (2018.01); *A61P 35/00* (2018.01); *C07D 519/00* (2013.01)

(58) Field of Classification Search
CPC ..... C07D 495/04; C07D 519/00; A61P 11/00; A61P 35/00
See application file for complete search history.

(56) References Cited

U.S. PATENT DOCUMENTS 7,041,298 B2 5/2006 Deshaies et al.
7,208,157 B2 4/2007 Dashaies et al.
(Continued)

FOREIGN PATENT DOCUMENTS

CN 103242341 A 8/2013
CN 106749513 A 5/2017
(Continued)

OTHER PUBLICATIONS

Leah L.N. Hubbard, Bethany B. Moore, Infectious Disease Reports 2010; vol. 2:e9. (Year: 2010).*
(Continued)

*Primary Examiner* — Clinton A Brooks
*Assistant Examiner* — Izabela Schmidt
(74) *Attorney, Agent, or Firm* — Element IP, PLC

(57) ABSTRACT

It is to provide a novel heterocyclic compound which has the effect of inducing degradation of interleukin-1 receptor-associated kinase-M (IRAK-M) protein and is expected to be useful for the prevention/treatment of cancer, fibrosis, infectious diseases, etc. The present invention provides a compound represented by the following formula (I) or a pharmaceutically acceptable salt thereof.

I

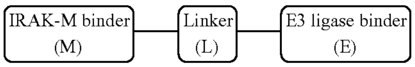

11 Claims, 1 Drawing Sheet

Specification includes a Sequence Listing.

(51) Int. Cl.
*A61P 35/00* (2006.01)
*C07D 519/00* (2006.01)

(56) References Cited

U.S. PATENT DOCUMENTS

| | | | | |
|---|---|---|---|---|
| 9,770,512 | B2 | 9/2017 | Bradner et al. | |
| 10,071,164 | B2 | 9/2018 | Crew et al. | |
| 10,125,114 | B2 | 11/2018 | Bradner et al. | |
| 11,639,354 | B2 * | 5/2023 | Tominari | C07D 495/14 514/210.16 |
| 12,202,829 | B2 * | 1/2025 | Tominari | C07D 403/06 |
| 2002/0068063 | A1 | 6/2002 | Deshaies et al. | |
| 2004/0038358 | A1 | 2/2004 | Dashaies et al. | |
| 2007/0093428 | A1 | 4/2007 | Laurent et al. | |
| 2013/0040957 | A1 | 2/2013 | Dhanoa | |
| 2013/0172264 | A1 | 7/2013 | Cohen et al. | |
| 2014/0135270 | A1 | 5/2014 | Borzilleri et al. | |
| 2014/0356322 | A1 | 12/2014 | Crews et al. | |
| 2015/0219657 | A1 | 8/2015 | Heath et al. | |
| 2015/0291562 | A1 | 10/2015 | Crew et al. | |
| 2016/0045607 | A1 | 2/2016 | Crew et al. | |
| 2016/0058872 | A1 | 3/2016 | Crew et al. | |
| 2016/0176916 | A1 | 6/2016 | Bradner et al. | |
| 2016/0214972 | A1 | 7/2016 | Jin et al. | |
| 2017/0008904 | A1 | 1/2017 | Crew et al. | |
| 2017/0065719 | A1 | 3/2017 | Qian et al. | |
| 2017/0121321 | A1 | 5/2017 | Crews et al. | |
| 2018/0072711 | A1 | 3/2018 | Crew et al. | |
| 2018/0099940 | A1 | 4/2018 | Crew et al. | |
| 2018/0118733 | A1 | 5/2018 | Harling et al. | |
| 2018/0134684 | A1 | 5/2018 | Bradner et al. | |
| 2018/0134688 | A1 | 5/2018 | Casillas et al. | |
| 2018/0155322 | A1 | 6/2018 | Crew et al. | |
| 2018/0169109 | A1 | 6/2018 | Bradner et al. | |
| 2018/0177750 | A1 | 6/2018 | Crew et al. | |
| 2018/0179183 | A1 | 6/2018 | Crew et al. | |
| 2018/0179522 | A1 | 6/2018 | Buckley et al. | |
| 2018/0186785 | A1 | 7/2018 | Crews et al. | |
| 2018/0193470 | A1 | 7/2018 | Crew et al. | |
| 2018/0215731 | A1 | 8/2018 | Crew et al. | |
| 2018/0228907 | A1 | 8/2018 | Crew et al. | |
| 2018/0237418 | A1 | 8/2018 | Crew et al. | |
| 2018/0256586 | A1 | 9/2018 | Crew et al. | |
| 2018/0327419 | A1 | 11/2018 | Bradner et al. | |
| 2019/0002578 | A1 | 1/2019 | Brayshaw et al. | |
| 2019/0062281 | A1 | 2/2019 | Schiltz et al. | |
| 2019/0119271 | A1 | 4/2019 | Casillas et al. | |
| 2019/0119358 | A1 | 4/2019 | Josephson et al. | |
| 2019/0127359 | A1 | 5/2019 | Crews et al. | |
| 2019/0151457 | A1 | 5/2019 | Bradner et al. | |
| 2019/0152946 | A1 * | 5/2019 | Harling | A61P 35/00 |
| 2019/0175612 | A1 | 6/2019 | Pillow et al. | |
| 2019/0192514 | A1 | 6/2019 | Crew et al. | |
| 2019/0233408 | A1 | 8/2019 | Crew et al. | |
| 2019/0233433 | A1 | 8/2019 | Crews et al. | |
| 2019/0255041 | A1 | 8/2019 | Jin et al. | |
| 2019/0263758 | A1 | 8/2019 | Nakache et al. | |
| 2019/0263759 | A1 | 8/2019 | Derbyshire et al. | |
| 2019/0276459 | A1 | 9/2019 | Crews et al. | |
| 2019/0276474 | A1 | 9/2019 | Chan et al. | |
| 2019/0300521 | A1 | 10/2019 | Crew et al. | |
| 2020/0038378 | A1 | 2/2020 | Crew et al. | |
| 2020/0038513 | A1 | 2/2020 | Crews et al. | |
| 2020/0055825 | A1 | 2/2020 | Crew et al. | |
| 2020/0085793 | A1 | 3/2020 | Crew et al. | |
| 2020/0121684 | A1 | 4/2020 | Crews et al. | |
| 2020/0140456 | A1 | 5/2020 | Phillips et al. | |
| 2020/0190079 | A1 | 6/2020 | Tang et al. | |

FOREIGN PATENT DOCUMENTS

| | | | | |
|---|---|---|---|---|
| CN | 106977584 | A | 7/2017 | |
| CN | 107382862 | A | 11/2017 | |
| CN | 107540608 | A | 1/2018 | |
| EP | 2985285 | A1 | 2/2016 | |
| GB | 2554071 | A | 3/2018 | |
| JP | 2012106958 | A | 6/2012 | |
| JP | 2012176934 | A | 9/2012 | |
| JP | 2013056837 | A | 3/2013 | |
| JP | 2019517559 | A | 6/2019 | |
| WO | 0220740 | A2 | 3/2002 | |
| WO | 2006091737 | A1 | 8/2006 | |
| WO | 2006113376 | A1 | 10/2006 | |
| WO | 2007104162 | A1 | 9/2007 | |
| WO | 2007106192 | A2 | 9/2007 | |
| WO | 2007131366 | A1 | 11/2007 | |
| WO | 2008016893 | A1 | 2/2008 | |
| WO | 2008045905 | A1 | 4/2008 | |
| WO | 2008079735 | A1 | 7/2008 | |
| WO | 2008128171 | A2 | 10/2008 | |
| WO | 2010142994 | A1 | 12/2010 | |
| WO | 2011002684 | A1 | 1/2011 | |
| WO | 2011098904 | A1 | 8/2011 | |
| WO | 2012143726 | A1 | 10/2012 | |
| WO | 2013019966 | A1 | 2/2013 | |
| WO | 2013106643 | A2 | 7/2013 | |
| WO | 2013106646 | A2 | 7/2013 | |
| WO | 2014023708 | A1 | 2/2014 | |
| WO | 2014060770 | A1 | 4/2014 | |
| WO | 2014108452 | A1 | 7/2014 | |
| WO | 2015000867 | A1 | 1/2015 | |
| WO | 2015000868 | A1 | 1/2015 | |
| WO | 2015160845 | A2 | 10/2015 | |
| WO | 2016040330 | A1 | 3/2016 | |
| WO | 2016105518 | A1 | 6/2016 | |
| WO | 2016118666 | A1 | 7/2016 | |
| WO | 2016146985 | A1 | 9/2016 | |
| WO | 2016149668 | A1 | 9/2016 | |
| WO | 2016169989 | A1 | 10/2016 | |
| WO | 2016172134 | A2 | 10/2016 | |
| WO | 2016197032 | A1 | 12/2016 | |
| WO | 2016197114 | A1 | 12/2016 | |
| WO | 2016204197 | A1 | 12/2016 | |
| WO | 2017007612 | A1 | 1/2017 | |
| WO | 2017011371 | A1 | 1/2017 | |
| WO | 2017011590 | A1 | 1/2017 | |
| WO | 2017024318 | A1 | 2/2017 | |
| WO | 2017030814 | A1 | 2/2017 | |
| WO | 2017117473 | A1 | 7/2017 | |
| WO | 2017117474 | A1 | 7/2017 | |
| WO | 2017181061 | A1 | 10/2017 | |
| WO | 2017182418 | A1 | 10/2017 | |
| WO | 2017185036 | A1 | 10/2017 | |
| WO | 2017197036 | A1 | 11/2017 | |
| WO | 2017197046 | A1 | 11/2017 | |
| WO | 2017197051 | A1 | 11/2017 | |
| WO | 2017197055 | A1 | 11/2017 | |
| WO | 2017197056 | A1 | 11/2017 | |
| WO | 2017201449 | A1 | 11/2017 | |
| WO | 2017204445 | A2 | 11/2017 | |
| WO | WO-2017211924 | A1 * | 12/2017 | C07D 401/12 |
| WO | 2018051107 | A1 | 3/2018 | |
| WO | 2018053354 | A1 | 3/2018 | |
| WO | 2018066545 | A1 | 4/2018 | |
| WO | 2018102067 | A2 | 6/2018 | |
| WO | 2018102725 | A1 | 6/2018 | |
| WO | 2018118598 | A1 | 6/2018 | |
| WO | 2018119357 | A1 | 6/2018 | |
| WO | 2018119441 | A1 | 6/2018 | |
| WO | 2018119448 | A1 | 6/2018 | |
| WO | 2018140809 | A1 | 8/2018 | |
| WO | 2018144649 | A1 | 8/2018 | |
| WO | 2018148443 | A1 | 8/2018 | |
| WO | 2018189554 | A1 | 10/2018 | |
| WO | 2018237026 | A1 | 12/2018 | |
| WO | 2019007869 | A1 | 1/2019 | |
| WO | 2019014429 | A1 | 1/2019 | |
| WO | 2019060742 | A1 | 3/2019 | |
| WO | 2019078522 | A1 | 4/2019 | |
| WO | 2019079357 | A1 | 4/2019 | |
| WO | 2019079701 | A1 | 4/2019 | |
| WO | 2019084026 | A1 | 5/2019 | |
| WO | 2019084030 | A1 | 5/2019 | |
| WO | 2019094718 | A1 | 5/2019 | |

(56) References Cited

FOREIGN PATENT DOCUMENTS

| | | | |
|---|---|---|---|
| WO | 2019094772 | A1 | 5/2019 |
| WO | 2019099926 | A1 | 5/2019 |
| WO | 2019109415 | A1 | 6/2019 |
| WO | 2019113071 | A1 | 6/2019 |
| WO | 2019114770 | A1 | 6/2019 |
| WO | 2019118893 | A1 | 6/2019 |
| WO | 2019123367 | A1 | 6/2019 |
| WO | 2019133531 | A1 | 7/2019 |
| WO | 2019140003 | A1 | 7/2019 |
| WO | 2019165189 | A1 | 8/2019 |
| WO | 2019165216 | A1 | 8/2019 |
| WO | 2019165229 | A1 | 8/2019 |
| WO | 2019170150 | A1 | 9/2019 |
| WO | 2019173224 | A1 | 9/2019 |
| WO | 2019173516 | A1 | 9/2019 |
| WO | 2019183523 | A1 | 9/2019 |
| WO | 2019195201 | A1 | 10/2019 |
| WO | 2019195609 | A2 | 10/2019 |
| WO | 2019199816 | A1 | 10/2019 |
| WO | 2019200217 | A1 | 10/2019 |
| WO | 2019201123 | A1 | 10/2019 |
| WO | 2019246570 | A1 | 12/2019 |
| WO | 2020006724 | A1 | 1/2020 |
| WO | 2020010204 | A1 | 1/2020 |
| WO | 2020014489 | A2 | 1/2020 |
| WO | 2020023851 | A1 | 1/2020 |
| WO | 2020027225 | A1 | 2/2020 |
| WO | 2020038415 | A1 | 2/2020 |
| WO | 2020041331 | A1 | 2/2020 |
| WO | 2020051564 | A1 | 3/2020 |
| WO | 2020069105 | A1 | 4/2020 |
| WO | 2020069106 | A1 | 4/2020 |
| WO | 2020069117 | A1 | 4/2020 |
| WO | 2020069125 | A1 | 4/2020 |
| WO | 2020076996 | A1 | 4/2020 |
| WO | 2020077278 | A1 | 4/2020 |
| WO | 2020092662 | A1 | 5/2020 |
| WO | 2020093370 | A1 | 5/2020 |
| WO | 2020119192 | A1 | 6/2020 |
| WO | 2020243373 | A1 | 12/2020 |
| WO | 2021065980 | A1 | 4/2021 |
| WO | 2021067799 | A1 | 4/2021 |

OTHER PUBLICATIONS

Troup et al., Explor Target Antitumor Ther. 2020;1:273-312. (Year: 2020).*
Zugazagoitia et al., Clin. Ther. 2016;38(7):1551-66 at p. 1564. (Year: 2016).*
Andrew R. Reynolds et. al., Cancer Discov (2023) 13 (5): 1058-1083. (Year: 2023).*
Jain A, Kaczanowska S, Davila E. IL-1 Receptor-Associated Kinase Signaling and Its Role in Inflammation, Cancer Progression, and Therapy Resistance. Front Immunol. Nov. 17, 2014;5:553. (Year: 2014).*
Extended European Search Report issued Nov. 13, 2023 in European Patent Application No. 20847962.6, 8 pages.
Nunes, Joao, et al., "Targeting IRAK4 for Degradation with PROTACs", ACS Medicinal Chemistry Letters, Jun. 14, 2019, vol. 10, No. 7, pp. 1081-1085, XP055785428.
"FIMECS Presents IRAK-M Protein Degraders for Immuno-oncology at the AACR Annual Meeting 2019", FIMECS, AACR Annual Meeting, 2019 (with English translation), 5 pages.
Alessandra Soares-Schanoski et al, "Impaired antigen presentation and potent phagocytic activity identifying tumor-tolerant human monocytes", Biochemical and Biophysical Research Communications, 423(2), 2012, pp. 331-337.
Ashton C. Lai et al, "Induced protein degradation: an emerging drug discovery paradigm", Nat Rev Drug Discov., 16(2), Feb. 2017, pp. 101-114.
Brenda F. Reader et al, "IRAK-M Regulates Monocyte Trafficking to the Lungs in Response to Bleomycin Challenge", The Journal of Immunology, 204, 2020, pp. 2661-2670.
Carlos del Fresno et al., "Tumor Cells Deactivate Human Monocytes by Up-Regulating IL-1 Receptor Associated Kinase-M Expression via CD44 and TLR4", The Journal of Immunology, 174, 2005, pp. 3032-3040.
Craig M. Crews, "Targeting the Undruggable Proteome: The Small Molecules of My Dreams", Chemistry & Biology Crosstalk, 17(6), Jun. 25, 2010, pp. 551-555.
Daniel P Bondeson et al, "Catalytic in vivo protein knockdown by small-molecule PROTACs", Nat Chem Biol., 11(8), Aug. 2015, pp. 611-617.
Daniel P. Bondeson et al., "Lessons in PROTAC Design from Selective Degradation with a Promiscuous Warhead", Cell Chemical Biology, 25(1), Jan. 18, 2018, pp. 78-87, e1-e5, supplemental information.
George M. Burslem, et al, "The Advantages of Targeted Protein Degradation Over Inhibition: An RTK Case Study", Cell Chem Biology, 25 (1), Jan. 18, 2018, pp. 67-77, e. 1-3.
Hao Zhou et al, "IRAK-M mediates Toll-like receptor/IL-1R-induced NFkB activation and cytokine production", 32(4), 2013, pp. 583-596.
Holger Wesche et al, "IRAK-M Is a Novel Member of the Pelle/Interleukin-1 Receptor-associated Kinase (IRAK) Family", The Journal of Biological Chemistry, vol. 274, No. 27, Jul. 2, 1999, pp. 19403-19410.
International Search Report issued Sep. 15, 2020 in PCT/JP2020/029589 (with English translation), 8 pages.
Jane C. Deng et al, "Sepsis-induced suppression of lung innate immunity is mediated by IRAK-M", The Journal of Clinical Investigation, 116(9), 2006, pp. 2532-2542.
Jane C. Deng et al, "Sepsis-induced suppression of lung innate immunity is mediated by IRAK-M", The Journal of Clinical Investigation, 116(9), Sep. 2006, 2532-2542.
Jemilat Salami et al, "Waste disposal—An attractive strategy for cancer therapy", Science, 355, 2017, pp. 1163-1167.
Jesús Villar et al, "Mechanical ventilation modulates TLR4 and IRAK-3 in a non-infectious, ventilator-induced lung injury model", Respiratory Research, 11(27), 2010, pp. 1-11.
John S. Schneekloth Jr. et al, "Chemical Approaches to Controlling Intracellular Protein Degradation", Chembiochem, 6(1), Jan. 2005, 16 pages.
Kanae Gamo et al, "Targeted IRAK-M degradation as a novel and efficacious cancer-immunotherapy overcoming innate-driven immunosuppression" Poster, FIMECS, Inc., #2354, Apr. 1, 2019, 1 page.
Kanae Gamo et al, "Targeted IRAK-M degradation as a novel and efficacious cancer-immunotherapy overcoming innate-driven immunosuppression", AACR Annual Meeting, Molecular Mechanisms in the Immune Response to Cancer, Apr. 1, 2019 (with English abstract), 4 pages.
Kanae Gamo, "Drug discovery research for novel cancer immunotherapeutic agents whose mechanism of action is the degradation of IRAK-M protein", Kyushu University Seminar, Mar. 11, 2019, 24 pages.
Koichi Kobayashi et al, "IRAK-M Is a Negative Regulator of Toll-like Receptor Signaling", Cell, vol. 110, Jul. 26, 2002, pp. 191-202.
Leah L. N. Hubbard et al, "A Role for IL-1 Receptor-Associated Kinase-M in Prostaglandin E 2-Induced Immunosuppression Post-Bone Marrow Transplantation", The Journal of Immunology, 184(11), Jun. 1, 2010, pp. 6299-6308.
Leah L.N. Hubbard et al, "IRAK-M regulation and function in host defense and immune homeostasis", Infectious Disease Reports, vol. 2:e9; 2010, pp. 22-29.
Lorna Ringwood et al, "The involvement of the interleukin-1 receptor-associated kinases (IRAKs) in cellular signaling networks controlling inflammation", Cytokine, 42, 2008, pp. 1-7.
Maciej Lech et al, "Macrophage Phenotype Controls Long-Term AKI Outcomes—Kidney Regeneration versus Atrophy", The American Society of Nephrology, 25, 2014, pp. 292-304.
Mark W. Julian et al., "Tolerance and Cross-Tolerance following Toll-Like Receptor (TLR)-4 and -9 Activation Are Mediated by IRAK-M and Modulated by IL-7 in Murine Splenocytes", PLoS ONE, 10(7), e0132921, 2015, pp. 1-26.

(56) References Cited

OTHER PUBLICATIONS

Martin Berglund et al, "IL-1 Receptor-associated Kinase M Downregulates DSS-induced Colitis", Inflamm Bowel Dis, 16, 2010, pp. 1778-1786.
Masafumi Seki et al, "Critical Role of IL-1 Receptor-Associated Kinase-M in Regulating Chemokine-Dependent Deleterious Inflammation in Murine Influenza Pneumonia", The Journal of Immunology, 184, 2010, pp. 1410-1418.
Megan N. Ballinger et al, "IRAK-M Promotes Alternative Macrophage Activation and Fibroproliferation in Bleomycin-Induced Lung Injury", The Journal of Immunology, 194(4), Feb. 15, 2015, pp. 1894-1904.
Megan N. Ballinger et al, "IRAK-M Promotes Alternative Macrophage Activation and Fibroproliferation in Bleomycin-Induced Lung Injury", The Journal of Immunology, 194(4), Feb. 2015, 1894-1904.
Meghan E Turnis et al, "Enhancement of dendritic cells as vaccines for cancer", Immunotherapy, 2(6), Nov. 2010, pp. 847-862.
Meghan E. Turnis et al, "IRAK-M Removal Counteracts Dendritic Cell Vaccine Deficits in Migration and Longevity", The Journal of Immunology, 185(7), Oct. 1, 2010, pp. 4223-4232.
Philipp M. Cromm et al, "Targeted Protein Degradation: from Chemical Biology to Drug Discovery", Cell Chemical Biology, 24 (9), Sep. 21, 2017, pp. 1181-1190.
Philipp Ottis et al, "Proteolysis-Targeting Chimeras: Induced Protein Degradation as a Therapeutic Strategy", ACS Chemical Biology, 12(4), Apr. 21, 2017, pp. 892-898.
Qifa Xie et al, "Loss of the innate immunity negative regulator IRAK-M leads to enhanced host immune defense against tumor growth", Molecular Immunology, 44, 2007, 3453-3461.
Qiyuan Tan et al, "IRAK-M Deficiency Promotes the Development of Type 1 Diabetes in NOD Mice", Diabetes, vol. 63, Aug. 2014, pp. 2761-2775.
Rebecca Kesselring et al, "IRAK-M Expression in Tumor Cells Supports Colorectal Cancer Progression through Reduction of Antimicrobial Defense and Stabilization of STAT3", Cancer Cell, 29, 2016, pp. 684-696 (plus Supplemental Information).
Sebastien L. Degorce et al., "Discovery of PROTAC molecules that selectively degrade the IRAK3 pseudokinase.", Journal of Medicinal Chemistry, 63(18), 2020, 71 pages.
Shyun Li et al, "IRAK-4: A novel member of the IRAK family with the properties of an IRAK-kinase", PNAS, 99(8), Apr. 16, 2002, pp. 5567-5572.
Sinead Flannery et al, "The interleukin-1 receptor-associated kinases: Critical regulators of innate immune signalling", Biochemical Pharmacology, 80, 2010, 1981-1991.
Su-Chang Lin et al, "Helical assembly in the MyD88-IRAK4-IRAK2 complex in TLR/IL-1R signalling", Nature, 465(17), 2010, 885-891.
TJ Standiford et al, "TGF-beta-induced IRAK-M expression in tumor-associated macrophages regulates lung tumor growth", Oncogene, 30 (21), 2011, pp. 2475-2484.
Yipeng Wang et al, "Role of IRAK-M in Alcohol Induced Liver Injury", PLoS ONE, 8(2), e57085, Feb. 2013, pp. 1-10.
Yusuke Tominari Ph.D., "2nd YUGOKAFe NExT", Shonan Health Innovation Park, The Society of Synthetic Organic Chemistry, Feb. 22, 2019, 14 pages.
Yusuke Tominari Ph.D., "Basics and global trends of target proteolysis inducers as a new modality", Kyushu University Seminar, Mar. 11, 2019, 34 pages.
Yusuke Tominari Ph.D., "Case Study of Targeted Protein Degradation for Immuno-oncology program, IRAK-M degrader", 20th Annual Drug Discovery Summit, Berlin, Jul. 12, 2019, 28 pages.
Yusuke Tominari Ph.D., "Drugging Undruggable Targets", Nikkei Biotech 2018, May 29, 2018, 24 pages.
Yusuke Tominari Ph.D., "Efficient discovery platform of the targeted protein degradation drugs", European Protein Degradation Congress, May 23, 2019, 23 pages.
Yusuke Tominari Ph.D., "Solutions for Drugging Undruggable Targets in FIMECS", Targeted Protein Degradation Summit 2018, Oct. 15, 2018, 28 pages.
Yusuke Tominari, "Pharmacia", vol. 56, No. 3, The Pharmaceutical Society of Japan, 2020, 4 pages.
Yusuke Tominari, Ph.D., "New Modality and Synthetic Organic Chemistry", The Society of Synthetic Organic Chemistry, Japan, Jul. 17, 2019, 32 pages.

* cited by examiner

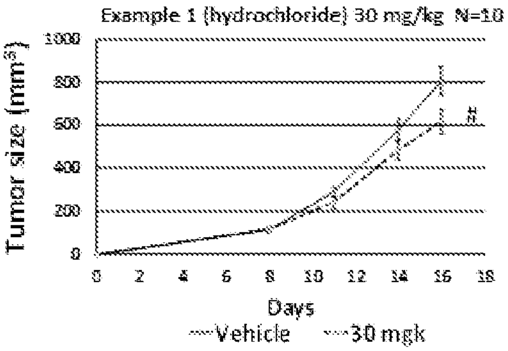
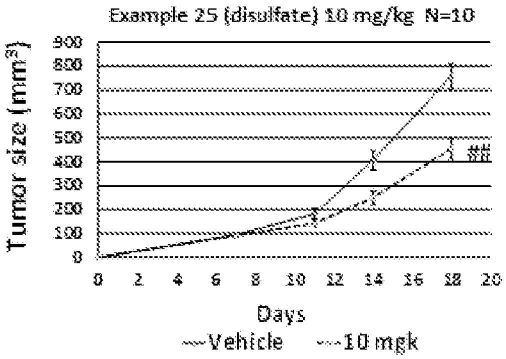
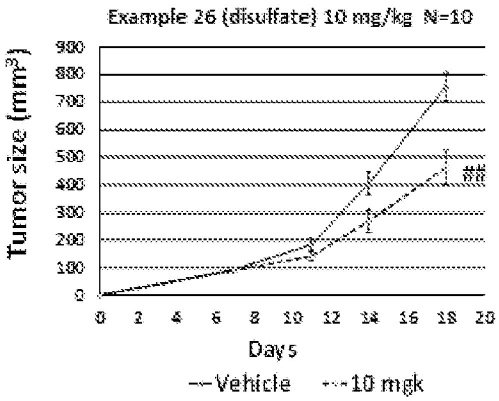
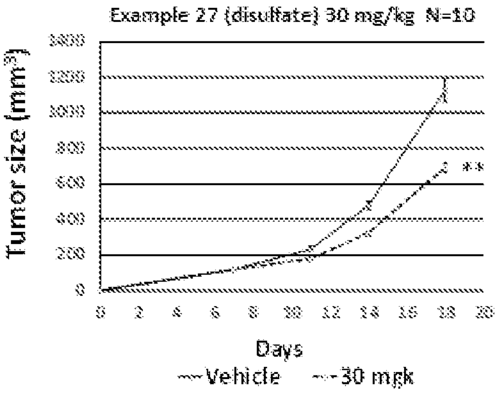
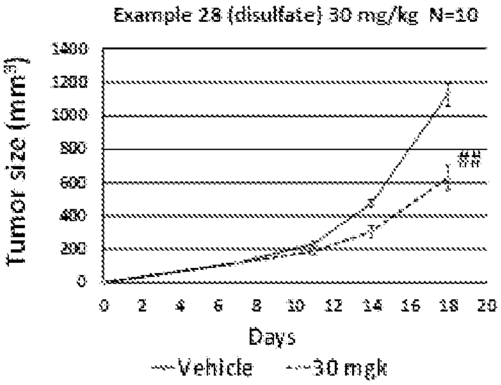
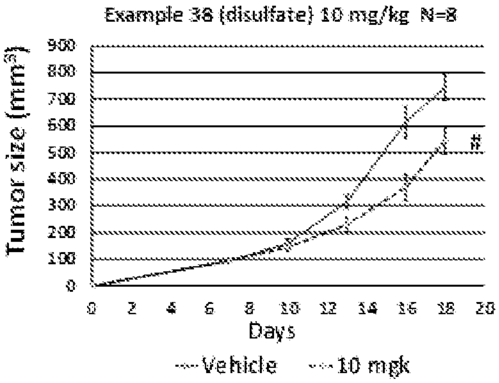
#; $p<0.05$, ##; $p<0.01$, t test
**; $p<0.01$ Welch's t test

HETEROCYCLIC COMPOUND

TECHNICAL FIELD

The present invention relates to a novel heterocyclic compound having the effect of inducing degradation of interleukin-1 receptor-associated kinase-M (IRAK-M) protein and expected to be useful for the prevention/treatment of cancer, fibrosis, infectious diseases, etc., and a drug containing the same.

BACKGROUND ART

Development of compounds that induce ubiquitination of target proteins and proteasome degradation by E3 ligase (referred to as Proteolysis Targeting Chimeras (PROTAC® or Specific and Nongenetic IAP-dependent Protein Eraser (SNIPER) and the like in some cases) has been attempted for the purpose of treatment by reducing disease-related proteins (Non-Patent Documents 1 to 9). IRAK-M is a member of the IRAK family of protein kinases and is a pseudokinase having no kinase activity (Non-Patent Document 10). IRAK-M is located downstream of all Toll-like receptors (TLRs) except TLR3 and a protein which acts as a negative feedback regulator of the TLR/interleukin-1 (IL-1) receptor signaling pathway in vivo (Non-Patent Document 11). It is located and expressed in some epithelial cells, including bile duct epithelial cells, lung epithelial cells and intestinal epithelial cells, and in immune cells, especially myeloid cells. IRAK-M plays an important role in maintaining immune homeostasis such as induction of endotoxin tolerance by negatively controlling TLR-mediated induction signals of inflammatory cytokines in innate immunocompetent cells such as macrophages and dendritic cells (Non-Patent Document 12). IRAK-M has been reported to contribute to cancer growth by contributing to immunosuppression by tumor-related macrophages in the tumor microenvironment, bone marrow-derived immunosuppressive cells, dendritic cells and so on (Non-Patent Documents 13 to 15). Furthermore, IRAK-M has been reported to act on alveolar macrophages' phagocytosis, defense against bacteria and collagen production promoting ability, and is involved in fibrosis, asthma, secondary infection after sepsis, and infectious complications of hematopoietic stem cell transplantation (Non-Patent Documents 16-18). Therefore, compounds that induce the degradation of IRAK-M by linking a E3 ligase binder, including the Von Hippel-Lindau (VHL) binder, the Cereblon (CRBN) binder, the X-Linked Inhibitor of Apoptosis Protein (XIAP) binder, the Murine Double Minute 2 (MDM2) binder and the DDB1/CUL4-associated factor (DCAF) 15 binder and the like, and the IRAK-M binder via a linker can be promising therapeutic agents for cancer, fibrosis, infectious diseases, and IRAK-M protein-related diseases.

Patent Document 1 reports a compound as an IRAK-M protein degradation inducer.

Patent Documents 2 and 3 report compounds as an IRAK (particularly IRAK-4) protein degradation inducer.

Patent Documents 4 to 16 report compounds that induce protein degradation by using IAP binders.

Patent Documents 17 to 35 report compounds as an IAP antagonist.

Patent Documents 36 to 39 reports compounds containing the structure of N-(piperidine-4-yl) thieno[3,2-d]pyrimidin-4-amine or N-(piperidine-4-yl) thieno[3,2-b] pyridine-7-amine.

CITATION LIST

Patent Document

Patent Document 1: WO2017/211924
Patent Document 2: WO2019/099926
Patent Document 3: WO2019/133531
Patent Document 4: WO2018/066545
Patent Document 5: Japanese Unexamined Patent Application Publication No. 2013-056837
Patent Document 6: WO2016/169989
Patent Document 7: WO2016/172134
Patent Document 8: WO2017/011590
Patent Document 9: WO2017/182418
Patent Document 10: WO2017/201449
Patent Document 11: US2018/0118733 A1
Patent Document 12: US2018/0134688 A1
Patent Document 13: WO2018/119448
Patent Document 14: WO2018/119357
Patent Document 15: US2019/0119271 A1
Patent Document 16: US2019/0175612 A1
Patent Document 17: WO2006/113376
Patent Document 18: WO2007/104162
Patent Document 19: WO2007/106192
Patent Document 20: WO2007/131366
Patent Document 21: US2007/0093428 A1
Patent Document 22: WO2008/016893
Patent Document 23: WO2008/045905
Patent Document 24: WO2008/079735
Patent Document 25: WO2008/128171
Patent Document 26: WO2010/142994
Patent Document 27: WO2011/002684
Patent Document 28: WO2011/098904
Patent Document 29: WO2012/143726
Patent Document 30: Japanese Unexamined Patent Application Publication No. 2012-106958
Patent Document 31: Japanese Unexamined Patent Application Publication No. 2012-176934
Patent Document 32: US2013/0172264 A1
Patent Document 33: US2014/0135270 A1
Patent Document 34: WO2014/023708
Patent Document 35: WO2014/0060770
Patent Document 36: WO2016/040330
Patent Document 37: WO2013/019966
Patent Document 38: US2013/0040957 A1
Patent Document 39: CN103242341 A

Non-Patent Document

Non-Patent Document 1: Science. 2017 Mar. 17; 355 (6330) 1163-1167.
Non-Patent Document 2: Cell Chem Biol. 2018 Jan. 18; 25(1):67-77.e3.
Non-Patent Document 3: Cell Chem. Biol. 2017 Sep. 21; 24(9) 1181-1190.
Non-Patent Document 4: ACS Chem Biol. 2017 Apr. 21; 12(4):892-898.
Non-Patent Document 5: Cell Chem Biol. 2018 Jan. 18; 25(1):78-87.e5.
Non-Patent Document 6: Nat Rev Drug Discov. 2017 February; 16(2):101-114.
Non-Patent Document 7: Nat Chem Biol. 2015 August; 11(8):611-7.
Non-Patent Document 8: Chemistry & Biology, 2010, 17(6):551-555
Non-Patent Document 9: Chembiochem, 2005, 6(1):40-46

Non-Patent Document 10: J Biol Chem, 1999 Jul. 2; 274(27): 19403-19410

Non-Patent Document 11: Cell, 2002 Jul. 26; 110(2): 191-202

Non-Patent Document 12: Infect Dis Rep, 2010 Jan. 1; 2(1). pii: e9

Non-Patent Document 13: Oncogene, 2011 May 26; 30(21): 2475-2484

Non-Patent Document 14: J Immunol, 2010 Oct. 1; 185 (7): 4223-4232

Non-Patent Document 15: Mol Immunol, 2007 July; 44(14): 3453-3461

Non-Patent Document 16: J Immunol, 2015 Feb. 15; 194(4): 1894-1904

Non-Patent Document 17: J Clin Invest, 2006 September; 116(9): 2532-2542, Epub 2006 Aug. 17

Non-Patent Document 18: J Immunol, 2010 Jun. 1; 184 (11): 6299-6308

SUMMARY OF THE INVENTION

Technical Problem

An object of the present invention is to provide a novel heterocyclic compound and a pharmaceutical compound containing thereof, which have an action of inducing degradation of IRAK-M protein and are expected to be useful for prevention and treatment of cancer, fibrosis, infectious diseases, etc.

Solution to Problem

The present inventors have diligently studied to find an IRAK-M protein degrader and resultantly found that the compound represented by the following formula provides an excellent degradation-inducing activity of IRAK-M protein, and that the compound may be useful for prevention or treatment of cancer, fibrosis, infectious diseases and the like, leading to completion of the present invention.

The present invention is below.

[1] A compound represented by the formula (I):

I

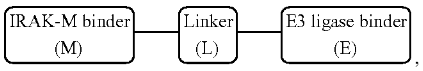

or a pharmaceutically acceptable salt thereof.

[2] The compound according to the above [1], wherein the E3 ligase binder is selected from the group consisting of an IAP binder, a CRBN binder, a VHL binder, a MDM2 binder and a DCAF15 binder, or a pharmaceutically acceptable salt thereof.

[3] The compound according to the above [1], wherein the IRAK-M binder (M) is represented by the following formula (II):

II

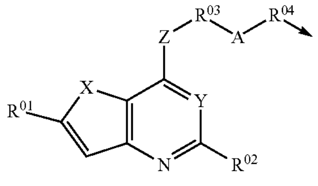

wherein X represents S, O or NR, wherein R represents a hydrogen atom or a C1-6 alkyl group, Y represents CH or N, Z represents O or NH, $R^{01}$ represents a hydrogen atom, a C1-6 alkyl group, a C2-6 alkenyl group, a C2-6 alkynyl group, a cyano group, a halogen atom, an optionally substituted phenyl group, an optionally substituted ester group, or an optionally substituted hetero 5-membered ring group, $R^{02}$ represents a hydrogen atom, a C1-6 alkyl group, or a halogen atom, $R^{03}$ represents an optionally substituted C1-6 alkylene group, an optionally substituted C6-C14 arylene group, an optionally substituted heterocyclic group, or a bond, A represents a group represented by the following structural formula:

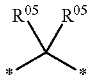

[wherein $R^{05}$ each independently represent a hydrogen atom, a halogen atom, a C1-6 alkyl group, or a C1-6 alkoxy group], *—$SO_2$—*, *—CO—$CH_2$—*, *—CO—NH—*, *—O—*, an optionally substituted C1-6 alkylene group, or a bond, $R^{04}$ represents a group represented by any one of the following structural formulae:

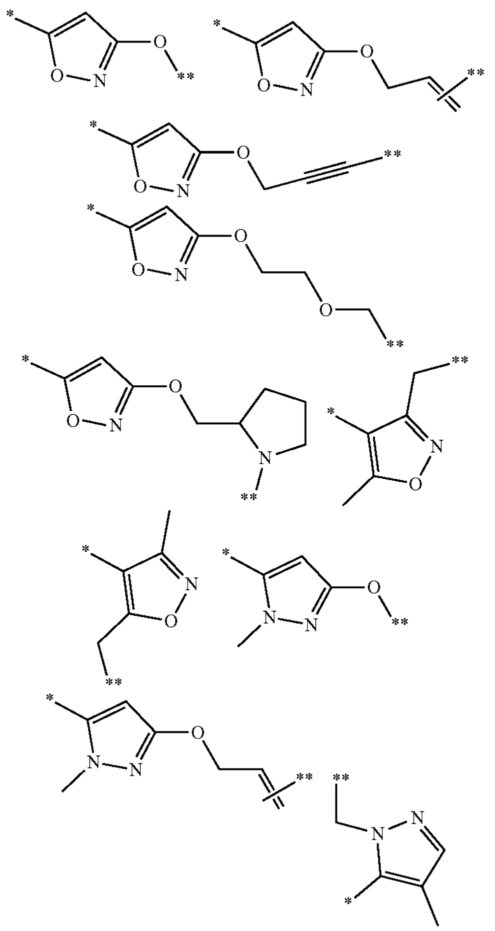

-continued

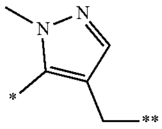
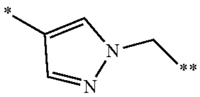
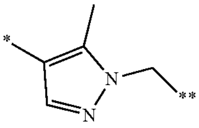
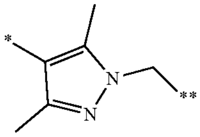
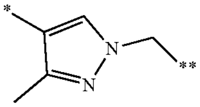
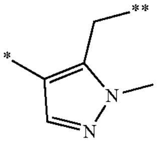
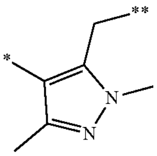
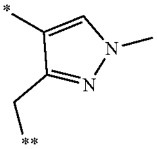
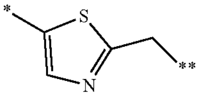
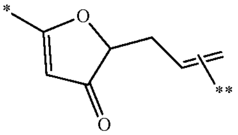
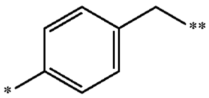
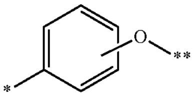
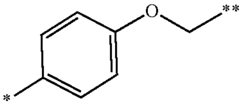
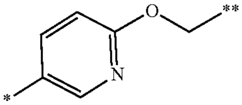
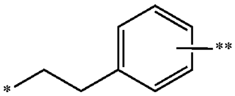
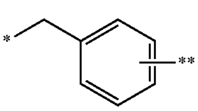
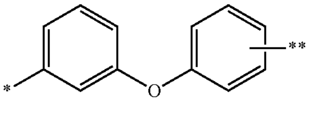
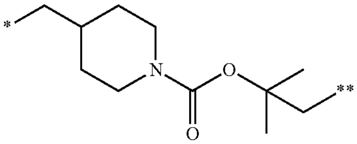
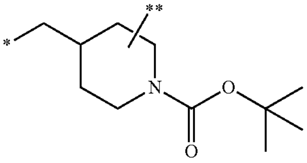
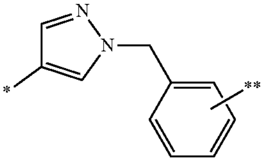
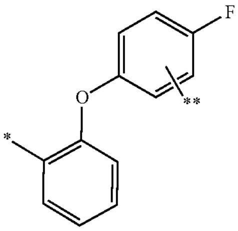

-continued

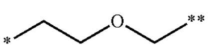
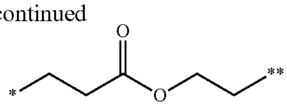

[wherein * represents the binding position to A, and ** represents the binding position to the linker], an optionally substituted C1-6 alkylene group, an optionally substituted C3-10 cycloalkylene group, an optionally substituted C6-14 arylene group, an optionally substituted hetero 5-6-membered ring group, an ester bond, or a bond, and the arrow represent the binding to the linker (L), or a pharmaceutically acceptable salt thereof.

[4] The compound according to the above [3], wherein in the formula (II) R°1 represents a hydrogen atom, a C1-6 alkyl group, a C2-6 alkynyl group, a cyano group, a halogen atom, an optionally substituted phenyl group, an optionally substituted ester group, or an optionally substituted hetero 5-membered ring group, $R^{03}$ represents an optionally substituted C6-C14 arylene group, an optionally substituted heterocyclic group, or a bond, $R^{04}$ is a group represented by any one of the following structural formulae:

$R^{04}$ is a group represented by any one of the following structural formulae:

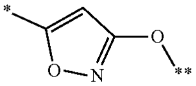
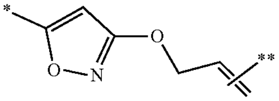
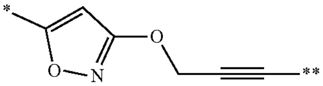
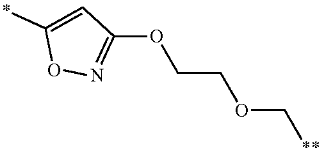
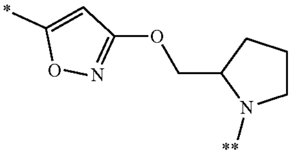
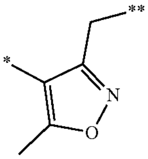
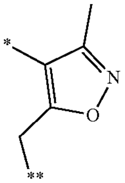
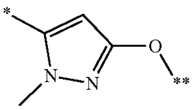
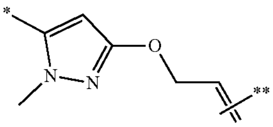
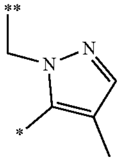

-continued

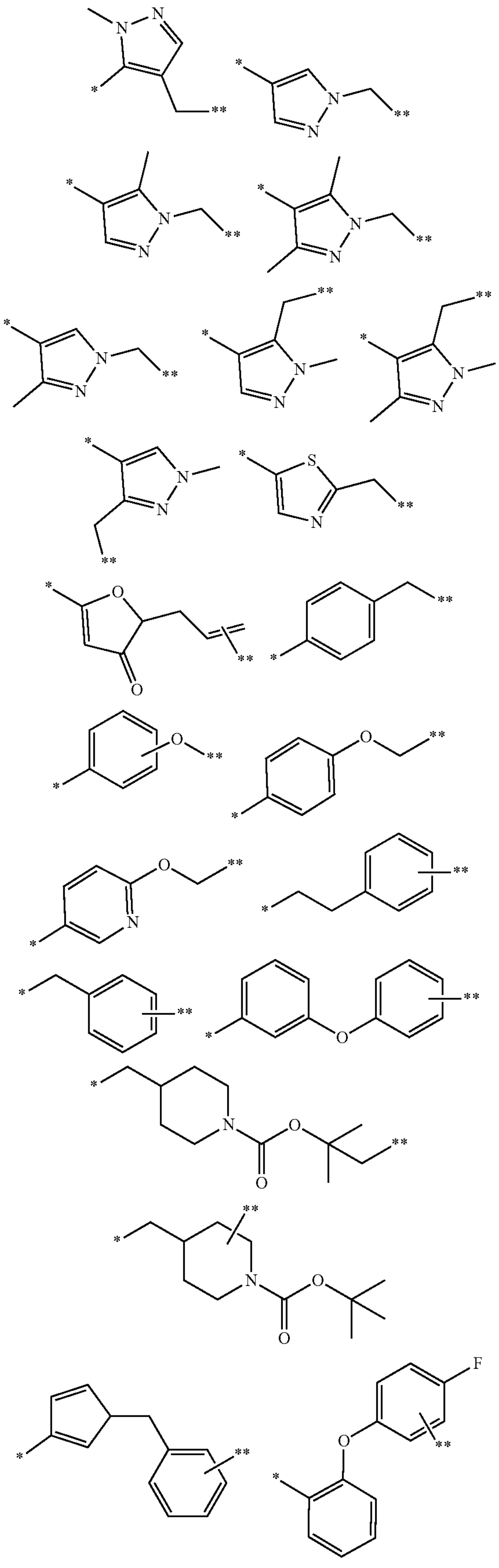

-continued

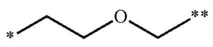 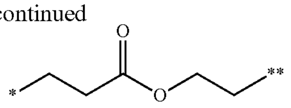

[wherein * represents the binding position to A, and ** represents the binding position to the linker], an optionally substituted C1-6 alkylene group, an optionally substituted C3-10 cycloalkylene group, an optionally substituted C6-14 arylene group, an optionally substituted pyrazolinediyl group, an optionally substituted oxazolidinediyl group, an optionally substituted isooxazolidinediyl group, an ester bond, or a bond, and the arrow represent the binding to the linker (L), or a pharmaceutically acceptable salt thereof.

[5] The compound according to the above [4], wherein in the formula (II)

$R^{01}$ represents a hydrogen atom, a methyl group, a cyano group, an iodine atom, a phenyl group, or a group represented by any one of the following structural formulae:

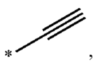, 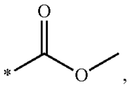, 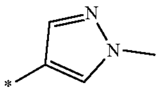

$R^{02}$ represents a hydrogen atom, a methyl group, or a chlorine atom, $R^{03}$ represents a group represented by any one of the following structural formulae:

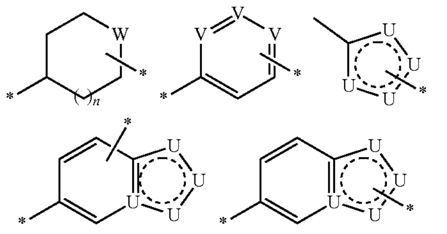

[wherein n is 0, 1 or 2, W represents NR [wherein R represents a hydrogen atom, a C1-6 alkyl group, or an acyl group], $SO_2$, SO, S or O, V each independently represent CH or N, provided that any one of V is CH, U each independently represent CH, N, NH, O or S, provided that no more than one U can be O or S], an optionally substituted C1-6 alkylene group, or a bond, $R^{04}$ represents a group represented by any one of the following structural formulae:

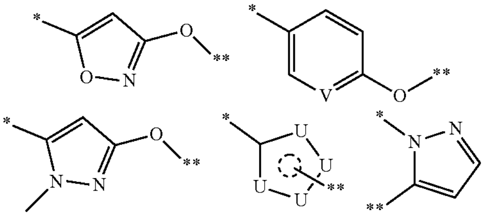

-continued

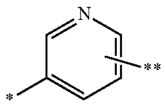
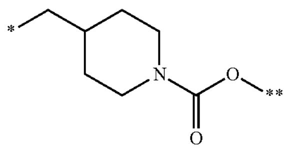
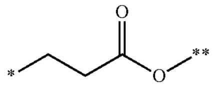
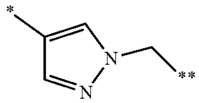
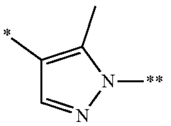

[wherein * represents the binding position to A, and ** represents the binding position to the linker, V represents CH or N, U each independently represent CH, N, NH, O or S, provided that no more than one U can be O or S], an optionally substituted C1-6 alkylene group, an optionally substituted C3-10 cycloalkylene group, an optionally substituted C6-C14 arylene group, or a bond, or a pharmaceutically acceptable salt thereof.

[6] The compound according to the above [5], wherein in the formula (II) X is S, Z is O, $R^{01}$ represents a hydrogen atom or a methyl group, $R^{02}$ is a hydrogen atom, $R^{03}$ is a group represented by the following structural formula:

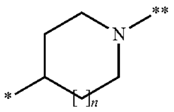

wherein * represents the binding position to 0, and ** represents the binding position to A, n is 0, 1 or 2, A is a group represented by the following structural formula:

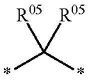

wherein $R^{05}$ each independently represent a hydrogen atom or a C1-6 alkyl group, $*—SO_2—*$, or $*—CO—CH_2—*$, $R^{04}$ represents a group represented by any one of the following structural formulae:

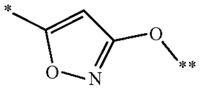
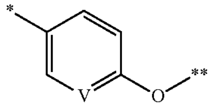
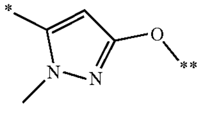

[wherein V is CH or N, * represents the binding position to A, and ** represents the binding position to the linker], an optionally substituted C1-6 alkylene group, an optionally substituted C3-10 cycloalkylene group, or an optionally substituted C6-C14 arylene group, or a pharmaceutically acceptable salt thereof.

[7] The compound according to the above [3], wherein the IRAK-M binder (M) is represented by the following formula (III):

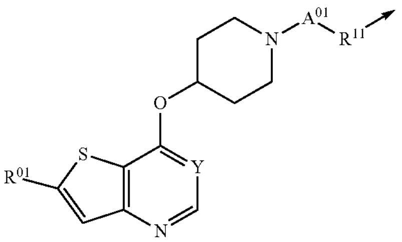

III wherein Y represents CH or N, $R^{01}$ represents a hydrogen atom, a C1-6 alkyl group, a C2-6 alkenyl group, a C2-3 alkynyl group, a cyano group, a halogen atom, an optionally substituted phenyl group, an optionally substituted ester group, or an optionally substituted hetero 5-membered ring group, $A^{01}$ is a group represented by the following structural formula:

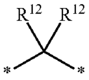

[wherein $R^{12}$ each independently represent a hydrogen atom or a C1-6 alkyl group], $*—SO_2—*$, or $*—CO—CH_2—*$, $R^{11}$ is a group represented by any one of the following structural formulae:

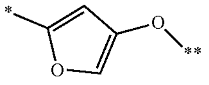
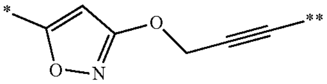
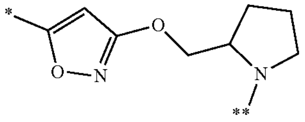
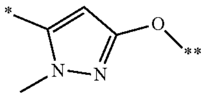
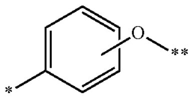
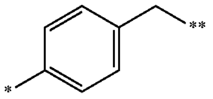
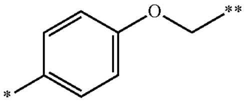
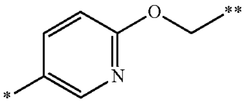
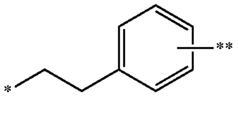
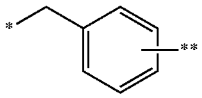

[wherein * represents the binding position to $A^{01}$, and ** represents the binding position to the linker], an optionally substituted C1-6 alkylene group, an optionally substituted C3-10 cycloalkylene group, an optionally substituted C6-14 arylene group, or a bond, and the arrow represent the binding to the linker (L), or a pharmaceutically acceptable salt thereof.

[8] The compound according to the above [7], wherein in the formula (III) $R^{01}$ represents a hydrogen atom or a methyl group, $A^{01}$ is a group represented by the following structural formula:

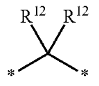

[wherein $R^{12}$ each independently represent a hydrogen atom or a C1-6 alkyl group], or *—$SO_2$—*, $R^{11}$ is a group represented by any one of the following structural formulae:

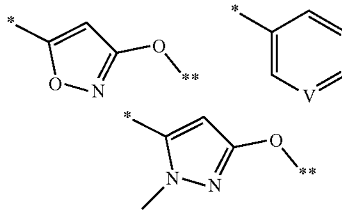

[wherein * represents the binding position to $A^{01}$, and ** represents the binding position to the linker], or a pharmaceutically acceptable salt thereof.

[9] The compound according to the above [3], wherein the IRAK-M binder (M) is a monovalent group derived from the compound selected from the group consisting of:

N-(3-(methylsulfonyl)phenyl)thieno[3,2-d]pyrimidin-4-amine:

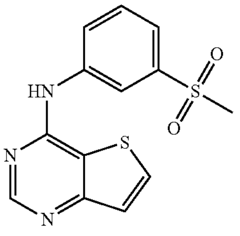 [SMILES: CS(=O)(=O)c1cccc(Nc2ncnc3ccsc23)c1]

4-((4-(thieno[3,2-d]pyrimidin-4-yloxy)piperidin-1-yl)sulfonyl)phenol:

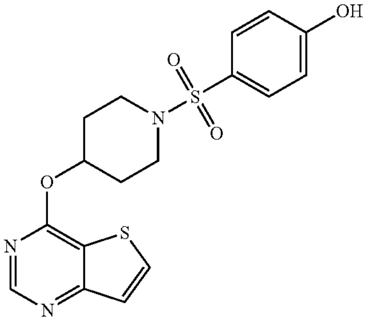 [SMILES: O=S(=O)(c1ccc(O)cc1)N1CCC(Oc2ncnc3ccsc23)CC1]

3-(allyloxy)-5-((4-(thieno[3,2-b]pyridin-7-yloxy)piperidin-1-yl)methyl)isoxazole:

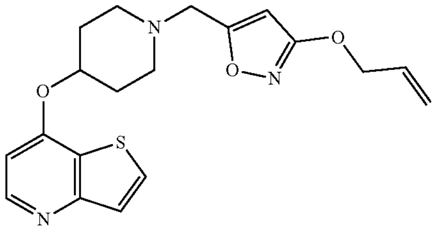 [SMILES: C=CCOc1cc(CN2CCC(Oc3ccnc4ccsc34)CC2)on1]

5-((4-(thieno[3,2-b]pyridin-7-yloxy)piperidin-1-yl)methyl)isoxazol-3-ol:

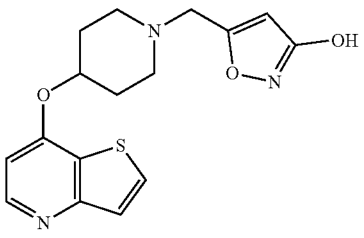 [SMILES: Oc1cc(CN2CCC(Oc3ccnc4ccsc34)CC2)on1]

3-(allyloxy)-5-(1-(4-(thieno[3,2-b]pyridin-7-yloxy)piperidin-1-yl)ethyl)isoxazole:

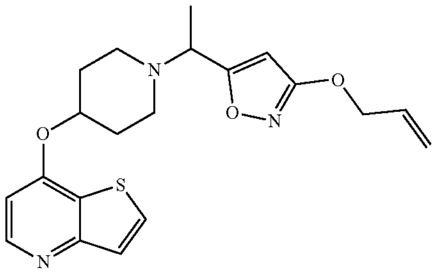 [SMILES: C=CCOc1cc(C(C)N2CCC(Oc3ccnc4ccsc34)CC2)on1]

3-(allyloxy)-5-(1-(4-((2-methylthieno[3,2-b]pyridin-7-yl)oxy)piperidin-1-yl)ethyl)isoxazole:

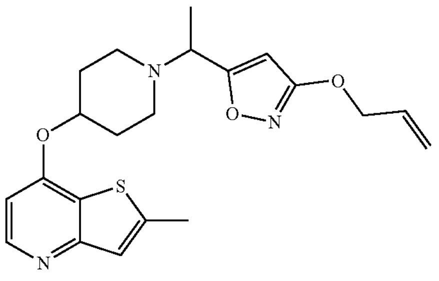 [SMILES: C=CCOc1cc(C(C)N2CCC(Oc3ccnc4cc(C)sc34)CC2)on1]

(S)-3-(pyrrolidin-2-ylmethoxy)-5-((4-(thieno[3,2-b]pyridin-7-yloxy)piperidin-1-yl)methyl)isoxazole:

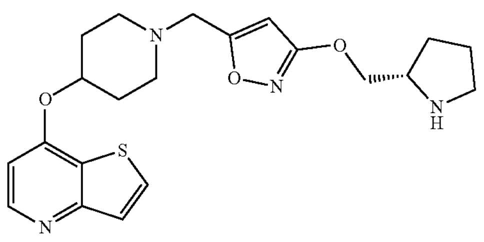 [SMILES: c1cc(OC2CCN(Cc3cc(OC[C@@H]4CCCN4)no3)CC2)c2sccc2n1]

3-((tetrahydrofuran-3-yl)oxy)-4-(thieno[3,2-d]pyrimidin-4-ylamino)benzamide:

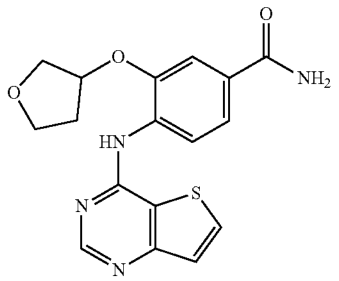 [SMILES: NC(=O)c1ccc(Nc2ncnc3ccsc23)c(OC2CCOC2)c1]

N,6-diphenylthieno[3,2-d]pyrimidin-4-amine:

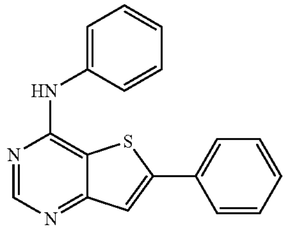 [SMILES: c1ccc(Nc2ncnc3cc(-c4ccccc4)sc23)cc1]

N-(2-methoxyphenyl)-6-phenylthieno[3,2-d]pyrimidin-4-amine:

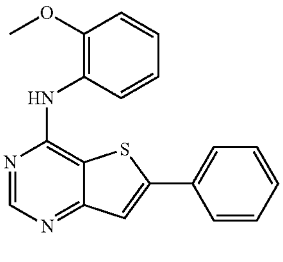 [SMILES: COc1ccccc1Nc1ncnc2cc(-c3ccccc3)sc12]

N-(cyclopropylmethyl)-6-phenylthieno[3,2-d]pyrimidin-4-amine:

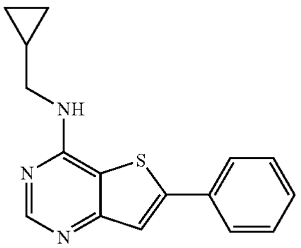 [SMILES: c1ccc(-c2cc3ncnc(NCC4CC4)c3s2)cc1]

6-phenyl-N-(pyridin-2-yl)thieno[3,2-d]pyrimidin-4-amine:

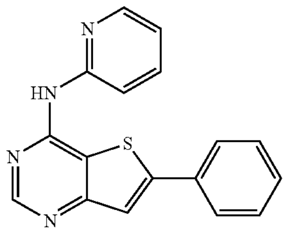 [SMILES: c1ccc(-c2cc3ncnc(Nc4ccccn4)c3s2)cc1]

6-phenyl-N-(pyridin-3-ylmethyl)thieno[3,2-d]pyrimidin-4-amine:

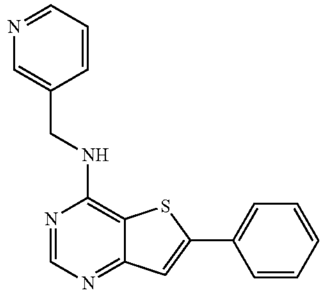 [SMILES: c1ccc(-c2cc3ncnc(NCc4cccnc4)c3s2)cc1]

N-phenethyl-6-phenphenylthieno[3,2-d]pyrimidin-4-amine:

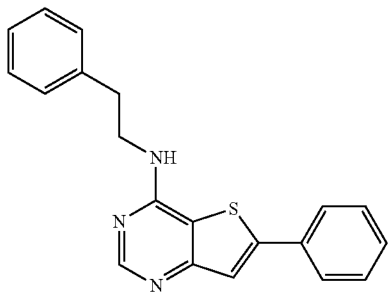 [SMILES: c1ccc(CCNc2ncnc3cc(-c4ccccc4)sc23)cc1]

4-(thieno[3,2-d]pyrimidin-4-ylamino)benzamide:

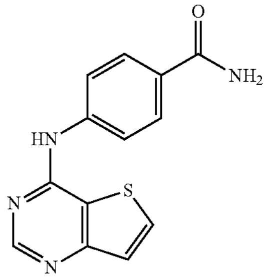 [SMILES: NC(=O)c1ccc(Nc2ncnc3ccsc23)cc1]

N-(2-((tetrahydrofuran-3-yl)oxy)phenyl)thieno[3,2-d]pyrimidin-4-amine:

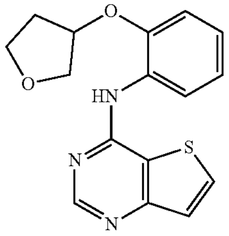 [SMILES: c1ccc(OC2CCOC2)c(Nc2ncnc3ccsc23)c1]

3-(thieno[3,2-d]pyrimidin-4-ylamino)benzamide:

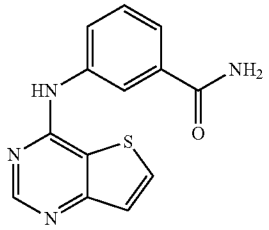 [SMILES: NC(=O)c1cccc(Nc2ncnc3ccsc23)c1]

N-(pyridin-4-yl)thieno[3,2-d]pyrimidin-4-amine:

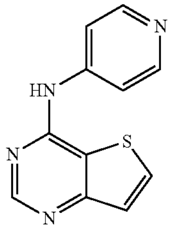 [SMILES: c1cc(Nc2ncnc3ccsc23)ccn1]

N-(2-(trifluoromethyl)pyridin-4-yl)thieno[3,2-d]pyrimidin-4-amine:

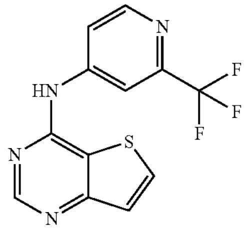 [SMILES: FC(F)(F)c1cc(Nc2ncnc3ccsc23)ccn1]

N-(2-methoxypyridin-4-yl)thieno[3,2-d]pyrimidin-4-amine:

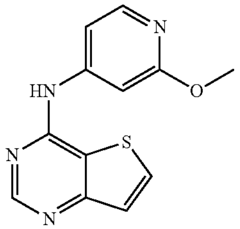 [SMILES: COc1cc(Nc2ncnc3ccsc23)ccn1]

N-(2-(trifluoromethyl)pyridin-3-yl)thieno[3,2-d]pyrimidin-4-amine:

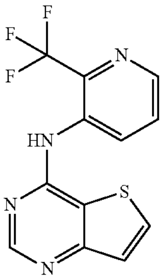 [SMILES: FC(F)(F)c1ncccc1Nc1ncnc2ccsc12]

N-(3-methyl-1-(pyridin-2-yl)-1H-pyrazol-5-yl)thieno[3,2-d]pyrimidin-4-amine:

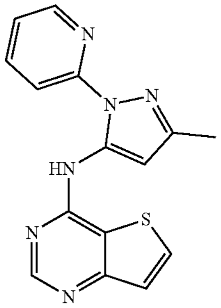 [SMILES: Cc1cc(Nc2ncnc3ccsc23)n(-c2ccccn2)n1]

N-(1H-benzo[d]imidazol-5-yl)thieno[3,2-d]pyrimidin-4-amine:

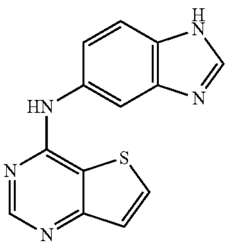 [SMILES: c1nc(Nc2ccc3[nH]cnc3c2)c2sccc2n1]

5-(thieno[3,2-d]pyrimidin-4-ylamino)isoindoline-1,3-dione:

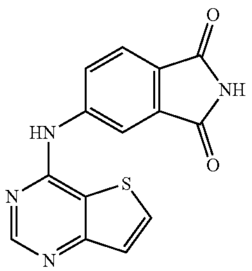 [SMILES: O=C1NC(=O)c2cc(Nc3ncnc4ccsc34)ccc21]

N-(1H-indazol-6-yl)thieno[3,2-d]pyrimidin-4-amine:

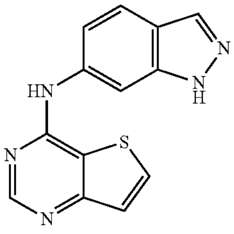 [SMILES: c1nc(Nc2ccc3cn[nH]c3c2)c2sccc2n1]

5-(thieno[3,2-d]pyrimidin-4-ylamino)isobenzofuran-1(3H)-one:

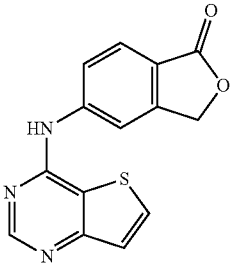 [SMILES: O=C1OCc2cc(Nc3ncnc4ccsc34)ccc21]

methyl 4-((cyclopropylmethyl)amino)thieno[3,2-d]pyrimidine-6-carboxylate:

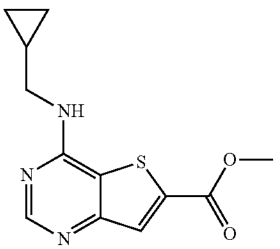 [SMILES: COC(=O)c1cc2ncnc(NCC3CC3)c2s1]

6-(1-methyl-1H-pyrazol-4-yl)-4-((1-methylpiperidin-4-yl)oxy)thieno[3,2-d]pyrimidine:

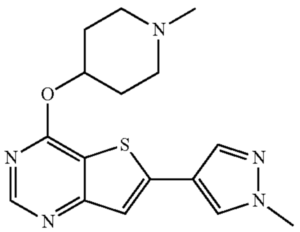 [SMILES: CN1CCC(Oc2ncnc3cc(-c4cnn(C)c4)sc23)CC1]

6-ethynyl-4-((1-methylpiperidin-4-yl)oxy)thieno[3,2-d]pyrimidine:

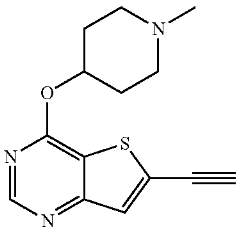 [SMILES: C#Cc1cc2ncnc(OC3CCN(C)CC3)c2s1]

4-((2-chlorothieno[3,2-d]pyrimidin-4-yl)amino)benzamide:

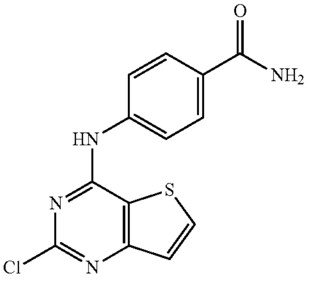 [SMILES: NC(=O)c1ccc(Nc2nc(Cl)nc3ccsc23)cc1]

6-iodo-4-((tetrahydro-2H-pyran-4-yl)oxy)thieno[3,2-d]pyrimidine:

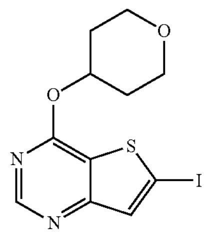 [SMILES: Ic1cc2ncnc(OC3CCOCC3)c2s1]

6-iodo-4-((tetrahydro-2H-thiopyran-4-yl)oxy)thieno[3,2-d]pyrimidine:

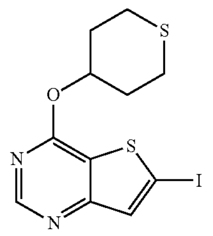 [SMILES: Ic1cc2ncnc(OC3CCSCC3)c2s1]

6-iodo-4-((1-methylpiperidin-4-yl)oxy)thieno[3,2-d]pyrimidine:

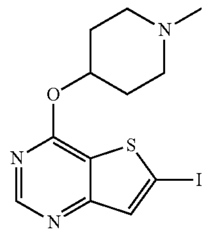 [SMILES: CN1CCC(Oc2ncnc3cc(I)sc23)CC1]

4-((6-iodothieno[3,2-d]pyrimidin-4-yl)oxy)tetrahydro-2H-thiopyran 1,1-dioxide:

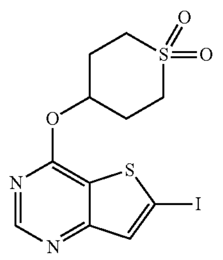 [SMILES: O=S1(=O)CCC(Oc2ncnc3cc(I)sc23)CC1]

4-((1-((2,6-difluorophenyl)sulfonyl)piperidin-4-yl)oxy)thieno[3,2-d]pyrimidine:

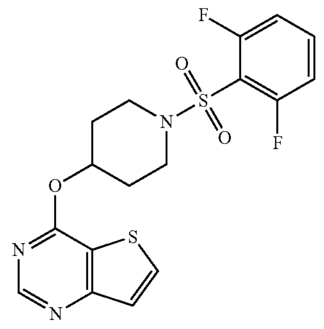 [SMILES: O=S(=O)(c1c(F)cccc1F)N1CCC(Oc2ncnc3ccsc23)CC1]

4-((1-(methylsulfonyl)piperidin-4-yl)oxy)thieno[3,2-d]pyrimidine:

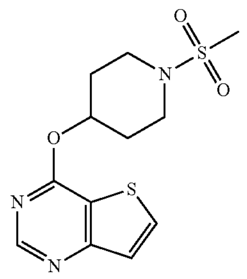 [SMILES: CS(=O)(=O)N1CCC(Oc2ncnc3ccsc23)CC1]

4-((1-((2-methoxyethyl)sulfonyl)piperidin-4-yl)oxy)thieno[3,2-d]pyrimidine:

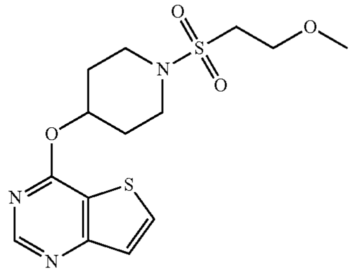 [SMILES: COCCS(=O)(=O)N1CCC(Oc2ncnc3ccsc23)CC1]

4-((1-(benzylsulfonyl)piperidin-4-yl)oxy)thieno[3,2-d]pyrimidine:

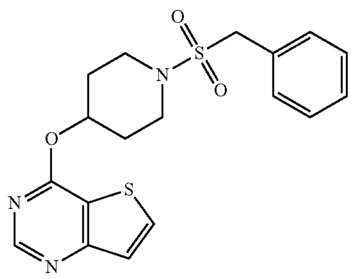 [SMILES: O=S(=O)(Cc1ccccc1)N1CCC(Oc2ncnc3ccsc23)CC1]

tert-butyl 4-(((4-(thieno[3,2-d]pyrimidin-4-yloxy)piperidin-1-yl)sulfonyl)methyl)piperidine-1-carboxylate:

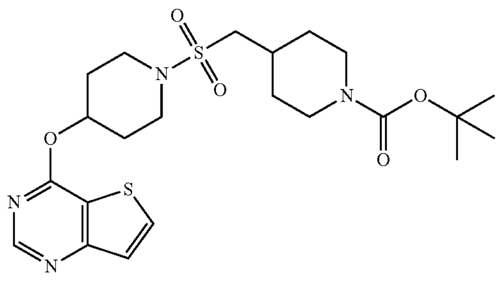 [SMILES: CC(C)(C)OC(=O)N1CCC(CS(=O)(=O)N2CCC(Oc3ncnc4ccsc34)CC2)CC1]

ethyl 3-((4-(thieno[3,2-d]pyrimidin-4-yloxy)piperidin-1-yl)sulfonyl)propanoate:

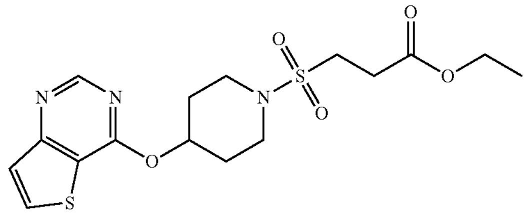 [SMILES: CCOC(=O)CCS(=O)(=O)N1CCC(Oc2ncnc3ccsc23)CC1]

4-((1-(cyclopropylsulfonyl)piperidin-4-yl)oxy)thieno[3,2-d]pyrimidine:

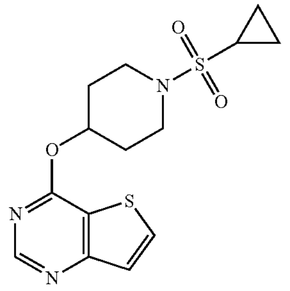 [SMILES: O=S(=O)(C1CC1)N1CCC(Oc2ncnc3ccsc23)CC1]

4-((1-((2-chlorophenyl)sulfonyl)piperidin-4-yl)oxy)thieno[3,2-d]pyrimidine:

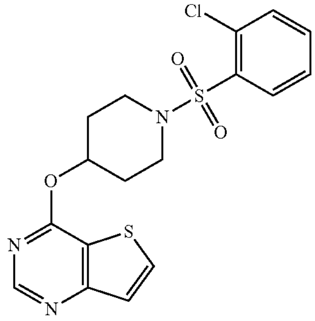 [SMILES: O=S(=O)(c1ccccc1Cl)N1CCC(Oc2ncnc3ccsc23)CC1]

4-((1-((2-methoxyphenyl)sulfonyl)piperidin-4-yl)oxy)thieno[3,2-d]pyrimidine:

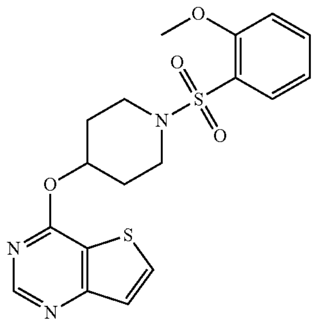 [SMILES: COc1ccccc1S(=O)(=O)N1CCC(Oc2ncnc3ccsc23)CC1]

4-((1-(o-tolylsulfonyl)piperidin-4-yl)oxy)thieno[3,2-d]pyrimidine:

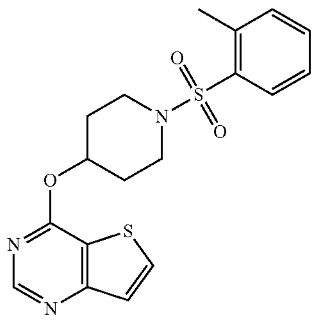 [SMILES: Cc1ccccc1S(=O)(=O)N1CCC(Oc2ncnc3ccsc23)CC1]

4-((1-((2-(4-fluorophenoxy)phenyl)sulfonyl)piperidin-4-yl)oxy)thieno[3,2-d]pyrimidine:

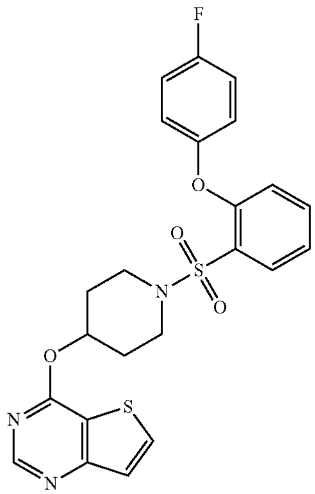 [SMILES: O=S(=O)(c1ccccc1Oc1ccc(F)cc1)N1CCC(Oc2ncnc3ccsc23)CC1]

4-((1-((2-fluorophenyl)sulfonyl)piperidin-4-yl)oxy)thieno[3,2-d]pyrimidine:

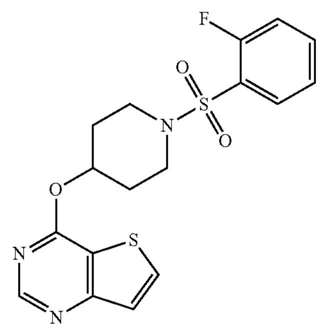 [SMILES: O=S(=O)(c1ccccc1F)N1CCC(Oc2ncnc3ccsc23)CC1]

4-((1-((2-(trifluoromethoxy)phenyl)sulfonyl)piperidin-4-yl)oxy)thieno[3,2-d]pyrimidine:

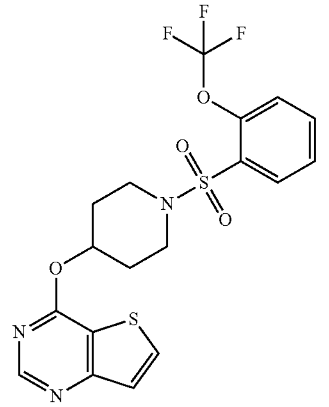 [SMILES: O=S(=O)(c1ccccc1OC(F)(F)F)N1CCC(Oc2ncnc3ccsc23)CC1]

4-((1-((4-methoxyphenyl)sulfonyl)piperidin-4-yl)oxy)thieno[3,2-d]pyrimidine:

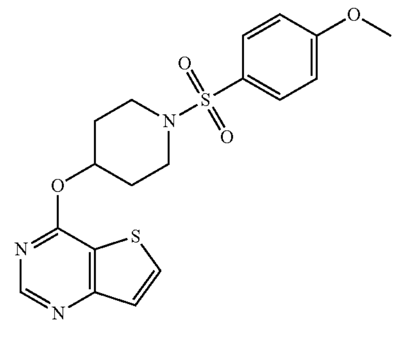

4-((1-((4-chlorophenyl)sulfonyl)piperidin-4-yl)oxy)thieno[3,2-d]pyrimidine:

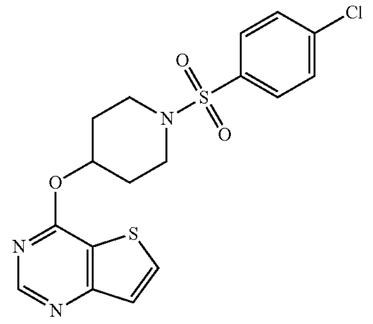 [SMILES: O=S(=O)(c1ccc(Cl)cc1)N1CCC(Oc2ncnc3ccsc23)CC1]

4-((1-((4-fluorophenyl)sulfonyl)piperidin-4-yl)oxy)thieno[3,2-d]pyrimidine:

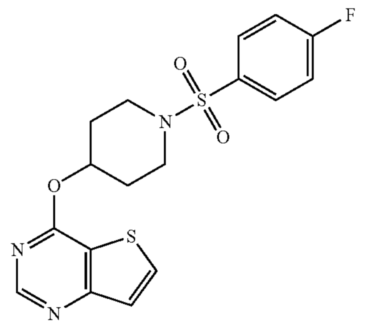 [SMILES: O=S(=O)(c1ccc(F)cc1)N1CCC(Oc2ncnc3ccsc23)CC1]

4-((1-((3-methoxyphenyl)sulfonyl)piperidin-4-yl)oxy)thieno[3,2-d]pyrimidine:

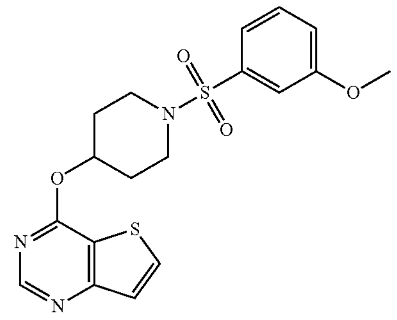 [SMILES: COc1cccc(S(=O)(=O)N2CCC(Oc3ncnc4ccsc34)CC2)c1]

4-((1-(4-methylbenzenesulfonyl)piperidin-4-yl)oxy)thieno[3,2-d]pyrimidine:

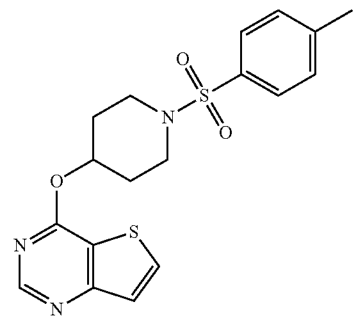 [SMILES: Cc1ccc(S(=O)(=O)N2CCC(Oc3ncnc4ccsc34)CC2)cc1]

4-((1-((3-fluorophenyl)sulfonyl)piperidin-4-yl)oxy)thieno[3,2-d]pyrimidine:

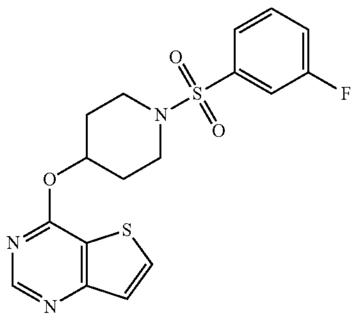 [SMILES: O=S(=O)(c1cccc(F)c1)N1CCC(Oc2ncnc3ccsc23)CC1]

4-((1-((3-chlorophenyl)sulfonyl)piperidin-4-yl)oxy)thieno[3,2-d]pyrimidine:

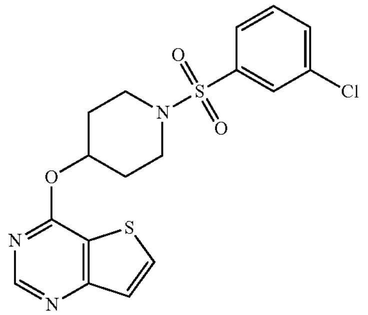 [SMILES: O=S(=O)(c1cccc(Cl)c1)N1CCC(Oc2ncnc3ccsc23)CC1]

4-((1-(pyridin-3-ylsulfonyl)piperidin-4-yl)oxy)thieno[3,2-d]pyrimidine:

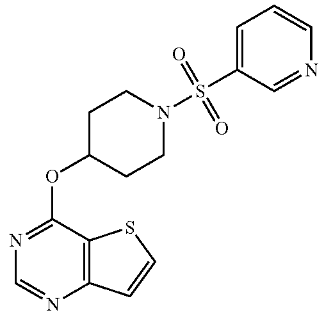 [SMILES: O=S(=O)(c1cccnc1)N1CCC(Oc2ncnc3ccsc23)CC1]

4-((1-((1-benzyl-1H-pyrazol-4-yl)sulfonyl)piperidin-4-yl)oxy)thieno[3,2-d]pyrimidine:

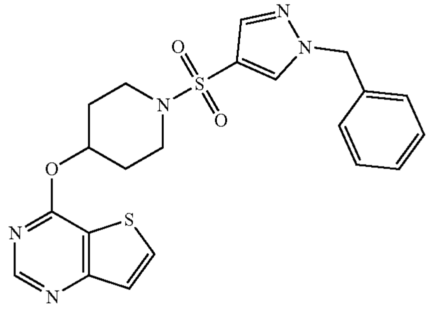 [SMILES: O=S(=O)(c1cnn(Cc2ccccc2)c1)N1CCC(Oc2ncnc3ccsc23)CC1]

4-((1-((6-methoxypyridin-3-yl)sulfonyl)piperidin-4-yl)oxy)thieno[3,2-d]pyrimidine:

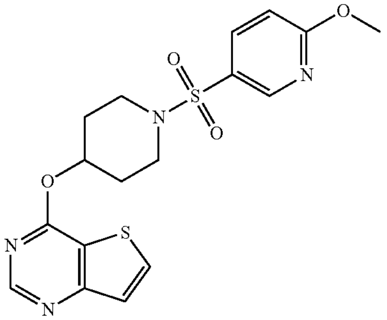 [SMILES: COc1ccc(S(=O)(=O)N2CCC(Oc3ncnc4ccsc34)CC2)cn1]

4-((1-((1,4-dimethyl-1H-pyrazol-5-yl)sulfonyl)piperidin-4-yl)oxy)thieno[3,2-d]pyrimidine:

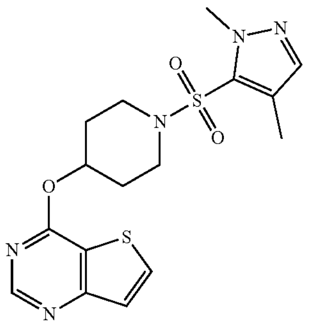 [SMILES: Cc1cnn(C)c1S(=O)(=O)N1CCC(Oc2ncnc3ccsc23)CC1]

4-((1-(isobutylsulfonyl)piperidin-4-yl)oxy)thieno[3,2-d]pyrimidine:

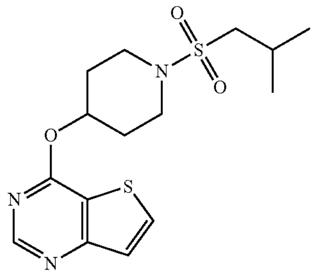 [SMILES: CC(C)CS(=O)(=O)N1CCC(Oc2ncnc3ccsc23)CC1]

4-((1-(phenethylsulfonyl)piperidin-4-yl)oxy)thieno[3,2-d]pyrimidine:

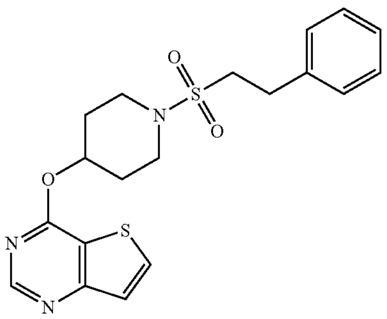 [SMILES: O=S(=O)(CCc1ccccc1)N1CCC(Oc2ncnc3ccsc23)CC1]

4-((1-((3-phenoxyphenyl)sulfonyl)piperidin-4-yl)oxy)thieno[3,2-d]pyrimidine:

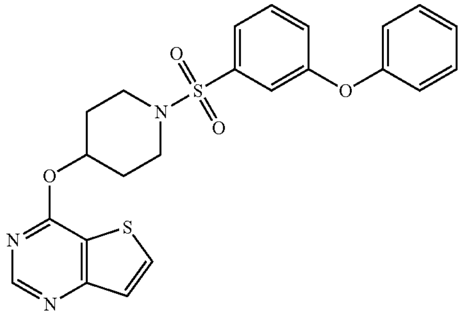 [SMILES: O=S(=O)(c1cccc(Oc2ccccc2)c1)N1CCC(Oc2ncnc3ccsc23)CC1]

N-(4-ethoxyphenyl)thieno[3,2-d]pyrimidin-4-amine:

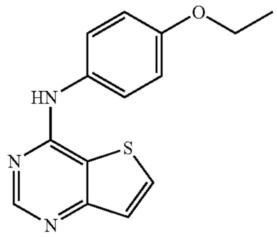 [SMILES: CCOc1ccc(Nc2ncnc3ccsc23)cc1]

N-(3,4-dimethoxyphenyl)-2,6-dimethylthieno[3,2-d]pyrimidin-4-amine:

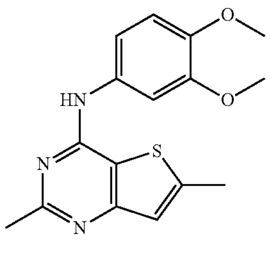

7-((1-(prop-2-yn-1-yl)piperidin-4-yl)oxy)thieno[3,2-b]pyridine:

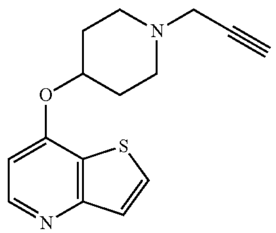 [SMILES: C#CCN1CCC(Oc2ccnc3ccsc23)CC1]

1-methyl-5-((4-(thieno[3,2-b]pyridin-7-yloxy)piperidin-1-yl)methyl)-1H-pyrazol-3-ol:

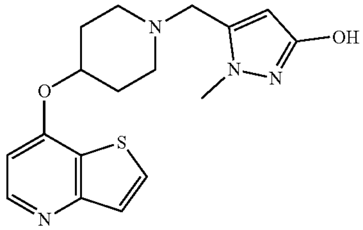 [SMILES: Cn1nc(O)cc1CN1CCC(Oc2ccnc3ccsc23)CC1]

7-((1-((3-(allyloxy)-1-methyl-1H-pyrazol-5-yl)methyl)piperidin-4-yl)oxy)thieno[3,2-b]pyridine:

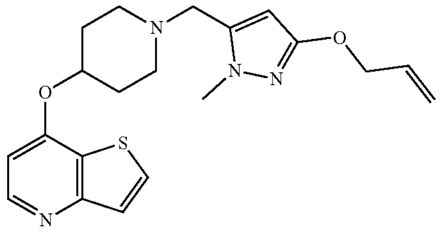 [SMILES: C=CCOc1cc(CN2CCC(Oc3ccnc4ccsc34)CC2)n(C)n1]

3-(allyloxy)-5-((4-(thieno[3,2-d]pyrimidin-4-yloxy)piperidin-1-yl)methyl)isoxazole:

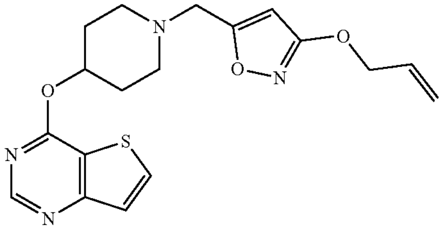 [SMILES: C=CCOc1cc(CN2CCC(Oc3ncnc4ccsc34)CC2)on1]

3-(prop-2-yn-1-yloxy)-5-((4-(thieno[3,2-b]pyridin-7-yloxy) piperidin-1-yl)methyl)isoxazole:

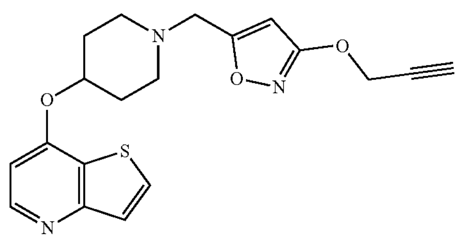 [SMILES: C#CCOc1cc(CN2CCC(Oc3ccnc4ccsc34)CC2)on1]

3-(allyloxy)-5-((4-((2-methylthieno[3,2-b]pyridin-7-yl)oxy) piperidin-1-yl)methyl)isoxazole:

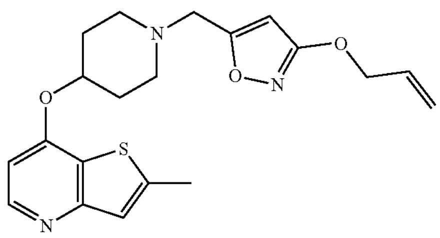 [SMILES: C=CCOc1cc(CN2CCC(Oc3ccnc4cc(C)sc34)CC2)on1]

7-((1-((1-methyl-1H-pyrazol-4-yl)methyl)piperidin-4-yl) oxy)thieno[3,2-b]pyridine:

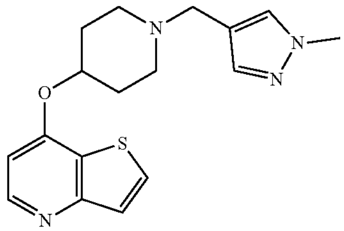 [SMILES: Cn1cc(CN2CCC(Oc3ccnc4ccsc34)CC2)cn1]

7-((1-((1,3-dimethyl-1H-pyrazol-4-yl)methyl)piperidin-4-yl)oxy)thieno[3,2-b]pyridine:

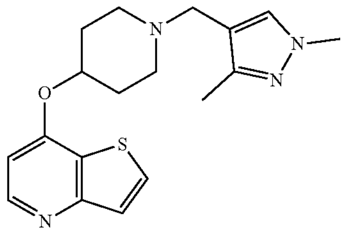 [SMILES: Cc1nn(C)cc1CN1CCC(Oc2ccnc3ccsc23)CC1]

7-((1-((1,3,5-trimethyl-1H-pyrazol-4-yl)methyl)piperidin-4-yl)oxy)thieno[3,2-b]pyridine:

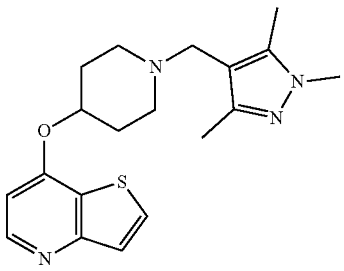 [SMILES: Cc1nn(C)c(C)c1CN1CCC(Oc2ccnc3ccsc23)CC1]

7-((1-((1,5-dimethyl-1H-pyrazol-4-yl)methyl)piperidin-4-yl)oxy)thieno[3,2-b]pyridine:

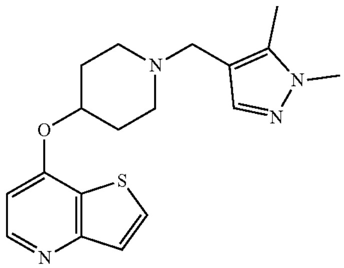 [SMILES: Cc1c(CN2CCC(Oc3ccnc4ccsc34)CC2)cnn1C]

7-((1-((1-methyl-1H-pyrazol-5-yl)methyl)piperidin-4-yl) oxy)thieno[3,2-b]pyridine:

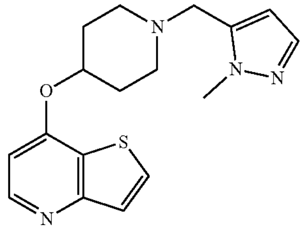 [SMILES: Cn1nccc1CN1CCC(Oc2ccnc3ccsc23)CC1]

3,5-dimethyl-4-((4-(thieno[3,2-b]pyridin-7-yloxy)piperidin-1-yl)methyl)isoxazole:

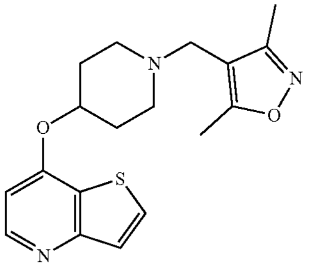 [SMILES: Cc1noc(C)c1CN1CCC(Oc2ccnc3ccsc23)CC1]

7-((1-(thiazol-2-ylmethyl)piperidin-4-yl)oxy)thieno[3,2-b]pyridine:

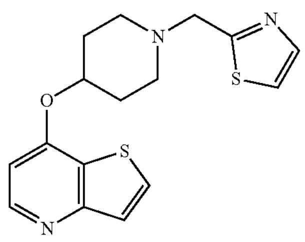 [SMILES: c1csc(CN2CCC(Oc3ccnc4ccsc34)CC2)n1]

7-((1-((2-methylthiazol-5-yl)methyl)piperidin-4-yl)oxy)thieno[3,2-b]pyridine:

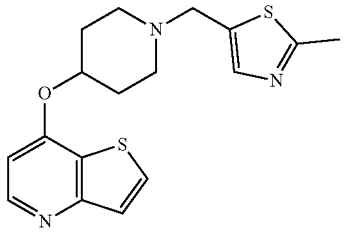 [SMILES: Cc1ncc(CN2CCC(Oc3ccnc4ccsc34)CC2)s1]

2-(1H-pyrazol-1-yl)-1-(4-(thieno[3,2-b]pyridin-7-yloxy)piperidin-1-yl)ethan-1-one:

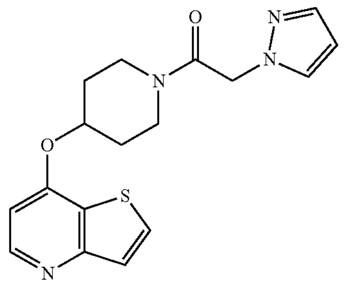 [SMILES: O=C(Cn1cccn1)N1CCC(Oc2ccnc3ccsc23)CC1]

1-(4-(thieno[3,2-b]pyridin-7-yloxy)piperidin-1-yl)-2-(2H-1,2,3-triazol-2-yl)ethan-1-one:

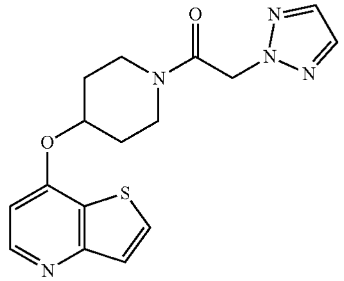 [SMILES: O=C(Cn1nccn1)N1CCC(Oc2ccnc3ccsc23)CC1]

2-allyl-5-((4-(thieno[3,2-b]pyridin-7-yloxy)piperidin-1-yl)methyl)isoxazol-3(2H)-one:

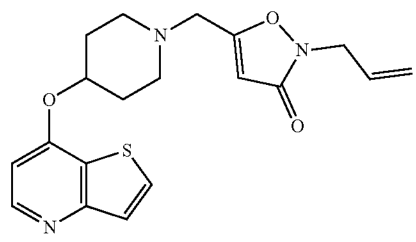 [SMILES: C=CCn1oc(CN2CCC(Oc3ccnc4ccsc34)CC2)cc1=O]

3-(2-methoxyethoxy)-5-((4-(thieno[3,2-b]pyridin-7-yloxy)piperidin-1-yl)methyl)isoxazole:

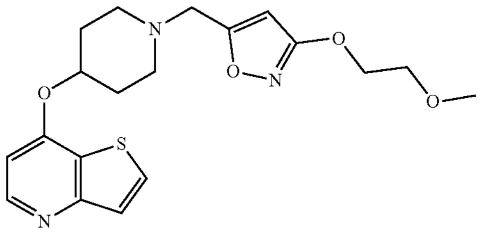 [SMILES: COCCOc1cc(CN2CCC(Oc3ccnc4ccsc34)CC2)on1]

7-((1-((3-(allyloxy)isoxazol-5-yl)methyl)piperidin-4-yl)oxy)thieno[3,2-b]pyridine-2-carbonitrile:

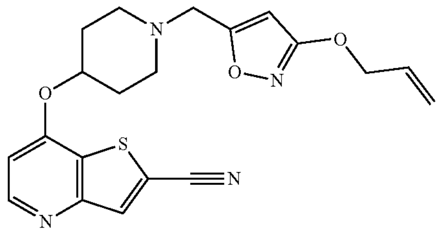 [SMILES: C=CCOc1cc(CN2CCC(Oc3ccnc4cc(C#N)sc34)CC2)on1]

5-((4-((2-methylthieno[3,2-b]pyridin-7-yl)oxy)piperidin-1-yl)methyl)isoxazol-3-ol:

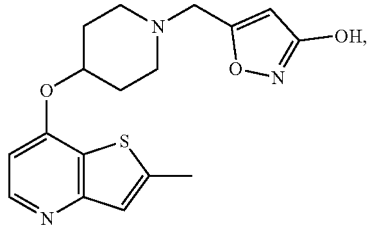 [SMILES: Cc1cc2nccc(OC3CCN(Cc4cc(O)no4)CC3)c2s1]

and 5-(1-(4-((2-methylthieno[3,2-b]pyridin-7-yl)oxy)piperidin-1-yl)ethyl)isoxazol-3-ol:

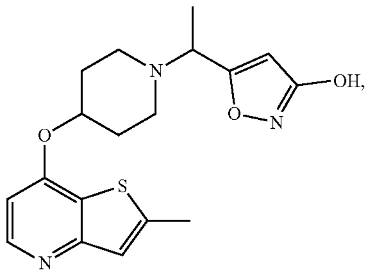 [SMILES: Cc1cc2nccc(OC3CCN(C(C)c4cc(O)no4)CC3)c2s1]

or a pharmaceutically acceptable salt thereof.

[10] The compound according to the above [9], wherein the IRAK-M binder (M) is a monovalent group derived from the compound selected from the group consisting of: 5-((4-(thieno[3,2-b]pyridin-7-yloxy)piperidin-1-yl)methyl)isoxazol-3-ol:

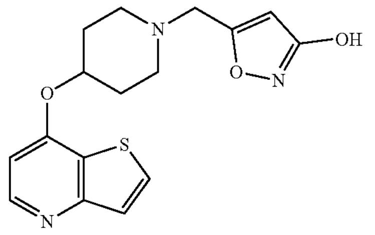 [SMILES: Oc1cc(CN2CCC(Oc3ccnc4ccsc34)CC2)on1]

5-((4-((2-methylthieno[3,2-b]pyridin-7-yl)oxy)piperidin-1-yl)methyl)isoxazol-3-ol:

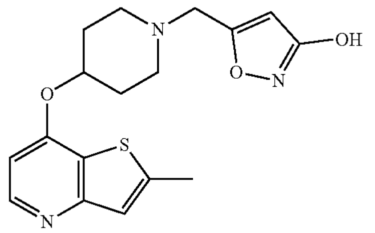 [SMILES: Cc1cc2nccc(OC3CCN(Cc4cc(O)no4)CC3)c2s1]

1-methyl-5-((4-(thieno[3,2-b]pyridin-7-yloxy)piperidin-1-yl)methyl)-1H-pyrazol-3-ol:

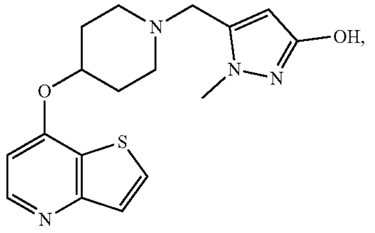 [SMILES: Cn1nc(O)cc1CN1CCC(Oc2ccnc3ccsc23)CC1]

and (4-((4-(thieno[3,2-d]pyrimidin-4-yloxy)piperidin-1-yl)sulfonyl)phenol:

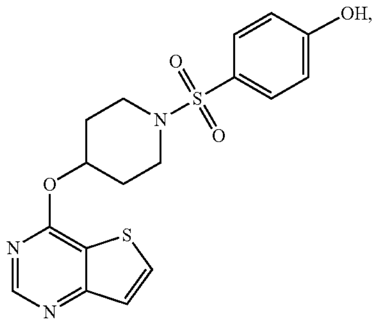 [SMILES: O=S(=O)(c1ccc(O)cc1)N1CCC(Oc2ncnc3ccsc23)CC1]

or a pharmaceutically acceptable salt thereof.

[11] The compound according to any one of the above [3] to [10], wherein the Linker (L) is represented by the formula (L1): $—B_1—B_2\text{-}L^1\text{-}L^2\text{-}L^3\text{-}L^4\text{-}L^5\text{-}L^6\text{-}L^7\text{-}$, wherein $B_1$ and $B_2$ each independently represent a group represented by the following structural formula:

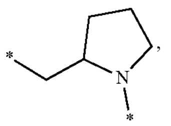 [SMILES: *CC1CCCN1*]

provided that both $B_1$ and $B_2$ are not the above structural formula, *—O—*, *—$NR^{06}$—* [wherein $R^{06}$ represents a hydrogen atom or a C1-6 alkyl group], *—$CO_2$—*, *—CO—*, *—$SO_2$—*, an optionally substituted C1-6 alkylene group, an optionally substituted C2-6 alkenylene group, an optionally substituted C2-6 alkynylene group, an optionally substituted C3-10 cycloalkylene group, an optionally substituted C6-14 arylene group, or a bond, $L^1$, $L^2$, $L^3$, $L^4$, $L^5$, $L^6$, and $L^7$ each independently represent a group represented by the following structural formula:

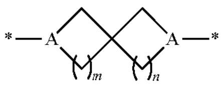

[wherein m represents an integer of 1 to 4, n represents an integer of 1 to 4, and A each independently represent N, CHCO or $CHCH_2O$, provided that any two or more of $L^1$ to $L^7$ are not the above structural formula], a bond, oxygen atom, sulfur atom, a C1-6 alkylene group, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolyldiyl group, a non-aromatic heterocyclic group which may be substituted with an optionally substituted C1-6 alkyl group or a halogen atom, a pyrrolidinediyl group optionally substituted with fluorine atom, a morpholinediyl group which may be substituted with an optionally substituted C1-6 alkyl group, an azetidinediyl group optionally substituted with fluorine atom, formula —$SO_2$—, formula —$CH_2CH_2O$—, formula $—OCH_2CH_2—$, formula $—COCH_2—$, formula $—CH_2CO—$, formula $—CO_2—$, formula —OCO—, formula $—COCHR^{101}NR^{102}—$, formula $—OCH_2CHR^{103}NR^{104}—$, formula $—N^{105}CHR^{106}CO—$, formula $—NR^{107}CO—$, formula $—CONR^{108}—$, formula $—SO_2NR^{109}—$, formula $—NR^{110}SO_2—$, or formula $—NR^{111}CHR^{112}CH_2O—$ [wherein in the above formulae $R^{101}$, $R^{103}$, $R^{106}$ and $R^{112}$ each independently represent a hydrogen atom, a C1-6 alkyl group, a 3-guanidinopropyl group, a carbamoylmethyl group, a carboxymethyl group, a mercaptomethyl group, a 2-carbamoyl ethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, an 4-hydroxyphenylmethyl group or a pyridylmethyl group, and $R^{102}$, $R^{104}$, $R^{105}$, $R^{107}$, $R^{108}$, $R^{109}$, $R^{110}$, and $R^{111}$ each independently represent a hydrogen atom or a C1-6 alkyl group], or together represent a bond, or a pharmaceutically acceptable salt thereof.

[12] The compound according to the above [11], wherein $B_1$ and $B_2$ each independently represent a group represented by the following structural formula:

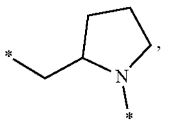

provided that both $B_1$ and $B_2$ are not the structural formula, *—O—*, $*—NR^{06}—*$ [wherein $R^{06}$ represents a hydrogen atom or a C1-6 alkyl group], *—CO—*, an optionally substituted C1-6 alkylene group, an optionally substituted C6-14 arylene group, an optionally substituted C2-6 alkynylene group, or a bond, or a pharmaceutically acceptable salt thereof.

[13] The compound according to the above [11], wherein $B_1$ and $B_2$ each independently represent a group represented by the following structural formula:

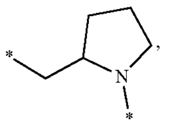

provided that both $B_1$ and $B_2$ are not the structural formula, *—O—*, a C1-6 alkylene group, or a bond, or a pharmaceutically acceptable salt thereof.

[14] The compound according to the above [11], wherein the Linker (L) represents a group represented by any one of the following formulae:

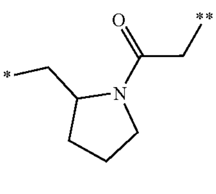

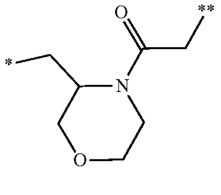

-continued

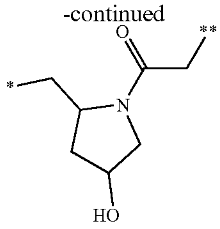

[wherein * represents the binding to the IRAK-M binder (M)], $*—(CH_2CH_2O)n(CH_2)m(NRCO)s(CH_2)t-*$ (n is an integer from 1 to 5, m is 0, 1, or 2, s is 0 or 1, t is 0 or 1, and R represents a hydrogen atom or a C1-6 alkyl group), or a bond, or a pharmaceutically acceptable salt thereof.

[15] The compound according to any one of the above [3] to [14], wherein the E3 ligase binder (E) is represented by the following formula (IV):

(IV)

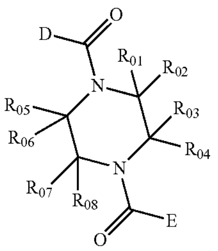

wherein D represents a fragment structure of a substance that binds to the IAP together with the piperazine ring, and E represents a nitrogen-containing aromatic heterocyclic group, $R_{01}$, $R_{02}$, $R_{03}$, $R_{04}$, $R_{05}$, $R_{06}$, $R_{07}$ and $R_{08}$ each independently represent a hydrogen atom or a C1-6 alkyl group which may form a ring with each other, and either D or E binds to the Linker (L), or a pharmaceutically acceptable salt thereof.

[16] The compound according to the above [15], wherein D represents the following formula (V):

(V)

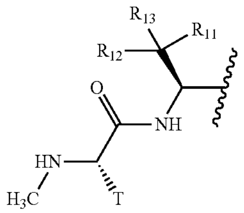

wherein $R_{11}$ represents a hydrogen atom or a hydroxyl group, and $R_{12}$ and $R_{13}$ each independently represent a hydrogen atom, a C1-6 alkyl group, a C3-10 cycloalkylene group, a carbonyl group, an imino group optionally substituted with a C1-6 alkyl group, an ethynylene group optionally substituted with a C1-6 alkyl group, a vinylene group optionally substituted with a C1-6 alkyl group, a pyrazole group optionally substituted with a C1-6 alkyl group, a C3-10 cycloalkenylene group, a phenylene group, a thiazolylene group, a pyrrolidinediyl group optionally substituted with a fluorine atom, an azetidinediyl group optionally substituted with a fluorine atom, or any of the above group bonded to the linker (L), provided that both $R_{12}$ and $R_{13}$ are not bonded to a linker, and T represents an optionally halogenated C1-3 alkyl group, or the following formula (VI):

(VI)

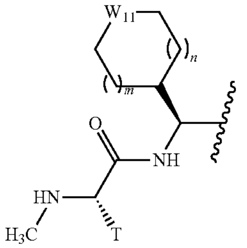

wherein m is 0, 1 or 2, n is 0, 1 or 2, $W_{11}$ represents a methylene group, a difluoromethylene group, O, S, SO, $SO_2$, or NR, wherein R represents a hydrogen atom, a C1-6 alkyl group, a C1-6 alkyl-carbonyl group, a C6-14 aryl-carbonyl group, a C1-6 alkylsulfonyl group, or the binding to the Linker, and T represents an optionally halogenated C1-3 alkyl group, or the following formula (VII):

(VII)

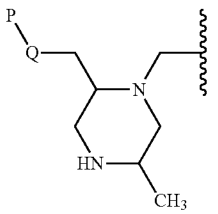

wherein Q represents an oxygen atom, formula —$NR^{21}$— [wherein $R^{21}$ represents a hydrogen atom, a C1-6 alkyl group, or a C1-6 alkyl group which may form a ring with P], or a bond, P represents a hydrogen atom, a C1-6 alkyl group or the binding to the Linker, including the formation of a ring with Q and binding to the Linker, or a pharmaceutically acceptable salt thereof.

[17] The compound according to the above [16], wherein D bonds to the Linker via any of $R_{12}$ or $R_{13}$ in the formula (V), $W_{11}$ in the formula (VI), or P in the formula (VII), or a pharmaceutically acceptable salt thereof.

[18] The compound according to the above [15] or [16], wherein E represents any one of the following formulae:

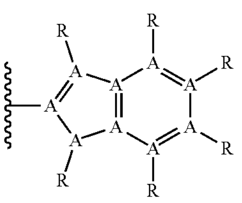
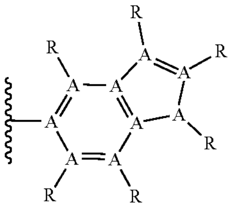

wherein A each independently represent C or N, and R bonded to N each independently represent a hydrogen atom, a C1-6 alkyl group, or an amido group, and other R each independently represent a hydrogen atom, a halogen atom, a C1-6 alkyl group, a C1-6 alkoxy group, or an amido group, wherein when E is bonded to the Linker, E is bonded to the Linker at any one position indicted by R in the above formulae, or a pharmaceutically acceptable salt thereof.

[19] The compound according to the above [18], wherein E is represented by any one of the following formulae:

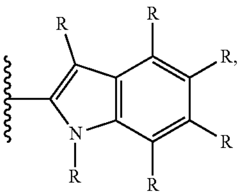
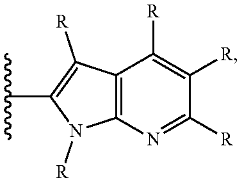
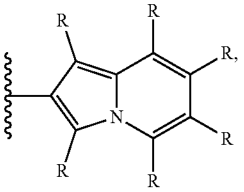
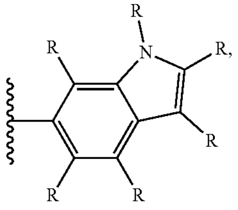
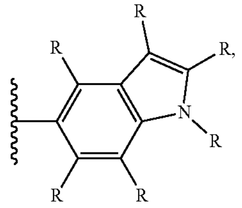
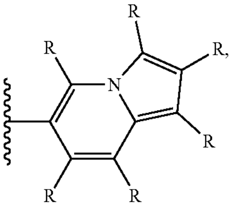
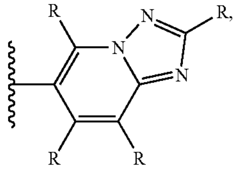
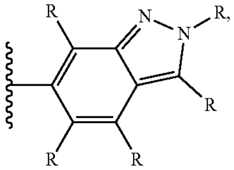
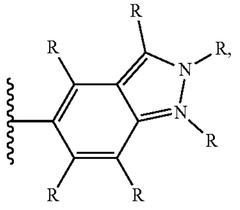
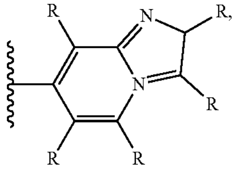
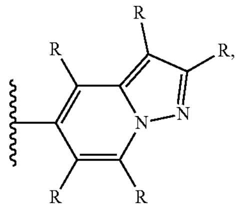
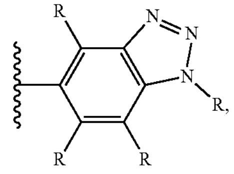
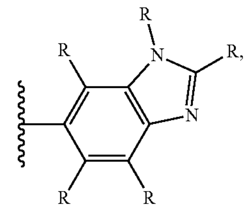
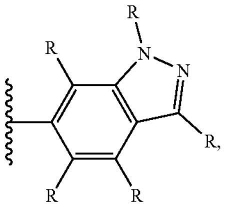

-continued

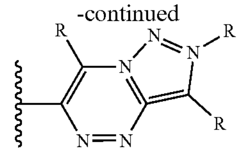

wherein R bonded to N each independently represent a hydrogen atom, a C1-6 alkyl group, or an amido group, and other R each independently represent a hydrogen atom, a halogen atom, a C1-6 alkyl group, a C1-6 alkoxy group, or an amido group, wherein when E is bonded to the Linker, E is bonded to the Linker at any one position indicted by R in the above formulae, or a pharmaceutically acceptable salt thereof.

[20] The compound according to the above [18], wherein E represents the following formula (VIII):

VIII

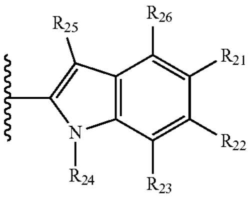

wherein $R_{21}$, $R_{22}$, and $R_{23}$ each independently represent a hydrogen atom, a halogen atom, a C1-6 alkyl group, a C1-6 alkoxy group, or an amido group, $R_{25}$ and $R_{26}$ each independently represent a hydrogen atom, a halogen atom, a C1-6 alkyl group, a C1-6 alkoxy group, an amido group, or the binding to the Linker, $R_{24}$ represents a hydrogen atom, a methyl group, or the binding to the linker, provided that the binding to the linker is any one of $R_{24}$, $R_{25}$, or $R_{26}$, or a pharmaceutically acceptable salt thereof.

[21] The compound according to the above [18], wherein E represents the following formula (IX):

IX

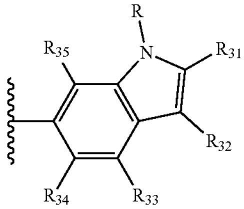

wherein $R_{31}$, $R_{32}$, $R_{33}$, $R_{34}$, and $R_{35}$ each independently represent a hydrogen atom, a halogen atom, a C1-6 alkyl group, a C1-6 alkoxy group, or an amido group, and R represents a hydrogen atom, C1-6 alkyl group, or the binding to the linker, or a pharmaceutically acceptable salt thereof.

[22] The compound according to the above [1], which compound is selected from the group consisting of:

2-(4-((S)-2-cyclohexyl-2-((S)-2-(methylamino)propanamido)acetyl)piperazine-1-carbonyl)-5,6-difluoro-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide:

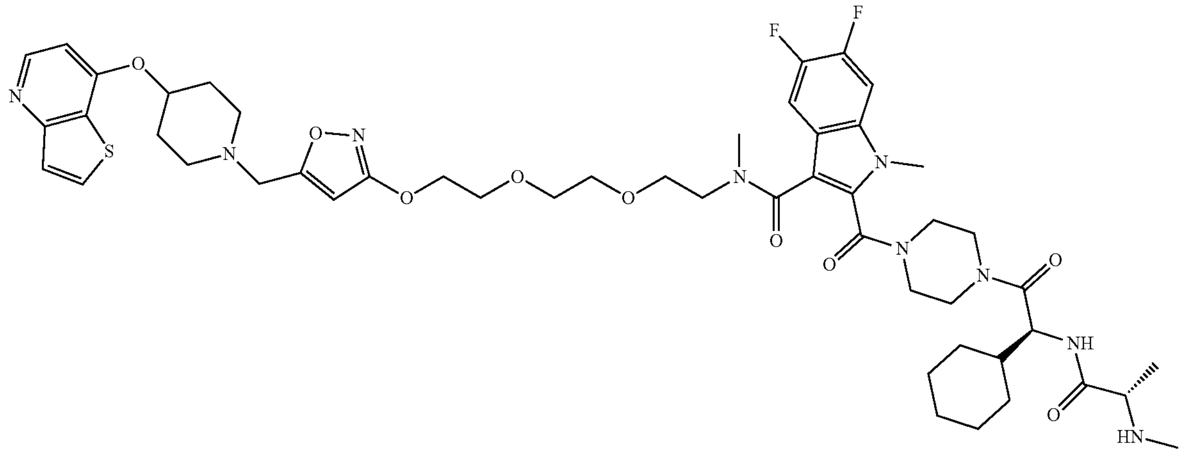 [SMILES: CN[C@@H](C)C(=O)N[C@H](C(=O)N1CCN(C(=O)c2c(C(=O)N(C)CCOCCOCCOc3cc(CN4CCC(Oc5ccnc6ccsc56)CC4)on3)c3cc(F)c(F)cc3n2C)CC1)C1CCCCC1]

2-(4-((S)-2-cyclohexyl-2-((S)-2-(methylamino)propanamido)acetyl)piperazine-1-carbonyl)-6-methoxy-1-methyl-N-(2-(2-(2-(4-((4-(thieno[3,2-d]pyrimidin-4-yloxy)piperidin-1-yl)sulfonyl)phenoxy)ethoxy)ethoxy)ethyl)-1H-indole-3-carboxamide:

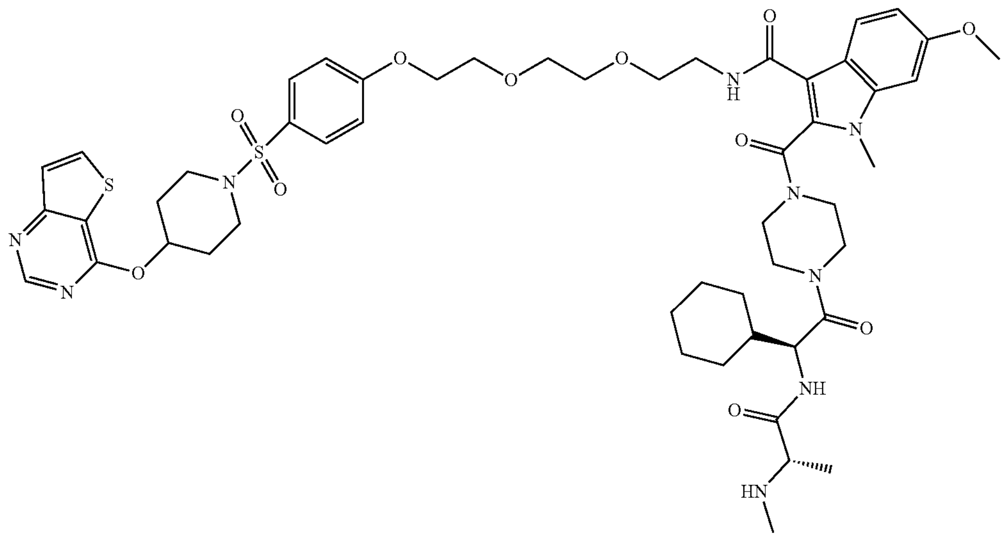 [SMILES: CN[C@@H](C)C(=O)N[C@H](C(=O)N1CCN(C(=O)c2c(C(=O)NCCOCCOCCOc3ccc(S(=O)(=O)N4CCC(Oc5ncnc6ccsc56)CC4)cc3)c3ccc(OC)cc3n2C)CC1)C1CCCCC1]

1-((R)-4-(5,6-difluoro-1-methyl-1H-indole-2-carbonyl)-2-methylpiperazin-1-yl)-2-((2R,5R)-5-methyl-2-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazin-1-yl)ethan-1-one:

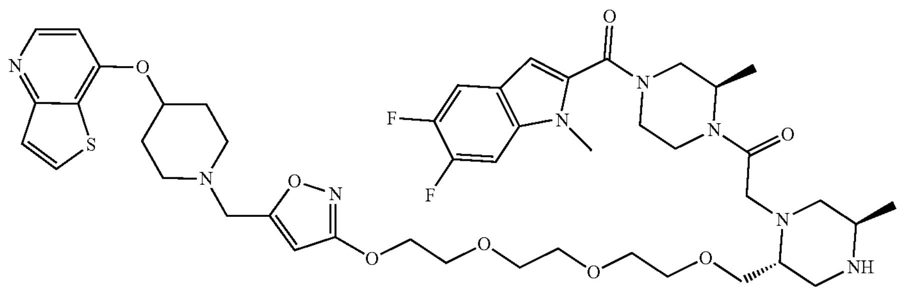 [SMILES: C[C@@H]1CN(CC(=O)N2CCN(C(=O)c3cc4cc(F)c(F)cc4n3C)C[C@H]2C)[C@@H](COCCOCCOCCOc2cc(CN3CCC(Oc4ccnc5ccsc45)CC3)on2)CN1]

(S)—N—((S)-1-cyclohexyl-2-(4-(5,6-difluoro-1-methyl-3-(2-(2-(2-((5-((4-(thieno[3,2-b]pyridin-7-yloxy)piperidin-1-yl)methyl)isoxazol-3-yl)oxy)ethoxy)ethoxy)ethoxy)-1H-indole-2-carbonyl)piperazin-1-yl)-2-oxoethyl)-2-(methylamino)propanamide:

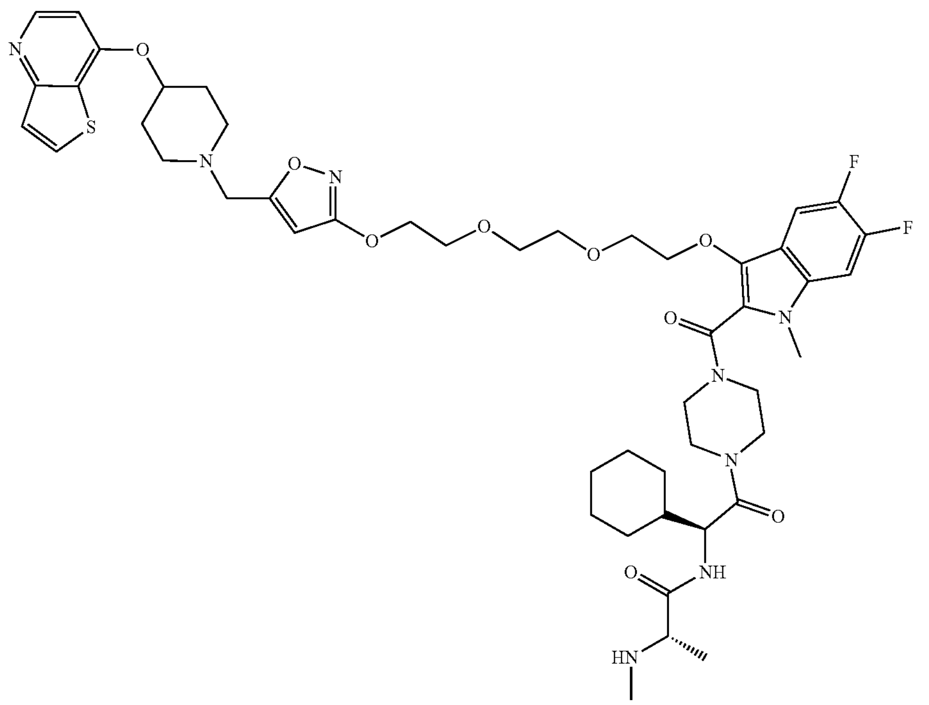 [SMILES: CN[C@@H](C)C(=O)N[C@H](C(=O)N1CCN(C(=O)c2c(OCCOCCOCCOc3cc(CN4CCC(Oc5ccnc6ccsc56)CC4)on3)c3cc(F)c(F)cc3n2C)CC1)C1CCCCC1]

(S)—N—((S)-1-cyclohexyl-2-(4-(5,6-difluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-aza-tetradecyl)-1H-indole-2-carbonyl)piperazin-1-yl)-2-oxoethyl)-2-(methylamino)propanamide:

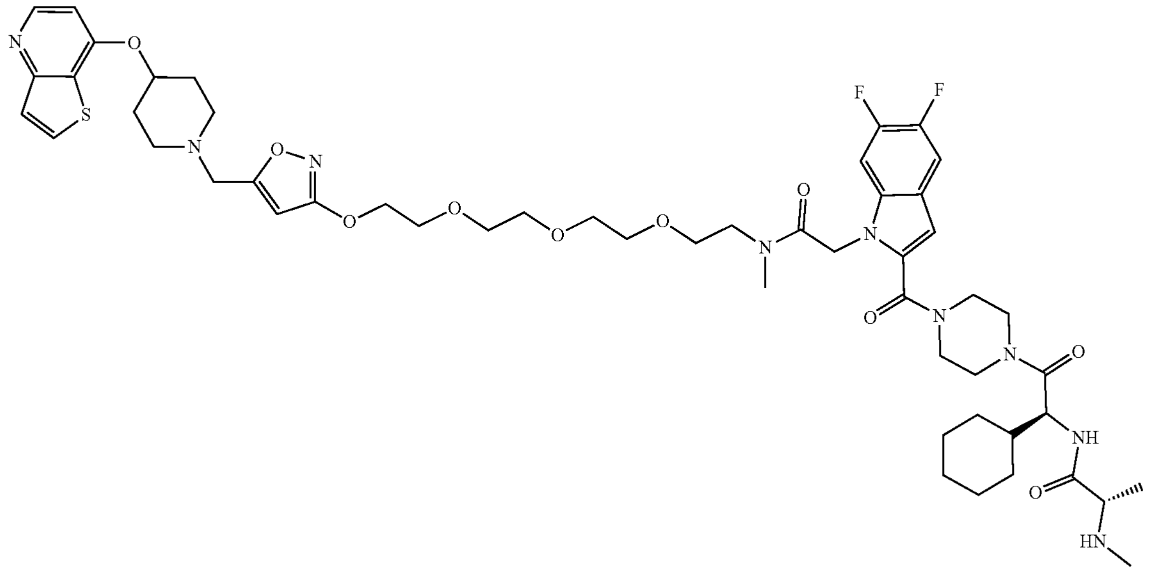 [SMILES: CN[C@@H](C)C(=O)N[C@H](C(=O)N1CCN(C(=O)c2cc3cc(F)c(F)cc3n2CC(=O)N(C)CCOCCOCCOCCOc2cc(CN3CCC(Oc4ccnc5ccsc45)CC3)on2)CC1)C1CCCCC1]

(S)—N—((S)-1-cyclohexyl-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide:

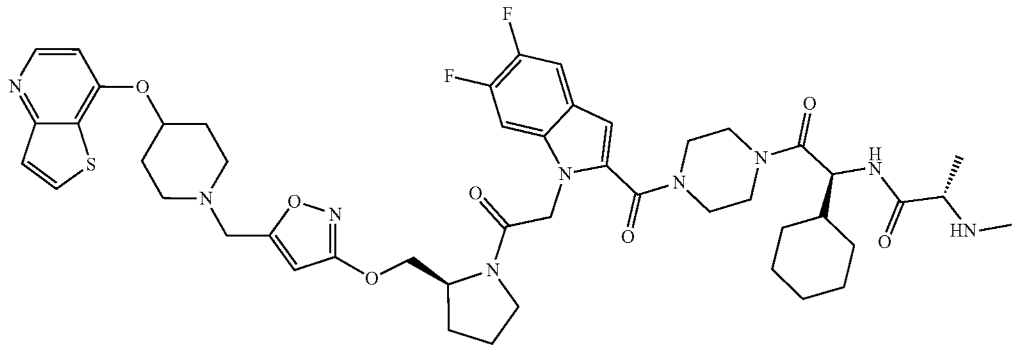 [SMILES: CN[C@@H](C)C(=O)N[C@H](C(=O)N1CCN(C(=O)c2cc3cc(F)c(F)cc3n2CC(=O)N2CCC[C@H]2COc2cc(CN3CCC(Oc4ccnc5ccsc45)CC3)on2)CC1)C1CCCCC1]

(S)—N—((S)-1-cyclohexyl-2-(4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide:

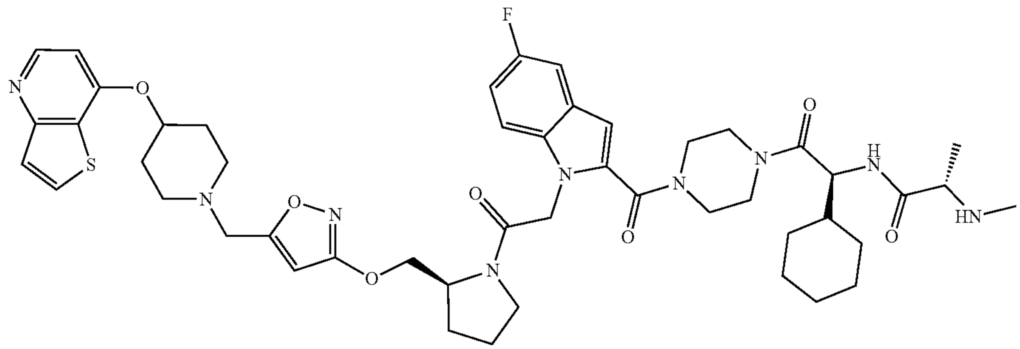 [SMILES: CN[C@@H](C)C(=O)N[C@H](C(=O)N1CCN(C(=O)c2cc3cc(F)ccc3n2CC(=O)N2CCC[C@H]2COc2cc(CN3CCC(Oc4ccnc5ccsc45)CC3)on2)CC1)C1CCCCC1]

(S)—N—((S)-1-cyclohexyl-2-((S)-4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide:

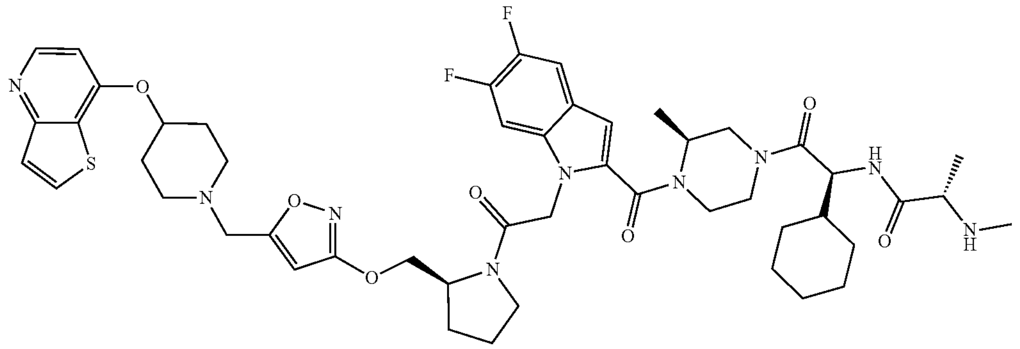 [SMILES: CN[C@@H](C)C(=O)N[C@H](C(=O)N1CCN(C(=O)c2cc3cc(F)c(F)cc3n2CC(=O)N2CCC[C@H]2COc2cc(CN3CCC(Oc4ccnc5ccsc45)CC3)on2)[C@@H](C)C1)C1CCCCC1]

(S)—N—((S)-1-cyclohexyl-2-((S)-4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide:

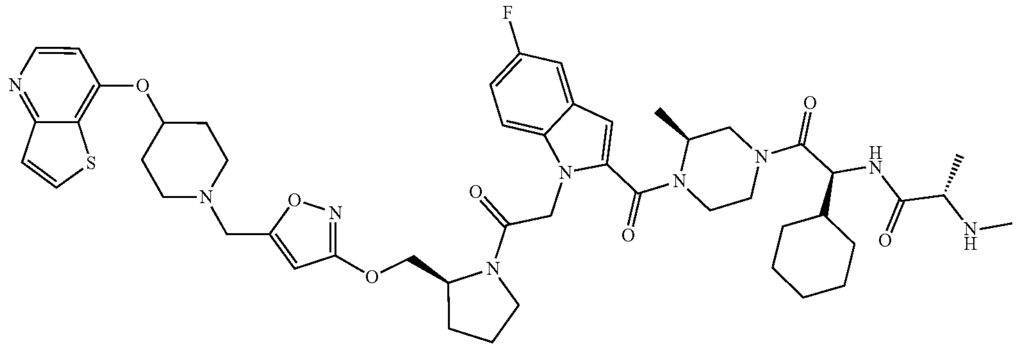 [SMILES: CN[C@@H](C)C(=O)N[C@H](C(=O)N1CCN(C(=O)c2cc3cc(F)ccc3n2CC(=O)N2CCC[C@H]2COc2cc(CN3CCC(Oc4ccnc5ccsc45)CC3)on2)[C@@H](C)C1)C1CCCCC1]

(S)—N—((S)-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-1-(4,4-difluorocyclohexyl)-2-oxoethyl)-2-(methylamino)propanamide

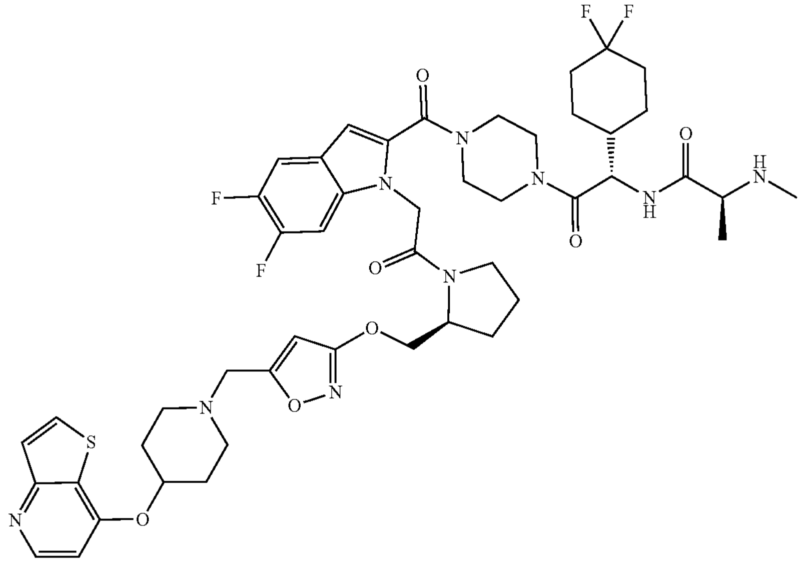 [SMILES: CN[C@@H](C)C(=O)N[C@H](C(=O)N1CCN(C(=O)c2cc3cc(F)c(F)cc3n2CC(=O)N2CCC[C@H]2COc2cc(CN3CCC(Oc4ccnc5ccsc45)CC3)on2)CC1)C1CCC(F)(F)CC1]

(S)—N—((S)-1-cyclohexyl-2-(4-(5,6-difluoro-1-methyl-4-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)-1H-indole-2-carbonyl)piperazin-1-yl)-2-oxoethyl)-2-(methylamino)propanamide:

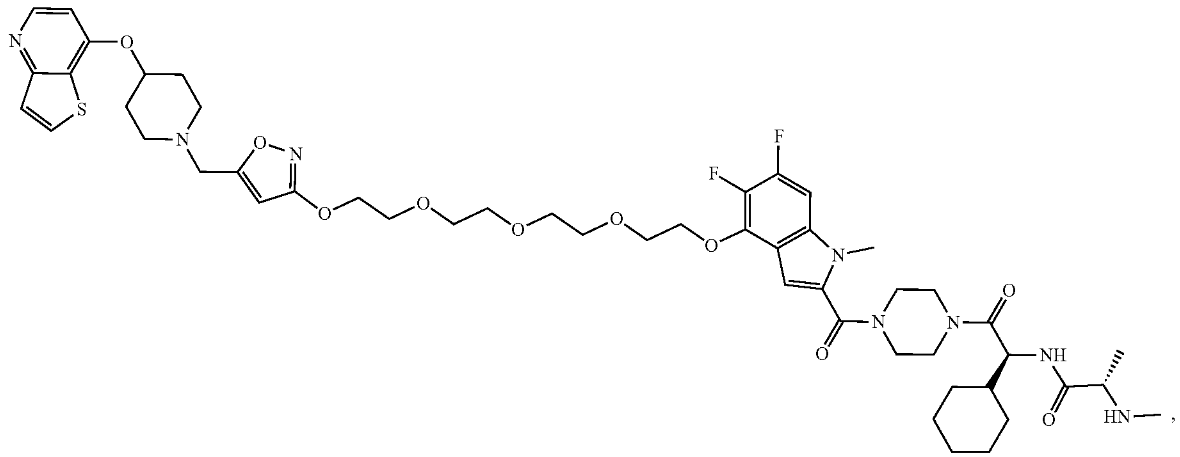 [SMILES: CN[C@@H](C)C(=O)N[C@H](C(=O)N1CCN(C(=O)c2cc3c(OCCOCCOCCOCCOc4cc(CN5CCC(Oc6ccnc7ccsc67)CC5)on4)c(F)c(F)cc3n2C)CC1)C1CCCCC1]

and (S)—N—((S)-1-cyclohexyl-2-(4-(2-methyl-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-5-carbonyl)piperazin-1-yl)-2-oxoethyl)-2-(methylamino)propanamide:

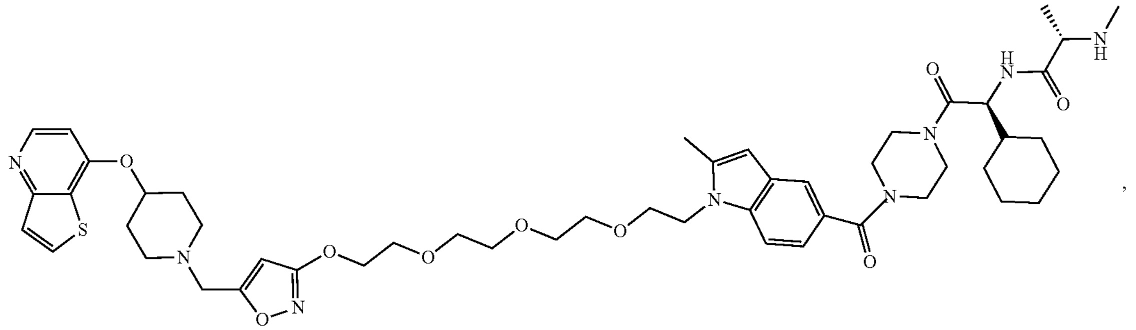

or a pharmaceutically acceptable salt thereof.

[23] The compound according to any one of the above [3] to [14], wherein the E3 ligase binder is a Smac peptide mimetics, or a pharmaceutically acceptable salt thereof.

[24] The compound according to the above [23], wherein the Smac peptide mimetics is an IAP binder represented by the following formula (Si):

S1

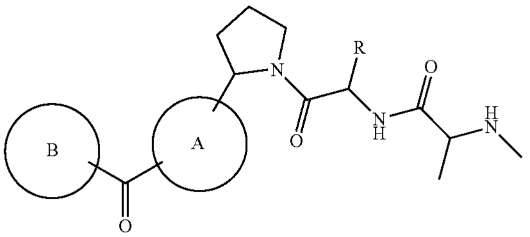

wherein R represents an optionally substituted alkyl group or an optionally substituted cycloalkyl group, ring A represents an optionally substituted heterocyclic group, ring B represents an optionally substituted ring, and either the ring B or R binds to the linker, or a pharmaceutically acceptable salt thereof.

[25] The compound according to the above [24], wherein in the formula S1 R represents a cycloalkyl group, B represents an optionally substituted aryl group, and A represents a thiazolediyl group, or a pharmacologically acceptable thereof.

[26] The compound according to the above [23], wherein the Smac peptide mimetics is an IAP binder represented by the following formulae (I-1), (I-2):

I-1

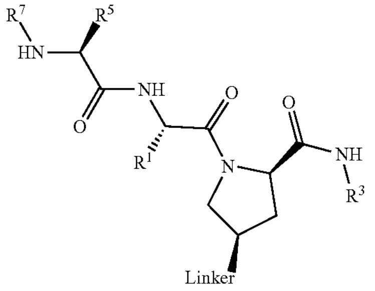

I-2

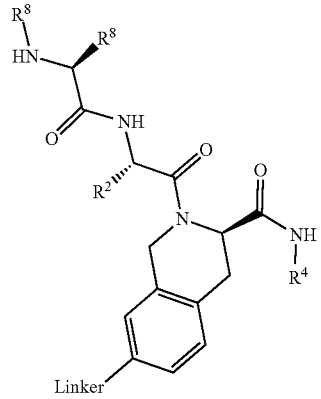

wherein, $R^1$ and $R^2$ each independently represent an optionally substituted alkyl group, an optionally substituted cycloalkyl group, or an optionally substituted aryl group, and $R^3$ and $R^4$ each independently represent an optionally substituted alkyl group, an optionally substituted cycloalkyl group, an optionally substituted aryl group, an optionally substituted alkoxy group, an optionally substituted heteroaryl group, or an optionally substituted heterocyclyl group, $R^5$, $R^6$, $R^7$, and $R^8$ each independently represent a hydrogen atom, an optionally substituted alkyl group, or an optionally substituted cycloalkyl group, and "Linker" indicates the binding to the linker, the following formula (I-3):

(I-3)

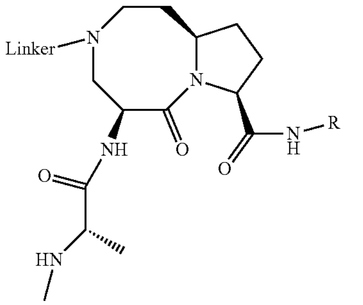

wherein R represents any one of the following formulae:

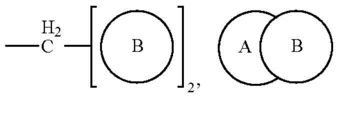

wherein ring A represents a C4-8-membered aliphatic ring, a C3-6 cycloalkylene, or $(CH_2)_{1-4}$, ring B represents an optionally substituted aryl ring or an optionally substituted heteroaryl ring containing a nitrogen atom, and "Linker" indicates the binding to the linker, the following formula (I-4):

(I-4)

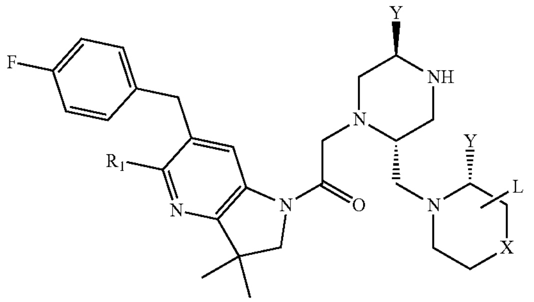

wherein Y each independently represent a hydrogen atom or a C1-3 alkyl group, X represents CH, O or N, $R_1$ represents a hydrogen atom, a methyl group or a hydroxymethyl group, and L indicates the binding to the linker, the following formulae (I-5), (I-6), (I-7):

I-5

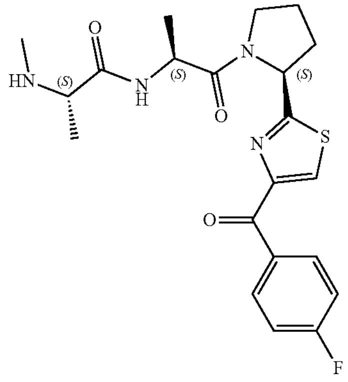

I-6

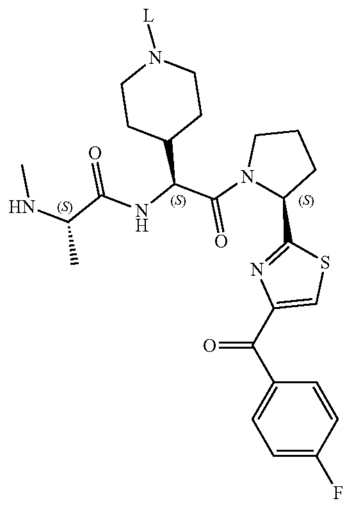

-continued

I-7

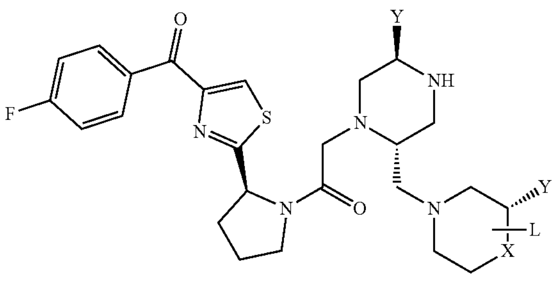

wherein Y each independently represent a hydrogen atom or C1-3 alkyl group, X represents CH, O or N, and L indicates the binding to the linker, or the following formula (I-8):

I-8

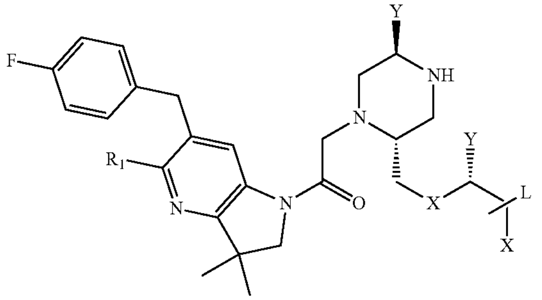

wherein Y each independently represent a hydrogen atom or a C1-3 alkyl group, X each independently represent $CH_2$, O, NH or NR [wherein R represents a C1-3 alkyl group] and X may form a ring with each other, $R_1$ represents a hydrogen atom, a methyl group or a hydroxymethyl group, and L indicates the binding to the linker, but L can bind to X, or a pharmacologically acceptable thereof.

[27] The compound according to any one of the above [3] to [14], wherein the E3 ligase binder is a CRBN binder selected from the group consisting of thalidomide, lenalidomide, pomalidomide, an isomer thereof, and a derivative thereof, or a pharmaceutically acceptable salt thereof.

[28] The compound according to the above [27], wherein the CRBN binder is represented by any one of the following formulae (C1-C6):

(C1)

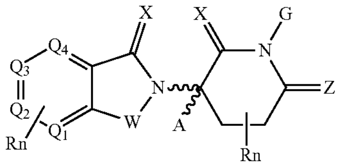

(C2)

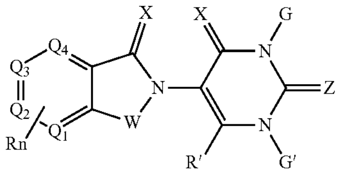

-continued (C3)

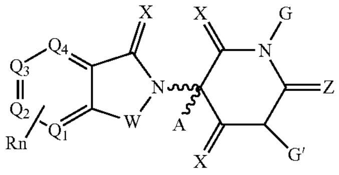

(C4)

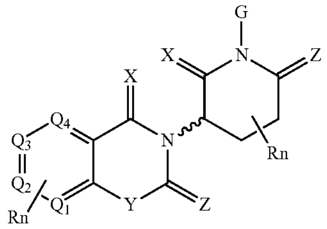

(C5)

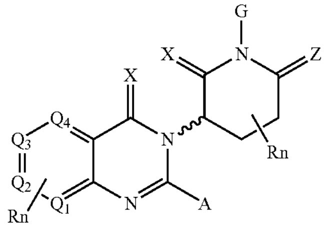

(C6)

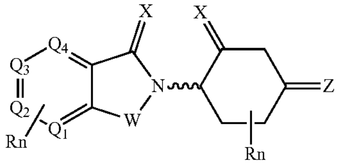

wherein W represents $CH_2$, CHR, C═O, $SO_2$, NH, or N-alkyl group, X each independently represent O, S, or $H_2$, Y represents $CH_2$, —C═CR', NH, N-alkyl group, N-aryl group, N-heteroaryl group, N-cycloalkyl group, N-heterocyclyl group, O or S, Z represents O, S, or $H_2$, G and G' each independently represent a hydrogen atom, an alkyl group, a hydroxy group, R'OCOOR, R'OCONRR", a $CH_2$-heterocyclyl group optionally substituted with R', or a benzyl group optionally substituted with R', $Q_1$, $Q_2$, $Q_3$, $Q_4$ represent R', N, or a carbon substituted with N-oxide, A represents a hydrogen atom, an optionally substituted alkyl group, an cycloalkyl group, Cl or F, R represents CONR'R", —OR', —NR'R", —SR', —$SO_2$R', —$SO_2$NR'R", —CR'R"—, —CR'NR'R"—, an aryl group, a hetaryl group, an alkyl group, a cycloalkyl group, a heterocyclyl group, —P(O)(OR')R", —P(O)R'R", —OP(O)(OR') R", —OP (O)R'R", a halogen atom, a trifluoromethyl group, a cyano group, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", a nitro group, —$CO_2$R', —C(C═N—OR')R", —CR'═CR'R", —CCR', —S(C═O)(C═N—R')R", a pentafluorosulfanyl or a trifluoromethoxy group, R' and R" each independently represent a bond, a hydrogen atom, an optionally substituted alkyl group, an optionally substituted cycloalkyl group, an optionally substituted aryl group, an optionally substituted heteroaryl group, an optionally substituted heterocyclic group, an optionally substituted —C(═O)R, or an optionally substituted heterocyclyl group, and wavy line represents that the bond is sterically specific ((R) or (S)), or non-stereospecific, Rn each independently represent 1 to 4 functional groups or atoms, n=1 represents the binding to the linker, and where n is 2, 3 or 4, one of them represents the binding to the linker, or a pharmacologically acceptable thereof.

[29] The compound according to any one of the above [3] to [14], wherein the E3 ligase binder is a VHL binder represented by the following formula (V1):

(V1)

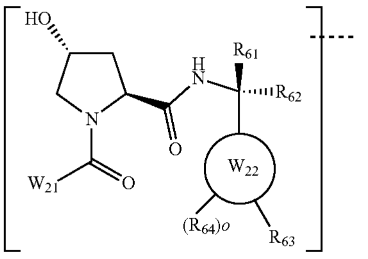

wherein $W_{21}$ represents an optionally substituted aryl group, an optionally substituted heteroaryl group, or the following formula:

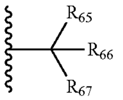

wherein $R_{65}$ and $R_{66}$ each independently represent a hydrogen atom, an optionally substituted alkyl group, an optionally substituted cycloalkyl group, or an optionally substituted heteroaryl group, or an optionally substituted cycloalkyl group formed by $R_{65}$, $R_{66}$ and the carbon atom(s) to which they are attached each other, $R_{67}$ represents an optionally substituted heterocyclyl group, an optionally substituted alkoxy group, an optionally substituted heteroaryl group, an optionally substituted aryl group, any one of the following formulae:

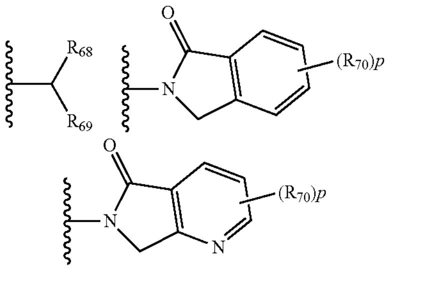

[wherein $R_{68}$ represents a hydrogen atom or an optionally substituted alkyl group, $R_6$ represents a hydrogen atom, an optionally substituted alkyl group, an optionally substituted alkylcarbonyl group, an optionally substituted (cycloalkyl) alkylcarbonyl group, an optionally substituted aralkylcarbonyl group, an optionally substituted arylcarbonyl group, an optionally substituted (heterocyclyl) carbonyl group, or an optionally substituted aralkyl group, $R_{70}$ each independently represent a halogen atom, an optionally substituted alkoxy group, a cyano group, an optionally substituted alkyl group, a haloalkyl group, a haloalkoxy group, or a bond to the linker, p indicates 0 to 3, provided that when $R_{70}$ represents the binding to the linker, p=1], or the binding to the linker; $R_6$ and $R_{62}$ each independently represent a hydrogen atom or an optionally substituted alkyl group; $W_{22}$ represents a benzene ring or a 5-10 membered heteroaryl ring; $R_{63}$ is a hydrogen atom, a halogen atom, a hydroxy group, $NO_2$, $NR_{61}R_{62}$, $OR_{62}$, $CONR_{61}R_{62}$, $NR_{61}COR_{62}$, $SO_2NR_{61}R_{62}$, $NR_{61}SO_2R_{62}$, an optionally substituted alkyl group, an optionally substituted alkoxy group, an optionally substituted aryl group, an optionally substituted heteroaryl group, an optionally substituted cycloalkyl group, or an optionally substituted heterocyclyl group; $R_{64}$ represents a hydrogen atom, a halogen atom, an optionally substituted alkyl group, a hydroxy group, an optionally substituted alkoxy group, or the binding to the linker, and o is 0, 1, 2, 3 or 4, provided that when $R_{64}$ represents the binding to the linker, o=1, or a pharmacologically acceptable thereof.

[30] The compound according to any one of the above [3] to [14], wherein the E3 ligase binder (E) is a MDM2 binder selected from the group consisting of an imidazoline derivative, a spiroindolinone derivative, a pyrrolidone derivative, a piperidinone derivative, a morpholinone derivative, a pyrolopyrimidin derivative, an imidazolopyridine derivative, a thiazoloimidazoline derivative, a pyrolopyrolidinone derivative, and an isoquinolinone derivative, or a pharmacologically acceptable thereof.

[31] The compound according to any one of the above [3] to [14], wherein the E3 ligase binder (E) is a DCAF15 binder selected from the group consisting of a compound represented by the following formula:

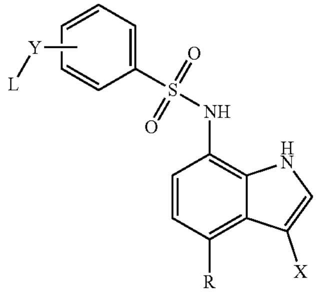

wherein X represents a halogen atom or a cyano group, R represents a hydrogen atom or a methyl group, Y represents a sulfonamide or $CH_2NH$, and L represents the binding to the linker, and a derivative thereof, or a pharmacologically acceptable thereof.

[32] A medicament containing the compound according to any one of the above [1] to [31], or a pharmaceutically acceptable salt thereof.

[33] The medicament according to the above [32], wherein the drug is an IRAK-M protein degrader.

[34] The medicament according to the above [32] or [33], which is a prophylactic or therapeutic agent for cancers.

[35] The medicament according to any one of the above [32] to [34], which is used in combination with another anticancer agent.

[36] A method for IRAK-M protein degradation, comprising administering to a patient in need of treatment an effective amount of the compound or pharmacologically acceptable salt thereof according to any one of the above [1] to [31].

[37] A method for prevention or treatment of cancers, comprising administering to a patient in need of treatment an effective amount of the compound or pharmacologically acceptable salt thereof according to any one of the above [1] to [31].

Advantageous Effect of the Invention

The compound of the present invention has an activity of inducing the degradation of IRAK-M protein and may be useful as a prophylactic or therapeutic agent for cancer, fibrosis and infectious diseases.

BRIEF DESCRIPTION OF DRAWINGS

FIG. 1 shows the results of the changes in tumor size over time in each group when subcutaneously administering the compounds of Examples 1, 25, 26, 27, 28 and 38 three times every three days into a Lewis lung cancer cell inoculation model. Each compound was used as its salt shown in the FIGURE. The mean±standard error is shown in the FIGURE.

DESCRIPTION OF EMBODIMENTS

Hereinafter, the present invention as well as compounds of the present invention and the method of producing them and their use will be illustrated with reference to the exemplary embodiments along with the preferred methods and materials which can be used in practice of the present invention. Unless otherwise specified in the sentences, any technical terms and scientific terms used in the present specification have the same meaning as those generally understood by those of ordinary skill in the art to which the present invention belongs. Any materials and methods equivalent or similar to those described in the present specification can be used for practicing the present invention. All publications and patents cited herein in connection with the present invention described herein are incorporated by reference, for example, as indicating methodology, materials, etc. that can be used in the present invention.

In addition, in the present specification, the description of "A-B" indicating a numerical range means a numerical range including A and B which are end points. The same applies to "A to B".

In the present specification, when describing a compound name of a substituent and so on, a common name may be used instead of the proper name, but they mean the same compound.

Hereinafter, the definition of each substituent used in the present specification will be described in detail. Unless otherwise specified, each substituent has the following definition.

In the present specification, the "halogen atom" includes, e.g., fluorine, chlorine, bromine and iodine.

In the present specification, the "C1-3 alkyl group" includes e.g., methyl, ethyl, propyl, isopropyl and cyclopropyl.

In the present specification, the "optionally halogenated C1-3 alkyl group" includes, e.g., a C1-3 alkyl group optionally having 1 to 5 halogen atoms. Specific examples thereof include methyl, chloromethyl, fluoromethyl, dichloromethyl, difluoromethyl, trichloromethyl, trifluoromethyl, ethyl, 2-bromoethyl, 2,2,2-trifluoroethyl, tetrafluoroethyl, pentafluoroethyl, 2-fluoroethyl, 2,2-difluoroethyl, propyl, 2,2-difluoropropyl, 3,3,3-trifluoropropyl, isopropyl, cyclopropyl, 1-fluorocyclopropyl, 2-chlorocyclopropyl, 2-fluorocyclopropyl, 2,2-difluorocyclopropyl and 2,3-difluorocyclopropyl.

In the present specification, the "C1-6 alkyl group" includes, e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, cyclopropyl, cyclobutyl, cyclopentyl and cyclohexyl.

In the present specification, the "optionally halogenated C1-6 alkyl group" includes, e.g., a C1-6 alkyl group optionally having 1 to 7, preferably 1 to 5 halogen atoms. Specific examples thereof include methyl, chloromethyl, fluoromethyl, dichloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, 2,2-difluorocyclopropyl, butyl, 4,4,4-trifluorobutyl, isobutyl, sec-butyl, tert-butyl, difluorocyclobutyl, pentyl, isopentyl, neopentyl, 5,5,5-trifluoropentyl, fluorocyclopentyl, hexyl and 6,6,6-trifluorohexyl, fluorocyclohexyl.

In the present specification, the "C2-6 alkenyl group" includes, e.g., ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, the "C2-6 alkynyl group" includes, e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl. In the present specification, the "C2-3 alkynyl group" means a group having two or three carbon atoms and includes, e.g., ethynyl, 1-propynyl and 2-propynyl.

In the present specification, the "C3-10 cycloalkyl group" includes, e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, the "C3-10 cycloalkenyl group" includes, e.g., cyclopropenyl, cyclobutenyl, cyclopentenyl, cyclohexenyl, cycloheptenyl and cyclooctenyl.

In the present specification, the "C6-14 aryl group" includes, e.g., phenyl, 1-naphthyl, 2-naphthyl, 1-anthryl, 2-anthryl and 9-anthryl.

In the present specification, the "C7-16 aralkyl group" includes, e.g., benzyl, phenethyl, naphthylmethyl and phenylpropyl.

In the present specification, the "C1-6 alkoxy group" includes, e.g., methoxy, ethoxy, propoxy, isopropoxy, butoxy, isobutoxy, sec-butoxy, tert-butoxy, pentyloxy and hexyloxy.

In the present specification, the "optionally halogenated C1-6 alkoxy group" includes, e.g., a C1-6 alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, the "C3-10 cycloalkyloxy group" includes, e.g., cyclopropyloxy, cyclobutyloxy, cyclopentyloxy, cyclohexyloxy, cycloheptyloxy and cyclooctyloxy.

In the present specification, the "C1-6 alkylthio group" includes, e.g., methylthio, ethylthio, propylthio, isopropylthio, butylthio, sec-butylthio, tert-butylthio, pentylthio and hexylthio.

In the present specification, the "optionally halogenated C1-6 alkylthio group" includes, e.g., a C1-6 alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, the "C3-10 cycloalkylthio group (the sulfur atom is optionally oxidized)" includes, e.g., cyclopropylthio, cyclohexylthio, cyclopenthylsulfiny and cyclohexylsulfonyl.

In the present specification, the "C1-6 alkyl-carbonyl group" includes, e.g., acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, the "optionally halogenated C1-6 alkyl-carbonyl group" includes, e.g., a C1-6 alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, the "C1-6 alkoxy-carbonyl group" includes, e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, the "C6-14 aryl-carbonyl group" includes, e.g., benzoyl, 1-naphthoyl and 2-naphthoyl.

In the present specification, the "C7-16 aralkyl-carbonyl group" includes, e.g., phenylacetyl and phenylpropionyl.

In the present specification, the "5- to 14-membered aromatic heterocyclylcarbonyl group" includes, e.g., nicotinoyl, isonicotinoyl, thenoyl and furoyl.

In the present specification, the "3- to 14-membered non-aromatic heterocyclylcarbonyl group" includes, e.g., morpholinylcarbonyl, piperidinylcarbonyl and pyrrolidinylcarbonyl.

In the present specification, the "mono- or di-C1-6 alkyl-carbamoyl group" includes, e.g., methylcarbamoyl, ethylcarbamoyl, dimethylcarbamoyl, diethylcarbamoyl and N-ethyl-N-methylcarbamoyl.

In the present specification, the "mono- or di-C7-16 aralkyl-carbamoyl group" include benzylcarbamoyl and phenethylcarbamoyl.

In the present specification, the "C1-6 alkylsulfonyl group" includes, e.g., methylsulfonyl, ethylsulfonyl, propylsulfonyl, isopropylsulfonyl, butylsulfonyl, sec-butylsulfonyl and tert-butylsulfonyl.

In the present specification, the "optionally halogenated C1-6 alkylsulfonyl group" includes, e.g., a C1-6 alkylsulfonyl group optionally having 1 to 7 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, the "C6-14 arylsulfonyl group" includes, e.g., phenylsulfonyl, 1-naphthylsulfonyl and 2-naphthylsulfonyl.

In the present specification, the "C6-14 arylene group" include, e.g., phenylene, 1,5-naphthylene, 1,4-naphthylene, 2,3-naphthylene, 1,8-anthrylene and 9,10-anthrylene.

In the present specification, the "substituent" includes, e.g., a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, the "hydrocarbon group" (including "hydrocarbon group" of "optionally substituted hydrocarbon group") includes, e.g., a C1-3 alkyl group, a C1-6 alkyl group, a C1-6 alkylene group, a C2-6 alkenyl group, a C2-6 alkynyl group, a C3-10 cycloalkyl group, a C3-10 cycloalkylene group, a C3-10 cycloalkenyl group, a C6-14 aryl group, a C6-14 arylene group and a C7-16 aralkyl group.

In the present specification, the "optionally substituted hydrocarbon group" includes, e.g., a hydrocarbon group optionally having substituent(s) selected from the following Substituent group A.

"Substituent Group A"

(1) a halogen atom,
(2) a nitro group,
(3) a cyano group,
(4) an oxo group,
(5) a hydroxy group,
(6) an optionally halogenated C1-6 alkoxy group,
(7) a C6-14 aryloxy group (e.g., phenoxy, naphthoxy),
(8) a C7-16 aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a C1-6 alkyl-carbonyloxy group (e.g., acetoxy, propanoyloxy),
(12) a C6-14 aryl-carbonyloxy group (e.g., benzoyloxy, 1-naphthoyloxy, 2-naphthoyloxy),
(13) a C1-6 alkoxy-carbonyloxy group (e.g., methoxycarbonyloxy, ethoxycarbonyloxy, propoxycarbonyloxy, butoxycarbonyloxy),
(14) a mono- or di-C1-6 alkyl-carbamoyloxy group (e.g., methylcarbamoyloxy, ethylcarbamoyloxy, dimethylcarbamoyloxy, diethylcarbamoyloxy),
(15) a C6-14 aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated C1-6 alkylsulfonyloxy group (e.g., methylsulfonyloxy, trifluoromethylsulfonyloxy),
(19) a C6-14 arylsulfonyloxy group optionally substituted by a C1-6 alkyl group (e.g., phenylsulfonyloxy, toluenesulfonyloxy),
(20) an optionally halogenated C1-6 alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated C1-6 alkyl-carbonyl group,
(26) a C6-14 aryl-carbonyl group,

(27) a 5- to 14-membered aromatic heterocyclylcarbonyl group,
(28) a 3- to 14-membered non-aromatic heterocyclylcarbonyl group,
(29) a C1-6 alkoxy-carbonyl group,
(30) a C6-14 aryloxy-carbonyl group (e.g., phenyloxycarbonyl, 1-naphthyloxycarbonyl, 2-naphthyloxycarbonyl),
(31) a C7-16 aralkyloxy-carbonyl group (e.g., benzyloxycarbonyl, phenethyloxycarbonyl),
(32) a carbamoyl group,
(33) a thiocarbamoyl group,
(34) a mono- or di-C1-6 alkyl-carbamoyl group,
(35) a C6-14 aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated C1-6 alkylsulfonyl group,
(39) a C6-14 arylsulfonyl group,
(40) a 5- to 14-membered aromatic heterocyclylsulfonyl group (e.g., pyridylsulfonyl, thienylsulfonyl),
(41) an optionally halogenated C1-6 alkylsulfinyl group,
(42) a C6-14 arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-C1-6 alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-C6-14 arylamino group (e.g., phenylamino),
(47) a 5- to 14-membered aromatic heterocyclylamino group (e.g., pyridylamino),
(48) a C7-16 aralkylamino group (e.g., benzylamino),
(49) a formylamino group,
(50) a C1-6 alkyl-carbonylamino group (e.g., acetylamino, propanoylamino, butanoylamino),
(51) a (C1-6 alkyl)(C1-6 alkyl-carbonyl)amino group (e.g., N-acetyl-N-methylamino),
(52) a C6-14 aryl-carbonylamino group (e.g., phenylcarbonylamino, naphthylcarbonylamino),
(53) a C1-6 alkoxy-carbonylamino group (e.g., methoxycarbonylamino, ethoxycarbonylamino, propoxycarbonylamino, butoxycarbonylamino, tert-butoxycarbonylamino),
(54) a C7-16 aralkyloxy-carbonylamino group (e.g., benzyloxycarbonylamino),
(55) a C1-6 alkylsulfonylamino group (e.g., methylsulfonylamino, ethylsulfonylamino),
(56) a C6-14 arylsulfonylamino group optionally substituted by a C1-6 alkyl group (e.g., phenylsulfonylamino, toluenesulfonylamino),
(57) an optionally halogenated C1-6 alkyl group,
(58) a C2-6 alkenyl group,
(59) a C2-6 alkynyl group,
(60) a C3-10 cycloalkyl group,
(61) a C3-10 cycloalkenyl group, and
(62) a C6-14 aryl group.

The number of the above-described substituents in the "optionally substituted hydrocarbon group" is, e.g., 1 to 5, preferably 1 to 3. When the number of the substituents is two or more, each substituent may be the same or different.

In the present specification, the "heterocyclic group" (including "heterocyclic group" of "optionally substituted heterocyclic group") includes, e.g., (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, the "optionally substituted C6-14 aryl group" includes, e.g., a C6-14 aryl group, optionally having a substituent(s) selected from Substituent Group A described above. The number of the substituents in the "optionally substituted C6-14 aryl group" is, e.g., 1 to 3. When the number of the substituents is two or more, each substituent may be the same or different.

In the present specification, the "aromatic heterocyclic group" (including "5- to 14-membered aromatic heterocyclic group") includes, e.g., 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom. Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, the "non-aromatic heterocyclic group" (including "3- to 14-membered non-aromatic heterocyclic group") includes, e.g., a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom. Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxolanyl, oxanyl, dioxanyl, thiolanyl, oxathianil, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl, triazaspirononyl (e. g., 1,3,7-triazaspironyl [4.4] nonyl), thiadiazaspirononyl (e.g., 7-thia-1,3-diazaspironyl [4.4] nonyl), dioxidethiadiazaspironil (e. g., 7,7-dioxide-7-thia-1,3-diazaspironyl [4.4] nonyl) and the like.

In the present specification, examples of the "nitrogen-containing aromatic heterocyclic group" include "aromatic heterocyclic groups" containing at least one nitrogen atom as a ring-constituting atom.

In the present specification, the "optionally substituted heterocyclic group" includes, e.g., a heterocyclic group optionally having a substituent(s) selected from the above-mentioned Substituent group A. The number of the substituents in the "optionally substituted heterocyclic group" is, e.g., 1 to 3. When the number of the substituents is two or more, each substituent may be the same or different.

In the present specification, the "acyl group" includes, e.g., a formyl group, a carboxy group, a carbamoyl group, a thiocarbamoyl group, a sulfino group, a sulfo group, a sulfamoyl group and a phosphono group, each optionally having "1 or 2 substituents selected from a C1-6 alkyl group, a C2-6 alkenyl group, a C3-10 cycloalkyl group, a C3-10 cycloalkenyl group, a C6-14 aryl group, a C7-16 aralkyl group, a 5- to 14-membered aromatic heterocyclic group and a 3- to 14-membered non-aromatic heterocyclic group, each of which optionally has 1 to 3 substituents selected from a halogen atom, an optionally halogenated C1-6 alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a C1-6 alkyl-carbonyl group, a C2-6 alkenyl-carbonyl group (e.g., crotonoyl), a C3-10 cycloalkylcarbonyl group (e.g., cyclobutanecarbonyl, cyclopentanecarbonyl, cyclohexanecarbonyl, cycloheptanecarbonyl), a C3-10 cycloalkenyl-carbonyl group (e.g., 2-cyclohexenecarbonyl), a C6-14 aryl-carbonyl group, a C7-16 aralkyl-carbonyl group, a 5- to 14-membered aromatic heterocyclylcarbonyl group, a 3- to 14-membered non-aromatic heterocyclylcarbonyl group, a C1-6 alkoxy-carbonyl group, a C6-14 aryloxycarbonyl group (e.g., phenyloxycarbonyl, naphthyloxycarbonyl), a C7-16 aralkyloxy-carbonyl group (e.g., benzyloxycarbonyl, phenethyloxycarbonyl), a carbamoyl group, a mono- or di-C1-6 alkyl-carbamoyl group, a mono- or di-C2-6 alkenyl-carbamoyl group (e.g., diallylcarbamoyl), a mono- or di-C3-10 cycloalkyl-carbamoyl group (e.g., cyclopropylcarbamoyl), a mono- or di-C6-14 aryl-carbamoyl group (e.g., phenylcarbamoyl), a mono- or di-C7-16 aralkyl-carbamoyl group, a 5- to 14-membered aromatic heterocyclylcarbamoyl group (e.g., pyridylcarbamoyl), a thiocarbamoyl group, a mono- or di-C1-6 alkyl-thiocarbamoyl group (e.g., methylthiocarbamoyl, N-ethyl-N-methylthiocarbamoyl), a mono- or di-C2-6 alkenyl-thiocarbamoyl group (e.g., diallylthiocarbamoyl), a mono- or di-C3-10 cycloalkyl-thiocarbamoyl group (e.g., cyclopropylthiocarbamoyl, cyclohexylthiocarbamoyl), a mono- or di-C6-14 aryl-thiocarbamoyl group (e.g., phenylthiocarbamoyl), a mono- or di-C7-16 aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a C1-6 alkylsulfinyl group (e.g., methylsulfinyl, ethylsulfinyl), a sulfo group, a C1-6 alkylsulfonyl group, a C6-14 arylsulfonyl group, a phosphono group and a mono- or di-C1-6 alkylphosphono group (e.g., dimethylphosphono, diethylphosphono, diisopropylphosphono, dibutylphosphono).

In the present specification, the "optionally substituted amino group" includes, e.g., an amino group optionally having "1 or 2 substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5- to 14-membered aromatic heterocyclylcarbonyl group, a 3- to 14-membered non-aromatic heterocyclylcarbonyl group, a C1-6 alkoxy-carbonyl group, a 5- to 14-membered aromatic heterocyclic group, a carbamoyl group, a mono- or di-C1-6 alkyl-carbamoyl group, a mono- or di-C7-16 aralkyl-carbamoyl group, a C1-6 alkylsulfonyl group and a C6-14 arylsulfonyl group, each of which optionally has 1 to 3 substituents selected from "Substituent group A".

Preferable examples of the optionally substituted amino group include an amino group, a mono- or di-(optionally halogenated C1-6 alkyl)amino group (e.g., methylamino, trifluoromethylamino, dimethylamino, ethylamino, diethylamino, propylamino, dibutylamino), a mono- or di-C2-6 alkenylamino group (e.g., diallylamino), a mono- or di-C3-10 cycloalkylamino group (e.g., cyclopropylamino, cyclohexylamino), a mono- or di-C6-14 arylamino group (e.g., phenylamino), a mono- or di-C7-16 aralkylamino group (e.g., benzylamino, dibenzylamino), a mono- or di-(optionally halogenated C1-6 alkyl)-carbonylamino group (e.g., acetylamino, propionylamino), a mono- or di-C6-14 aryl-carbonylamino group (e.g., benzoylamino), a mono- or di-C7-16 aralkylcarbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-C1-6 alkoxy-carbonylamino group (e.g., tert-butoxycarbonylamino), a 5- to 14-membered aromatic heterocyclylamino group (e.g., pyridylamino), a carbamoylamino group, a (mono- or di-C1-6 alkyl-carbamoyl)amino group (e.g., methylcarbamoylamino), a (mono- or di-C7-16 aralkyl-carbamoyl)amino group (e.g., benzylcarbamoylamino), a C1-6 alkylsulfonylamino group (e.g., methylsulfonylamino, ethylsulfonylamino), a C6-14 arylsulfonylamino group (e.g., phenylsulfonylamino), a (C1-6 alkyl)(C1-6 alkyl-carbonyl) amino group (e.g., N-acetyl-N-methylamino) and a (C1-6 alkyl)(C6-14 aryl-carbonyl)amino group (e.g., N-benzoyl-N-methylamino).

In the present specification, the "optionally substituted carbamoyl group" includes, e.g., a carbamoyl group optionally having "1 or 2 substituents selected from a C1-6 alkyl group, a C2-6 alkenyl group, a C3-10 cycloalkyl group, a C6-14 aryl group, a C7-16 aralkyl group, a C1-6 alkylcarbonyl group, a C6-14 aryl-carbonyl group, a C7-16 aralkyl-carbonyl group, a 5- to 14-membered aromatic heterocyclylcarbonyl group, a 3- to 14-membered nonaromatic heterocyclylcarbonyl group, a C1-6 alkoxy-carbonyl group, a 5- to 14-membered aromatic heterocyclic group, a carbamoyl group, a mono- or di-C1-6 alkyl-carbamoyl group and a mono- or di-C7-16 aralkyl-carbamoyl group, each of which optionally has 1 to 3 substituents selected from "Substituent group A".

Preferable examples of the optionally substituted carbamoyl group include a carbamoyl group, a mono- or di-C1-6 alkyl-carbamoyl group, a mono- or di-C2-6 alkenyl-carbamoyl group (e.g., diallylcarbamoyl), a mono- or di-C3-10 cycloalkyl-carbamoyl group (e.g., cyclopropylcarbamoyl, cyclohexylcarbamoyl), a mono- or di-C6-14 aryl-carbamoyl group (e.g., phenylcarbamoyl), a mono- or di-C7-16 aralkyl-carbamoyl group, a mono- or di-C1-6 alkyl-carbonyl-carbamoyl group (e.g., acetylcarbamoyl, propionylcarbamoyl), a mono- or di-C6-14 aryl-carbonyl-carbamoyl group (e.g., benzoylcarbamoyl) and a 5- to 14-membered aromatic heterocyclylcarbamoyl group (e.g., pyridylcarbamoyl).

In the present specification, the "optionally substituted thiocarbamoyl group" includes, e.g., a thiocarbamoyl group optionally having 1 or 2 substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5- to 14-membered aromatic heterocyclylcarbonyl group, a 3- to 14-membered nonaromatic heterocyclylcarbonyl group, a C1-6 alkoxy-carbonyl group, a 5- to 14-membered aromatic heterocyclic group, a carbamoyl group, a mono- or di-C1-6 alkyl-carbamoyl group and a mono- or di-C7-16 aralkyl-carbamoyl group, each of which optionally has 1 to 3 substituents selected from "Substituent group A".

Preferable examples of the optionally substituted thiocarbamoyl group include a thiocarbamoyl group, a mono- or di-C1-6 alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-C2-6 alkenyl-thiocarbamoyl group (e.g., diallylthiocarbamoyl), a mono- or di-C3-10 cycloalkyl-thiocarbamoyl group (e.g., cyclopropylthiocarbamoyl, cyclohexylthiocarbamoyl), a mono- or di-C6-14 aryl-thiocarbamoyl group (e.g., phenylthiocarbamoyl), a mono- or di-C7-16 aralkyl-thiocarbamoyl group (e.g., benzylthiocarbamoyl, phenethylthiocarbamoyl), a mono- or di-C1-6 alkyl-carbonyl-thiocarbamoyl group (e.g., acetylthiocarbamoyl, propionylthiocarbamoyl), a mono- or di-C6-14 aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, the "optionally substituted sulfamoyl group" includes, e.g., a sulfamoyl group optionally having 1 or 2 substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5- to 14-membered aromatic heterocyclylcarbonyl group, a 3- to 14-membered nonaromatic heterocyclylcarbonyl group, a C1-6 alkoxy-carbonyl group, a 5- to 14-membered aromatic heterocyclic group, a carbamoyl group, a mono- or di-C1-6 alkyl-carbamoyl group and a mono- or di-C7-16 aralkyl-carbamoyl group, each of which optionally has 1 to 3 substituents selected from "Substituent group A".

Preferable examples of the optionally substituted sulfamoyl group include a sulfamoyl group, a mono- or di-C1-6 alkyl-sulfamoyl group (e.g., methylsulfamoyl, ethylsulfamoyl, dimethylsulfamoyl, diethylsulfamoyl, N-ethyl-N-methylsulfamoyl), a mono- or di-C2-6 alkenyl-sulfamoyl group (e.g., diallylsulfamoyl), a mono- or di-C3-10 cycloalkyl-sulfamoyl group (e.g., cyclopropylsulfamoyl, cyclohexylsulfamoyl), a mono- or di-C6-14 arylsulfamoyl group (e.g., phenylsulfamoyl), a mono- or di-C7-16 aralkyl-sulfamoyl group (e.g., benzylsulfamoyl, phenethylsulfamoyl), a mono- or di-C1-6 alkyl-carbonylsulfamoyl group (e.g., acetylsulfamoyl, propionylsulfamoyl), a mono- or di-C6-14 aryl-carbonyl-sulfamoyl group (e.g., benzoylsulfamoyl) and a 5- to 14-membered aromatic heterocyclylsulfamoyl group (e.g., pyridylsulfamoyl).

In the present specification, the "optionally substituted hydroxy group" include a hydroxy group optionally having a substituent selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5- to 14-membered aromatic heterocyclylcarbonyl group, a 3- to 14-membered non-aromatic heterocyclylcarbonyl group, a C1-6 alkoxy-carbonyl group, a 5- to 14-membered aromatic heterocyclic group, a carbamoyl group, a mono- or di-C1-6 alkylcarbamoyl group, a mono- or di-C7-16 aralkyl-carbamoyl group, a C1-6 alkylsulfonyl group and a C6-14 arylsulfonyl group, each of which optionally has 1 to 3 substituents selected from "Substituent group A".

Preferable examples of the optionally substituted hydroxy group include a hydroxy group, a C1-6 alkoxy group, a C2-6 alkenyloxy group (e.g., allyloxy, 2-butenyloxy, 2-pentenyloxy, 3-hexenyloxy), a C3-10 cycloalkyloxy group (e.g., cyclohexyloxy), a C6-14 aryloxy group (e.g., phenoxy, naphthyloxy), a C7-16 aralkyloxy group (e.g., benzyloxy, phenethyloxy), a C1-6 alkyl-carbonyloxy group (e.g., acetyloxy, propionyloxy, butyryloxy, isobutyryloxy, pivaloyloxy), a C6-14 aryl-carbonyloxy group (e.g., benzoyloxy), a C7-16 aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a C1-6 alkoxy-carbonyloxy group (e.g., tert-butoxycarbonyloxy), a 5- to 14-membered aromatic heterocyclyloxy group (e.g., pyridyloxy), a carbamoyloxy group, a C1-6 alkyl-carbamoyloxy group (e.g., methylcarbamoyloxy), a C7-16 aralkyl-carbamoyloxy group (e.g., benzylcarbamoyloxy), a C1-6 alkylsulfonyloxy group (e.g., methylsulfonyloxy, ethylsulfonyloxy) and a C6-14 arylsulfonyloxy group (e.g., phenylsulfonyloxy).

In the present specification, the "optionally substituted sulfanyl group" includes, e.g., a sulfanyl group optionally having a substituent selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group and a 5- to 14-membered aromatic heterocyclic group, each of which optionally has 1 to 3 substituents selected from "Substituent group A" and a halogenated sulfanyl group.

Preferable examples of the optionally substituted sulfanyl group include a sulfanyl (—SH) group, a C1-6 alkylthio group, a C2-6 alkenylthio group (e.g., allylthio, 2-butenylthio, 2-pentenylthio, 3-hexenylthio), a C3-10 cycloalkylthio group (e.g., cyclohexylthio), a C6-14 arylthio group (e.g., phenylthio, naphthylthio), a C7-16 aralkylthio group (e.g., benzylthio, phenethylthio), a C1-6 alkyl-carbonylthio group (e.g., acetylthio, propionylthio, butyrylthio, isobutyrylthio, pivaloylthio), a C6-14 aryl-carbonylthio group (e.g., benzoylthio), a 5- to 14-membered aromatic heterocyclylthio group (e.g., pyridylthio) and a halogenated thio group (e.g., pentafluorothio).

In the present specification, the "optionally substituted silyl group" includes, e.g., a silyl group optionally having 1 to 3 substituents selected from a C1-6 alkyl group, a C2-6 alkenyl group, a C3-10 cycloalkyl group, a C6-14 aryl group and a C7-16 aralkyl group, each of which optionally has 1 to 3 substituents selected from "Substituent group A". Examples of the optionally substituted silyl group include a tri-C1-6 alkylsilyl group (e.g., trimethylsilyl, tert-butyl(dimethyl)silyl).

In the present specification, the term "linker" refers to any chemical moiety (structure) to be used to link a portion of a compound of interest to another compound. Exemplary linkers are described herein. For example, in any of the compounds described herein, a chemical structure used to bind a portion structure of a compound to a portion structure of another compound is available as a linker and is corresponded to the liker defined in the specification. Examples of the linker preferably used in the present invention include a structure represented by "LX" (x is an arbitrary number) herein, and the structure to which one or more atomic groups are further attached, but not limited to these.

In the present specification, the "C1-6 alkylene group" includes, e.g., methylene, 1,2-ethylene, 1,1-ethylene, 1,2-propylene, 1,3-propylene, 2,2-propylene, 1,4-butylene, 1,2-butylene, 1,3-butylene, 2,2-butylene, 1,5-pentylene, 3,3-pentylene and 1,6-hexylene.

In the present specification, the "C3-10 cycloalkylene group" includes, e.g., 1,1-cyclopropylene, cis-1,2-cyclopropylene, trans-1,2-cyclopropylene, 1,1-cyclobutylene, cis-1,2-cyclobutylene, trans-1,2-cyclobutylene, cis-1,3-cyclobutylene, trans-1,3-cyclobutylene, 1,1-cyclopentylene, cis-1,2-cyclopentylene, trans-1,2-cyclopentylene, cis-1,3-cyclopentylene, trans-1,3-cyclopentylene, 1,1-cyclohexylene, cis-1,2-cyclohexylene, trans-1,2-cyclohexylene, cis-1,3-cyclohexylene, trans-1,3-cyclohexylene, cis-1,4-cyclohexylene, trans-1,4-cyclohexylene, 1,1-cycloheptynylene, 1,1-cyclooctynylene, 2,2-dimethyl-1,1-cyclopropylene, 2,3-dimethyl-1,1-cyclopropylene, 2,2,3,3,4,4-tetramethyl-1,1-cyclobutylene, 7,7-norcaranylene, 7,7-norpinanylene and 7,7-norbornanylene.

In the present specification, the "C3-10 cycloalkenylene group" includes, e.g., 1,2-cyclopropenylene, 1,2-cyclobutenylene, 1,2-cyclopentenylene, 1,2-cyclohexenylene and 2-bornen-2,3-yl.

In the present specification, the term "bond" indicates a state in which two adjacent groups are bonded by a single bond. Further, when a plurality of the "single bonds" are connected, it indicates a state in which all of them are connected together by a single bond.

Hereinafter, each symbol of the formula (II) will be described.

X represents S, O, or NR [wherein R is a hydrogen atom or a C1-6 alkyl group, preferably a methyl group], and preferably S.

Y represents CH or N, preferably CH.

Z represents O or NH, preferably O.

The arrow means the binding to the Linker (L).

$R^{01}$ represents a hydrogen atom, a C1-6 alkyl group, a C2-6 alkenyl group, a C2-6 alkynyl group, a cyano group, a halogen atom, an optionally substituted phenyl group, an optionally substituted ester group, or an optionally substituted hetero 5-membered ring group, preferably a hydrogen atom, a C1-6 alkyl group, a C2-3 alkynyl group, a cyano group, a halogen atom, an optionally substituted phenyl group, an optionally substituted ester group, or an optionally substituted hetero 5-membered ring group, more preferably a hydrogen atom, a methyl group, a cyano group, an iodine atom, a phenyl group, or any group represented by the following structural formulae:

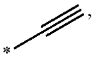,
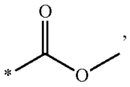,
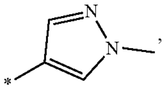, particularly preferably a hydrogen atom.

An example of the "substituent" of "an optionally substituted phenyl group," "an optionally substituted ester group," or "an optionally substituted hetero 5-membered ring group" shown in $R^{01}$ is a substituent selected from "Substituent group A." The number of the substituents is, for example, 1 to 5, preferably 1 to 3. When the number of the substituents is two or more, each substituent may be the same or different.

An example of the "hetero 5-membered ring group" of "an optionally substituted hetero 5-membered ring group" shown in $R^{01}$ is, e.g., pyrazole, imidazole, thiazole, oxazole, isoxazole, thiophene, furan, pyrrol, thiadiazole, oxadiazole, thiatriazole, or oxatriazole, preferably pyrazole.

$R^{02}$ represents a hydrogen atom, a C1-6 alkyl group, or a halogen atom, preferably a hydrogen atom, a methyl group, or a chlorine atom, more preferably a hydrogen atom.

$R^{03}$ represents an optionally substituted C1-6 alkylene group, an optionally substituted C6-14 arylene group, an optionally substituted heterocyclic group, or a bond, preferably an optionally substituted C6-14 arylene group, an optionally substituted heterocyclic group, or a bond, more preferably any group represented by the following structural formulae:

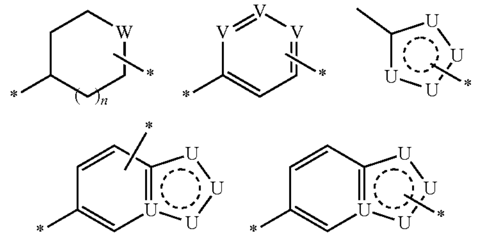

wherein n is 0, 1 or 2, W represents NR [wherein R represents a hydrogen atom, a C1-6 alkyl group, or an acyl group], $SO_2$, SO, S or O, V each independently represent CH or N, provided that any one of V is CH, U each independently represent CH, N, NH, O or S, provided that no more than one U can be O or S, an optionally substituted C1-6 alkylene group, or a bond, more preferably a group represented by the following structural formula:

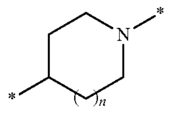

wherein n is 0, 1 or 2, most preferably a group represented by the following structural formula:

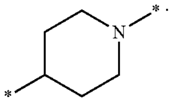 [SMILES: *C1CCN(*)CC1]

An example of the "substituent" of "an optionally substituted C1-6 alkylene group," "an optionally substituted C6-C14 arylene group," "an optionally substituted heterocyclic group" shown in $R^{03}$ is a substituent selected from the "Substituent group A." The number of the substituents is for example 1 to 4. When the number of the substituent is two or more, each substituent may be the same or different.

A represents a group represented by the following structural formula:

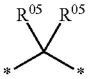

[wherein $R^{05}$ each independently represent a hydrogen atom, a halogen atom, a C1-6 alkyl group, or a C1-6 alkoxy group], $*—SO_2—*$, $*—CO—CH_2—*$, *—CO—NH—*, *—O—*, an optionally substituted C1-6 alkylene group, or a bond, preferably a group represented by the following structural formula:

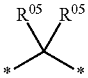

[wherein $R^{05}$ each independently represent a hydrogen atom or a C1-6 alkyl group], $*—SO_2—*$, or $*—CO—CH_2—*$.

An example of the "substituent" of "an optionally substituted C1-6 alkylene group" shown in A is a substituent selected from the "Substituent group A." The number of the substituents is for example 1 to 7. When the number of the substituents is two or more, each substituent may be the same or different. A preferred example of the C1-6 alkyl group is a C1-3 alkyl group.

$R^{04}$ represents a group represented by any one of the following structural formulae:

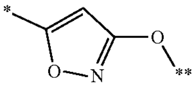
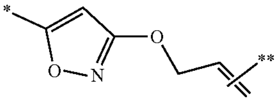
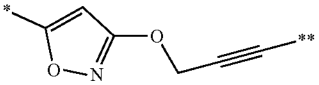
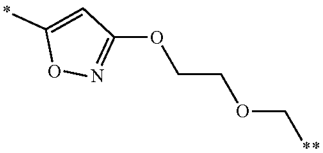

-continued

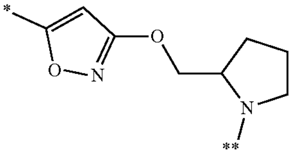
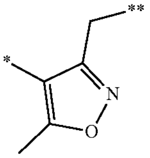
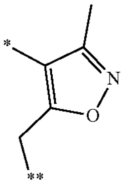
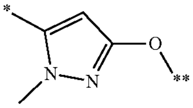
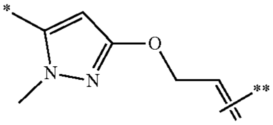
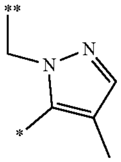
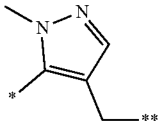
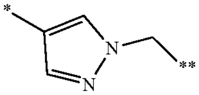
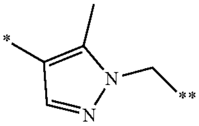
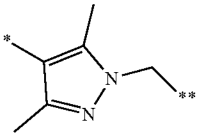
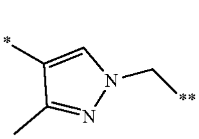
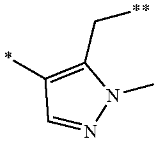
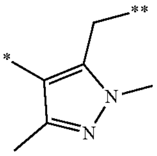
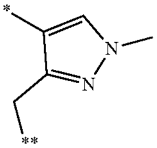
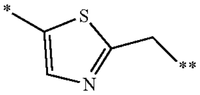
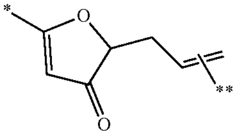
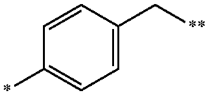
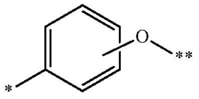
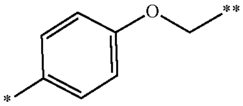
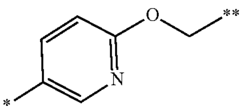
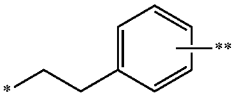
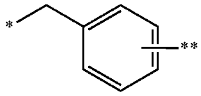
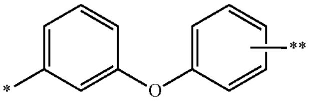

-continued

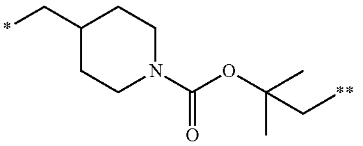

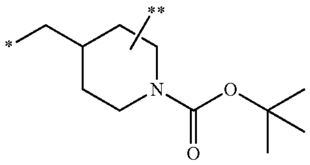

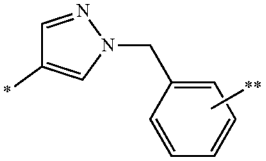

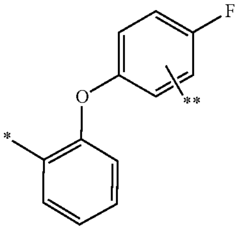

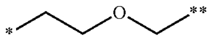

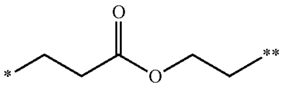

[wherein * represents the binding position to A, and ** represents the binding position to the linker], an optionally substituted C1-6 alkylene group, an optionally substituted C3-10 cycloalkylene group, an optionally substituted C6-14 arylene group, an optionally substituted hetero 5-6-membered ring group, an ester bond, or a bond, preferably a group represented by any one of the following structural formulae:

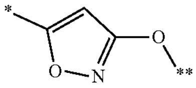

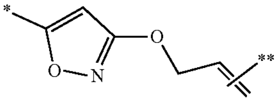

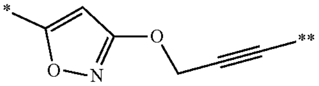

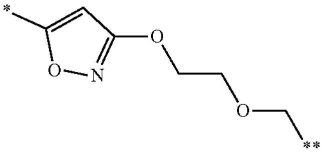

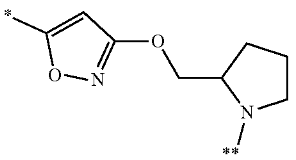

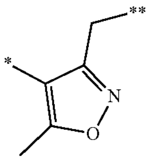

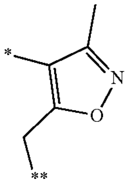

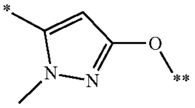

-continued

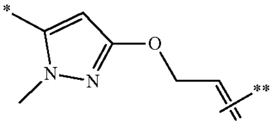

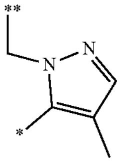

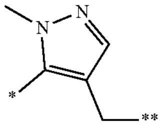

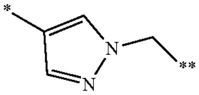

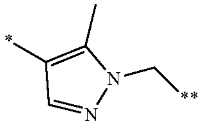

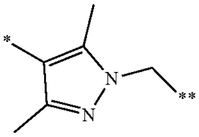

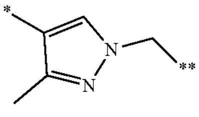

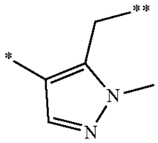

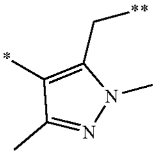

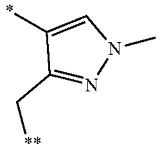

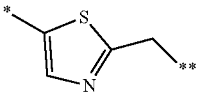

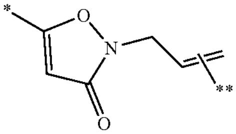

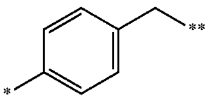

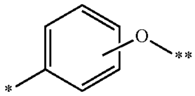

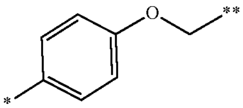

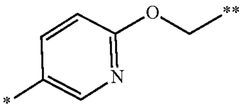

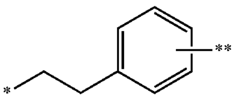

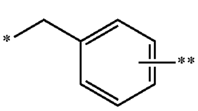

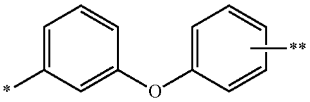

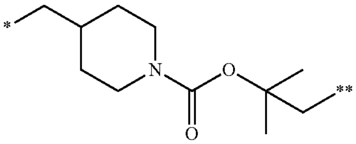

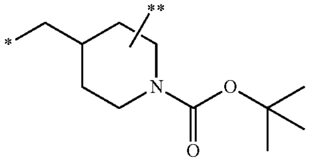

-continued

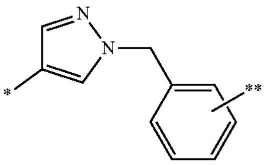
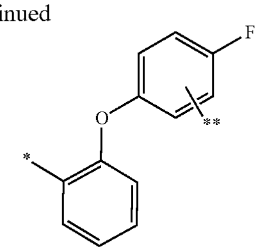
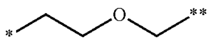
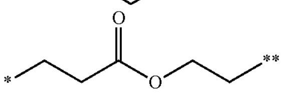

[wherein * represents the binding position to A, and ** represents the binding position to the linker], an optionally substituted C1-6 alkylene group, an optionally substituted C3-10 cycloalkylene group, an optionally substituted C6-14 arylene group, an optionally substituted pyrazolinediyl group, an optionally substituted oxazolinediyl group, an optionally substituted isoxazolinediyl group, an ester bond, or a bond, more preferably a group represented by any one of the following structural formulae:

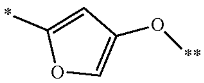
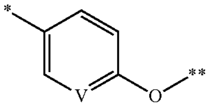
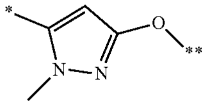
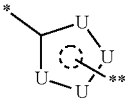
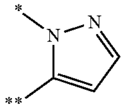
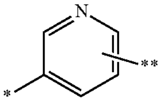
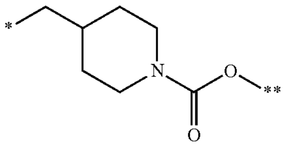
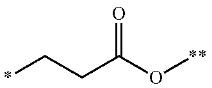
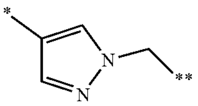
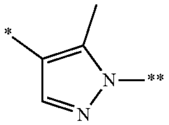

[wherein * represents the binding position to A, and ** represents the binding position to the linker, V represents CH or N, U each independently represent CH, N, NH, O or S, provided that no more than one U can be O or S], an optionally substituted C1-6 alkylene group, an optionally substituted C3-10 cycloalkylene group, an optionally substituted C6-C14 arylene group, or a bond, further preferably a group represented by any one of the following structural formulae:

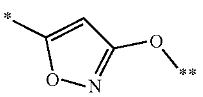
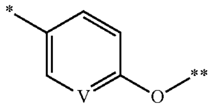

-continued

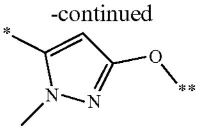

[wherein V is CH or N, * represents the binding position to A, and ** represents the binding position to the linker].

An example of the "substituent" of "an optionally substituted C1-6 alkylene group," "an optionally substituted C3-10 cycloalkylene group," "an optionally substituted C6-14 arylene group," "an optionally substituted hetero 5-6-membered ring group," "an optionally substituted pyrazolinediyl group," "an optionally substituted oxazolidinediyl group," or "an optionally substituted isooxazolidinediyl group" shown in $R^{04}$ is a substituent selected from the "Substituent group A." The number of the substituents is for example 1 to 4. When the number of the substituents is two or more, each substituent may be the same or different. An example of the "hetero 5-membered ring group" of "an optionally substituted hetero 5-membered ring group" shown in $R^{04}$ is, e.g., a divalent group derived from pyrazole, imidazole, thiazole, oxazole, isoxazole, thiophene, furan, pyrrol, thiadiazole, oxadiazole, thiatriazole, oxatriazole, pyridine, pyrazine, pyrimidine, or pyridazine, preferably pyrazole, oxazole or isoxazole.

Hereinafter, each symbol of the formula (III) will be described.

$R^{01}$ is the same as described in the formula (II). The arrow means the binding to the Linker (L).

$A^0$ represents a group represented by the following structural formula:

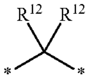

[wherein $R^{12}$ each independently represent a hydrogen atom or a C1-6 alkyl group], $*-SO_2-*$, or $*-CO-CH_2-*$, preferably the above formula or $*-SO_2-*$.

$R^{11}$ represents a group represented by any one of the following structural formulae:

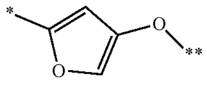
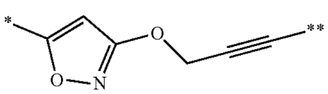
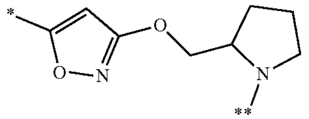
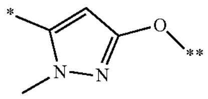
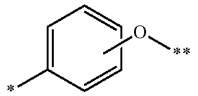
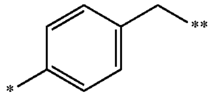
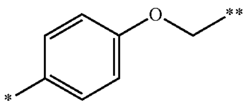
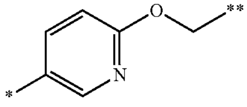
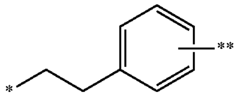
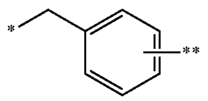

[wherein represents the binding position to A, and represents the binding position to the linker], an optionally substituted C1-6 alkylene group, an optionally substituted C3-10 cycloalkylene group, an optionally substituted C6-14 arylene group, or a bond, preferably a group represented by any one of the following structural formula:

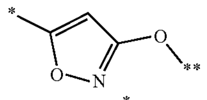

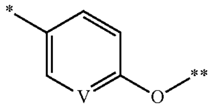

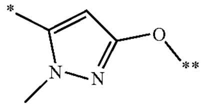

[wherein * represents the binding position to A, and ** represents the binding position to the linker], an optionally substituted C1-6 alkylene group, an optionally substituted C3-10 cycloalkylene group, an optionally substituted C6-14 arylene group, or a bond, more preferably a group represented by any one of the following structural formulae:

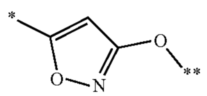

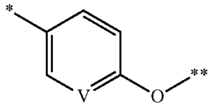

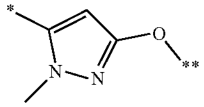

wherein * represents the binding position to A, and ** represents the binding position to the linker.

An example of the "substituent" of "an optionally substituted C1-6 alkylene group," "an optionally substituted C3-10 cycloalkylene group," or "an optionally substituted C6-14 arylene group" shown in R11 is a substituent selected from the "Substituent group A." The number of the substituents is for example 1 to 3. When the number of the substituents is two or more, each substituent may be the same or different.

Hereinafter, each symbol of the formula (IV) will be described.

$R_{01}$, $R_{02}$, $R_{03}$, $R_{04}$, $R_{05}$, $R_{06}$, $R_{07}$ and $R_{08}$ each independently represent a hydrogen atom or a C1-6 alkyl group which may form a ring with each other, preferably each independently represent a hydrogen atom or a C1-6 alkyl group, more preferably each independently represent a hydrogen atom or a C1-3 alkyl group.

Either D or E binds to the linker (L).

D represents a fragment structure of a substance that binds to the IAP together with the piperazine ring.

For example, D is represented by the following formula (V):

(V)

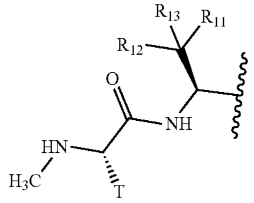

wherein $R_{11}$ represents a hydrogen atom or a hydroxyl group, and $R_{12}$ and $R_{13}$ each independently represent a hydrogen atom, a C1-6 alkyl group, a C3-10 cycloalkylene group, a carbonyl group, an imino group optionally substituted with a C1-6 alkyl group, an ethynylene group optionally substituted with a C1-6 alkyl group, a vinylene group optionally substituted with a C1-6 alkyl group, a pyrazole group optionally substituted with a C1-6 alkyl group, a C3-10 cycloalkenylene group, a phenylene group, a thiazolylene group, a pyrrolidinediyl group optionally substituted with a fluorine atom, an azetidinediyl group optionally substituted with a fluorine atom, or any of the above group bonded to the linker (L), provided that both $R_{12}$ and $R_{13}$ are not bonded to a linker, and T represents an optionally halogenated C1-3 alkyl group, or the following formula (VI):

(VI)

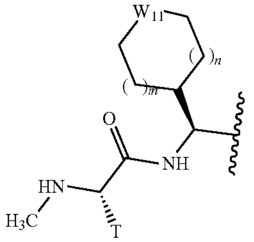

wherein m is 0, 1, or 2, n is, 1, or 2, $W_{11}$ represents a methylene group, a difluoromethylene group, O, S, SO, $SO_2$, or NR [wherein R represents a hydrogen atom, a C1-6 alkyl group, a C1-6 alkyl-carbonyl group, a C6-14 aryl-carbonyl group, a C1-6 alkylsulfonyl group, or the binding to the linker], and T represents an optionally halogenated C1-3 alkyl group, or the following formula (VII):

(VII)

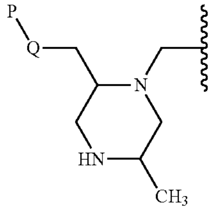

wherein Q represents an oxygen atom, formula —$NR^{21}$— [wherein, $R^{21}$ represents a hydrogen atom, a C1-6 alkyl group, or a C1-6 alkyl group which may form a ring with P], or a bond, P represents a hydrogen atom, a C1-6 alkyl group or the binding to the linker (including the formation of a ring with Q and binding to the linker).

D can bind to the linker (L) at any of $R_{12}$ or $R_{13}$ in the formula (V), $W_{11}$ in the formula (VI), or P in the formula (VII).

E represents a nitrogen-containing aromatic heterocyclic group.

For example, E is represented by any one of the following formulae:

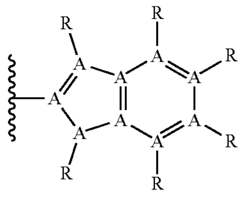

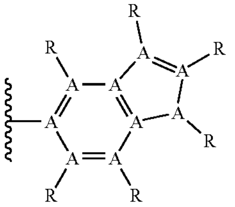

wherein A each independently represent C or N, and R bonded to N each independently represent a hydrogen atom, a C1-6 alkyl group, or an amido group, and other R each independently represent a hydrogen atom, a halogen atom, a C1-6 alkyl group, a C1-6 alkoxy group, or an amido group, wherein when E is bonded to the Linker, E is bonded to the Linker at any one position indicated by R in the above formulae, preferably is represented by any one of the following formulae:

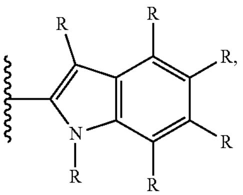

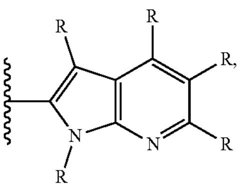

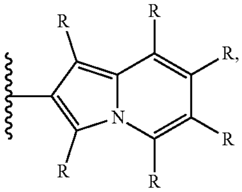

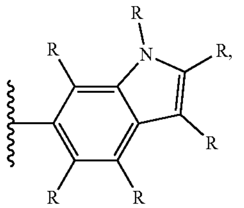

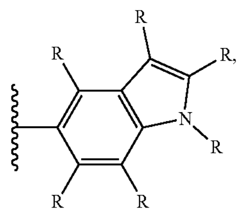

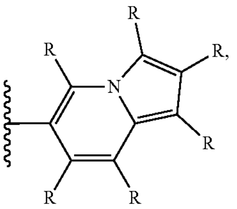

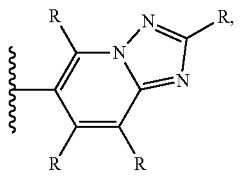

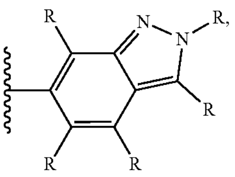

-continued

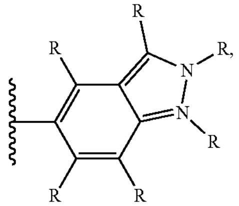

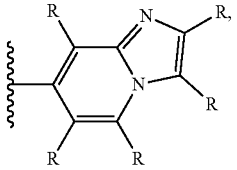

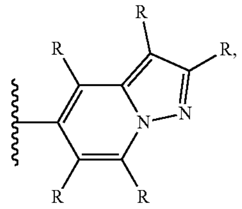

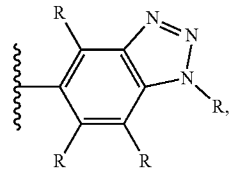

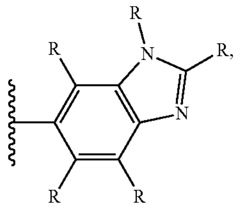

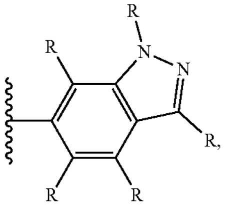

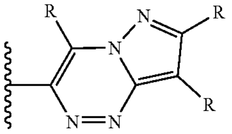

wherein R bonded to N each independently represent a hydrogen atom, a C1-6 alkyl group, or an amido group, and other R each independently represent a hydrogen atom, a halogen atom, a C1-6 alkyl group, a C1-6 alkoxy group, or an amido group, wherein when E is bonded to the linker, E is bonded to the linker at any one position indicted by R in the above formulae.

One preferred example of E is represented by the following formula (VIII):

VIII

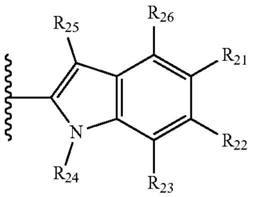

wherein $R_{21}$, $R_{22}$, and $R_{23}$ each independently represent a hydrogen atom, a halogen atom, a C1-6 alkyl group, a C1-6 alkoxy group, or an amido group, $R_{25}$ and $R_{26}$ each independently represent a hydrogen atom, a halogen atom, a C1-6 alkyl group, a C1-6 alkoxy group, an amido group, or the binding to the linker, $R_{24}$ represents a hydrogen atom, a methyl group, or the binding to the linker, provided that the binding to the linker is any one of $R_{24}$, $R_{25}$ or $R_{26}$.

Another preferred example of E is represented by the following formula (IX):

IX

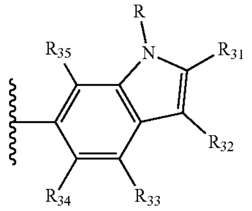

wherein $R_{31}$, $R_{32}$, $R_{33}$, $R_{34}$, and $R_{35}$ each independently represent a hydrogen atom, a halogen atom, a C1-6 alkyl group, a C1-6 alkoxy group, or an amido group, and R represents a hydrogen atom, C1-6 alkyl group, or the binding to the linker.

Hereinafter, the linker of the formula (I) will be described.

The Linker (L) is represented by the formula (L1): $—B_1—B_2$-$L^1$-$L^2$-$L^3$-$L^4$-$L^5$-$L^6$-$L^7$-, wherein $B_1$ and $B_2$ each independently represent a group represented by the following structural formula:

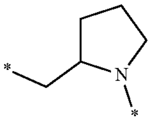
, provided that both $B_1$ and $B_2$ are not the above structural formula, *—O—*, *—$NR^{06}$—* [wherein $R^{06}$ represents a hydrogen atom or a C1-6 alkyl group], *—$CO_2$—*, *—CO—*, *—$SO_2$—*, an optionally substituted C1-6 alkylene group, an optionally substituted C2-6 alkenylene group, an optionally substituted C2-6 alkynylene group, an optionally substituted C3-10 cycloalkylene group, an optionally substituted C6-14 arylene group, or a bond, $L^1$, $L^2$, $L^3$, $L^4$, $L^5$, $L^6$, and $L^7$ each independently represent a group represented by the following structural formula:

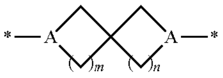

wherein m represents an integer of 1 to 4, n represents an integer of 1 to 4, and A each independently represent N, CHCO or $CHCH_2O$, provided that any two or more of $L^1$ to $L^7$ are not the above structural formula, a bond, oxygen atom, sulfur atom, a C1-6 alkylene group, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolyldiyl group, a non-aromatic heterocyclic group which may be substituted with an optionally substituted C1-6 alkyl group or a halogen atom, a pyrrolidinediyl group optionally substituted with fluorine atom, a morpholinediyl group which may be substituted with an optionally substituted C1-6 alkyl group, an azetidinediyl group optionally substituted with fluorine atom, formula $—SO_2—$, formula $—CH_2CH_2O—$, formula $—OCH_2CH_2—$, formula $—COCH_2—$, formula $—CH_2CO—$, formula $—CO_2—$, formula —OCO—, formula $—COCHR^{101}NR^{102}—$, formula $—OCH_2CHR^{103}NR^{104}—$, formula $—NR^{105}CHR^{106}CO—$, formula $—NR^{107}CO—$, formula $—CONR^{108}—$, formula $—SO_2NR^{109}—$, formula $—NR^{110}SO_2—$, or formula $—NR^{111}CHR^{112}CH_2O—$ [wherein in the above formulae $R^{101}$, $R^{103}$, $R^{106}$ and $R^{112}$ each independently represent a hydrogen atom, a C1-6 alkyl group, a 3-guanidinopropyl group, a carbamoylmethyl group, a carboxymethyl group, a mercaptomethyl group, a 2-carbamoyl ethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, an 4-hydroxyphenylmethyl group or a pyridylmethyl group, and $R^{102}$, $R^{104}$, $R^{105}$, $R^{107}$, $R^{108}$, $R^{109}$, $R^{110}$, and $R^{111}$ each independently represent a hydrogen atom or a C1-6 alkyl group], or together represent a bond.

$B_1$ and $B_2$ each independently represent a group represented by the following structural formula:

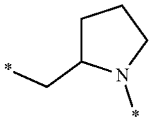
, provided that both $B_1$ and $B_2$ are not the above structural formula, *—O—*, *—$NR^{06}$—* [wherein $R^{06}$ represents a hydrogen atom or a C1-6 alkyl group], *—CO—*, an optionally substituted C1-6 alkylene group, an optionally substituted C6-14 arylene group, an optionally substituted C2-6 alkynylene group, or a bond, preferably a group represented by the following structural formula:

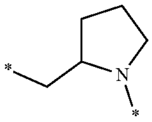
, provided that both $B_1$ and $B_2$ are not the above structural formula, *—O—*, a C1-6 alkylene group, or a bond, more preferably the above structural formula, provided that both $B_1$ and $B_2$ are not the above structural formula, or a bond.

The Linker (L) preferably represents a group represented by any one of the following formulae:

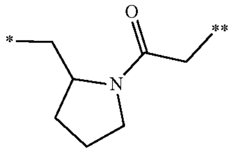

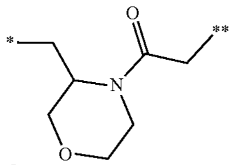

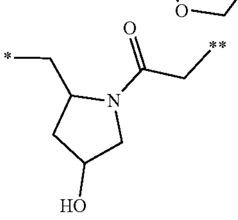

[wherein * represents the binding to the IRAK-M binder (M)],

*—$(CH_2CH_2O)n(CH_2)m(NRCO)s(CH_2)t$-* (n is an integer from 1 to 5, m is 0, 1, or 2, s is 0 or 1, t is 0 or 1, and R represents a hydrogen atom or a C1-6 alkyl group), or a bond, more preferably represents a group represented by the following formula:

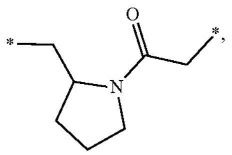

or *—$(CH_2CH_2O)n(CH_2)m(NRCO)s(CH_2)t$-* (n is an integer from 1 to 5, m is 0, 1, or 2, s is 0 or 1, t is 0 or 1, and R represents a hydrogen atom or a C1-6 alkyl group).

An example of the "substituent" of "an optionally substituted C1-6 alkylene group," "an optionally substituted C2-6 alkenylene group," "an optionally substituted C2-6 alkynylene group," "an optionally substituted C3-10 cycloalkylene group," and "an optionally substituted C6-14 arylene group" shown in the Linker is a substituent selected from the "Substituent group A." The number of the substituent is for example 1 to 4. When the number of the substituent is two or more, each substituent may be the same or different.

In the present specification, the "compound that adds a function" means a ligand of any protein present in a living body, a cell penetrating peptide (CPP), or a kinetophore that keeps a compound in the intestinal tract (e.g., polyethylene oxides capped with a short-chain peptide, a sugar and quaternary ammonium; etc.).

In the present specification, the "Smac peptide mimetics" means a compound that binds to the space same as the space occupied by the Smac N-terminal peptide AVPIAQK (SEQ ID NO: 1) (particularly AVPI (SEQ ID NO: 2) when binding to XIAP and that has an inhibitory effect on the binding of the Smac peptide.

In the present specification, the "IRAK-M protein related disease(s)" is a disease or an illness that is described or speculated in association to abnormalities in the IRAK-M protein itself or its regulation. Protein abnormalities include, but are not limited to, abnormal expression or enhancement of a protein in a living body, and the presence of mutant proteins.

A compound included in compound (I) can be used as a synthetic intermediate in producing another compound (I) of the present invention, and is also used as a synthetic intermediate in producing an IRAK-M protein degrader other than compound (I).

When compound (I) is in a form of a salt, the salt includes, e.g., metal salts, ammonium salts, salts with organic base, salts with inorganic acid, salts with organic acid, salts with basic or acidic amino acid, and the like. Suitable examples of the metal salt include, e.g., alkali metal salts such as sodium salts, potassium salts and the like; alkaline-earth metal salts such as calcium salts, magnesium salts, barium salts and the like; aluminum salts, and the like. Suitable examples of the salt with organic base include, e.g., salts with trimethylamine, triethylamine, pyridine, picoline, 2,6-rutidine, ethanolamine, diethanolamine, triethanolamine, cyclohexylamine, dicyclohexylamine, N,N'-dibenzylethylenediamine and the like. Suitable examples of the salt with inorganic acid include, e.g., salts with hydrochloric acid, hydrobromic acid, nitric acid, sulfuric acid, phosphoric acid and the like. Suitable examples of the salt with organic acid include, e.g., salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with basic amino acid include, e.g., salts with arginine, lysine, ornithine and the like, and suitable examples of the salts with acidic amino acids include, e.g., salts with aspartic acid, glutamic acid and the like.

Among them, pharmaceutically acceptable salts are preferred. For example, when an acidic functional group is present in a compound, the salt includes inorganic salts such as alkali metal salts (e.g., sodium salts, potassium salts, etc.) and alkaline-earth metal salts (e.g., calcium salts, magnesium salts, etc.) and ammonium salts, while when a basic functional group is present in a compound, the salt includes salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is explained in the followings. The raw material and reagent used and the compound obtained in each step in the following production method may be each in a form of a salt, and examples of such salt include those similar to the salts of the compound of the present disclosure.

When the compound obtained in each step is in a free form, it can be converted to the objective salt according to a method known per se. When the compound obtained in each step is in a salt form, it can be converted to the free form or the objective other salt form according to a method known per se.

The compound obtained in each step can be used directly as the resultant reaction mixture or as a resultant crude product for the next reaction. Alternatively, the compound obtained in each step can be isolated and/or purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min to 48 hr, preferably 10 min to 8 hr, unless otherwise specified.

In the reaction in each step, while the reaction temperature varies depending on the kind of the reagent and solvent to be used, it is generally −78° C. to 300° C., preferably −78° C. to 150° C., unless otherwise specified.

In the reaction in each step, while the pressure varies depending on the kind of the reagent and solvent to be used, it is generally 1 atm to 20 atm, preferably 1 atm to 3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature to 300° C., preferably 50° C. to 250° C., unless otherwise specified. While the reaction time varies depending on the kind of the reagent and solvent to be used, it is generally 1 min to 48 hr, preferably 1 min to 8 hr, unless otherwise specified.

In the reaction in each step, the reagent is used in an amount of 0.5 equivalent to 20 equivalents, preferably 0.8 equivalent to 5 equivalents, relative to the substrate, unless otherwise specified. When the reagent is used as a catalyst, the reagent is used in an amount of 0.001 equivalent to 1 equivalent, preferably 0.01 equivalent to 0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

anhydrides: acetic anhydride and the like;

organic acids: formic acid, acetic acid, trifluoroacetic acid and the like;

inorganic acids: hydrochloric acid, sulfuric acid and the like;

esters: ethyl acetate and the like;

ketones: acetone, methyl ethyl ketone and the like;

water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide and the like;

basic salts: sodium carbonate, calcium carbonate, sodium hydrogencarbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like;

Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5$^{th}$ Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like or a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; and carbonate ester type protecting groups such as tert-butylcarbonate and the like.

Examples of the protecting group for a carbonyl group of an aldehyde include acetal type protecting groups such as dimethylacetal and the like; and cyclic acetal-type protecting groups such as 1,3-dioxane and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; and hydrazone-type protecting groups such as N,N-dimethylhydrazone and the like.

Examples of the protecting group for a carboxyl group include ester-type protecting groups such as methyl ester and the like; and amide-type protecting groups such as N,N-dimethylamide and the like.

Examples of the protecting group for a thiol include ether-type protecting groups such as benzyl thioether and the like; and ester-type protecting groups such as thioacetate ester, thiocarbonate, thiocarbamate and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; and sulfonamide-type protecting groups such as methanesulfonamide and the like.

The protecting groups can be removed according to a method known per se, such as a method using acid, base, ultraviolet rays, hydrazine, phenylhydrazine, sodium N-methyldithiocarbamate, tetrabutylammonium fluoride, palladium acetate or trialkylsilyl halide (e.g., trimethylsilyl iodide, trimethylsilyl bromide), or a reduction method.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxido-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboran in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole) and a base (e.g., a basic salt, an organic base) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; alkylmagnesium halides such as methylmagnesium bromide and the like. The Grignard reagent can be prepared according to a method known per se, for example, by reacting an alkyl halide or an aryl halide with metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen and formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD), ditert-butyl azodicarboxylate etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy 1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; 2,4,6-tripropyl-1,3,5,2,4,6-trioxatriphosphorinane-2,4,6-trioxide (T3P); combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis (diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases, basic salts and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis (4-methoxyphenyl)-1,3,2,4-dithiadiphosphetane-2,4-disulfide (Lawesson's reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two-step reaction comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. When acid hydrolysis reaction of t-butyl ester is carried out, formic acid, triethylsilane and the like may be added to reductively trap t-butyl cation which is by-produced.

When dehydration reaction is carried out in each step, examples of the dehydrating agent to be used include sulfuric acid, diphosphorus pentoxide, phosphorus oxychloride, N,N'-dicyclohexylcarbodiimide, alumina, polyphosphoric acid and the like.

When the alkylation reaction of alcohols or amines or aromatic heterocyclics having an NH group in the ring (e.g., imidazole, pyrazole) is performed in each step, the alkylating agent includes optionally substituted alkyl halides (e.g., iodomethane), optionally substituted alkyls having an optionally substituted C1-6 alkylsulfonyloxy group as a leaving group, optionally substituted alkyls having a C6-14 arylsulfonyloxy group optionally substituted with a C1-6 alkyl group, sodium 2-chloro-2,2-difluoroacetate, 2,2-difluoro-2-(fluorosulfonyl)acetate, and the like. Further, the base to be used includes organic lithiums, metal alkoxides, inorganic bases, organic bases, and the like.

When the fluorination reaction is performed in each step, the fluorinating agent to be used includes DAST (diethylaminosulfur trifluoride), bis(2-methoxyethyl)aminosulfur trifluoride, 1-chloromethyl-4-fluoro-1,4-diazoniabicyclo [2.2.2]octane bis (tetrafluoroborate) (Selectfluor), 4-tert-butyl-2,6-dimethylphenylsulfur trifluoride (FLUOLEAD) and the like.

When the Huisgen reaction is performed in each step, an azide compound and an alkyne compound are used as the agent used. The catalyst includes monovalent copper ions, for example, copper iodide, copper chloride, copper cyanide and the like.

When the coupling reaction is performed in each step, the coupling reaction includes Suzuki coupling, Stille coupling, Buchwald-Hartwig coupling, Negishi coupling, Mizoroki-Heck reaction, cyanation reaction using copper cyanide or zinc cyanide, and the like. Reagents such as metal catalysts, phosphine ligands, bases and the like used in the coupling reaction can be used in methods known per se [methods described in, e.g., J. F. Hartwig, S. Shekhar, Q. Shen, F. Barrios-Landeros, in The Chemistry of Anilines, Z. Rappoport, Ed., Wiley-Intersicence, New York (2007); L. Jiang, S. L. Buchwald, in Metal-Catalyzed Cross-Coupling Reactions, 2nd Ed., A. de Meijere, F. Diederich, Eds., Wiley-VCH, Weinheim, Germany (2004); J. F. Hartwig, in Handbook of Organopalladium Chemistry for Organic Synthesis, A. de Meijere, F. Diederich, Eds., Wiley, New York (2002); J. F. Hartwig, in Modern Amination Methods, A. Ricci, Ed., Wiley-VCH, Weinheim, (2000)] or methods according to them, in addition to reagents described above.

Hereinafter, a method for producing compound (I) will be described.

Each symbol in the following reaction schemes has the same meaning as described above unless otherwise specified. When a specific production method is not described, a commercially available raw material compound can be easily obtained, or a raw material compound can be produced by a method known per se or a method similar thereto, and a method described in Examples.

When performing a reaction in each step, if there is a reactive site where a reaction other than the intended reaction occurs, a protecting group is introduced into the reactive site in advance by means known per se as necessary, and the desired reaction is performed, and thereafter, the protecting group may be removed also by means known per se. For example, when the raw material compounds or the intermediates have an amino group, a carboxy group or a hydroxyl group as a substituent, these groups may be protected with a protecting group generally used in peptide chemistry and the like. In this case, after the reaction, the target compound can be obtained by removing the protecting group(s) as necessary.

Compound (I) can be synthesized from the compound (1) which is an IRAK-M binder or the compound (4) which is an E3 ligase binder by the method shown in the scheme below. In each scheme, compound (I) and each reaction intermediate may independently form salts.

Scheme 1

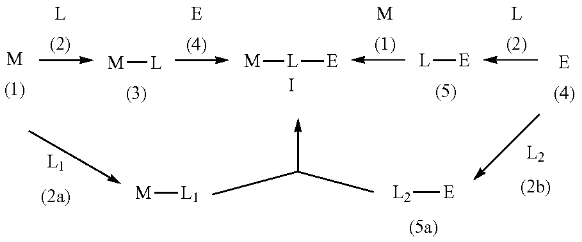

The compound (3) can be produced by subjecting the compound (1) or a reactive derivative thereof and the compound (2) which is a linker (L) or a reactive derivative thereof to an amidation reaction, a Mitsunobu reaction, an alkylation reaction, a coupling reaction, and the like. Compound (I) can be obtained by subjecting the compound (3) or a reactive derivative thereof and the compound (4) or a reactive derivative thereof to an amidation reaction, the Mitsunobu reaction, an alkylation reaction or a coupling reaction, and the like.

The compound (5) can be produced by subjecting the compound (4) or a reactive derivative thereof and compound (2) or a reactive derivative thereof to an amidation reaction, a Mitsunobu reaction, an alkylation reaction, a coupling reaction, and the like. Compound (I) can be obtained by subjecting the compound (5) or a reactive derivative thereof and the compound (1) or a reactive derivative thereof to an amidation reaction, the Mitsunobu reaction, an alkylation reaction, a coupling reaction, and the like.

The compound (3a) can be produced by subjecting the compound (1) or a reactive derivative thereof and compound (2a) or a reactive derivative thereof to an amidation reaction, a Mitsunobu reaction, an alkylation reaction, a coupling reaction, and the like. The compound (5a) can be produced by subjecting the compound (4) or a reactive derivative thereof and compound (2b) or a reactive derivative thereof to an amidation reaction, the Mitsunobu reaction, an alkylation reaction, a coupling reaction, and the like. Compound (I) can be obtained by subjecting the compound (3a) and the compound (5a) or reactive derivatives thereof to an amidation reaction, the Mitsunobu reaction, an alkylation reaction, a coupling reaction, the Huisgen reaction and the like.

The method for producing the IRAK-M binder (M) (compound (1)) represented by the following formula (II), which constitutes a part of compound (I), will be described below.

Scheme 2

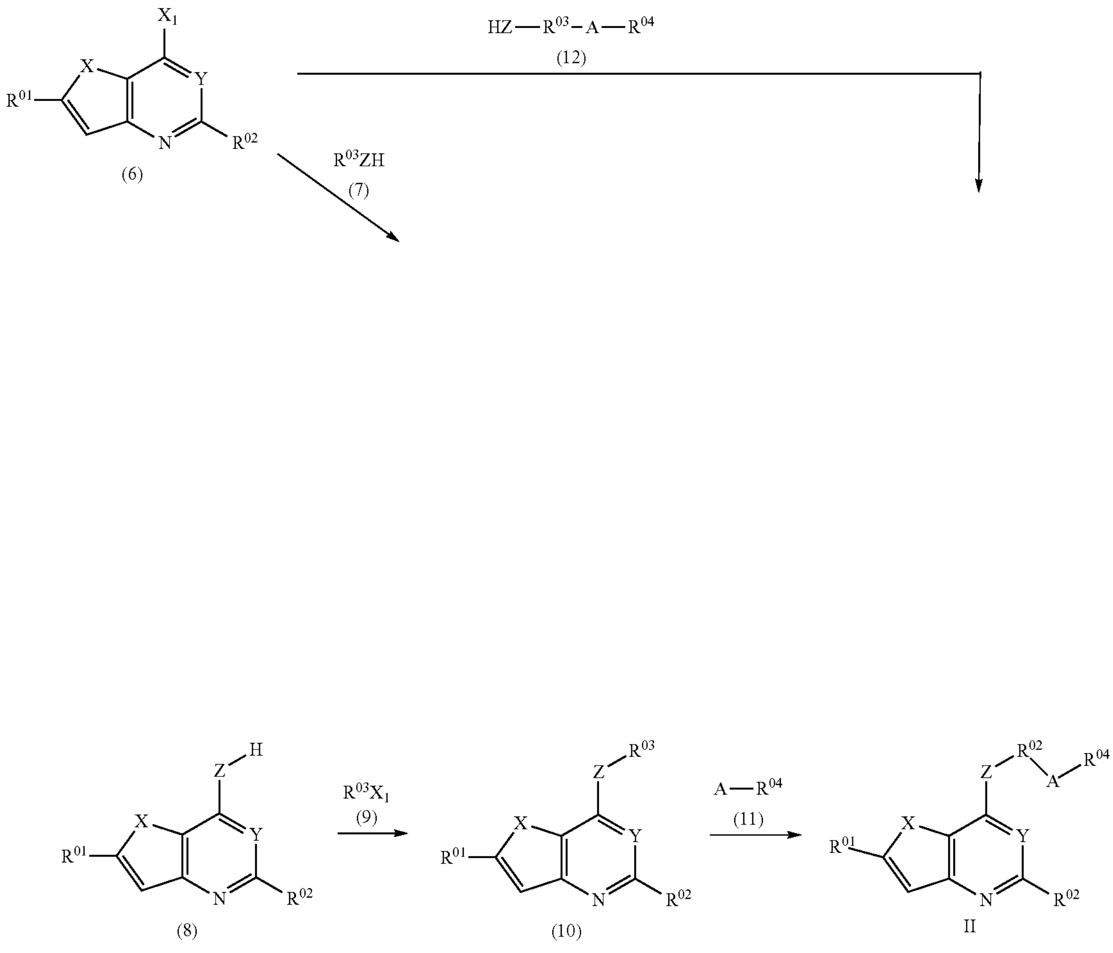

In the Scheme 2, $X_1$ represents a halogen atom or a leaving group.

The compound (10) can be produced by subjecting the compound (6) and the compound (7) to an aromatic nucleophilic substitution reaction, a coupling reaction, and the like. In addition, the compound (10) can be produced by subjecting the compound (8) and the compound (9) to an alkylation reaction, an aromatic nucleophilic substitution reaction, a coupling reaction, and the like.

The compound (II) can be produced by subjecting the compound (10) and the compound (11) or a reactive derivative thereof to an amidation reaction, a Mitsunobu reaction, an alkylation reaction, a sulfonylation reaction, a reductive amination reaction, a coupling reaction, and the like. In addition, the compound (II) can be produced by subjecting the compound (6) and the compound (12) to an aromatic nucleophilic substitution reaction, a coupling reaction, and the like.

The "L" (the compound (2)) is a linker (L) constituting a part of compound (I), and "$L_1$" (the compound (2a)) and the "$L_2$" (the compound (2b)) are a part of the linker (L), all of which may be a commercially available product to be used as is or can be produced by a method known per se or a method similar thereto.

The "E" (the compound (4)) which is a E3 ligase binder constituting a part of compound (I) may be a commercially available product to be used as is or can be produced by a method known per se or a method similar thereto, or the method described below.

The production method will be described below when the "E" (the compound (4)) is a compound represented by the following formula (IV-I).

Scheme 3

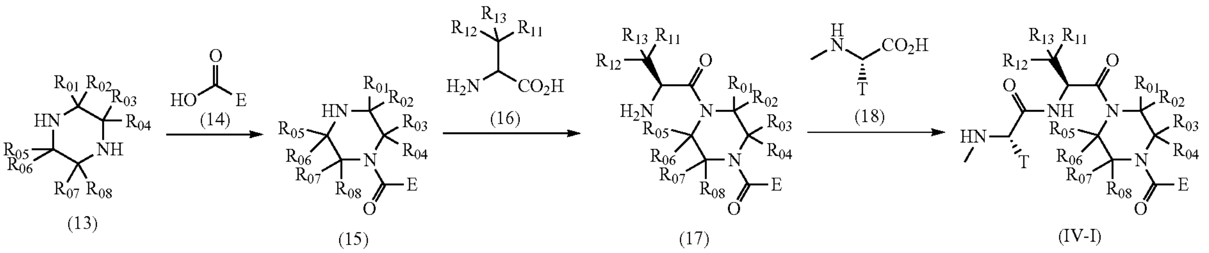

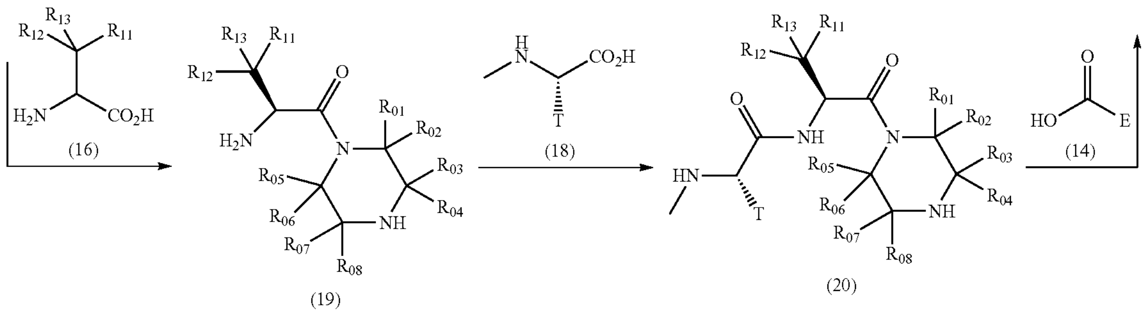

The compound (15) can be produced by subjecting the compound (13) and the compound (14) or a reactive derivative thereof to an amidation reaction and the like. The compound (17) can be produced by subjecting the compound (15) and the compound (16) to an amidation reaction and the like. The compound (IV-I) can be produced by subjecting the compound (17) and the compound (18) or a reactive derivative thereof to an amidation reaction and the like.

In addition, the compound (19) can be produced by subjecting the compound (13) and the compound (16) or a reactive derivative thereof to an amidation reaction and the like. The compound (20) can be produced by subjecting the compound (19) and the compound (18) or a reactive derivative thereof to an amidation reaction and the like. The compound (IV-I) can be produced by subjecting the compound (20) and the compound (14) or a reactive derivative thereof to an amidation reaction and the like.

The production method will be described below when the "E" (the compound (4)) is a compound represented by the following formula (IV-II).

Scheme 4

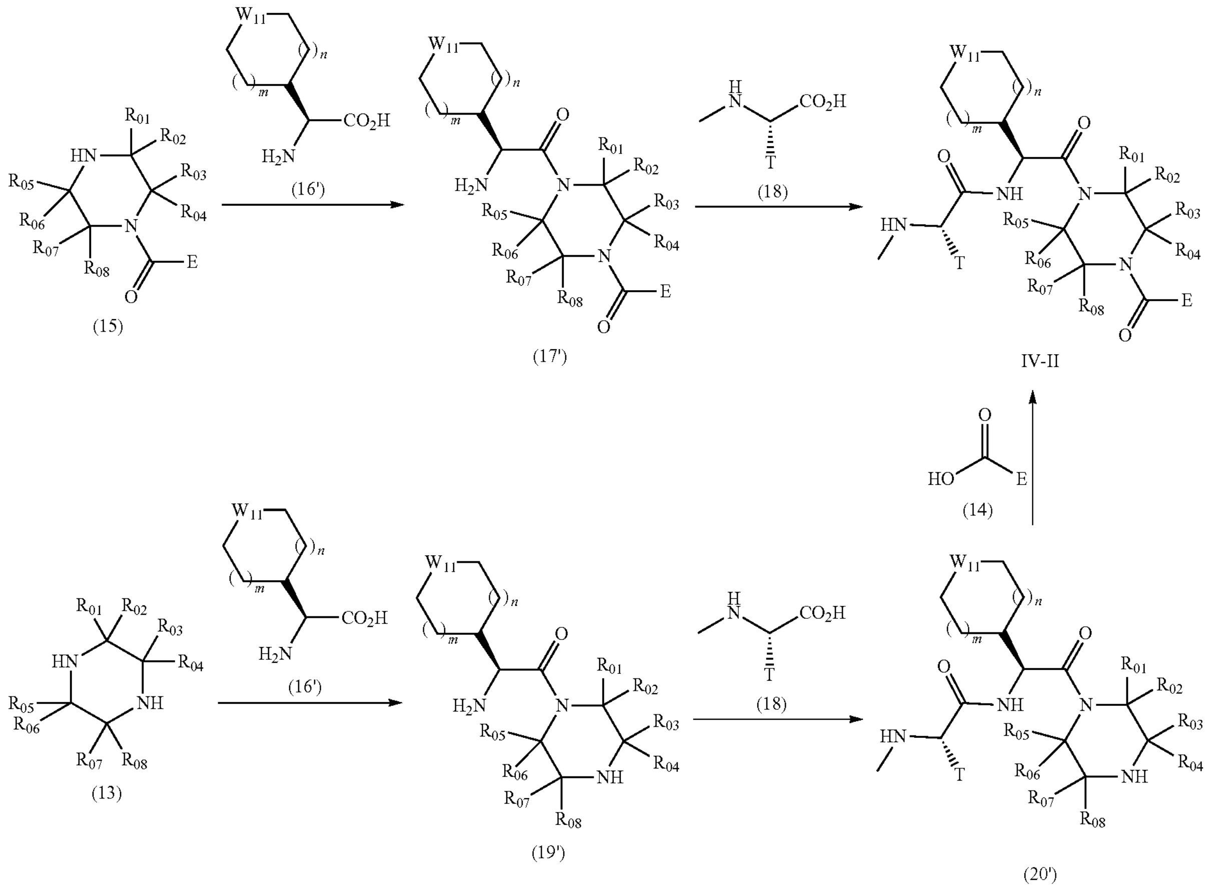

(15) (16') (17') (18) IV-II (14) (13) (16') (19') (18) (20')

The compound (17') can be produced by subjecting the compound (15') and the compound (16') or a reactive derivative thereof to an amidation reaction and the like. The compound (IV-II) can be produced by subjecting the compound (17') and the compound (18) or a reactive derivative thereof to an amidation reaction and the like.

In addition, the compound (19') can be produced by subjecting the compound (13) and the compound (16') or a reactive derivative thereof to an amidation reaction and the like. The compound (20') can be produced by subjecting the compound (19') and the compound (18) or a reactive derivative thereof to an amidation reaction and the like. The compound (IV-II) can be produced by subjecting the compound (20') and the compound (14) or a reactive derivative thereof to an amidation reaction and the like.

The production method will be described below when the "E" (the compound (4)) is a compound represented by the following formula (IV-III).

Scheme 5

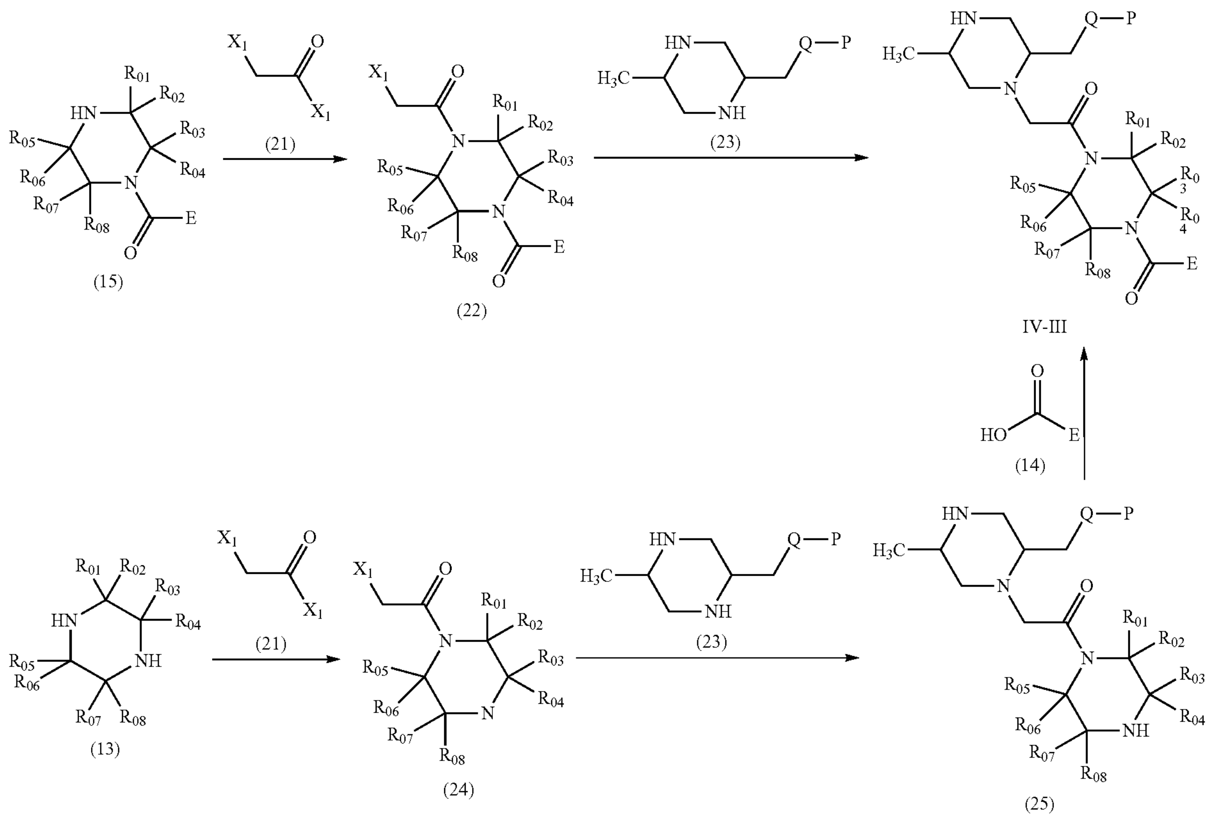

The compound (22) can be produced by subjecting the compound (15) and the compound (21) to an amidation reaction and the like. The compound (IV-III) can be produced by subjecting the compound (22) and the compound (23) to an alkylation reaction and the like. In addition, the compound (24) can be produced by subjecting the compound (13) and the compound (21) to an amidation reaction and the like. The compound (25) can be produced by subjecting the compound (24) and the compound (23) to an alkylation reaction and the like. The compound (IV-III) can be produced by subjecting the compound (25) and the compound (14) or a reactive derivative thereof to an amidation reaction and the like.

By converting substituents of compound (I) thus obtained or each intermediate by means known per se (that is, introduction of a substituent or conversion of a functional group), another compound contained in compound (I) can be produced. Intermediates corresponding thereto or salts thereof can also be produced.

Compound (I) obtained by the above production method can be isolated and purified by known means, e.g., solvent extraction, solution pH conversion, phase transfer, crystallization, recrystallization or chromatography.

When compound (I) contains an optical isomer, a stereoisomer, a regioisomer, and a rotational isomer, these are also contained as the compound (I), and each compound can be obtained as a single item by a synthesis method and a separation method known per se. For example, when compound (I) has an optical isomer, the optical isomer resolved from the compound is also included in the compound (I).

Here, the optical isomer can be produced by a method known per se.

Compound (I) may be a crystal.

The crystal of compound (I) (hereinafter sometimes abbreviated as crystals of the present invention) can be produced by crystallization of compound (I) by applying a crystallization method known per se.

Compound (I) may be a pharmaceutically acceptable co-crystal or a salt thereof. Here, the co-crystal or the salt thereof mean a crystalline substance constituted of two or more special solids at room temperature, each having different physical properties (e.g., structure, melting point, heat of fusion, hygroscopicity, solubility, and stability). The co-crystal or the salt thereof can be produced according to a co-crystallization method known per se.

Compound (I) may be a hydrate, a non-hydrate, a non-solvate, or a solvate.

Furthermore, deuterium converted materials obtained by converting $^{1}H$ into $^{2}H(D)$ are also included in the compound (I).

Compound (I) may be labeled with an isotope (e.g., $^{3}H$, $^{13}C$, $^{4}C$, $^{18}F$, $^{35}S$, $^{125}I$) and the like. The compound (I) labeled or substituted with an isotope can be used, e.g., as a tracer (PET tracer) for use in positron emission tomography (PET) and is expected to be useful in fields such as medical diagnosis and the like.

Compound (I) may be used as a prodrug.

A prodrug of compound (I) means a compound which is converted into compound (I) with a reaction due to an enzyme, a gastric acid, etc. under the physiological condition in a living body, that is, a compound which is enzymatically oxidized, reduced, hydrolyzed, etc. to be converted into compound (I), or a compound which is hydrolyzed with gastric acid, etc., to be converted into compound (I).

A prodrug of compound (I) includes; a compound in which an amino group of compound (I) is acylated, alkylated or phosphorylated (e.g., compounds in which an amino group of compound (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated or tert-butylated); a compound in which a hydroxy group of compound (I) is acylated, alkylated, phosphorylated or borated (e.g., compounds in which a hydroxy group of compound (I) is acetylated, palmitoylated, propanoylated, pivaloylated, succinylated, fumarylated, alanylated or dimethylaminomethylcarbonylated); a compound in which a carboxy group of compound (I) is esterified or amidated (e.g., compounds in which a carboxy group of compound (I) is ethylesterified, phenylesterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated), and the like. These compounds can be produced from compound (I) by a method known per se.

Further, a prodrug of compound (I) may be a compound which is converted to compound (I) under physiological conditions as described in "IYAKUHIN no KAIHATSU (Development of Pharmaceuticals)", Vol. 7, Design of Molecules, p. 163-198, published by HIROKAWA SHOTEN (1990).

In the present specification, the prodrug may be in a form of a salt, and examples of such salt include those exemplified as the salt of the compound represented by the formula (I) described above.

Compound (I) may be conjugated with a compound that adds a function, e.g., a cell penetrating peptide (CPP), or a kinetophore which keeps a compound in the intestinal tract (e.g., polyethylene oxides capped with a short-chain peptide, sugar and quaternary ammonium; etc.), and the compound (I) may bind directly or via a linker to a compound that adds a function.

Compound (I) can also be used as a payload (the moiety corresponding to the drug described above) in an antibody (or peptidic antigen recognition sequence)-drug conjugate. When compound (I) is used as a payload, compound (I) may bind to an antibody (or a peptidic antigen recognition sequence) directly or via a linker.

When compound (I) is used as a payload, the linker as described in Chem. Rev., 114, 9154-9218 (2014), Pharma. Res. 32, 3526-3540 (2015), Bioconjugate Chem. 21, 5-13 (2010), The AAPS journal, 17, 339-351 (2015), WO2011/005761, and the like, may be used in addition to the linkers exemplified in the present specification.

Compound (I) or a prodrug thereof (herein, these may be collectively abbreviated as "the compound of the present invention") has activity of inducing degradation of IRAK-M and can be useful as a prophylactic or therapeutic agent for cancer, a cancer growth inhibitor, a cancer metastasis inhibitor.

The compound of the present invention exhibits activity of inducing protein degradation of IRAK-M, and the compound of the present invention is useful as a medicament, since it is superior in at least one of the points in terms of drug efficacy, pharmacokinetics (e.g., absorption, distribution, metabolism, excretion), solubility (e.g., water solubility), interaction with other medicaments (e.g., drug-metabolizing enzyme inhibitory action), safety (e.g., acute toxicity, chronic toxicity, genetic toxicity, reproductive toxicity, cardiotoxicity, carcinogenicity, central toxicity), and stability (e.g., chemical stability, stability to an enzyme). Among them, it is expected to be effective for the treatment or prophylaxis of cancer, but it is not limited to this.

The compound of the present invention also has activity of inducing degradation of IRAK-M protein for mammals (e.g., mouse, rat, hamster, rabbit, cat, dog, cow, sheep, monkey, and human), and in view of the mechanism of action can be used as a medicament of a prophylaxis or treatment agent for diseases correlated with IRAK-M protein (herein, these may be collectively abbreviated as "IRAK-M associated diseases"): e.g., cancers [e.g., colon cancer (e.g. rectal cancer, anus cancer, familial colorectal cancer, hereditary nonpolyposis colorectal cancer, gastrointestinal stromal tumor), lung cancers (e.g., non-small-cell lung cancer, small-cell lung cancer, malignant mesothelioma), mesothelioma, pancreatic cancers (e.g., pancreatic ductal adenocarcinoma, pancreatic endocrine tumor), pharyngeal cancer, laryngeal cancer, esophageal cancer, stomach cancers (e.g., papillary adenocarcinoma, mucinous adenocarcinoma, adenosquamous carcinoma), duodenal cancer, small intestinal cancer, breast cancers (e.g., invasive ductal carcinoma, non-invasive ductal carcinoma, inflammatory breast cancer), ovarian cancers (e.g., ovarian epithelial cancer, extragonadal germ cell tumor, ovarian germ cell tumor, ovarian low-malignant potential tumors), testis tumors, prostate cancers (e.g., hormone-dependent prostate cancer, non-hormone dependent prostate cancer, castration-resistant prostate cancer), liver cancers (e.g., hepatocellular cancer, primary liver cancer, extrahepatic bile duct cancer), thyroid cancers (e.g., medullary thyroid carcinoma), renal cancers (e.g., renal cell carcinomas (e.g., clear cell renal cell carcinoma), transitional cell cancer of the renal pelvis and ureter), uterine cancers (e.g., cervical cancer, uterine body cancer, uterus sarcoma), gestational choriocarcinoma, brain tumors (e.g., medulloblastoma, glioma, pineal astrocytic tumor, pilocytic astrocytoma, diffuse astrocytoma, anaplastic astrocytoma, pituitary adenoma), retinoblastoma, skin cancers (e.g., basalioma, malignant melanoma), sarcomas (e.g., rhabdomyosarcoma, leiomyosarcoma, soft tissue sarcoma, spindle cell sarcoma), malignant bone tumor, bladder cancer, blood cancers (e.g., multiple myeloma, leukemias (e.g., acute myeloid leukemia, chronic lymphocytic leukemia), malignant lymphoma (B-cell lymphoma, diffuse large B-cell lymphoma, MALT lymphoma, follicular lymphoma, mantle cell lymphoma), Hodgkin's disease, chronic myeloproliferative disease), cancer of unknown primary]; an inhibition agent of a cancer growth; a suppression agent of metastasis; a promotion agent of apoptosis; or a therapeutic agent of precancerous lesions (e.g., myelodysplastic syndrome).

Further, IRAK-M associated diseases other than cancer include, e.g., asthma, inflammatory bone disease, inflammatory lung disease, idiopathic pulmonary fibrosis, inflammatory bowel disease (e.g., Crohn's disease, ulcerative colitis, etc.), multiple sclerosis, systemic inflammatory response syndrome (SIRS), sepsis, infectious complications of hematopoietic stem cell transplantation, influenza infection, acute respiratory syndrome (COVID-19, MERS, SARS), acute bacterial meningitis, *Helicobacter pylori* infection, invasive *Staphylococcus aureus* infection, tuberculosis, systemic fungal infection, herpes simplex virus infection, varicella zoster virus infection, human papillomavirus infection, acute viral encephalitis, encephalitis, meningitis, decreased immune function associated with infection and the like.

The compound of the present invention may be administered orally or parenterally as it is or in a mixture with a pharmacologically acceptable carrier as a medicament to a mammal (preferably, humans).

Hereinafter, the medicament containing the compound of the present invention (sometimes to be abbreviated as "the medicament of the present invention") is described in detail. Examples of the dosage form of the medicament of the present invention include oral preparations such as tablets (e.g., sugar-coated tablets, film-coated tablets, sublingual tablets, buccal tablets, orally disintegrating tablets), pills, granules, powders, capsules (e.g., soft capsules, microcapsules), syrups, emulsions, suspensions, films (e.g., orally disintegrating films, oral mucosa-sticking films) and the like. Further, examples of the dosage form of the medicament of the present invention include also parenteral preparations such as injections, drip infusions, transdermal absorption type preparations (e.g., iontophoretic transdermal absorption type preparations), suppositories, ointments, nasal preparations, pulmonary preparations, and eye drops and the like. Also, the medicament of the present invention may be a release control preparation such as an immediate-release preparation or a sustained-release preparation (e.g., a sustained-release microcapsule) and the like.

As a dosage form of the medicament of the present invention, a nanoparticle preparation or a preparation using a bacterial-derived membrane can also be used.

The medicament of the present invention may be prepared by a known preparation method generally used in the field of preparation technology (e.g., the method described in the Japanese Pharmacopoeia). The medicament of the present invention may contain a suitable amount of an additive such as an excipient, a binder, a disintegrant, a lubricant, a sweeting agent, a surfactant, a suspending agent, an emulsifier, a colorant, a preservative, an aromatic, a corrigent, a stabilizer, a thickening agent and the like generally used in the field of preparation as necessary.

Examples of the above-mentioned pharmacologically acceptable carriers include these additives.

For example, tablet may be prepared using an excipient, a binder, a disintegrant, a lubricant and the like, and pill and granule may be prepared using an excipient, a binder and a disintegrant. Also, powder and capsule may be prepared using an excipient and the like, syrup may be prepared using a sweeting agent and the like, and emulsion or suspension may be prepared using a suspending agent, a surfactant, an emulsifier and the like.

Examples of the excipient include lactose, white sugar, glucose, starch, sucrose, crystalline cellulose, powdered glycyrrhiza, mannitol, sodium hydrogencarbonate, calcium phosphate and calcium sulfate.

Examples of the binder include 5 to 10 wt % starch liquid paste, 10 to 20 wt % gum arabic solution or gelatin solution, 1 to 5 wt % tragacanth solution, carboxymethyl cellulose solution, sodium alginate solution and glycerin.

Examples of the disintegrant include starch and calcium carbonate.

Examples of the lubricant include magnesium stearate, stearic acid, calcium stearate and purified talc.

Examples of the sweeting agent include glucose, fructose, invert sugar, sorbitol, xylitol, glycerin and simple syrup.

Examples of the surfactant include sodium lauryl sulfate, polysorbate 80, sorbitan mono-fatty acid ester and polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin and polysorbate 80.

For example, when the medicament of the present invention is a tablet, the tablet may be prepared, e.g., by adding an excipient (e.g., lactose, sucrose, starch), a disintegrant (e.g., starch, calcium carbonate), a binder (e.g., starch, gum arabic, carboxymethyl cellulose, polyvinyl pyrrolidone, hydroxypropyl cellulose) or a lubricant (e.g., talc, magnesium stearate, polyethylene glycol 6000) to the compound of the present invention, compression-molding according to a method known per se, and then, if necessary, coating it for the purpose of taste masking, enteric property or durability to give a tablet according to a method known per se. As the coating agent used for coating, e.g., hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (methacrylic acid/acrylic acid copolymer, Rohm, Germany) and pigments (e.g., iron oxide red, titanium dioxide) may be used.

Examples of the above-described injection include intravenous injection as well as subcutaneous injection, intradermal injection, intramuscular injection, intraperitoneal injection, drip injection and the like.

Such injections are prepared according to a method known per se, that is, by dissolving, suspending or emulsifying the compound of the present invention in a sterilized aqueous liquid or oily liquid. Examples of the aqueous liquid include physiological saline, isotonic solutions containing glucose or other auxiliary drugs (e.g., D-sorbitol, D-mannitol, sodium chloride) and the like. The aqueous liquid may contain a suitable solubilizer, e.g., an alcohol (e.g., ethanol), a polyalcohol (e.g., propylene glycol, polyethylene glycol), a nonionic surfactant (e.g., polysorbate 80, HCO-50). Examples of the oily liquid include sesame oil and soybean oil and the like. The oily liquid may contain a suitable solubilizing agent. Examples of the solubilizing agent include benzyl benzoate, benzyl alcohol and the like. In addition, the injection may be blended with a buffer (e.g., phosphate buffer, sodium acetate buffer), a soothing agent (e.g., benzalkonium chloride, procaine hydrochloride), a stabilizer (e.g., human serum albumin, polyethylene glycol), a preservative (e.g., benzyl alcohol, phenol) and the like. A prepared injection solution may be usually filled into an ampoule.

The content of the compound of the present invention in the medicament of the present invention varies depending on the form of the pharmaceutical preparation, and is usually about 0.01 to about 100 wt %, preferably about 2 to about 85 wt %, more preferably about 5 to about 70 wt %, based on the whole preparation.

The content of the additive in the medicament of the present invention varies depending on the form of the pharmaceutical preparation, and is usually about 1 to about 99.9 wt %, preferably about 10 to about 90 wt %, based on the whole preparation.

The compound of the present invention is stable and has low toxicity and may be used safely. The daily dose of the compound of the present invention varies depending on the condition and body weight of a patient, the kind of compound, administration route and the like, in the case of, for example, oral administration to patients for the purpose of treating cancer, the daily dose for an adult (body weight about 60 kg) is about 1 to about 1000 mg, preferably about 3 to about 300 mg, and more preferably about 10 to about 200 mg, as the compound of the present invention, which may be administered once or in two or three divided doses.

When the compound of the present invention is administered parenterally, it is usually administered in the form of a liquid (e.g., injection). The dose of the compound of the present invention varies depending on the subject of administration, target organ, symptoms, administration method and the like, and for example, it is usually about 0.01 to about 100 mg, preferably about 0.01 to about 50 mg, more preferably about 0.01 to about 20 mg, as the compound of the present invention, relative to 1 kg of body weight, which is preferably given by intravenous injection or subcutaneous injection.

The compound of the present invention may be used concurrently with other drugs. Specifically, the compound of the present invention may be used together with a medicament such as hormonal therapeutic agents, chemotherapeutic agents, immunotherapeutic agents, or medicaments inhibiting the action of cell growth factors or their receptors and the like. Hereinafter, drugs that can be used in combination or concurrently with the compound of the present invention are abbreviated as concomitant drugs.

As the "hormonal therapeutic agents" include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testololactone, aminoglutethimide, LH-RH agonists (e.g. goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgens (e.g., flutamide, bicalutamide, nilutamide, enzalutamide), 5α-reductase inhibitors (e.g., finasteride, epristeride, dutasteride), adrenal cortex hormone drugs (e.g., dexamethasone, prednisolone, betamethasone, triamcinolone), androgen synthesis inhibitors (e.g., abiraterone), retinoids and drugs that retard the metabolism of retinoids (e.g., liarozole), thyroid hormone, and their DDS (Drug Delivery System) preparations may be used.

As the "chemotherapeutic agents", e.g., alkylating agents, antimetabolites, anticancer antibiotics and plant-derived anticancer agents may be used.

As the "alkylating agents", e.g., nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucide, carboplatin, cisplatin, miboplatin, nedaplatin, oxaliplatin, altretamine, ambamustine, dibrospidium hydrochloride, fotemustine, prednimustine, pumitepa, ribomustine, temozolomide, treosulfan, trofosfamide, zinostatin stimalamer, adozelesin, cystemustine, bizelesin and their DDS preparations thereof may be used.

As the "antimetabolits", e.g., mercaptopurine, 6-mercaptopurine riboside, thioinosine, methotrexate, pemetrexed, enocitabine, cytarabine, cytarabine ocfosphate, ancitabine hydrochloride, 5-FU drugs (e.g., fluorouracil, tegafur, UFT, doxifluridine, carmofur, galocitabine, emitefur, capecitabine), aminopterin, nelzarabine, leucovorin calcium, thioguanine, butocine, calcium folinate, levofolinate calcium, cladribine, emitefur, fludarabine, gemcitabine, hydroxycarbamide, pentostatine, piritrexim, idoxuridine, mitoguazone, thiazofurin, ambamustine, bendamustine and their DDS preparations thereof may be used.

As the "anticancer antibiotics", e.g., actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and their DDS preparations (e.g., doxorubicin-encapsulated PEG liposomes) may be used.

As the "plant-derived anticancer agents", e.g., etoposide, etoposide phosphate, vinblastine sulfate, vincristine sulfate, vindesine sulfate, teniposide, paclitaxel, docetaxel, cabazitaxel, vinorelbine and their DDS preparations thereof may be used.

As the "immunotherapeutic agents", e.g., picibanil, krestin, schizophyllan, lentinan, ubenimex, interferons, interleukins, macrophage colony stimulating factor, granulocyte colony stimulating factor, erythropoietin, lymphotoxin, BCG vaccine, *Corynebacterium parvum*, levamisole, Toll-like receptor (TLR) agonist, polysaccharide K, procodazole, anti-CTLA4 antibodies (e.g., ipilimumab, tremelimumab), anti-PD-1 antibodies (e.g., nivolumab, pembrolizumab, cemiplimab, tislelizmab, sintilimab, toripalimab), anti-PD-L1 antibody (e.g., atezolizumab, avelumab, durvalumab), and oncolytic viruses may be used.

The "cell growth factors" in the "medicaments inhibiting the action of cell growth factors or their receptors" may be any substance that promote cell growth, and usually include peptides having a molecular weight of 20,000 or less and exhibiting the action at low concentrations by binding to a receptor, and specifically, (1) EGF (epidermal growth factor) or substances having substantially the same activity as EGF (e.g., TGF$\alpha$); (2) insulin or substances having substantially the same activity as insulin (e.g., insulin, IGF (insulin-like growth factor)-1, IGF-2), (3) FGF (fibroblast growth factor) or substances having substantially the same activity as FGF (e.g., acidic FGF, basic FGF, KGF (keratinocyte growth factor), FGF-10), and (4) other cell growth factors [e.g., CSF (colony stimulating factor), EPO (erythropoietin), IL-2 (interleukin-2), NGF (nerve growth factor), PDGF (platelet-derived growth factor), TGF-$\beta$ (transforming growth factor $\beta$), HGF (hepatocyte growth factor), VEGF (vascular endothelial growth factor), heregulin, angiopoietin may be used.

The "cell growth factor receptors" may be any receptor as long as it has the ability to bind to the above-mentioned cell growth factors, and specifically, EGF receptor, heregulin receptor (e.g., HER3), insulin receptor, IGF receptor-1, IGF receptor-2, FGF receptor-1 or FGF receptor-2, NGF receptor, TGF$\beta$ receptor, HGF receptor, VEGF receptor, angiopoietin receptor (e.g., Tie2), PDGF receptor and the like may be used.

As the "medicament inhibiting the action of cell growth factors or their receptors", EGF inhibitor, TGF$\alpha$ inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGF$\beta$ inhibitor, HGF inhibitor, VEGF inhibitor, angiopoietin inhibitor, EGF receptor inhibitor, HER2 inhibitor, HER3 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, RORi inhibitor, Trk inhibitor, Ret inhibitor, mTOR inhibitor, Aurora inhibitor, PLK inhibitor, MEK(MEK1/2) inhibitor, MET inhibitor, CDK inhibitor, Akt inhibitor, ERK inhibitor, PI3K inhibitor and the like may be used. More specifically, anti-VEGF antibody (e.g., Bevacizumab, Ramucirumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d]pirimidine-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate ester (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2(R),3-dihydroxypropoxy]-3,4-difluoro-2-(2-fluoro4-iodophenylamino)benzamide (PD-0325901), Bosutinib, Regorafenib, Afatinib, Idelalisib, Ceritinib, Dabrafenib, Ponatinib, Lenvatinib, Midostaurin, Pazopanib and the like may be used.

In addition to the above-mentioned drugs, L-asparaginase, L-arginase, arginine deiminases, aceglaton, procarbazine hydrochloride, protoporphyrin-cobalt complex salt, mercury hematoporphyrin-sodium, topoisomerase I inhibitors (e.g., irinotecan, topotecan, indotecan, indimitecan), topoisomerase II inhibitors (e.g., sobuzoxane)), differentiation-inducing agents (e.g., retinoid, vitamin D), other angiogenesis inhibitors (e.g., fumagillin, shark extract, COX-2 inhibitor), $\alpha$-blockers (e.g., tamsulosin hydrochloride), bisphosphonic acids (e.g., pamidronate, zoledronate), thalidomide, lenalidomide, pomalidomide, 5-azacitidine, decitabine, proteasome inhibitors (e.g., bortezomib, carfilzomib, ixazomib), NEDD8 inhibitors (e.g., Pevonedistat), UAE inhibitors, PARP inhibitors (e.g., Olaparib, Niraparib, Veliparib), anti-tumor antibodies such as anti-CD20 antibodies (e.g., Rituximab, Obinutuzumab), anti-CCR4 antibodies (e.g., Mogamulizumab) and the like, antibody drug conjugates (e.g., Trastuzumab emtansine, Brenximab vedotin) and the like may also be used as a concomitant drug.

When the compound of the present invention is used for purposes of IRAK-M associated diseases other than cancer, besides the above-mentioned concomitants, e.g., antibacterial drugs, antifungal drugs, nonsteroidal anti-inflammatory drugs, steroid drugs, bronchodilating preparations, anticoagulants, antiplatelet drugs, thrombolytic drugs, immunomodulators, antiprotozoal drugs, antitussives/expectorants, sedatives, anesthetics, narcotic antagonists, anti-ulcer drugs, vitamins, vitamins derivatives, antiallergic drugs, anti-asthmatic drugs, therapeutic drugs for dermatitis atopic, signal transduction inhibitors, inflammatory mediator action suppressants, inflammatory mediator action suppression antibodies, inflammatory mediator production suppressants, anti-inflammatory mediator action suppressants, anti-inflammatory mediator action suppression antibodies, anti-inflammatory mediator production suppressants, antifibrotic drug, al-adrenergic agonist, antiemetic, methemoglobin elevation inhibitors, and the like may be used as a concomitant drugs.

(1) Antibacterial Drugs (i) Sulfa Drugs

Sulfamethizole, sulfisoxazole, sulfamonomethoxine, sulfamethizole, salazosulfapyridine, silver sulfadiazine, etc.

(ii) Quinoline Antibacterial Drugs nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin, etc.

(iii) Antiphthisics isoniazid, ethambutol (ethambutol hydrochloride), para-aminosalicylic acid (calcium para-aminosalicylate), pyrazinamide, ethionamide, prothionamide, rifampicin, streptomycin sulfate, kanamycin sulfate, cycloserine, etc.

(iv) Antiacidfast Bacterium Drug diaminodiphenyl sulfone, rifampicillin, etc.

(v) Antiviral Drugs idoxuridine, aciclovir, vidarabine, ganciclovir, favipiravir, etc.

(vi) Anti-HIV Drugs zidovudine, didanosine, zalcitabine, indinavir sulfate ethanolate, ritonavir, etc.

(vii) Anti-Spirochete Drugs (viii) Antibiotics tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cefalotin, cephapirin, cefaloridine, cefaclor, cefalexin, cefroxadine, cefadroxil, cefamandole, cefuroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefmenoxime, cefmetazole, cefininox, cefoxitin, cefbuperazone, latamoxef, flomoxef, cefazolin, cefotaxime, cefoperazone, ceftizoxime, moxalactam, thienamycin, sulfazecin, aztreonam or salts thereof, griseofulvin, lankacidin, etc.

(2) Antifungal Drugs (i) Polyene antibiotics (e.g., amphotericin B, nystatin, trichomycin)

(ii) Griseofulvin, pyrrolnitrin, etc.

(iii) Cytosine antimetabolites (e.g., flucytosine)

(iv) Imidazole derivatives (e.g., econazole, clotrimazole, miconazole nitrate, bifonazole, croconazole)

(v) Triazole derivatives (e.g., fluconazole, itraconazole, azole compounds [2-[(1R,2R)-2-(2,4-difluorophenyl)-2-hydroxy-1-methyl-3-(1H-1,2,4-triazol-1-yl) propyl]-4-[4-(2,2,3,3-tetrafluoropropoxy)phenyl]-3-(2H,4H)-1,2,4-triazolone]

(vi) Thiocarbamic acid derivatives (e.g., tolnaftate)

(vii) Echinocandin derivatives (e.g., caspofungin, micafungin, anidulafungin), etc.

(3) Non-Steroidal Anti-Inflammatory Drugs acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesylate, ulinastatin, colchicine, probenecid, sulfinpyrazone, benzbromarone, allopurinol, gold sodium thiomalate, sodium hyaluronate, sodium salicylate, morphine hydrochloride, salicylic acid, atropine, scopolamine, morphine, pethidine, levorphanol, ketoprofen, naproxen, oxymorphone, meloxicam, celecoxib, rofecoxib, or salts thereof.

(4) Steroid Drugs dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclometasone propionate, estriol, etc.

(5) Bronchodilating Preparations

Metaproterenol, salmeterol, formoterol, carmoterol, etc.

(6) Anticoagulants heparin sodium, sodium citrate, activated protein C, tissue factor pathway inhibitor, antithrombin III, dalteparin sodium, warfarin potassium, argatroban, gabexate, sodium citrate, etc.

(7) Antiplatelet Drugs ozagrel sodium, ethyl icosapentate, beraprost sodium, alprostadil, ticlopidine hydrochloride, pentoxifylline, dipyridamole, etc.

(8) Thrombolytic Drugs tisokinase, urokinase, streptokinase, etc.

(9) Immunomodulators cyclosporin, tacrolimus, gusperimus, azathioprine, antilymphocyte serum, freeze-dried sulfonated normal immunoglobulin, erythropoietin, colony stimulating factor, interleukin, interferon, etc.

(10) Antiprotozoal Drugs metronidazole, tinidazole, diethylcarbamazine citrate, quinine hydrochloride, quinine sulfate, etc.

(11) Antitussive and Expectorant Drugs ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextropetorphan hydrobromide, oxycodone hydrochloride, dimorphane phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocysteine, etc.

(12) Sedatives chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromvalerylurea, chloral hydrate, triclofos sodium, etc.

(13) Anesthetics (13-1) Local Anesthetics cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine, etc.

(13-2) General Anesthetics (i) Inhalation anesthetics (e.g., ether, halothane, nitrous oxide, isoflurane, enflurane), (ii) Intravenous anesthetics (e.g., ketamine hydrochloride, droperidol, thiopental sodium, thiamylal sodium, pentobarbital), etc.

(14) Narcotic Antagonists levallorphan, nalorphine, naloxone or a salt thereof, etc.

(15) Anti-Ulcer Drugs metoclopramide, histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin, etc.

(16) Vitamin Drugs (i) Vitamin A: vitamin A1, vitamin A2 and retinol palmitate (ii) Vitamin D: Vitamin D1, D2, D3, D4 and D5

(iii) Vitamin E: α-tocopherol, β-tocopherol, γ-tocopherol, δ-tocopherol, dl-α-tocopherol nicotinate (iv) Vitamin K: vitamin K1, K2, K3 and K4

(v) Folic acid (vitamin M)

(vi) Vitamin B: vitamin B1, vitamin B2, vitamin B3, vitamin B5, vitamin B6 and vitamin B12

(vii) Biotin (vitamin H), etc.

(17) Vitamin Derivatives various derivatives of vitamins, e.g., ascorbic acid, vitamin D3 derivatives such as 5,6-trans-cholecalciferol, 2,5-hydroxycholecalciferol, 1-α-hydroxycholecalciferol, etc., vitamin D2 derivatives such as 5,6-trans-ergocalciferol, etc., etc.

(18) Antiallergic Drugs diphenhydramine, chlorpheniramine, tripelennamine, clemizole, diphenylpyraline, methoxyphenamine, sodium cromoglicate, tranilast, repirinast, amlexanox, ibudilast, ketotifen, terfenadine, mequitazine, azelastine, epinastine, ozagrel hydrochloride, pranlukast hydrate, seratrodast, etc.

(19) Anti-Asthmatic Drugs isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, ibudilast, ketotifen, terfenadine, mequitazine, azelastine, epinastine, ozagrel hydrochloride, pranlukast hydrate, seratrodast, dexamethasone, prednisolone, hydrocortisone, beclomethasone propionate, etc.

(20) Therapeutic Drugs for Dermatitis Atopic sodium cromoglicate, etc.

(21) Antiemetics phenothiazine derivatives, 5-HT3 receptor antagonists, etc.

(22) Methemoglobin Elevation Inhibitors methylene blue, ascorbic acid, etc.

(23) Integrin Inhibitors natalizumab, vedolizumab, AJM300, TRK-170, E-6007, etc.

(24) Antifibrotic Drugs pirfenidone nintedanib β-aminopropionitrile (BAPN), ursodeoxycholic acid, etc.

(25) Others hydroxycam, diacerein, megestrol acetate, nicergoline, prostaglandins, etc.

By combining the compound of the present invention and a concomitant drug, a superior effect may be obtained such as (1) the dose of the compound of the present invention or the concomitant drug may be reduced as compared with a case where the compound is administered alone, (2) the drug to be used in combination with the compound of the present invention may be selected depending on the patient's condition (mild case, severe case, etc.), (3) the treatment period may be set longer, (4) a therapeutic effect maintaining longer is designed, and (5) by using the compound of the present invention in combination with a concomitant drug, a synergistic effect may be obtained.

Hereinafter, when the compound of the present invention is used in combination with a concomitant drug, it is referred to as the "combination drug of the present invention".

When using the combination drug of the present invention, the administration time of the compound of the present invention and the concomitant drug is not limited, and the compound of the present invention and the concomitant drug may be administered simultaneously to a subject to be administered, or with a time interval. When the administration is carried out with a time interval, the time interval varies depending on the effective ingredient to be administered, dosage form and administration method, and for example, when the concomitant drug is administered first, the compound of the present invention may be administered within 1 minute to 3 days, preferably within 10 minutes to 1 day, more preferably within 15 minutes to 1 hour after administration of the concomitant drug. When the compound of the present invention is administered first, the concomitant drug may be administered within 1 minute to 1 day, preferably within 10 minutes to 6 hours, more preferably within 15 minutes to 1 hour after administering the compound of the present invention. The dosage of the concomitant drug may be in accordance with the dose clinically used, and may be appropriately selected depending on the administration subject, administration route, disease, combination, and the like.

Examples of the administration mode when the compound of the present invention and the concomitant drug are used concurrently include (1) administration of a single preparation obtained by simultaneously preparing the compound of the present invention and the concomitant drug, (2) simultaneous administration by the same administration route of two preparations obtained by separately preparing the compound of the present invention and a concomitant drug, (3) administration with an time interval by the same administration route of two preparations obtained by separately preparing the compound of the present invention and a concomitant drug, (4) simultaneous administration by the different administration routes of two preparations obtained by separately preparing the compound of the present invention and a concomitant drug, and (5) administration with a time interval by the different administration routes of two preparations obtained by separately preparing the compound of the present invention and a concomitant drug (e.g., administration in the order of the compound of the present invention and the concomitant drug, or administration in the reverse order).

The dose of the concomitant drug may be appropriately determined based on the clinically used dose. The ratio of the compound of the present invention and the concomitant drug may be appropriately determined depending on the administration subject, administration route, target disease, symptom, combination and the like. For example, when the administration subject is a human, the concomitant drug may be used in an amount of 0.01 to 100 parts by weight relative to 1 part by weight of the compound of the present invention.

Further, the compound of the present invention or the combination drug of the present invention may be used in combination with non-drug therapy. Specifically, the compound of the present invention or the combination drug of the present invention may be combined with non-drug therapy such as (1) surgery, (2) hypertensive chemotherapy using angiotensin II and the like, (3) gene therapy, (4) thermotherapy, (5) cryotherapy, (6) laser cauterization and (7) radiotherapy.

For example, by using the compound of the present invention or the combination drug of the present invention before or after the above-mentioned surgery and the like, or using the compound or the drug before or after a combined treatment of two or three kinds thereof, effects may be obtained such as prevention of the onset of resistance, prolongation of disease-free survival, suppression of metastasis or recurrence of cancer, prolongation of life, and the like.

Further, it is possible to combine a treatment with the compound of the present invention or the combination drug of the present invention with a supportive therapy [(i) administration of antibiotics (e.g., β-lactam type such as pansporin and the like, macrolide type such as clarithromycin and the like) for the complication with various infectious diseases, (ii) administration of high-calorie transfusion, amino acid preparation or multivitamin preparation for improving malnutrition, (iii) morphine administration for pain relief, (iv) administration of a drug for ameliorating side effects such as nausea, vomiting, anorexia, diarrhea, leukopenia, thrombocytopenia, decreased hemoglobin concentration, hair loss, liver damage, renal damage, DIC, fever and the like, and (v) administration of a drug for suppressing multiple drug resistance of cancer, etc..

Further, the present invention is explained in detail by referring to the following References, Examples, Experimental Examples and Formulation Examples, which are not to be construed as limitative, and the disclosure may be changed within the scope of the present invention.

In the following Examples, the "room temperature" generally means about 10° C. to about 35° C. The ratios indicated for mixed solvents are volume mixing ratios, unless otherwise specified. "%" means "wt %," unless otherwise specified.

In silica gel column chromatography, "NH" means use of aminopropyl silane-bound silica gel and "C18" means use of octadecyl-bound silica gel. In HPLC (high-performance liquid chromatography), "C18" means use of octadecyl-bonded silica gel. The ratios of elution solvents are volume mixing ratios, unless otherwise specified.

In Examples, the following abbreviations are used.

MS: mass spectrum

M: mol concentration

DMSO-$d_6$: deuterated dimethyl sulfoxide $^1$H NMR: proton nuclear magnetic resonance LC/MS: liquid chromatograph mass spectrometer ESI: Electrospray ionization APCI: Atmospheric pressure chemical ionization DCM: dichloromethane DIEA: diisopropylethylamine DMAP: 4-dimethylaminopyridine DMF: N,N-dimethylformamide HATU: 2-(7-azabenzotriazol-1-yl)-1,1,3,3-tetrametyluroniumhexafluorophosphate TBTU: 1-[bis(dimethylamino)methylene]-1H-benzotriazolium 3-oxide tetrafluoroborate TEA: triethylamine THF: tetrahydrofuran TFA: trifluoroacetate $^1$H NMR was measured by Fourier-transform type NMR. For the analysis, ACD/SpecManager (trade name) or MestreNova (trade name) and the like were used. Peaks with very mild protons such as a hydroxy group, an amino group and the like are not described.

MS was measured by LC/MS. As an ionization method, ESI method or APCI method was used. The data indicates actual measured value (found). Generally, a molecular ion peak ([M+H]+, [M−H]$^-$, etc.) is observed. In the case of a compound having a tert-butoxycarbonyl group, a peak after elimination of a tert-butoxycarbonyl (Boc) group or a tert-butyl (tBu) group may be observed as a fragment ion. In the case of a compound having a carboxyl group, a peak of sodium adduct thereof may be observed. In the case of a compound having a hydroxy group, a peak after elimination of water may be observed as a fragment ion. In the case of a salt, a molecular ion peak or fragment ion peak of free form is generally observed.

Sample concentration (c) used in the optical rotation ($[\alpha]_D$) is g/100 mL.

Elemental analysis value (Anal.) indicates both calculated value (Calcd) and measured value (Found).

Reference Example 1

N-(3-(Methylsulfonyl)phenyl)thieno[3,2-d]pyrimidin-4-amine

To a mixture of 4-chlorothieno[3,2-d]pyrimidine (14 mg) and 2-propanol (1 mL) were added 3-(methylsulfonyl)aniline (16.4 mg) and concentrated hydrochloric acid (2.06 μL). The reaction mixture was stirred at 80° C. overnight, the solvent was removed under reduced pressure, and the residue was purified by preparative HPLC (C18, mobile phase: acetonitrile/10 mM aqueous ammonium bicarbonate) to give the title compound (10.1 mg).

$^1$H NMR (400 MHz, DMSO-$d_6$) δ 3.23 (3H, s), 7.52 (1H, d, J=5.4 Hz), 7.61-7.68 (2H, m), 8.28-8.33 (2H, m), 8.42 (1H, s), 8.67 (1H, s), 10.09 (1H, s).

Reference Example 2

4-((4-(Thieno[3,2-d]pyrimidin-4-yloxy)piperidin-1-yl)sulfonyl)phenol A) tert-Butyl 4-(thieno[3,2-d]pyrimidin-4-yloxy)piperidine-1-carboxylate To a mixture of tert-butyl-4-hydroxypiperidine-1-carboxylate (2.42 g) and DMF (60.1 mL) was added sodium hydride (60%, dispersion in paraffin liquid, 0.577 g). After the reaction mixture was stirred for 30 min, 4-chlorothieno[3,2-d]pyrimidine (2.05 g) was added thereto, the mixture was stirred for 1 h at room temperature and diluted with ethyl acetate and water, and the aqueous layer was extracted with ethyl acetate. The organic layer was dried over anhydrous magnesium sulfate, and the solvent was removed under reduced pressure. The residue was purified by silica gel column chromatography (ethyl acetate/hexane) to give the title compound (3.75 g).

MS: $[M+H]^+$ 336.0.

B) 4-(Piperidin-4-yloxy)thieno[3,2-d]pyrimidine hydrochloride

To a mixture of tert-butyl 4-(thieno[3,2-d]pyrimidin-4-yloxy)piperidine-1-carboxylate (3.75 g) and ethyl acetate (22.4 ml) was added 4M hydrogen chloride/ethyl acetate solution (55.9 mL). After the reaction mixture was stirred for 30 min, the solvent was removed under reduced pressure. The residue was washed with ethyl acetate to give the title compound (3.25 g).

$^1$H NMR (300 MHz, DMSO-$d_6$) δ 2.00-2.12 (2H, m), 2.17-2.33 (2H, m), 3.02-3.37 (4H, m), 5.52-5.67 (1H, m), 7.62 (1H, d, J=5.29 Hz), 8.40 (1H, d, J=5.29 Hz), 8.79 (1H, s), 8.98-9.34 (2H, M).

C) 4-((4-(Thieno[3,2-d]pyrimidin-4-yloxy)piperidin-1-yl)sulfonyl)phenol

To a mixture of 4-(piperidin-4-yloxy)thieno[3,2-d]pyrimidine hydrochloride (215 mg) and pyridine (2.64 mL)

was added 4-hydroxybenzene-1-sulfonyl chloride (152 mg). The reaction mixture was stirred for 16 h, and the solvent was removed under reduced pressure. The residue was purified by silica gel column chromatography (C18, acetonitrile/5 mM aqueous ammonium acetate solution) to give the title compound (43.5 mg).

$^1$H NMR (300 MHz, DMSO-$d_6$) δ 1.75-1.95 (2H, m), 2.00-2.19 (2H, m), 2.83-3.01 (2H, m), 3.05-3.21 (2H, m), 5.15-5.51 (1H, m), 6.96 (2H, d, J=8.69 Hz), 7.46-7.72 (3H, m), 8.32 (1H, d, J=5.29 Hz), 8.70 (1H, s), 10.10-11.07 (1H, m).

Reference Example 3

3-(Allyloxy)-5-((4-(thieno[3,2-b]pyridin-7-yloxy) piperidin-1-yl)methyl)isoxazole A) 7-(Piperidin-4-yloxy)thieno[3,2-b]pyridine dihydrochloride To a mixture of tert-butyl 4-hydroxypiperidine-1-carboxylate (14.9 g) and DMF (100 mL) was added sodium hydride (60%, dispersion in paraffin liquid, 3.0 g) under ice-cooling. The reaction mixture was stirred for 10 min, 7-chlorothieno[3,2-b]pyridine (10.4 g) was added thereto, and stirred at 60° C. overnight. To the reaction mixture was added water, and the mixture was extracted with ethyl acetate. The organic layer was washed with water and brine, and dried over anhydrous magnesium sulfate, and the solvent was removed under reduced pressure. To a mixture of tert-butyl 4-(thieno[3,2-b]pyridin-7-yloxy)piperidine-1-carboxylate thus obtained and ethyl acetate (100 mL) was added 4M hydrogen chloride/ethyl acetate solution (100 mL). The reaction mixture was stirred at room temperature for 2 h, diisopropyl ether (70 mL) was added thereto, and the precipitates were collected by filtration to give the title compound (16.8 g).

MS: $[M+H]^+$ 235.2.

B) Methyl 3-(allyloxy)isoxazole-5-carboxylate

To a mixture of methyl 3-hydroxyisoxazole-5-carboxylate (15.0 g), potassium carbonate (17.4 g) and DMF (200 mL) was added 3-bromoprop-1-ene (24 mL), and the reaction mixture was stirred at 60° C. for 16 h. The reaction mixture was diluted with ethyl acetate and water, and the aqueous layer was extracted with ethyl acetate. The organic layer was washed with water and brine. and dried over anhydrous magnesium sulfate, and the solvent was removed under reduced pressure. The residue was purified by silica gel column chromatography (ethyl acetate/hexane) to give the title compound (16.6 g).

MS: $[M+H]^+$ 184.3.

C) (3-(Allyloxy)isoxazol-5-yl)methanol

To a mixture of methyl 3-(allyloxy)isoxazole-5-carboxylate (16.6 g) and methanol (300 mL) was added sodium borohydride (4.80 g). The reaction mixture was stirred at room temperature for 16 h, and the solvent was removed under reduced pressure. The residue was diluted with ethyl acetate and water, and the aqueous layer was extracted with ethyl acetate. The organic layer was washed with water and brine, and dried over anhydrous magnesium sulfate, and the solvent was removed under reduced pressure to give the title compound (13.2 g).

MS: $[M+H]^+$ 156.3.

D) (3-(Allyloxy)isoxazol-5-yl)methyl methanesulfonate

To a mixture of (3-(allyloxy)isoxazol-5-yl)methanol (13.2 g), TEA (24 mL) and THF (200 mL) was added methanesulfonyl chloride (9.94 mL) under ice-cooling. The reaction mixture was stirred at room temperature for 1 h, diluted with water, and the aqueous layer was extracted with ethyl acetate. The organic layer was washed with brine, and dried over anhydrous magnesium sulfate, and the solvent was removed under reduced pressure to give the title compound (18.9 g).

MS: $[M+H]^+$ 234.2.

E) 3-(Allyloxy)-5-((4-(thieno[3,2-b]pyridin-7-yloxy) piperidin-1-yl)methyl)isoxazole A mixture of 7-(piperidin-4-yloxy)thieno[3,2-b]pyridine dihydrochloride (6.16 g), (3-(allyloxy)isoxazol-5-yl)methyl methanesulfonate (5.14 g), tetrabutylammonium iodide (4.44 g), potassium carbonate (9.70 g) and DMF (100 mL) was stirred at room temperature for 24 h. To the reaction mixture was added water and the resultant mixture was filtered, and the filtrate was extracted with ethyl acetate. The organic layer was washed with water and brine, and dried over anhydrous magnesium sulfate, and the solvent was removed under reduced pressure. The residue was purified by silica gel column chromatography (NH, ethyl acetate/hexane) to give the title compound (6.25 g).

$^1$H NMR (300 MHz, DMSO-$d_6$) δ 1.68-1.85 (2H, m), 1.95-2.10 (2H, m), 2.36-2.49 (2H, m), 2.63-2.76 (2H, m), 3.63 (2H, s), 4.64-4.74 (2H, m), 4.74-4.87 (1H, m), 5.25-5.35 (1H, m), 5.35-5.49 (1H, m), 6.05 (1H, ddt, J=17.3, 10.7, 5.4 Hz), 6.20 (1H, s), 7.07 (1H, d, J=5.5 Hz), 7.50 (1H, d, J=5.3 Hz), 8.04 (1H, d, J=5.4 Hz), 8.50 (1H, d, J=5.4 Hz).

Reference Example 4

5-((4-(Thieno[3,2-b]pyridin-7-yloxy)piperidin-1-yl) methyl)isoxazol-3-ol

To a mixture of 3-(allyloxy)-5-((4-(thieno[3,2-b]pyridin-7-yloxy)piperidin-1-yl)methyl)isoxazole (5.68 g), triethylsilane (7.3 mL) and THF (100 mL) was added tetrakistriphenylphosphinepalladium (884 mg). The reaction mixture was stirred at room temperature for 1 h, and the solvent was removed under reduced pressure. The residue was purified by silica gel column chromatography (methanol), and the compound thus obtained was washed with ethyl acetate to give the title compound (2.50 g).

$^1$H NMR (300 MHz, DMSO-$d_6$) δ 1.68-1.84 (2H, m), 1.95-2.09 (2H, m), 2.35-2.49 (2H, m), 2.63-2.75 (2H, m), 3.58 (2H, s), 4.74-4.87 (1H, m), 5.93 (1H, s), 7.07 (1H, d, J=5.5 Hz), 7.50 (1H, d, J=5.6 Hz), 8.04 (1H, s) d, J=5.4 Hz), 8.50 (1H, d, J=5.4 Hz), 11.16 (1H, s).

Reference Example 5

3-(Allyloxy)-5-(1-(4-(thieno[3,2-b]pyridin-7-yloxy) piperidin-1-yl)ethyl)isoxazole (enantiomer)

A) 3-(Allyloxy)isoxazole-5-carboxylic acid

To a mixture of methyl 3-(allyloxy)isoxazole-5-carboxylate (1 g), THF (10 mL) and methanol (2 mL) were added lithium hydroxide monohydrate (687 mg) and water (2 mL). The reaction mixture was stirred at room temperature for 3 h, diluted with water and washed with ethyl acetate. The aqueous layer was adjusted to pH 3 with potassium hydrogen sulfate, and then extracted with ethyl acetate. The organic layer was washed with brine and dried over anhydrous sodium sulfate, and the solvent was removed under reduced pressure to give the title compound (670 mg).

$^1$H NMR (400 MHz, DMSO-$d_6$) δ 4.76 (2H, d, J=5.56 Hz), 5.31 (1H, d, J=10.44 Hz), 5.43 (1H, d, J=17.32 Hz), 6.01-6.08 (1H, m), 6.96 (1H, s), 13.7-14.9 (1H, brs).

B) 3-(Allyloxy)-N-methoxy-N-methylisoxazole-5-carboxamide

To a mixture of 3-(allyloxy)isoxazole-5-carboxylic acid (660 mg), N, O-dimethylhydroxylamine hydrochloride (570 mg) and DMF (20 mL) were added DIEA (3.4 mL) and TBTU (2.5 g), and the reaction mixture was stirred at room temperature for 16 h. The reaction mixture was diluted with ethyl acetate, washed with water and brine and dried over anhydrous sodium sulfate, and the solvent was removed under reduced pressure. The residue was purified by silica gel column chromatography (ethyl acetate/hexane) to give the title compound (700 mg).

MS: $[M+H]^+$ 213.1.

C) 1-(3-(Allyloxy)isoxazol-5-yl)ethane-1-one

To a mixture of 3-(allyloxy)-N-methoxy-N-methylisoxazole-5-carboxamide (600 mg) and THF (20 mL) was added 3M methylmagnesium bromide diethyl ether solution (1.41 mL) at −78° C. The reaction mixture was allowed to warm to room temperature over 2 h, water was added thereto, and the mixture was extracted with ethyl acetate. The organic layer was washed with brine and dried over anhydrous sodium sulfate, and the solvent was removed under reduced pressure to give the title compound (350 mg).

$^1$H NMR (400 MHz, $CDCl_3$) δ 2.54 (3H, s), 4.79 (2H, d, J=4.6 Hz), 5.33 (1H, dd, J=1.0, 10.6 Hz), 5.43 (1H, dd, J=1.3, 17.2 Hz), 5.96-6.13 (1H, m), 6.49 (1H, s).

D) 1-(3-(Allyloxy)isoxazol-5-yl)ethan-1-ol

To a mixture of 1-(3-(allyloxy)isoxazol-5-yl)ethan-1-one (250 mg) and methanol (20 mL) was added sodium borohydride (85 mg) under ice-cooling. The reaction mixture was stirred at room temperature for 2 h, water was added thereto, and the mixture was extracted with DCM. The organic layer was washed with brine, dried over anhydrous sodium sulfate, and the solvent was removed under reduced pressure to give the title compound (225 mg).

MS: $[M+H]^+$ 170.0.

E) 1-(3-(Allyloxy)isoxazol-5-yl)ethyl methanesulfonate

To a mixture of 1-(3-(allyloxy)isoxazol-5-yl)ethan-1-ol (220 mg) and DCM (20 mL) were added DIEA (0.45 mL) and methanesulfonyl chloride (0.152 mL) under ice-cooling. The reaction mixture was stirred at room temperature for 1 h, and the solvent was removed under reduced pressure. The residue was purified by silica gel column chromatography (ethyl acetate/hexane) to give the title compound (190 mg).

$^1$H NMR (400 MHz, DMSO-$d_6$) δ 1.64 (3H, d, J=6.6 Hz), 3.25 (3H, s), 4.72 (2H, d, J=5.5 Hz), 5.30 (1H, d, J=10.5 Hz), 5.42 (1H, d, J=17.2 Hz), 5.83 (1H, q, J=6.6 Hz), 5.98-6.12 (1H, m), 6.48 (1H, s).

F) 3-(Allyloxy)-5-(1-(4-(thieno[3,2-b]pyridin-7-yloxy)piperidin-1-yl)ethyl)isoxazole (racemate)

To a mixture of 7-(piperidin-4-yloxy)thieno[3,2-b]pyridine (270 mg) and methanol (20 mL) was added TEA (0.32 mL). After the reaction mixture was stirred for 10 min, 1-(3-(allyloxy)isoxazol-5-yl)ethyl methanesulfonate (211 mg) was added thereto. The reaction mixture was stirred at 80° C. for 16 h, and the solvent was removed under reduced pressure. The residue was purified by silica gel column chromatography (ethyl acetate/hexane) to give the title compound (70 mg).

MS: $[M+H]^+$ 385.8.

G) 3-(Allyloxy)-5-(1-(4-(thieno[3,2-b]pyridin-7-yloxy)piperidin-1-yl)ethyl)isoxazole (enantiomer)

3-(Allyloxy)-5-(1-(4-(thieno[3,2-b]pyridin-7-yloxy)piperidin-1-yl)ethyl)isoxazole (racemate) (60 mg) was purified by HPLC (Chiralpak IA (21×250 mm), mobile phase: ethanol/ethyl acetate/hexane (0.1% isopropylamine-containing system)) to give the title compound (12 mg, shorter retention time).

$^1$H NMR (400 MHz, $CDCl_3$) δ 1.44 (3H, d, J=7.0 Hz), 1.86-2.03 (2H, m), 2.03-2.18 (2H, m), 2.24-2.66 (2H, m), 2.72-2.96 (2H, m), 3.78-3.96 (1H, m), 4.56-4.68 (1H, m), 4.74 (2H, d, J=5.7 Hz), 5.31 (1H, d, J=10.5 Hz), 5.43 (1H, d, J=17.0 Hz), 5.76 (1H, s), 5.99-6.14 (1H, m), 6.65 (1H, d, J=5.5 Hz), 7.50 (1H, d, J=5.6) Hz), 7.66 (1H, d, J=5.4 Hz), 8.51 (1H, d, J=5.4 Hz).

Reference Example 6

3-(Allyloxy)-5-(1-(4-(thieno[3,2-b]pyridin-7-yloxy)piperidin-1-yl)ethyl)isoxazole (enantiomer)

3-(Allyloxy)-5-(1-(4-(thieno[3,2-b]pyridine-7-yloxy)piperidin-1-yl)ethyl)isoxazole (racemate) (60 mg) was purified by HPLC (Chiralpak IA (21×250 mm), mobile phase: ethanol/ethyl acetate/hexane (0.1% isopropylamine-containing system)) gave the title compound (10 mg, longer retention time).

$^1$H NMR (400 MHz, $CDCl_3$) δ 1.45 (3H, d, J=7.0 Hz), 1.87-2.03 (2H, m), 2.03-2.22 (2H, m), 2.26-2.69 (2H, m), 2.69-2.96 (2H, m), 3.77-3.99 (1H, m), 4.56-4.69 (1H, m), 4.74 (2H, d, J=5.8 Hz), 5.31 (1H, d, J=10.5 Hz), 5.43 (1H, d, J=17.4 Hz), 5.77 (1H, s), 5.99-6.14 (1H, m), 6.65 (1H, d, J=5.5 Hz), 7.50 (1H, d, J=5.4) Hz), 7.66 (1H, d, J=5.5 Hz), 8.52 (1H, d, J=5.5 Hz).

Reference Example 7

3-(Allyloxy)-5-(1-(4-((2-methylthieno[3,2-b]pyridin-7-yl)oxy)piperidin-1-yl)ethyl)isoxazole (racemate)

A) 7-Chloro-2-methylthieno[3,2-b]pyridine

To a mixture of 7-chlorothieno[3,2-b]pyridine (2 g) and THF (30 mL) was added 2M lithium diisopropylamide THF solution (12.96 mL) under an argon atmosphere at −78° C. The reaction mixture was stirred at 0° C. for 1 h, and methyl iodide (2.35 mL) was added. The reaction mixture was stirred at 0-25° C. for 2 h, water was added thereto, and the mixture was extracted with ethyl acetate. The organic layer was washed with brine and dried over anhydrous sodium sulfate, and the solvent was removed under reduced pressure. The residue was purified by silica gel column chromatography (ethyl acetate/hexane) to give the title compound (1.9 g).

MS: $[M+H]^+$ 183.8.

B) tert-Butyl 4-((2-methylthieno[3,2-b]pyridin-7-yl)oxy)piperidin-1-carboxylate

To a mixture of 7-chloro-2-methylthieno[3,2-b]pyridine (1.9 g), tert-butyl 4-hydroxypiperidine-1-carboxylate (2.29 g) and DMF (30 mL) was added sodium hydride (60%, dispersion in paraffin liquid, 620 mg). The reaction mixture was stirred at room temperature for 3 h, diluted with ethyl acetate and then washed with water. The organic layer was washed with brine and dried over anhydrous sodium sulfate, and the solvent was removed under reduced pressure. The residue was purified by silica gel column chromatography (ethyl acetate/hexane) to give the title compound (2 g).

MS: $[M+H]^+$ 348.5.

C) 2-Methyl-7-(piperidin-4-yloxy)thieno[3,2-b]pyridine trifluoroacetate To a mixture of tert-butyl 4-((2-methylthieno[3,2-b]pyridin-7-yl)oxy)piperidine-1-carboxylate (2 g) and DCM (20 mL) was added TFA (4.4 mL). The reaction mixture was stirred at room temperature for 2 h, and the solvent was removed under reduced pressure to give the title compound (1.4 g).

$^1$H NMR (400 MHz, DMSO-$d_6$) δ 1.93-2.08 (2H, m), 2.16-2.31 (2H, m), 2.74 (3H, s), 3.05-3.42 (4H, m), 5.25-5.34 (1H, m), 7.51 (1H, d, J=1.5 Hz), 7.61 (1H, d, J=6.8 Hz), 8.60-8.88 (2H, m), 8.89 (1H, d, J=6.8 Hz).

D) 3-(Allyloxy)-5-(1-(4-((2-methylthieno[3,2-b]pyridin-7-yl)oxy)piperidin-1-yl)ethyl)isoxazole (racemate)

To a mixture of 2-methyl-7-(piperidin-4-yloxy)thieno[3,2-b]pyridine trifluoroacetate (100 mg) and methanol (5 mL) was added TEA (0.08 mL). The reaction mixture was stirred at room temperature for 10 min, and 1-(3-(allyloxy)isoxazol-5-yl)ethyl methanesulfonate (74.3 mg) was added thereto. The reaction mixture was stirred at 80° C. for 16 h, and the solvent was removed under reduced pressure. The residue was purified by silica gel column chromatography (ethyl acetate/hexane) to give the title compound (38 mg).

$^1$H NMR (400 MHz, DMSO-$d_6$) δ 1.34 (3H, d, J=7.04 Hz), 1.71-1.73 (2H, m), 1.90-2.12 (2H, m), 2.29-2.32 (1H, m), 2.44-2.50 (2H, m), 2.57 (3H, s), 2.71-2.87 (1H, m), 3.89-3.90 (1H, m), 4.69-4.73 (3H, m), 5.29 (1H, d, J=10.4 Hz), 5.40-5.44 (1H, m), 6.02-6.09 (1H, m), 6.16 (1H, s), 6.97 (1H, d, J=5.52 Hz), 7.18 (1H, s), 8.38 (1H, d, J=5.44 Hz).

Reference Example 8

3-(Allyloxy)-5-(1-(4-((2-methylthieno[3,2-b]pyridin-7-yl)oxy)piperidin-1-yl)ethyl)isoxazole (enantiomer)

3-(Allyloxy)-5-(1-(4-((2-methylthieno[3,2-b]pyridin-7-yl)oxy)piperidin-1-yl)ethyl)isoxazole (racemate) (30 mg) was purified by HPLC (Chiralpak IA (21×250 mm), mobile phase: ethanol/ethyl acetate/hexane (0.1% isopropylamine-containing system)) to give the title compound (8 mg, shorter retention time).

$^1$H NMR (400 MHz, DMSO-$d_6$) δ 1.34 (3H, d, J=7.0 Hz), 1.60-1.82 (2H, m), 1.91-2.06 (2H, m), 2.25-2.35 (1H, m)), 2.44-2.54 (1H, m), 2.58 (3H, s), 2.60-2.69 (1H, m), 2.69-2.81 (1H, m), 3.89 (1H, q, J=7.1 Hz), 4.67-4.76 (3H, m), 5.30 (1H, d, J=10.9 Hz), 5.42 (1H, d, J=17.1 Hz), 5.98-6.13 (1H, m), 6.16 (1H, s), 6.97 (1H), d, J=5.5 Hz), 7.18 (1H, d, J=1.5 Hz), 8.38 (1H, d, J=5.4 Hz).

Reference Example 9

3-(Allyloxy)-5-(1-(4-((2-methylthieno[3,2-b]pyridin-7-yl)oxy)piperidin-1-yl)ethyl)isoxazole (enantiomer)

3-(Allyloxy)-5-(1-(4-((2-methylthieno[3,2-b]pyridin-7-yl)oxy)piperidin-1-yl)ethyl)isoxazole (racemate) (30 mg) was purified by HPLC (Chiralpak IA (21×250 mm), mobile phase: ethanol/ethyl acetate/hexane (0.1% isopropylamine-containing system)) to give the title compound (8 mg, longer retention time).

$^1$H NMR (400 MHz, DMSO-$d_6$) δ 1.34 (3H, d, J=7.0 Hz), 1.62-1.80 (2H, m), 1.92-2.07 (2H, m), 2.24-2.37 (1H, m)), 2.40-2.48 (1H, m), 2.58 (3H, s), 2.58-2.70 (1H, m), 2.68-2.82 (1H, m), 3.89 (1H, q, J=7.0 Hz), 4.67-4.78 (3H, m), 5.30 (1H, d, J=10.5 Hz), 5.42 (1H, d, J=17.3 Hz), 5.99-6.13 (1H, m), 6.16 (1H, s), 6.97 (1H, d, J=5.6 Hz), 7.19 (1H, d, J=1.5 Hz), 8.38 (1H, d, J=5.5 Hz).

Reference Example 10

(S)-3-(Pyrrolidin-2-ylmethoxy)-5-((4-(thieno[3,2-b]pyridin-7-yloxy)piperidin-1-yl)methyl)isoxazole trihydrochloride A mixture of methyl 3-hydroxyisoxazole-5-carboxylate (3.79 g), tert-butyl (S)-2-(hydroxymethyl)pyrrolidine-1-carboxylate (4.84 g) and triphenylphosphine (6.94 g) was azeotroped with toluene. To a mixture of the residue and toluene (50 mL) was added 40% diethyl azodicarboxylate toluene solution (14 mL) under ice-cooling. The reaction mixture was stirred at room temperature for 1 h, the solvent was reduced to half volume under reduced pressure, and the mixture was purified by silica gel column chromatography (ethyl acetate/hexane). To a mixture of methyl (S)-3-((1-(tert-butoxycarbonyl)pyrrolidin-2-yl)methoxy)isoxazole-5-carboxylate thus obtained and methanol (100 mL) was added sodium borohydride (1.18 g). The reaction mixture was stirred at room temperature for 4 h, water was added thereto, and extracted with ethyl acetate. The organic layer was washed with brine, dried over anhydrous magnesium sulfate, and the solvent was removed under reduced pressure. To a mixture of tert-butyl (S)-2-(((5-(hydroxymethyl)isoxazol-3-yl)oxy)methyl)pyrrolidine-1-carboxylate thus obtained and THF (100 mL) was added methanesulfonyl chloride (2.10 mL). The reaction mixture was stirred at room temperature for 2 h, saturated aqueous sodium bicarbonate was added thereto, and the mixture was extracted with ethyl acetate. The organic layer was washed with brine, and dried over anhydrous magnesium sulfate, and the solvent was removed under reduced pressure. A mixture of tert-butyl (S)-2-(((5-(((methylsulfonyl)oxy)methyl)isoxazol-3-yl)oxy)methyl)pyrrolidine-1-carboxylate thus obtained, 7-(piperidin-4-yloxy)thieno[3,2-b]pyridine dihydrochloride (8.85 g), potassium carbonate (19.9 g), tetrabutylammonium iodide (5.32 g) and DMF (50 mL) was stirred at room temperature for 16 h. To the reaction mixture were added water and ethyl acetate, and the mixture was extracted with ethyl acetate. The organic layer was washed with water and brine and dried over anhydrous magnesium sulfate, and the solvent was removed under reduced pressure. The residue was purified by silica gel column chromatography (NH, ethyl acetate/hexane). To a mixture of tert-butyl (S)-2-(((5-((4-(thieno[3,2-b]pyridin-7-yloxy)piperidin-1-yl)methyl)isoxazole-3-yl)oxy)methyl)pyrrolidine-1-carboxylate thus obtained and ethyl acetate (20 mL) was added 4M hydrogen chloride/ethyl acetate solution (40 mL). The reaction mixture was stirred at room temperature for 1 h, and the solvent was removed under reduced pressure to give the title compound (8.03 g).

$^1$H NMR (300 MHz, $CD_3OD$) δ 1.82-1.95 (m, 1H), 2.05-2.18 (m, 2H), 2.23-2.43 (m, 3H), 2.45-2.69 (m, 2H), 3.35-3.40 (m, 3H), 3.50-3.67 (m, 4H), 4.03-4.12 (m, 1H), 4.41-4.48 (m, 1H), 4.60-4.65 (m, 3H), 5.38-5.47 (m, 1H), 6.62 (d, J=5.4 Hz, 1H), 7.64-7.69 (m, 1H), 7.71 (dd, J=6.1, 1.8 Hz, 1H), 8.47-8.55 (m, 1H), 8.85 (dd, J=6.6, 1.8 Hz, 1H).

The reference example compounds produced according to the above-mentioned production methods or the methods shown in the reference examples, or similar methods thereto are described below. The MS value described below the compound indicates the measured value.

Reference Example Number 1: N-(3-(methylsulfonyl)phenyl)thieno[3,2-d]pyrimidin-4-amine

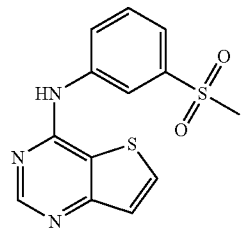

MS: 306.1

Reference Example Number 2: 4-((4-(thieno[3,2-d]pyrimidin-4-yloxy)piperidin-1-yl)sulfonyl)phenol

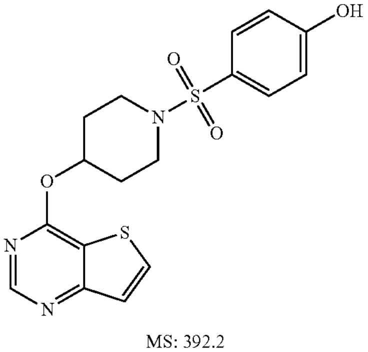 [SMILES: O=S(=O)(c1ccc(O)cc1)N1CCC(Oc2ncnc3ccsc23)CC1]

MS: 392.2

Reference Example Number 3: 3-(allyloxy)-5-((4-(thieno[3,2-b]pyridin-7-yloxy)piperidin-1-yl)methyl)isoxazole

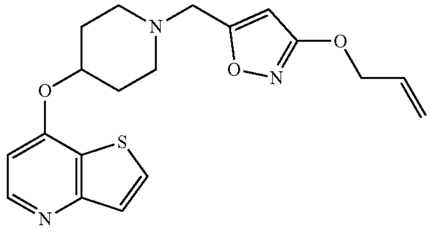

MS: 372.2

Reference Example Number 4: 5-((4-(thieno[3,2-b]pyridin-7-yloxy)piperidin-1-yl)methyl)isoxazol-3-ol

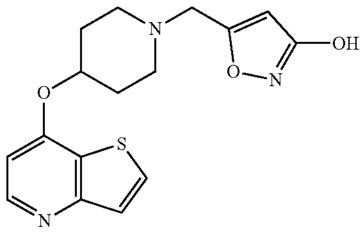

MS: 332.2

Reference Example Number 5: 3-(allyloxy)-5-(1-(4-(thieno[3,2-b]pyridin-7-yloxy)piperidin-1-yl)ethyl)isoxazole (enantiomer)

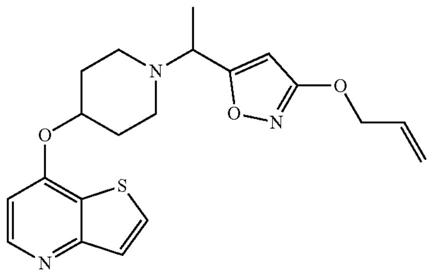

MS: 385.8

Reference Example Number 6: 3-(allyloxy)-5-(1-(4-(thieno[3,2-b]pyridin-7-yloxy)piperidin-1-yl)ethyl) isoxazole (enantiomer)

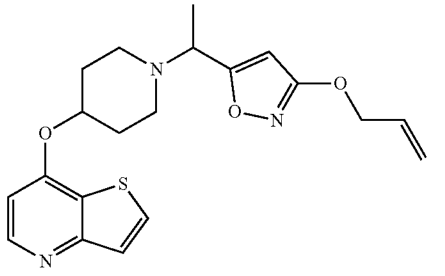

MS: 385.9

Reference Example Number 7: 3-(allyloxy)-5-(1-(4-((2-methylthieno[3,2-b]pyridin-7-yl)oxy)piperidin-1-yl)ethyl)isoxazole (racemate)

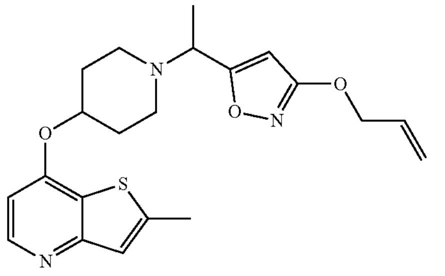

MS: 399.7

Reference Example Number 8: 3-(allyloxy)-5-(1-(4-((2-methylthieno[3,2-b]pyridin-7-yl)oxy)piperidin-1-yl)ethyl)isoxazole (enantiomer)

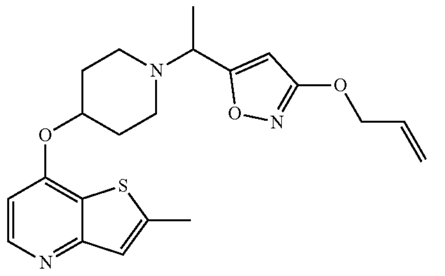

MS: 399.7

Reference Example Number 9: 3-(allyloxy)-5-(1-(4-((2-methylthieno[3,2-b]pyridin-7-yl)oxy)piperidin-1-yl)ethyl)isoxazole (enantiomer)

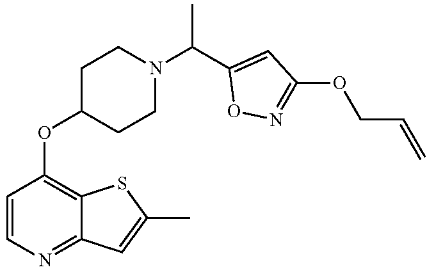

MS: 399.7

Reference Example Number 10: (S)-3-(pyrrolidin-2-ylmethoxy)-5-((4-(thieno[3,2-b]pyridin-7-yloxy) piperidin-1-yl)methyl)isoxazole

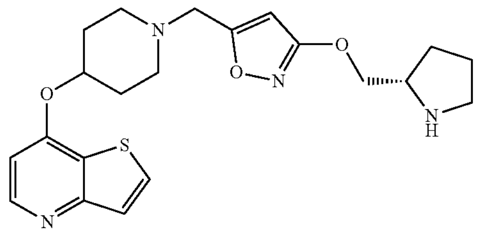

Salt type: 3HCl; MS: 415.2

Reference Example Number 11: 3-((tetrahydro-furan-3-yl)oxy)-4-(thieno[3,2-d]pyrimidin-4-ylamino)benzamide

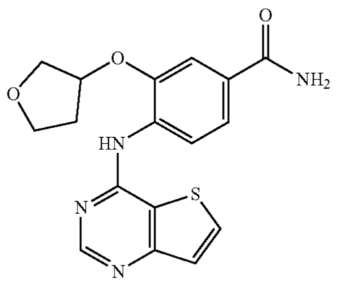

MS: 357.2

Reference Example Number 12: N,6-diphenylthieno[3,2-d]pyrimidin-4-amine

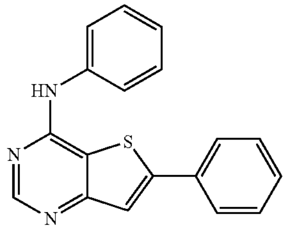

MS: 304.2

Reference Example Number 13: N-(2-methoxyphenyl)-6-phenylthieno[3,2-d]pyrimidin-4-amine

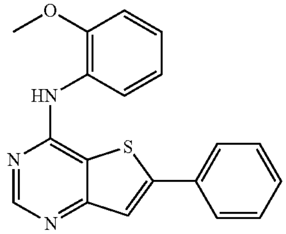

MS: 334.2

Reference Example Number 14: N-(cyclopropylmethyl)-6-phenylthieno[3,2-d]pyrimidin-4-amine

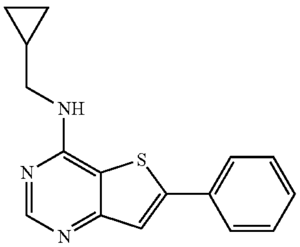

MS: 282.2

Reference Example Number 15: 6-phenyl-N-(pyridin-2-yl)thieno[3,2-d]pyrimidin-4-amine

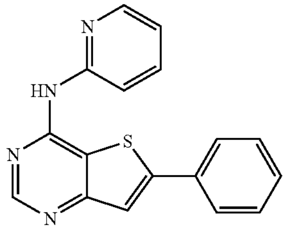

MS: 305.2

Reference Example Number 16: 6-phenyl-N-(pyridin-3-ylmethyl)thieno[3,2-d]pyrimidin-4-amine

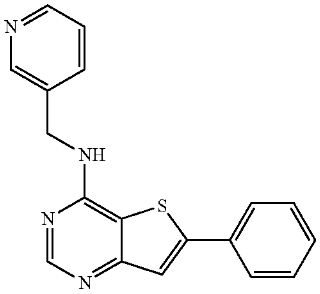

MS: 319.2

Reference Example Number 17: N-phenethyl-6-phenylthieno[3,2-d]pyrimidin-4-amine (N-phenethyl-6-phenylthieno[3,2-d]pyrimidin-4-amine)

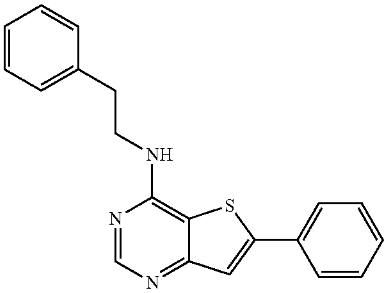

MS: 332.2

Reference Example Number 18: 4-(thieno[3,2-d]pyrimidin-4-ylamino)benzamide (4-(thieno[3,2-d]pyrimidin-4-ylamino)benzamide)

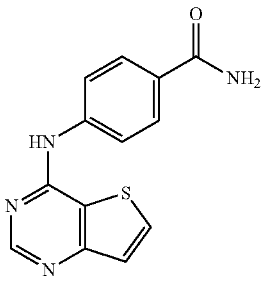

MS: 271.2

Reference Example Number 19: N-(2-((tetrahydrofuran-3-yl)oxy)phenyl)thieno[3,2-d]pyrimidin-4-amine

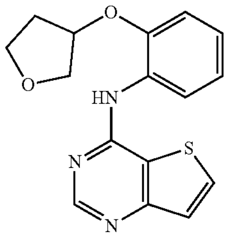

MS: 314.2

Reference Example Number 20: 3-(thieno[3,2-d]pyrimidin-4-ylamino)benzamide

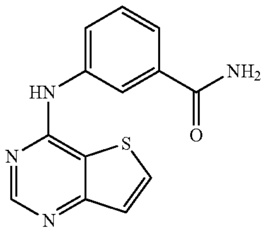

MS: 271.1

Reference Example Number 21: N-(pyridin-4-yl)thieno[3,2-d]pyrimidin-4-amine

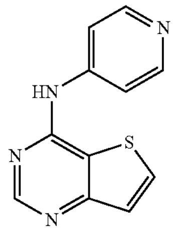

MS: 229.1

Reference Example Number 22: N-(2-(trifluoromethyl)pyridin-4-yl)thieno[3,2-d]pyrimidin-4-amine

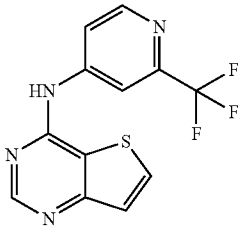

MS: 297.0

Reference Example Number 23: N-(2-methoxypyridin-4-yl)thieno[3,2-d]pyrimidin-4-amine

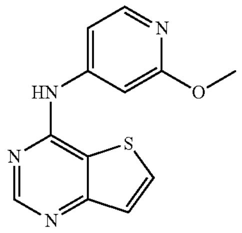

MS: 259.1

Reference Example Number 24: N-(2-(trifluoromethyl)pyridin-3-yl)thieno[3,2-d]pyrimidin-4-amine

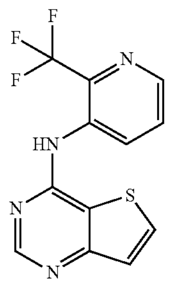

MS: 297.1

Reference Example Number 25: N-(3-methyl-1-(pyridin-2-yl)-1H-pyrazol-5-yl)thieno[3,2-d]pyrimidin-4-amine

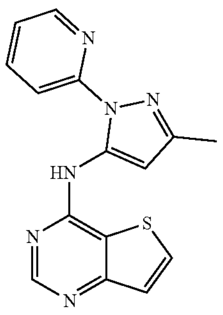

MS: 309.1

Reference Example Number 26: N-(1H-benzo[d]imidazol-5-yl)thieno[3,2-d]pyrimidin-4-amine)

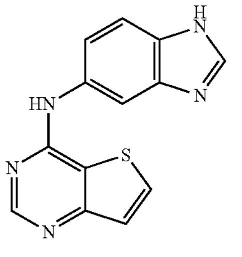

MS: 268.1

Reference Example Number 27: 5-(thieno[3,2-d]pyrimidin-4-ylamino)isoindoline-1,3-dione

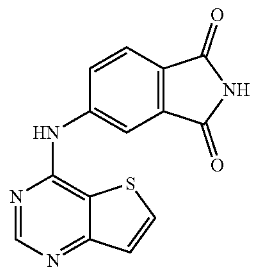

MS: 297.1

Reference Example Number 28: N-(1H-indazol-6-yl)thieno[3,2-d]pyrimidin-4-amine

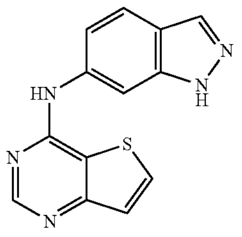

MS: 268.1

Reference Example Number 29: 5-(thieno[3,2-d]pyrimidin-4-ylamino)isobenzofuran-1(3H)-one

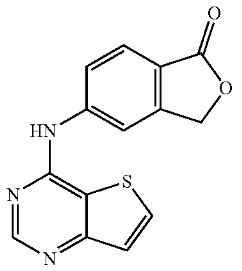

MS: 284.1

Reference Example Number 30: methyl 4-((cyclopropylmethyl)amino)thieno[3,2-d]pyrimidine-6-carboxylate

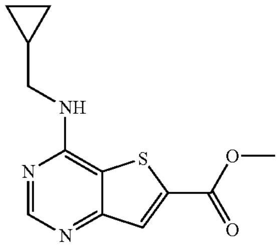

MS: 264.1

Reference Example Number 31: 6-(1-methyl-1H-pyrazol-4-yl)-4-((1-methylpiperidin-4-yl)oxy)thieno[3,2-d]pyrimidine

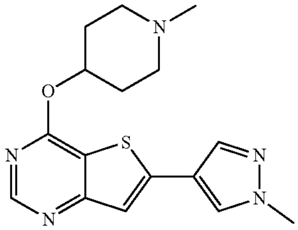

MS: 330.2

Reference Example Number 32: 6-ethynyl-4-((1-methylpiperidin-4-yl)oxy)thieno[3,2-d]pyrimidine

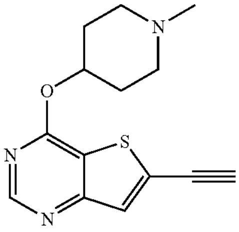

MS: 274.1

Reference Example Number 33: 4-((2-chlorothieno[3,2-d]pyrimidin-4-yl)amino)benzamide

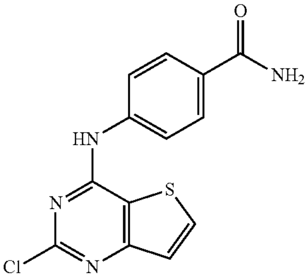

MS: 305.0

Reference Example Number 34: 6-iodo-4-((tetrahydro-2H-pyran-4-yl)oxy)thieno[3,2-d]pyrimidine

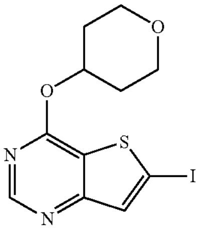

MS: 363.1

Reference Example Number 35: 6-iodo-4-((tetrahydro-2H-thiopyran-4-yl)oxy)thieno[3,2-d]pyrimidine

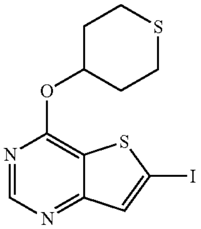

MS: 379.1

Reference Example Number 36: 6-iodo-4-((1-methylpiperidin-4-yl)oxy)thieno[3,2-d]pyrimidine

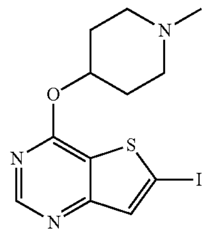

MS: 376.1

Reference Example Number 37: 4-((6-iodothieno[3,2-d]pyrimidin-4-yl)oxy)tetrahydro-2H-thiopyran 1,1-dioxide

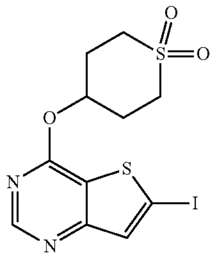

MS: 411.1

Reference Example Number 38: 4-((1-((2,6-difluorophenyl)sulfonyl)piperidin-4-yl)oxy)thieno[3,2-d]pyrimidine

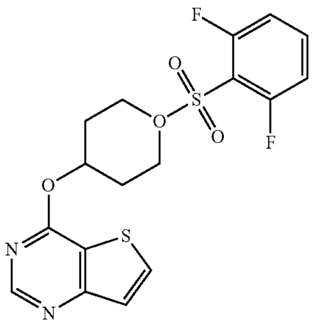

MS: 412.0

MS: 412.0

Reference Example Number 39: 4-((1-(methylsulfonyl)piperidin-4-yl)oxy)thieno[3,2-d]pyrimidine

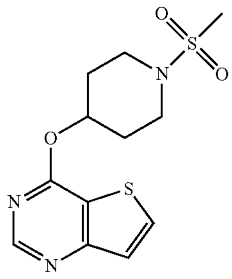

MS: 314.1

MS: 314.1

Reference Example Number 40: 4-((1-((2-methoxyethyl)sulfonyl)piperidin-4-yl)oxy)thieno[3,2-d]pyrimidine

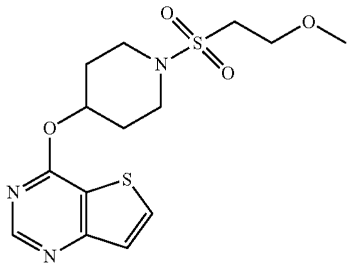

MS: 358.2

MS: 358.2

Reference Example Number 41: 4-((1-(benzylsulfonyl)piperidin-4-yl)oxy)thieno[3,2-d]pyrimidine

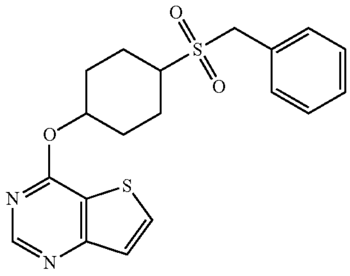

MS: 390.1

MS: 390.1

Reference Example Number 42: tert-butyl 4-(((4-(thieno[3,2-d]pyrimidin-4-yloxy)piperidin-1-yl)sulfonyl)methyl)piperidine-1-carboxylate

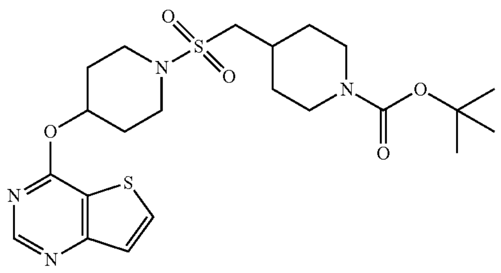

MS: 497.3

MS: 497.3

Reference Example Number 43: ethyl 3-((4-(thieno[3,2-d]pyrimidin-4-yloxy)piperidin-1-yl)sulfonyl)propanoate

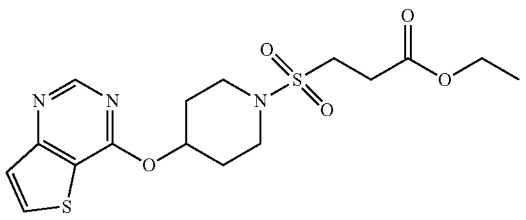

MS: 400.1

MS: 400.1

Reference Example Number 44: 4-((1-(cyclopropylsulfonyl)piperidin-4-yl)oxy)thieno[3,2-d]pyrimidine

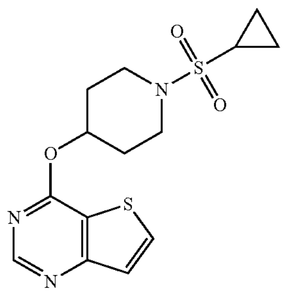

MS: 340.0

Reference Example Number 45: 4-((1-((2-chlorophenyl)sulfonyl)piperidin-4-yl)oxy)thieno[3,2-d]pyrimidine

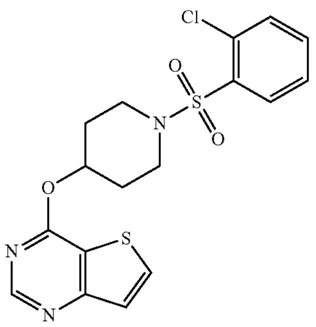

MS: 410.0

Reference Example Number 46: 4-((1-((2-methoxyphenyl)sulfonyl)piperidin-4-yl)oxy)thieno[3,2-d]pyrimidine

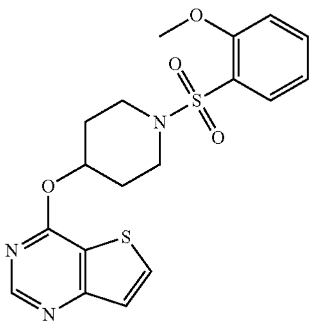

MS: 406.1

Reference Example Number 47: 4-((1-(o-tolylsulfonyl)piperidin-4-yl)oxy)thieno[3,2-d]pyrimidine

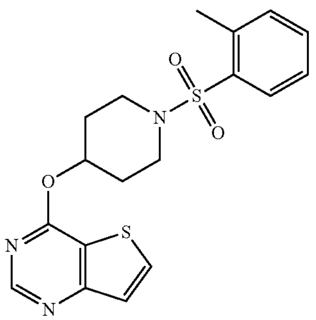

MS: 390.1

Reference Example Number 48: 4-((1-((2-(4-fluorophenoxy)phenyl)sulfonyl)piperidin-4-yl)oxy)thieno[3,2-d]pyrimidine (4-((1-((2-(4-fluorophenoxy)phenyl)sulfonyl)piperidin-4-yl)oxy)thieno[3,2-d]pyrimidine)

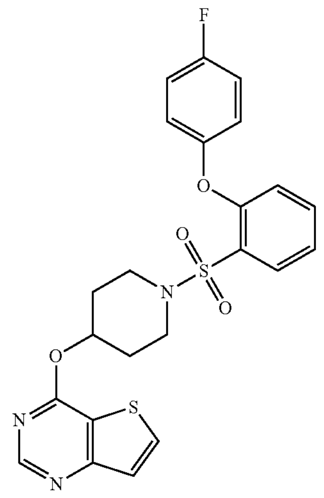

MS: 486.1

Reference Example Number 49: 4-((1-((2-fluorophenyl)sulfonyl)piperidin-4-yl)oxy)thieno[3,2-d]pyrimidine

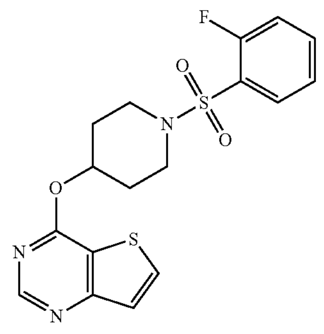

MS: 394.1

Reference Example Number 50: 4-((1-((2-(trifluoromethoxy)phenyl)sulfonyl)piperidin-4-yl)oxy)thieno[3,2-d]pyrimidine

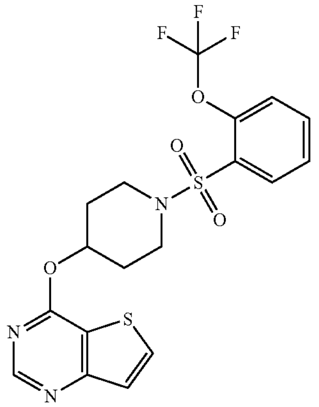

MS: 460.0

Reference Example Number 51: 4-((1-((4-methoxyphenyl)sulfonyl)piperidin-4-yl)oxy)thieno[3,2-d]pyrimidine

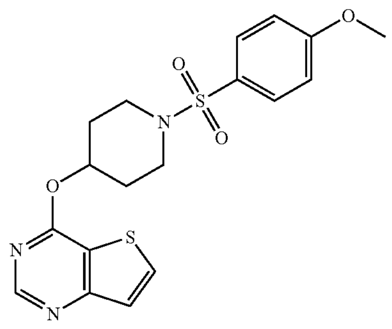

MS: 406.1

Reference Example Number 52: 4-((1-((4-chlorophenyl)sulfonyl)piperidin-4-yl)oxy)thieno[3,2-d]pyrimidine

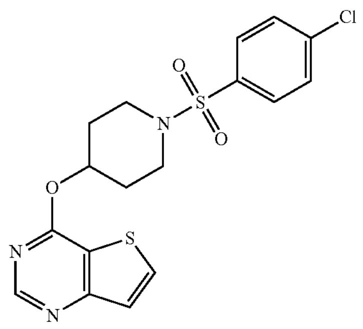

MS: 410.0

Reference Example Number 53: 4-((1-((4-fluorophenyl)sulfonyl)piperidin-4-yl)oxy)thieno[3,2-d]pyrimidine

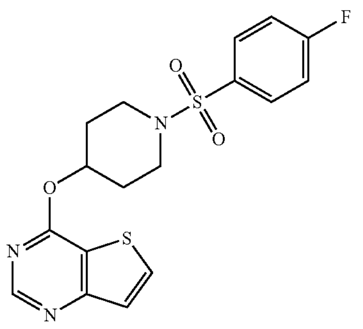

MS: 394.1

Reference Example Number 54: 4-((1-((3-methoxyphenyl)sulfonyl)piperidin-4-yl)oxy)thieno[3,2-d]pyrimidine

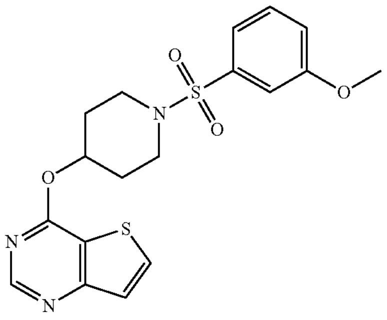

MS: 406.1

Reference Example Number 55: 4-((1-(4-methylbenzenesulfonyl)piperidin-4-yl)oxy)thieno[3,2-d]pyrimidine

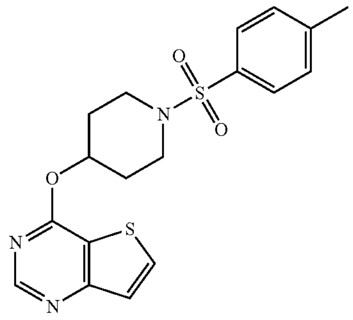

MS: 390.1

Reference Example Number 56: 4-((1-((3-fluorophenyl)sulfonyl)piperidin-4-yl)oxy)thieno[3,2-d]pyrimidine

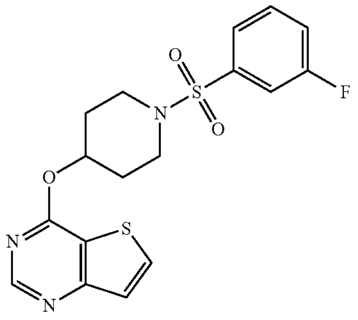

MS: 394.1

Reference Example Number 57: 4-((1-((3-chlorophenyl)sulfonyl)piperidin-4-yl)oxy)thieno[3,2-d]pyrimidine

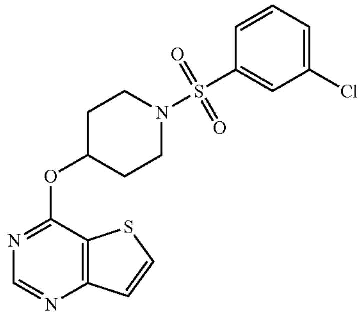

MS: 410.0

Reference Example Number 58: 4-((1-(pyridin-3-ylsulfonyl)piperidin-4-yl)oxy)thieno[3,2-d]pyrimidine

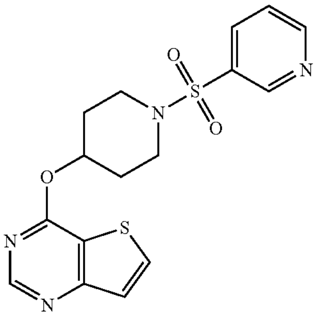

MS: 377.1

Reference Example Number 59: 4-((1-((1-benzyl-1H-pyrazol-4-yl)sulfonyl)piperidin-4-yl)oxy)thieno[3,2-d]pyrimidine

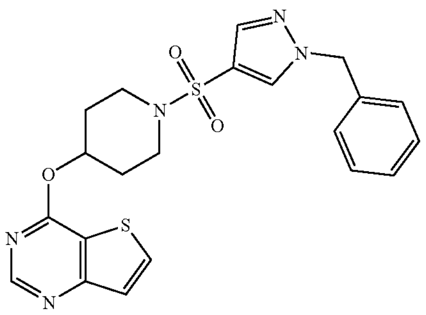

MS: 456.1

Reference Example Number 60: 4-((1-((6-methoxypyridin-3-yl)sulfonyl)piperidin-4-yl)oxy)thieno[3,2-d]pyrimidine

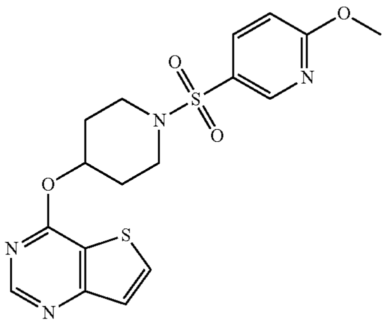

MS: 407.1

Reference Example Number 61: 4-((1-((1,4-dimethyl-1H-pyrazol-5-yl)sulfonyl)piperidin-4-yl)oxy)thieno[3,2-d]pyrimidine

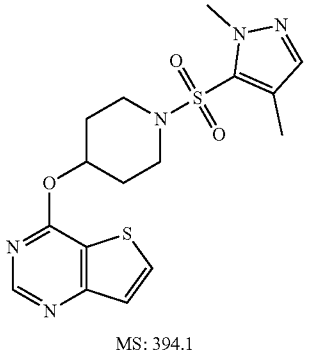 [SMILES: Cc1cnn(C)c1S(=O)(=O)N1CCC(Oc2ncnc3ccsc23)CC1]

MS: 394.1

Reference Example Number 62: 4-((1-(isobutylsulfonyl)piperidin-4-yl)oxy)thieno[3,2-d]pyrimidine

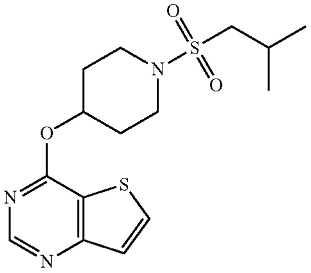

MS: 356.1

Reference Example Number 63: 4-((1-(phenethylsulfonyl)piperidin-4-yl)oxy)thieno[3,2-d]pyrimidine

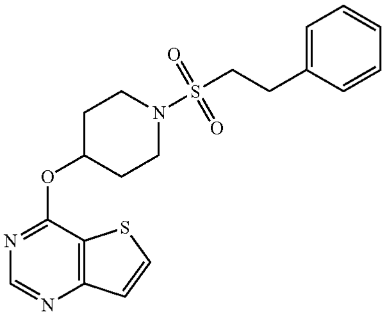

MS: 404.1

Reference Example Number 64: 4-((1-((3-phenoxyphenyl)sulfonyl)piperidin-4-yl)oxy)thieno[3,2-d]pyrimidine

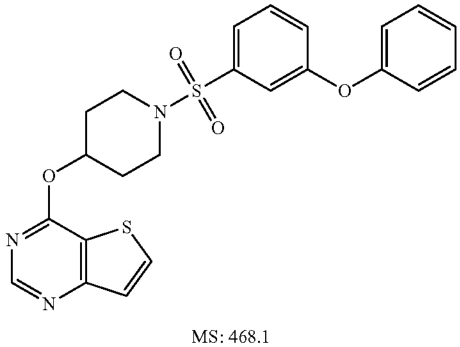 [SMILES: O=S(=O)(c1cccc(Oc2ccccc2)c1)N1CCC(Oc2ncnc3ccsc23)CC1]

MS: 468.1

Reference Example Number 65: N-(4-ethoxyphenyl)thieno[3,2-d]pyrimidin-4-amine

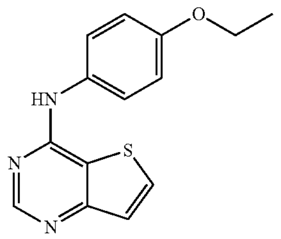

MS: 272.2

Reference Example Number 66: N-(3,4-dimethoxyphenyl)-2,6-dimethylthieno[3,2-d]pyrimidin-4-amine

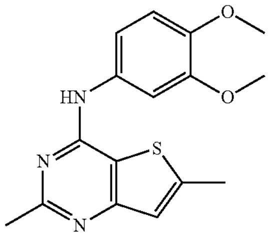

MS: 316.2

Reference Example Number 67: 7-((1-(prop-2-yn-1-yl)piperidin-4-yl)oxy)thieno[3,2-b]pyridine

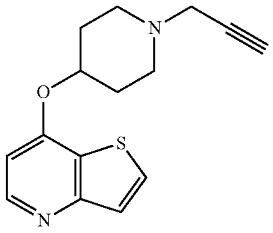

MS: 272.8

Reference Example Number 68: 1-methyl-5-((4-(thieno[3,2-b]pyridin-7-yloxy)piperidin-1-yl)methyl)-1H-pyrazol-3-ol

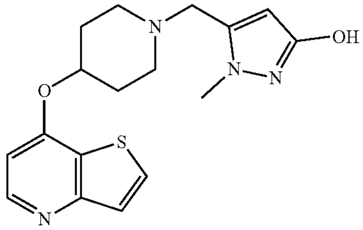

MS: 345.2

Reference Example Number 69: 7-((1-((3-(allyloxy)-1-methyl-1H-pyrazol-5-yl)methyl)piperidin-4-yl)oxy)thieno[3,2-b]pyridine

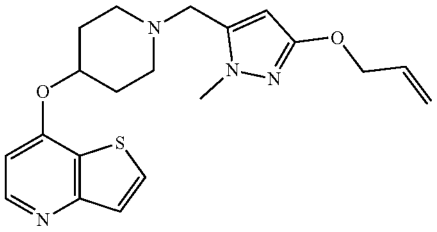

MS: 384.9

Reference Example Number 70: 3-(allyloxy)-5-((4-(thieno[3,2-d]pyrimidin-4-yloxy)piperidin-1-yl)methyl)isoxazole

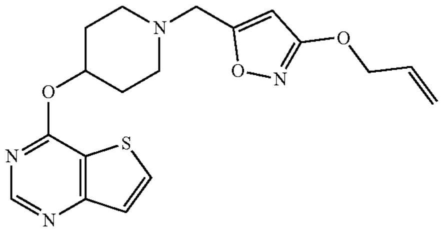

MS: 372.7

Reference Example Number 71: 3-(prop-2-yn-1-yloxy)-5-((4-(thieno[3,2-b]pyridin-7-yloxy)piperidin-1-yl)methyl)isoxazole

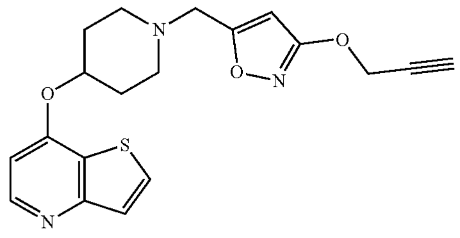

MS: 369.8

Reference Example Number 72: 3-(allyloxy)-5-((4-((2-methylthieno[3,2-b]pyridin-7-yl)oxy)piperidin-1-yl)methyl)isoxazole

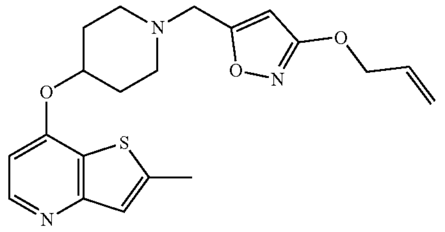

MS: 386.3

Reference Example Number 73: 7-((1-((1-methyl-1H-pyrazol-4-yl)methyl)piperidin-4-yl)oxy)thieno[3,2-b]pyridine

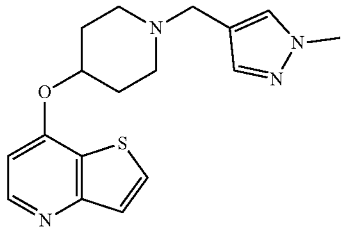

MS: 329.2

Reference Example Number 74: 7-((1-((1,3-dimethyl-1H-pyrazol-4-yl)methyl)piperidin-4-yl)oxy)thieno[3,2-b]pyridine

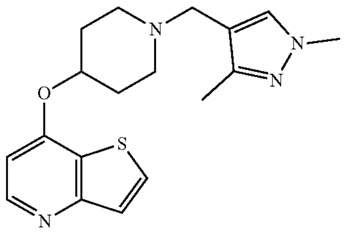

MS: 343.0

Reference Example Number 75: 7-((1-((1,3,5-trimethyl-1H-pyrazol-4-yl)methyl)piperidin-4-yl)oxy)thieno[3,2-b]pyridine

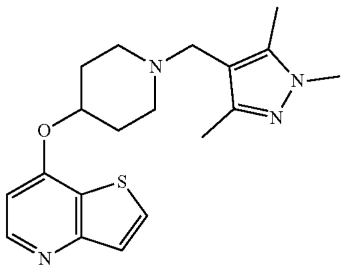

MS: 357.0

Reference example number 76: 7-((1-((1,5-dimethyl-1H-pyrazol-4-yl)methyl)piperidin-4-yl)oxy)thieno[3,2-b]pyridine

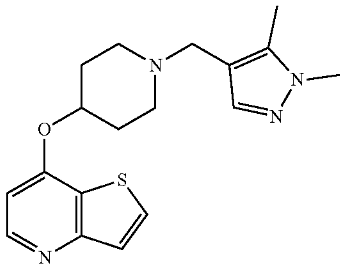

MS: 343.0

Reference Example Number 77: 7-((1-((1-methyl-1H-pyrazol-5-yl)methyl)piperidin-4-yl)oxy)thieno[3,2-b]pyridine

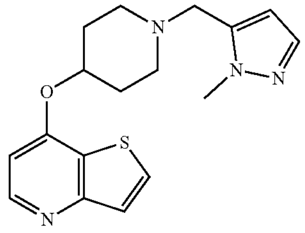

MS: 329.2

Reference Example Number 78: 3,5-dimethyl-4-((4-(thieno[3,2-b]pyridin-7-yloxy)piperidin-1-yl)methyl)isoxazole

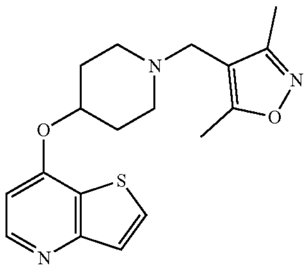

MS: 344.1

Reference Example Number 79: 7-((1-(thiazol-2-ylmethyl)piperidin-4-yl)oxy)thieno[3,2-b]pyridine

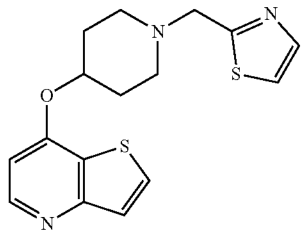

MS: 331.8

Reference Example Number 80: 7-((1-((2-methylthiazol-5-yl)methyl)piperidin-4-yl)oxy)thieno[3,2-b]pyridine

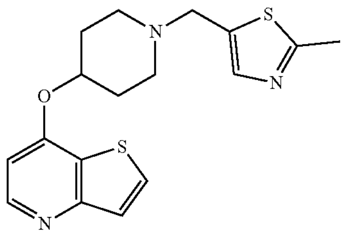

MS: 346.2

Reference Example Number 81: 2-(1H-pyrazol-1-yl)-1-(4-(thieno[3,2-b]pyridin-7-yloxy)piperidin-1-yl)ethan-1-one

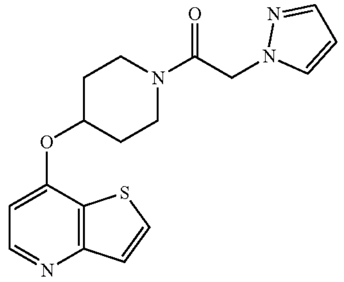

MS: 343.2

Reference Example Number 82: 1-(4-(thieno[3,2-b]pyridin-7-yloxy)piperidin-1-yl)-2-(2H-1,2,3-triazol-2-yl)ethan-1-one

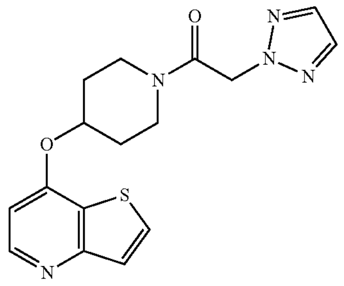

MS: 344.0

Reference Example Number 83: 3-(allyloxy)-5-(1-(4-(thieno[3,2-b]pyridin-7-yloxy)piperidin-1-yl)ethyl)isoxazole

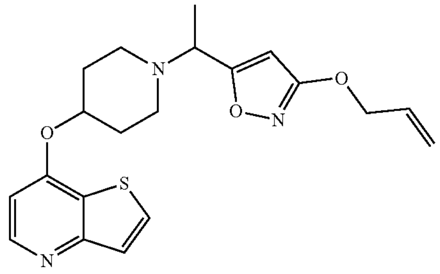

MS: 385.8

Reference Example Number 84: 2-allyl-5-((4-(thieno[3,2-b]pyridin-7-yloxy)piperidin-1-yl)methyl)isoxazol-3(2H)-one

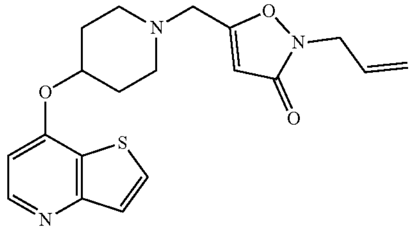

MS: 372.2

Reference Example Number 85: 3-(2-methoxy-ethoxy)-5-((4-(thieno[3,2-b]pyridin-7-yloxy)piperidin-1-yl)methyl)isoxazole

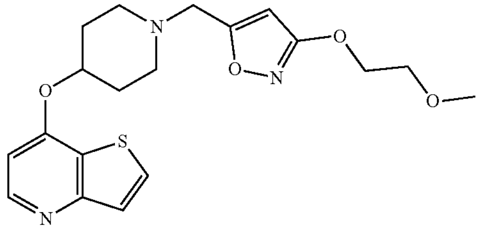

MS: 389.8

Reference Example Number 86: 7-((1-((3-(allyloxy)isoxazol-5-yl)methyl)piperidin-4-yl)oxy)thieno[3,2-b]pyridine-2-carbonitrile

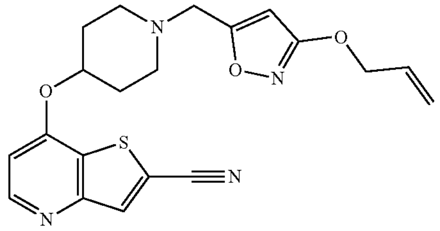

MS: 396.6

Reference Example Number 87: 5-((4-((2-methylthieno[3,2-b]pyridin-7-yl)oxy)piperidin-1-yl)methyl)isoxazol-3-ol

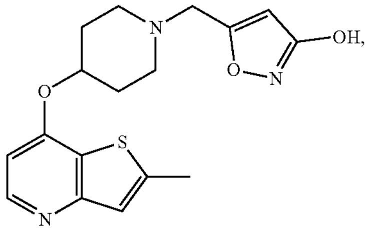

MS: 345.9

Reference Example Number 88: 5-(1-(4-((2-methyl-thieno[3,2-b]pyridin-7-yl)oxy)piperidin-1-yl)ethyl)isoxazol-3-ol

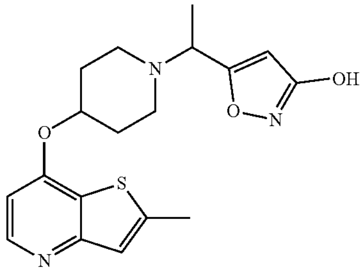

MS: 360.0

Example 1

2-(4-((S)-2-Cyclohexyl-2-((S)-2-(methylamino)propanamido)acetyl)piperazine-1-carbonyl)-5,6-difluoro-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide hydrochloride A) Benzyl (S)-4-(2-((tert-butoxycarbonyl)amino)-2-cyclohexylacetyl)piperazine-1-carboxylate To a mixture of (S)-2-((tert-butoxycarbonyl)amino)-2-cyclohexylacetic acid (2.5 g), benzyl piperazine-1-carboxylate (2.14 g), DIEA (5.09 mL) and DMF (48.6 mL) was added HATU (5.54 g) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate, and the solvent was removed under reduced pressure. The residue was purified by silica gel column chromatography (ethyl acetate/hexane) to give the title compound (4.34 g).

MS: $[M+H]^+$ 460.2.

B) Benzyl (S)-4-(2-amino-2-cyclohexylacetyl)piperazine-1-carboxylate hydrochloride To a mixture of benzyl (S)-4-(2-((tert-butoxycarbonyl)amino)-2-cyclohexylacetyl)piperazine-1-carboxylate (4.34 g) and ethyl acetate (18.9 mL) was added 4M hydrogen chloride/ethyl acetate solution (18.9 mL) at room temperature, and the reaction mixture was stirred at 45° C. for 1 h. The reaction mixture was concentrated under reduced pressure, and the crude product was recrystallized from ethyl acetate/hexane to give the title compound (2.96 g).

MS: $[M+H]^+$ 360.2.

C) Benzyl 4-((S)-2-((S)-2-((tert-butoxycarbonyl)(methyl)amino)propanamido)-2-cyclohexylacetyl)piperazine-1-carboxylate To a mixture of (S)-2-((tert-butoxycarbonyl)(methyl)amino)propanoic acid (1.63 g), benzyl (S)-4-(2-amino-2-cyclohexylacetyl)piperazine-1-carboxylate hydrochloride (2.96 g), DIEA (5.22 mL) and DMF (37.4 mL) was added HATU (4.26 g) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate, and the solvent was removed under reduced pressure. The residue was purified by silica gel column chromatography (ethyl acetate/hexane) to give the title compound (3.62 g).

MS: $[M+H]^+$ 545.4.

D) tert-Butyl ((S)-1-(((S)-1-cyclohexyl-2-oxo-2-(piperazin-1-yl)ethyl)amino)-1-oxopropan-2-yl)(methyl)carbamate A mixture of benzyl 4-((S)-2-((S)-2-((tert-butoxycarbonyl)(methyl)amino)propanamido)-2-cyclohexylacetyl)piperazine-1-carboxylate (3.62 g), 10% palladium on carbon (362 mg) and ethyl acetate (67 mL) was stirred under the normal pressure hydrogen atmosphere at room temperature for 1 h. The catalysts were filtered off, and the filtrate was concentrated under reduced pressure to give the title compound (2.46 g).

MS: $[M+H]^+$ 411.3.

E) Methyl 5,6-difluoro-1-methyl-1H-indole-2-carboxylate

To a mixture of 5,6-difluoro-1H-indole-2-carboxylic acid (20 g) and DMF (200 mL) were added potassium carbonate (42.0 g) and iodomethane (18.9 mL) at room temperature. The reaction mixture was stirred at the same temperature for 18 h and then stirred at 40° C. for 6 h. To the reaction mixture was added water, and the precipitates were collected by filtration and washed with hexane to give the title compound (20 g).

$^1$H NMR (400 MHz, DMSO-$d_6$) δ 3.85 (3H, s), 3.99 (3H, s), 7.26 (1H, s), 7.70 (1H, dd, J=8.24 Hz, 10.84 Hz), 7.78 (1H, dd, J=6.96 Hz, 11.68 Hz).

F) Methyl 5,6-difluoro-3-formyl-1-methyl-1H-indole-2-carboxylate

To a mixture of methyl 5,6-difluoro-1-methyl-1H-indole-2-carboxylate (2 g) and DCM (20 mL) were added 1 M titanium tetrachloride/DCM solution (17.8 mL) and a mixture of dichloromethyl methyl ether (1.7 mL) and DCM (2 mL) at −78° C. The reaction mixture was stirred at the same temperature for 2 h. The reaction mixture was diluted with water and neutralized with saturated aqueous sodium bicarbonate. The precipitates were filtered off with Celite®, and the filtrate was extracted with DCM. The organic layer was dried over anhydrous sodium sulfate, and the solvent was removed under reduced pressure to give the title compound (1.9 g).

$^1$H NMR (400 MHz, DMSO-d6) δ 3.99 (3H, s), 4.02 (3H, s), 8.0 (1H, dd, J=6.92 Hz, 11.4 Hz), 8.12 (1H, dd, J=8.24 Hz, 10.76 Hz), 10.34 (1H, s).

G) 5,6-Difluoro-3-formyl-1-methyl-1H-indole-2-carboxylic acid

To a mixture of methyl 5,6-difluoro-3-formyl-1-methyl-1H-indole-2-carboxylate (15 g), THF (225 mL), methanol (75 mL) and water (75 mL) was added lithium hydroxide monohydrate (3.73 g), and the reaction mixture was stirred at room temperature for 3 h. The reaction mixture was concentrated under reduced pressure and acidified with aqueous potassium hydrogen sulfate. The precipitates were collected by filtration to give the title compound (13 g).

MS: $[M+H]^+$ 240.1.

H) 2-(4-((S)-2-((S)-2-((tert-Butoxycarbonyl)(methyl)amino)propanamido)-2-cyclohexylacetyl)piperazine-1-carbonyl)-5,6-difluoro-1-methyl-1H-indole-3-carboxylic acid To a mixture of tert-butyl ((S)-1-(((S)-1-cyclohexyl-2-oxo-2-(piperazin-1-yl)ethyl)amino)-1-oxopropan-2-yl)(methyl)carbamate (4.63 g), 5,6-difluoro-3-formyl-1-methyl-1H-indole-2-carboxylic acid (2.45 g), DIEA (2.7 mL) and DMF (50 mL) was added HATU (4.67 g). After the reaction mixture was stirred at room temperature for 2 h, water was added thereto, and extracted with ethyl acetate. The organic layer was washed with 0.1 M hydrochloric acid, saturated aqueous sodium bicarbonate and brine respectively and then dried over anhydrous magnesium sulfate, and the solvent was removed under reduced pressure. The residue was purified by silica gel column chromatography (ethyl acetate/hexane). To a mixture of tert-butyl ((S)-1-(((S)-1-cyclohexyl-2-(4-(5,6-difluoro-3-formyl-1-methyl-1H-indole-2-carbonyl)piperazin-1-yl)-2-oxoethyl)amino)-1-oxopropan-2-yl)(methyl)carbamate thus obtained, sodium dihydrogen phosphate (4.90 g), 2-methylbut-2-ene (3.58 g), tert-butanol (90 mL) and water (30 mL) was added sodium chlorite (2.24 g). The reaction mixture was stirred at room temperature overnight, aqueous sodium thiosulfate solution was added thereto, and extracted with ethyl acetate. The organic layer was washed with water and brine and dried over anhydrous magnesium sulfate, and the solvent was removed under reduced pressure. The residue was purified by silica gel column chromatography (ethyl acetate/hexane and methanol/ethyl acetate) to give the title compound (5.46 g).

MS: $[M+H]^+$ 648.5.

I) tert-Butyl ((S)-1-(((S)-1-cyclohexyl-2-(4-(5,6-difluoro-3-((2-(2-(2-hydroxyethoxy)ethoxy)ethyl)(methyl)carbamoyl)-1-methyl-1H-indole-2-carbonyl)piperazin-1-yl)-2-oxoethyl)amino)-1-oxopropan-2-yl)(methyl)carbamate To a mixture of 2-(4-((S)-2-((S)-2-((tert-butoxycarbonyl)(methyl)amino)propanamido)-2-cyclohexylacetyl)piperazine-1-carbonyl)-5,6-difluoro-1-methyl-1H-indole-3-carboxylic acid (5.46 g), 2-(2-(2-(methylamino)ethoxy)ethoxy)ethan-1-ol (1.65 g), DIEA (2.26 mL) and DMF (8 mL) was added HATU (3.85 g). The reaction mixture was stirred at room temperature for 3 h, water was added thereto, and extracted with ethyl acetate. The organic layer was washed with saturated aqueous sodium bicarbonate and brine and dried over anhydrous magnesium sulfate, and the solvent was removed under reduced pressure. The residue was purified by silica gel column chromatography (methanol/ethyl acetate) to give the title compound (3.10 g).

MS: $[M+H]^+$ 793.5.

J) 5-((4-(Thieno[3,2-b]pyridin-7-yloxy)piperidin-1-yl)methyl)isoxazol-3-ol

To a mixture of 3-(allyloxy)-5-((4-(thieno[3,2-b]pyridin-7-yloxy)piperidin-1-yl)methyl)isoxazole (5.68 g), triethylsilane (7.3 mL) and THF (100 mL) was added tetrakistriphenylphosphine palladium (884 mg). The reaction mixture was stirred at room temperature for 1 h, and the solvent was removed under reduced pressure. The residue was purified by silica gel column chromatography (methanol), and the compound thus obtained was washed with ethyl acetate to give the title compound (2.50 g).

$^1H$ NMR (300 MHz, DMSO-$d_6$) δ 1.68-1.84 (2H, m), 1.95-2.09 (2H, m), 2.35-2.49 (2H, m), 2.63-2.75 (2H, m), 3.58 (2H, s), 4.74-4.87 (1H, m), 5.93 (1H, s), 7.07 (1H, d, J=5.5 Hz), 7.50 (1H, d, J=5.6 Hz), 8.04 (1H, d, J=5.4 Hz), 8.50 (1H, d, J=5.4 Hz), 11.16 (1H, s).

K) tert-Butyl ((S)-1-(((S)-1-cyclohexyl-2-(4-(5,6-difluoro-1-methyl-3-(methyl(2-(2-(2-((5-((4-(thieno[3,2-b]pyridin-7-yloxy)piperidin-1-yl)methyl)isoxazol-3-yl)oxy)ethoxy)ethoxy)ethyl)carbamoyl)-1H-indole-2-carbonyl)piperazin-1-yl)-2-oxoethyl)amino)-1-oxopropan-2-yl)(methyl)carbamate To a mixture of 5-((4-(thieno[3,2-b]pyridin-7-yloxy)piperidin-1-yl)methyl)isoxazol-3-ol (1.50 g), tert-butyl ((S)-1-(((S)-1-cyclohexyl-2-(4-(5,6-difluoro-3-((2-(2-(2-hydroxyethoxy)ethoxy)ethyl)(methyl)carbamoyl)-1-methyl-1H-indole-2-carbonyl)piperazin-1-yl)-2-oxoethyl)amino)-1-oxopropan-2-yl)(methyl)carbamate (3.59 g), triphenylphosphine (5.94 g) and toluene (25 mL) was added di-tert-butyl azodicarboxylate (3.13 g). The reaction mixture was stirred at room temperature for 1 h, and the solvent was removed under reduced pressure. The residue was purified by silica gel column chromatography (C18, acetonitrile/5 mM aqueous ammonium acetate) to give the title compound (2.37 g).

MS: $[M+H]^+$ 1106.6.

L) 2-(4-((S)-2-cyclohexyl-2-((S)-2-(methylamino)propanamido)acetyl)piperazine-1-carbonyl)-5,6-difluoro-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide hydrochloride To a mixture of tert-butyl ((S)-1-(((S)-1-cyclohexyl-2-(4-(5,6-difluoro-1-methyl-3-(methyl(2-(2-(2-((5-((4-(thieno[3,2-b]pyridin-7-yloxy)piperidin-1-yl)methyl)isoxazol-3-yl)oxy)ethoxy)ethoxy)ethyl)carbamoyl)-1H-indole-2-carbonyl)piperazin-1-yl)-2-oxoethyl)amino)-1-oxopropan-2-yl)(methyl)carbamate (2.37 g) and ethyl acetate (10 mL) was added 4M hydrogen chloride/ethyl acetate solution (16.1 mL), and the reaction mixture was stirred at room temperature for 1 h. The reaction mixture was concentrated under reduced pressure to give the title compound (2.16 g).

$^1H$ NMR (300 MHz, DMSO-$d_6$) δ 0.72-1.26 (7H, m), 1.35 (3H, d, J=6.8 Hz), 1.50-1.83 (7H, m), 2.11-2.48 (7H, m), 2.97 (3H, s), 3.20-3.97 (21H, m), 4.13-4.37 (2H, m), 4.39-4.82 (3H, m), 4.90-5.59 (2H, m), 6.65 (1H, s), 7.46 (1H, dd, J=10.9, 7.9 Hz), 7.54-7.96 (4H, m), 8.53 (1H, d, J=5.6 Hz), 8.66-9.12 (2H, m), 9.27-9.65 (1H, m), 11.79-12.71 (1H, m).

Example 2

2-(4-((S)-2-Cyclohexyl-2-((S)-2-(methylamino)propanamido)acetyl)piperazine-1-carbonyl)-6-methoxy-1-methyl-N-(2-(2-(2-(4-((4-(thieno[3,2-d]pyrimidin-4-yloxy)piperidin-1-yl)sulfonyl)phenoxy)ethoxy)ethoxy)ethyl)-1H-indole-3-carboxamide A) Methyl 6-methoxy-1-methyl-1H-indole-2-carboxylate To a mixture of methyl 6-methoxy-1H-indole-2-carboxylate (11.6 g) and DMF (100 mL) was added sodium hydride (60%, dispersion in paraffin liquid, 2.93 g) under ice-cooling. After the reaction mixture was stirred at the same temperature for 15 min, iodomethane (3.88 mL) was added to the reaction mixture, and the reaction mixture was stirred at the same temperature for 1 h. To the reaction mixture were added water (150 mL) and 1M hydrochloric acid (250 mL) under ice-cooling, and the aqueous layer was extracted with diethyl ether. The organic layer was washed with brine and then dried over anhydrous magnesium sulfate, and the solvent was removed under reduced pressure to give the title compound (11.4 g).

MS: $[M+H]^+$ 220.0.

B) 6-Methoxy-1-methyl-1H-indole-2-carboxylic acid

To a mixture of methyl 6-methoxy-1-methyl-1H-indole-2-carboxylate (11.4 g) and methanol (100 mL) was added 2M aqueous sodium hydroxide (52.0 mL) at room temperature and the reaction mixture was stirred at 60° C. for 1 h. The reaction mixture was cooled under ice-cooling and neutralized with 1M hydrochloric acid (110 mL), and the precipitates were collected by filtration to give the title compound (9.87 g).

MS: $[M+H]^+$ 206.0.

C) tert-Butyl 4-(6-methoxy-1-methyl-1H-indole-2-carbonyl)piperazine-1-carboxylate To a mixture of 6-methoxy-1-methyl-1H-indole-2-carboxylic acid (9.87 g), tert-butyl piperazine-1-carboxylate (9.41 g), 1-hydroxy-1H-benzotriazole monohydrate (8.10 g) and DMF (150 mL) was added 1-ethyl-3-(3-dimethylaminopropyl)carbodiimide hydrochloride (10.14 g), and the reaction mixture was stirred at room temperature for 2 h. The reaction mixture was cooled under ice-cooling, water was added thereto, and the precipitates were collected by filtration to give the title compound (16.8 g).

MS: $[M+H]^+$ 374.1.

D) tert-Butyl 4-(3-formyl-6-methoxy-1-methyl-1H-indole-2-carbonyl)piperazine-1-carboxylate To a mixture of tert-butyl 4-(6-methoxy-1-methyl-1H-indole-2-carbonyl)piperazine-1-carboxylate (10.4 g) and DMF (100 mL) was added (chloromethylene)dimethylammonium chloride (7.13 g), and the reaction mixture was stirred at room temperature for 2 h. To the reaction mixture was added water, the resultant mixture was stirred for 30 min, and then the aqueous layer was extracted with ethyl acetate. The organic layer was washed with water and brine and then dried over anhydrous magnesium sulfate, and the solvent was removed under reduced pressure to give the title compound (10.6 g).

MS: $[M+H]^+$ 402.1.

E) 6-Methoxy-1-methyl-2-(piperazine-1-carbonyl)-1H-indole-3-carbaldehyde hydrochloride To a mixture of tert-butyl 4-(3-formyl-6-methoxy-1-methyl-1H-indole-2-carbonyl)piperazine-1-carboxylate (10.6 g), dimethyl sulfide (25 mL) and ethyl acetate (100 mL) was added 4M hydrogen chloride/ethyl acetate solution (198 mL), and the reaction mixture was stirred at room temperature for 1 h. To the reaction mixture was added diisopropyl ether, and the precipitates were collected by filtration and washed with diisopropyl ether to give the title compound (8.1 g).

MS: $[M+H]^+$ 302.0.

F) tert-Butyl ((S)-1-(((S)-1-cyclohexyl-2-(4-(3-formyl-6-methoxy-1-methyl-1H-indole-2-carbonyl)piperazin-1-yl)-2-oxoethyl)amino)-1-oxopropan-2-yl)(methyl)carbamate To a mixture of (S)-2-((tert-butoxycarbonyl)amino)-2-cyclohexylacetic acid (1.96 g), 6-methoxy-1-methyl-2-(piperazine-1-carbonyl)-1H-indole-3-carbaldehyde hydrochloride (2.57 g), DIEA (2.66 mL) and DMF (38 mL) was added HATU (3.47 g) at room temperature, and the reaction mixture was stirred at the same temperature for 1 h. The reaction mixture was diluted with ethyl acetate and water, and the aqueous layer was extracted with ethyl acetate. The organic layer was dried over anhydrous magnesium sulfate, and the solvent was removed under reduced pressure. The residue was purified by silica gel column chromatography (ethyl acetate/hexane). To a mixture of the product thus obtained and ethyl acetate (38 mL) was added 4M hydrogen chloride/ethyl acetate solution (38 mL) at room temperature, and the reaction mixture was stirred at the same temperature for 1 h, and the reaction mixture was concentrated under reduced pressure. To a mixture of (S)-2-(4-(2-amino-2-cyclohexylacetyl)piperazine-1-carbonyl)-6-methoxy-1-methyl-1H-indole-3-carbaldehyde (3.35 g) thus obtained, (S)-2-((tert-butoxycarbonyl)(methyl)amino)propanoic acid (1.55 g), DIEA (6.65 mL) and DMF (38.1 mL) was added HATU (4.34 g) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate, and the solvent was removed under reduced pressure. The residue was purified by silica gel column chromatography (ethyl acetate/hexane) to give the title compound (2.12 g).

MS: $[M+H]^+$ 626.3.

G) 2-(4-((S)-2-((S)-2-((tert-Butoxycarbonyl)(methyl)amino)propanamido)-2-cyclohexylacetyl)piperazine-1-carbonyl)-6-methoxy-1-methyl-1H-indole-3-carboxylic acid To a mixture of tert-butyl ((S)-1-(((S)-1-cyclohexyl-2-(4-(3-formyl-6-methoxy-1-methyl-1H-indole-2-carbonyl)piperazin-1-yl)-2-oxoethyl)amino)-1-oxopropan-2-yl)(methyl)carbamate (2.30 g), sodium dihydrogen phosphate (1.76 g), 2-methylbut-2-ene (1.95 mL), tert-butyl alcohol (29.4 mL) and water (7.4 mL) was added sodium chlorite (665 mg) at room temperature. The reaction mixture was stirred at the same temperature for 4 h. The reaction mixture was diluted with ethyl acetate and saturated aqueous sodium thiosulfate, and the aqueous layer was extracted with ethyl acetate. The organic layer was washed with water and brine sequentially and dried over anhydrous magnesium sulfate, and the solvent was removed under reduced pressure. The residue was purified by silica gel column chromatography (methanol/ethyl acetate) to give the title compound (770 mg).

MS: $[M+H]^+$ 642.4.

H) tert-Butyl ((S)-1-(((S)-1-cyclohexyl-2-(4-(3-((2-(2-(2-hydroxyethoxy)ethoxy)ethyl)carbamoyl)-6-methoxy-1-methyl-1H-indole-2-carbonyl)piperazin-1-yl)-2-oxoethyl)amino)-1-oxopropan-2-yl)(methyl)carbamate A mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (147 mg), triethylene glycol monoamine (41.0 mg), DIEA (120 μL), HATU (131 mg) and DMF (1.15 mL) was stirred at room temperature for 1 h. The reaction mixture was diluted with water and ethyl acetate and extracted with ethyl acetate. The organic layer was dried over anhydrous magnesium sulfate, and the solvent was removed under reduced pressure. The residue was purified by silica gel column chromatography (C18, acetonitrile/5 mM aqueous ammonium acetate) to give the title compound (133 mg).

MS: $[M+H]^+$ 773.5.

I) 2-(4-((S)-2-Cyclohexyl-2-((S)-2-(methylamino)propanamido)acetyl)piperazine-1-carbonyl)-6-methoxy-1-methyl-N-(2-(2-(2-(4-((4-(thieno[3,2-d]pyrimidin-4-yloxy)piperidin-1-yl)sulfonyl)phenoxy)ethoxy)ethoxy)ethyl)-1H-indole-3-carboxamide To a mixture of 4-((4-(thieno[3,2-d]pyrimidin-4-yloxy)piperidin-1-yl)sulfonyl)phenol (35.5 mg), tert-butyl ((S)-1-

(((S)-1-cyclohexyl-2-(4-(3-((2-(2-(2-hydroxyethoxy)ethoxy)ethyl)carbamoyl)-6-methoxy-1-methyl-1H-indole-2-carbonyl)piperazin-1-yl)-2-oxoethyl)amino)-1-oxopropan-2-yl)(methyl)carbamate (70.0 mg), triphenylphosphine (119 mg) and toluene (0.45 mL) was added di-tert-butyl azodicarboxylate (62.6 mg). The reaction mixture was stirred at room temperature for 2 h, and the solvent was removed under reduced pressure. The residue was purified by silica gel column chromatography (C18, acetonitrile/5 mM aqueous ammonium acetate). To the product thus obtained were added ethyl acetate (0.2 mL) and then 4M hydrogen chloride/ethyl acetate solution (679 μL). After being stirred at room temperature for 1 h, the solvent was removed under reduced pressure. The residue was purified by silica gel column chromatography (C18, acetonitrile/5 mM aqueous ammonium acetate). The product thus obtained was dissolved in methanol, desalted by Amberlyst A21, and the solvent was removed under reduced pressure to give the title compound (19.5 mg).

$^1$H NMR (300 MHz, DMSO-$d_6$) δ 0.63-4.78 (54H, m) 5.26-5.43 (1H, m) 6.75-6.95 (1H, m) 7.05-7.20 (3H, m) 7.37-7.51 (1H, m) 7.55 (1H, d, J=5.29 Hz) 7.65 (2H, d, J=9.06 Hz) 7.75-7.85 (1H, m) 7.88-7.99 (1H, m) 8.30 (1H, d, J=5.29 Hz) 8.69 (1H, s).

Example 17

1-((R)-4-(5,6-Difluoro-1-methyl-1H-indole-2-carbonyl)-2-methylpiperazin-1-yl)-2-((2R,5R)-5-methyl-2-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazin-1-yl)ethan-1-one hydrochloride

A) 5,6-Difluoro-1-methyl-1H-indole-2-carboxylic acid

To a mixture of methyl 5,6-difluoro-1-methyl-1H-indole-2-carboxylate (2 g), THF (14 mL), methanol (7 mL) and water (7 mL) was added lithium hydroxide monohydrate (1.1 g), and the reaction mixture was stirred at room temperature for 4 h. The reaction mixture was concentrated under reduced pressure, and the residue was dissolved in water, acidified by adding aqueous potassium hydrogen sulfate, and extracted with ethyl acetate. The organic layer was washed with brine and dried over anhydrous sodium sulfate, and the solvent was removed under reduced pressure to give the title compound (1.8 g).

MS: $[M-H]^{-+}$ 210.0.

B) (R)-(5,6-Difluoro-1-methyl-1H-indol-2-yl)(3-methylpiperazin-1-yl)methanone To a mixture of 5,6-difluoro-1-methyl-1H-indole-2-carboxylic acid (1.8 g) and DMF (45 mL) were added DIEA (4.4 mL), (R)-2-methylpiperazine (1.02 g) and HATU (4.8 g). The reaction mixture was stirred at room temperature for 3 h, poured into ice-cold water, and extracted with ethyl acetate. The organic layer was washed with brine and dried over anhydrous sodium sulfate, and the solvent was removed under reduced pressure. The residue was purified by silica gel column chromatography (methanol/DCM) to give the title compound (1.9 g).

MS: $[M+H]^+$ 294.4.

C) (R)-2-Chloro-1-(4-(5,6-difluoro-1-methyl-1H-indole-2-carbonyl)-2-methylpiperazin-1-yl)ethan-1-one To a mixture of (R)-(5,6-difluoro-1-methyl-1H-indol-2-yl)(3-methylpiperazin-1-yl)methanone (1.9 g) and DCM (25 mL) were added TEA (1.35 mL) and chloroacetyl chloride (0.6 mL) under ice-cooling. The reaction mixture was stirred at room temperature for 3 h, diluted with DCM, and washed with water and brine. The organic layer was dried over anhydrous sodium sulfate, and the solvent was removed under reduced pressure. The residue was purified by silica gel column chromatography (ethyl acetate/hexane) to give the title compound (1.8 g).

MS: $[M+H]^+$ 370.2.

D) 2-(2-(2-(Benzyloxy)ethoxy)ethoxy)ethyl methanesulfonate

To a mixture of 2-(2-(2-benzyloxyethoxy)ethoxy)ethanol (2 g) and DCM (15 mL) were added TEA (1.7 mL) and methanesulfonyl chloride (0.77 mL) under ice-cooling. The reaction mixture was stirred at room temperature for 12 h, diluted with DCM, washed with water and brine, and then dried over anhydrous sodium sulfate, and the solvent was removed under reduced pressure to give the title compound (2.5 g).

$^1$H NMR (400 MHz, $CDCl_3$) δ 3.02-3.05 (3H, m), 3.61-3.65 (8H, m), 3.74-3.76 (2H, m), 4.34-4.36 (2H, m), 4.54 (2H, s), 7.27-7.33 (5H, m).

E) tert-Butyl (2R,5R)-4-benzyl-2-methyl-5-(12-phenyl-2,5,8,11-tetraoxadodecyl)piperazine-1-carboxylate To a mixture of tert-butyl (2R,5R)-4-benzyl-5-hydroxymethyl-2-methyl-piperazine-1-carboxylate (700 mg) and DMF (10 mL) was added sodium hydride (60%, dispersion in paraffin liquid, 105 mg). The reaction mixture was stirred for 1 h, 2-(2-(2-(benzyloxy)ethoxy)ethoxy)ethyl methanesulfonate (695 mg) was added thereto, and the mixture was additionally stirred at 60° C. for 4 h. The reaction mixture was cooled to room temperature, 2-(2-(2-(benzyloxy)ethoxy)ethoxy)ethyl methanesulfonate (556 mg) was added thereto, and the mixture was additionally stirred at 60° C. for 5 h. To the reaction mixture was added water, and the aqueous layer was extracted with ethyl acetate. The organic layer was washed with brine and then dried over anhydrous sodium sulfate, and the solvent was removed under reduced pressure. The residue was purified by silica gel column chromatography (ethyl acetate/hexane) to give the title compound (900 mg).

MS: $[M+H]^+$ 543.2.

F) tert-Butyl (2R,5R)-5-((2-(2-(2-hydroxyethoxy)ethoxy) ethoxy) methyl)-2-methylpiperazine-1-carboxylate To a mixture of tert-butyl (2R,5R)-4-benzyl-2-methyl-5-(12-phenyl-2,5,8,11-tetraoxadodecyl) piperazine-1-carboxylate (900 mg), acetic acid (0.1 mL) and ethanol (10 mL) was added 10% palladium on carbon (200 mg). The reaction mixture was stirred under the normal pressure hydrogen atmosphere at room temperature for 16 h and filtered with Celite®, and the filtrate was concentrated under reduced pressure. To the residue was added 10% methanol/DCM, and the organic layer was washed with saturated aqueous sodium bicarbonate and dried over anhydrous sodium sulfate. The solvent was removed under reduced pressure to give the title compound (600 mg).

1 H NMR (400 MHz, DMSO-$d_6$) δ 1.12 (3H, d, J=6.72 Hz), 1.39 (9H, s), 2.41 (1H, dd, J=2.74, 12.5 Hz), 2.88-2.94 (2H, m), 3.07 (1H, dd, J=4.16, 13.5 Hz), 3.31-3.52 (15H, m), 3.60-3.62 (1H, m), 3.98 (1H, brs) (1H, bs).

$^1$H NMR (400 MHz, DMSO-$d_6$) δ 1.12 (3H, d, J=6.72 Hz), 1.39 (9H, s), 2.41 (1H, dd, J=2.74, 12.5 Hz), 2.88-2.94 (2H, m), 3.07 (1H, dd, J=4.16, 13.5 Hz), 3.31-3.52 (15H, m), 3.60-3.62 (1H, m), 3.98 (1H, bs).

G) tert-Butyl (2R,5R)-4-(2-((R)-4-(5,6-difluoro-1-methyl-1H-indole-2-carbonyl)-2-methylpiperazin-1-yl)-2-oxoethyl)-5-((2-(2-(2-hydroxyethoxy)ethoxy)ethoxy)methyl)-2-methylpiperazine-1-carboxylate To a mixture of tert-butyl (2R,5R)-5-((2-(2-(2-hydroxyethoxy)ethoxy)ethoxy)methyl)-2-methylpiperazine-1-carboxylate (592 mg) and THF (15 mL) were added TEA (0.3 mL), (R)-2-chloro-1-(4-(5,6-difluoro-1-methyl-1H-indole-2-carbonyl)-2-methylpiperazin-1-yl)ethan-1-one (550 mg) and tetrabutylammonium iodide (549 mg), and the resultant mixture was stirred at 60° C. for 24 h. To the reaction mixture was added ethyl acetate, the mixture was washed with water and brine subsequently, the organic layer was dried over anhydrous sodium sulfate, and the solvent was removed under reduced pressure. The residue was purified by silica gel column chromatography (methanol/ethyl acetate) to give the title compound (740 mg).

MS: $[M+H]^+$ 696.5.

H) tert-Butyl (2R,5R)-4-(2-((R)-4-(5,6-difluoro-1-methyl-1H-indole-2-carbonyl)-2-methylpiperazin-1-yl)-2-oxoethyl)-2-methyl-5-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazine-1-carboxylate To a mixture of tert-butyl (2R,5R)-4-(2-((R)-4-(5,6-difluoro-1-methyl-1H-indole-2-carbonyl)-2-methylpiperazin-1-yl)-2-oxoethyl)-5-((2-(2-(2-hydroxyethoxy)ethoxy)ethoxy)methyl)-2-methylpiperazine-1-carboxylate (30 mg), 5-((4-(thieno[3,2-b]pyridin-7-yloxy)piperidin-1-yl)methyl)isoxazol-3-ol (17.1 mg), triphenylphosphine (56.5 mg) and toluene (2 mL) was added di-tert-butyl azodicarboxylate (29.7 mg). The reaction mixture was stirred at room temperature for 16 h, and the solvent was removed under reduced pressure. The residue was purified by preparative thin layer chromatography to give the title compound (26 mg).

MS: $[M+H]^+$ 1008.8.

I) 1-((R)-4-(5,6-Difluoro-1-methyl-1H-indole-2-carbonyl)-2-methylpiperazin-1-yl)-2-((2R,5R)-5-methyl-2-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazin-1-yl)ethan-1-one hydrochloride To a mixture of tert-butyl (2R,5R)-4-(2-((R)-4-(5,6-difluoro-1-methyl-1H-indole-2-carbonyl)-2-methylpiperazin-1-yl)-2-oxoethyl)-2-methyl-5-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazine-1-carboxylate (25 mg) and DCM (1 mL) was added 4M hydrogen chloride/dioxane solution (0.3 mL) under ice-cooling. The reaction mixture was stirred at room temperature for 1 h, and the solvent was removed under reduced pressure. The residue was washed with ether and pentane to give the title compound (19 mg).

$^1$H NMR (400 MHz, DMSO-$d_6$, 100° C.) δ 1.15-1.28 (6H, m), 2.19-2.36 (4H, m), 2.76-2.98 (3H, m), 3.20-4.36 (36H, m), 5.15 (1H, m), 5.66 (1H, s), 6.56 (1H, s), 7.30 (1H, d, J=8.0 Hz), 7.53-7.59 (2H, m), 7.63 (1H, d, J=8.0 Hz), 8.22 (1H, d, J=8.0 Hz), 8.68 (1H, d, J=8.0 Hz), 9.01-9.40 (1H, m).

Example 21

(S)—N—((S)-1-Cyclohexyl-2-(4-(5,6-difluoro-1-methyl-3-(2-(2-(2-((5-((4-(thieno[3,2-b]pyridin-7-yloxy)piperidin-1-yl)methyl)isoxazol-3-yl)oxy)ethoxy)ethoxy)ethoxy)-1H-indole-2-carbonyl)piperazin-1-yl)-2-oxoethyl)-2-(methylamino)propanamide hydrochloride A) Methyl 5,6-difluoro-3-hydroxy-1-methyl-1H-indole-2-carboxylate To a mixture of methyl 5,6-difluoro-3-formyl-1-methyl-1H-indole-2-carboxylate (3.5 g) and chloroform (50 mL) were added 3-chloroperoxybenzoic acid (5.88 g) and p-toluenesulfonic acid (3.15 g) at 5 to 10° C. The reaction mixture was stirred at the same temperature for 2 h. To the reaction mixture was added 2M ammonia/methanol solution (30 mL), and the reaction mixture was stirred at room temperature for 30 min. The solvent was removed under reduced pressure, and the residue was diluted with saturated aqueous sodium bicarbonate and extracted with DCM. The organic layer was washed with 10% aqueous sodium thiosulfate and dried over anhydrous sodium sulfate, and the solvent was removed under reduced pressure to give the title compound (3 g).

$^1$H NMR (400 MHz, DMSO-$d_6$) δ 3.81 (3H, s), 3.82 (3H, s), 7.56-7.69 (2H, m), 9.36 (1H, s).

B) tert-Butyl 4-(5,6-difluoro-3-hydroxy-1-methyl-1H-indole-2-carbonyl)piperazine-1-carboxylate To a mixture of methyl 5,6-difluoro-3-hydroxy-1-methyl-1H-indole-2-carboxylate (4.4 g), tert-butyl piperazine-1-carboxylate (5.1 g) and toluene (45 mL) was added and 2M trimethylaluminum/toluene solution (18.2 mL) under argon atmosphere at room temperature. The reaction mixture was stirred at 100° C. for 3 h. To the reaction mixture was added water, the precipitates were filtered off, and the filtrate was extracted with ethyl acetate. The organic layer was dried over anhydrous sodium sulfate, and the solvent was removed under reduced pressure. The residue was purified by silica gel column chromatography (ethyl acetate/hexane) to give the title compound (3 g).

MS: $[M+H]^+$ 393.8.

C) 2-(2-(2-(benzyloxy)ethoxy)ethoxy)ethyl 4-methylbenzenesulfonate

To a mixture of 2-(2-(2-(benzyloxy)ethoxy)ethoxy)ethan-1-ol (5 g) and DCM (100 mL) were added TEA (4.4 mL), DMAP (1.27 g) and p-toluenesulfonyl chloride (4.8 g) under ice-cooling, and the reaction mixture was stirred at room temperature for 2 h. The reaction mixture was diluted with DCM and washed with water and brine sequentially. The organic layer was dried over anhydrous sodium sulfate, and the solvent was removed under reduced pressure. The residue was purified by silica gel column chromatography (ethyl acetate/hexane) to give the title compound (5.2 g).

MS: $[M+H]^+$ 395.0.

D) tert-Butyl 4-(3-(2-(2-(2-(benzyloxy)ethoxy)ethoxy)ethoxy)-5,6-difluoro-1-methyl-1H-indole-2-carbonyl)piperazine-1-carboxylate To a mixture of tert-butyl 4-(5,6-difluoro-3-hydroxy-1-methyl-1H-indole-2-carbonyl)piperazine-1-carboxylate (1 g) and DMF (10 mL) were added cesium carbonate (2.06 g) and 2-(2-(2-(benzyloxy)ethoxy)ethoxy)ethyl 4-methylbenzensulfonate (1.49 g), and the reaction mixture was stirred at room temperature for 6 h. To the reaction mixture was added water, and the reaction mixture was extracted with ethyl acetate. The organic layer was washed with brine and dried over anhydrous sodium sulfate, and the solvent was removed under reduced pressure. The residue was purified by silica gel column chromatography (ethyl acetate/hexane) to give the title compound (1.26 g).

MS: $[M+H]^+$ 618.0.

E) (3-(2-(2-(2-(Benzyloxy)ethoxy)ethoxy)ethoxy)-5,6-difluoro-1-methyl-1H-indol-2-yl)(piperazin-1-yl)methanone hydrochloride To a mixture of tert-butyl 4-(3-(2-(2-(2-(benzyloxy)ethoxy)ethoxy)ethoxy)-5,6-difluoro-1-methyl-1H-indole-2-carbonyl)piperazine-1-carboxylate (1.2 g) and DCM (12 mL) was added 4M hydrogen chloride/dioxane solution (2 mL) under ice-cooling. The reaction mixture was stirred at room temperature for 4 h, and the solvent was removed under reduced pressure. The residue was washed with diethyl ether to give the title compound (1 g).

MS: $[M+H]^+$ 517.9.

F) tert-Butyl (S)-(2-(4-(3-(2-(2-(2-(benzyloxy)ethoxy)ethoxy)ethoxy)-5,6-difluoro-1-methyl-1H-indole-2-carbonyl)piperazin-1-yl)-1-cyclohexyl-2-oxoethyl)carbamate To a mixture of (3-(2-(2-(2-benzyloxyethoxy)ethoxy)ethoxy)-5,6-difluoro-1-methyl-1H-indol-2-yl)(piperazin-1-yl)methanone hydrochloride (1.1 g) and DMF (10 mL) was added DIEA (0.694 mL). The reaction mixture was stirred at room temperature for 15 min, and (S)-tert-butoxycarbonylaminocyclohexylacetic acid (0.512 g), 1-hydroxybenzotriazole (366 mg) and 1-ethyl-3-(3-dimethylaminopropyl)carbodiimide hydrochloride (458 mg) were added thereto. The reaction mixture was stirred at room temperature for 2 h, poured into ice-cold water, and extracted with ethyl acetate. The organic layer was dried over anhydrous sodium sulfate, and the solvent was removed under reduced pressure to give the title compound (1.1 g).

MS: $[M+H]^+$ 757.0.

G) (S)-2-Amino-1-(4-(3-(2-(2-(2-(benzyloxy)ethoxy)ethoxy)ethoxy)-5,6-difluoro-1-methyl-1H-indole-2-carbonyl)piperazin-1-yl)-2-cyclohexylethan-1-one hydrochloride To a mixture of tert-butyl (S)-(2-(4-(3-(2-(2-(2-(benzyloxy)ethoxy)ethoxy)ethoxy)-5,6-difluoro-1-methyl-1H-indole-2-carbonyl)piperazin-1-yl)-1-cyclohexyl-2-oxoethyl)carbamate (1.1 g) and DCM (10 mL) was added 4M hydrogen chloride/dioxane solution (10 mL) under ice-cooling. The reaction mixture was stirred at room temperature for 3 h, and the solvent was removed under reduced pressure to give the title compound (1.1 g).

MS: $[M+H]^+$ 657.2.

H) tert-Butyl ((S)-1-(((S)-2-(4-(3-(2-(2-(2-(benzyloxy)ethoxy)ethoxy)ethoxy)-5,6-difluoro-1-methyl-1H-indole-2-carbonyl)piperazin-1-yl)-1-cyclohexyl-2-oxoethyl)amino)-1-oxopropan-2-yl)(methyl)carbamate To a mixture of (S)-2-amino-1-(4-(3-(2-(2-(2-(benzyloxy)ethoxy)ethoxy)ethoxy)-5,6-difluoro-1-methyl-1H-indole-2-carbonyl)piperazin-1-yl)-2-cyclohexylethan-1-one hydrochloride (1.1 g) and DMF (10 mL) was added DIEA (0.83 mL). The reaction mixture was stirred for 15 min, (S)-2-(tert-butoxycarbonyl-methyl-amino)-propionic acid (0.323 g) and HATU (0.905 g) were added thereto, and the reaction mixture was stirred at room temperature for 16 h. The reaction mixture was poured into ice-cold water and extracted with ethyl acetate. The organic layer was washed with brine and dried over anhydrous sodium sulfate, and the solvent was removed under reduced pressure. The residue was purified by silica gel column chromatography (ethyl acetate/hexane) to give the title compound (850 mg).

MS: $[M+H]^+$ 842.1.

I) tert-Butyl ((S)-1-(((S)-1-cyclohexyl-2-(4-(5,6-difluoro-3-(2-(2-(2-hydroxyethoxy)ethoxy)ethoxy)-1-methyl-1H-indole-2-carbonyl)piperazin-1-yl)-2-oxoethyl)amino)-1-oxopropan-2-yl)(methyl)carbamate To a mixture of tert-butyl ((S)-1-(((S)-2-(4-(3-(2-(2-(2-(benzyloxy)ethoxy)ethoxy)ethoxy)-5,6-difluoro-1-methyl-1H-indole-2-carbonyl)piperazin-1-yl)-1-cyclohexyl-2-oxoethyl)amino)-1-oxopropan-2-yl)(methyl)carbamate (850 mg) and ethanol (10 mL) was added 10% palladium on carbon (200 mg) at room temperature, and the reaction mixture was stirred under the normal pressure hydrogen atmosphere for 3 h. The reaction mixture was filtered with Celite® and washed with ethanol, and the filtrate was concentrated under reduced pressure to give the title compound (740 mg).

MS: $[M+H]^+$ 752.6.

J) tert-Butyl ((S)-1-(((S)-1-cyclohexyl-2-(4-(5,6-difluoro-1-methyl-3-(2-(2-(2-((5-((4-(thieno[3,2-b]pyridin-7-yloxy)piperidin-1-yl)methyl)isoxazol-3-yl)oxy)ethoxy)ethoxy)ethoxy)-1H-indole-2-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(5,6-difluoro-3-(2-(2-(2-hydroxyethoxy)ethoxy)ethoxy)-1-methyl-1H-indole-2-carbonyl)piperazin-1-yl)-2-oxoethyl)amino)-1-oxopropan-2-yl)(methyl)carbamate (40 mg), 5-((4-(thieno[3,2-b]pyridin-7-yloxy)piperidin-1-yl)methyl)isoxazol-3-ol (21.1 mg), triphenylphosphine (69.7 mg) and toluene (1.5 mL) was added di-tert-butyl azodicarboxylate (36.7 mg), and the reaction mixture was stirred at room temperature for 16 h and concentrated under reduced pressure. The residue was purified by preparative thin layer chromatography to give the title compound (36 mg).

MS: $[M+H]^+$ 1064.8.

K) (S)—N—((S)-1-Cyclohexyl-2-(4-(5,6-difluoro-1-methyl-3-(2-(2-(2-((5-((4-(thieno[3,2-b]pyridin-7-yloxy)piperidin-1-yl)methyl) isoxazol-3-yl)oxy) ethoxy) ethoxy) ethoxy)-1H-indole-2-carbonyl) piperazin-1-yl)-2-oxoethyl)-2-(methylamino) propanamide hydrochloride To a mixture of tert-butyl ((S)-1-(((S)-1-cyclohexyl-2-(4-(5,6-difluoro-1-methyl-3-(2-(2-(2-((5-((4-(thieno[3,2-b] pyridin-7-yloxy)piperidin-1-yl)methyl) isoxazol-3-yl)oxy) ethoxy) ethoxy) ethoxy)-1H-indole-2-carbonyl) piperazin-1-yl)-2-oxoethyl)amino)-1-oxopropan-2-yl) (methyl) carbamate (36 mg) and DCM (1 mL) was added 4M hydrogen chloride/dioxane solution (0.3 mL) under ice-cooling, and the reaction mixture was stirred at room temperature for 2 h. The reaction mixture was concentrated under reduced pressure, and the residue was washed with diethyl ether and pentane to give the title compound (24 mg).

$^1$H NMR (400 MHz, DMSO-$d_6$) δ 1.03-1.23 (5H, m), 1.33 (3H, d, J=6.76 Hz), 1.60-1.68 (4H, m), 2.16 (2H, m), 2.32 (2H, m), 3.12-3.20 (3H, m), 3.47-3.50 (8H, m), 3.57-3.74 (15H, m), 3.85-3.86 (2H, m), 4.14 (2H, s), 4.31 (2H, s), 4.54-4.64 (3H, m), 5.08-5.29 (2H, m), 6.63 (1H, s), 7.46 (1H, m), 7.65-7.69 (2H, m), 8.35 (1H, m), 8.79-8.80 (2H, m), 9.14 (1H, s), 11.7 (1H, brs).

Example 24

(S)—N—((S)-1-Cyclohexyl-2-(4-(5,6-difluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl) piperazin-1-yl)-2-oxoethyl)-2-(methylamino) propanamide hydrochloride A) tert-Butyl ((S)-1-(((S)-1-cyclohexyl-2-(4-(5,6-difluoro-1H-indole-2-carbonyl)piperazin-1-yl)-2-oxoethyl)amino)-1-oxopropan-2-yl)(methyl)carbamate To a mixture of tert-butyl ((S)-1-(((S)-1-cyclohexyl-2-oxo-2-(piperazin-1-yl)ethyl)amino)-1-oxopropan-2-yl) (methyl)carbamate (2.29 g), 5,6-difluoro-1H-indole-2-carboxylic acid (1.00 g), DIEA (2.72 mL) and DMF (20 mL) was added HATU (2.89 g), and the reaction mixture was stirred at room temperature for 1 h. To the reaction mixture were added water and ethyl acetate, and the aqueous layer was extracted with ethyl acetate. The organic layer was dried over anhydrous magnesium sulfate, and the solvent was removed under reduced pressure to give the title compound (2.64 g).

MS: $[M+H]^+$ 490.3.

B) Methyl 2-(2-(4-((S)-2-((S)-2-((tert-butoxycarbonyl)(methyl)amino)propanamido)-2-cyclohexylacetyl)piperazine-1-carbonyl)-5,6-difluoro-1H-indol-1-yl)acetate A mixture of tert-butyl ((S)-1-(((S)-1-cyclohexyl-2-(4-(5,6-difluoro-1H-indole-2-carbonyl)piperazin-1-yl)-2-oxoethyl)amino)-1-oxopropan-2-yl)(methyl)carbamate (2.64 g), potassium carbonate (681 mg), methyl 2-bromoacetate (753 mg) and DMF (20 mL) was stirred at room temperature for 16 h. The reaction mixture was diluted with water and ethyl acetate, and the aqueous layer was extracted with ethyl acetate. The organic layer was dried over anhydrous magnesium sulfate, and the solvent was removed under reduced pressure. The residue was purified by silica gel column chromatography (ethyl acetate/hexane) to give the title compound (2.96 g).

MS: $[M+H]^+$ 662.4.

C) 2-(2-(4-((S)-2-((S)-2-((tert-Butoxycarbonyl)(methyl)amino)propanamido)-2-cyclohexylacetyl)piperazine-1-carbonyl)-5,6-difluoro-1H-indol-1-yl)acetic acid To a mixture of methyl 2-(2-(4-((S)-2-((S)-2-((tert-butoxycarbonyl)(methyl)amino)propanamido)-2-cyclohexylacetyl)piperazine-1-carbonyl)-5,6-difluoro-1H-indol-1-yl)acetate (2.76 g) and methanol (20 mL) was added 2M aqueous sodium hydroxide (10.4 mL). The reaction mixture was stirred at room temperature for 2 h, acidified with 1M hydrochloric acid, and extracted with ethyl acetate. The organic layer was dried over anhydrous magnesium sulfate, and the solvent was removed under reduced pressure to give the title compound (2.16 g).

MS: $[M+H]^+$ 648.4.

D) tert-Butyl ((S)-1-(((S)-1-cyclohexyl-2-(4-(5,6-difluoro-1-(14-hydroxy-3-methyl-2-oxo-6,9,12-trioxa-3-azatetradecyl)-1H-indole-2-carbonyl)piperazin-1-yl)-2-oxoethyl)amino)-1-oxopropan-2-yl)(methyl)carbamate To a mixture of 2-(2-(4-((S)-2-((S)-2-((tert-butoxycarbonyl)(methyl)amino)propanamido)-2-cyclohexylacetyl)piperazine-1-carbonyl)-5,6-difluoro-1H-indol-1-yl)acetic acid (1.20 g), 5,8,11-trioxa-2-azatridecan-13-ol (422 mg), DIEA (0.65 mL) and DMF (9.3 mL) was added HATU (986 mg), and the reaction mixture was stirred at room temperature for 1 h. The reaction mixture was diluted with water and ethyl acetate and extracted with ethyl acetate. The organic layer was dried over anhydrous magnesium sulfate, and the solvent was removed under reduced pressure. The residue was purified by silica gel column chromatography (ethyl acetate/hexane) to give the title compound (695 mg).

MS: $[M+H]^+$ 837.5.

E) tert-Butyl ((S)-1-(((S)-1-cyclohexyl-2-(4-(5,6-difluoro-1-(3-methyl-2-oxo-14-((5-((4-(thieno[3,2-b] pyridin-7-yloxy)piperidin-1-yl)methyl)isoxazol-3-yl) oxy)-6,9,12-trioxa-3-azatetradecyl)-1H-indole-2-carbonyl)piperazin-1-yl)-2-oxoethyl)amino)-1-oxopropan-2-yl)(methyl)carbamate To a mixture of 5-((4-(thieno[3,2-b]pyridin-7-yloxy)piperidin-1-yl)methyl)isoxazol-3-ol (265 mg), tert-butyl ((S)-1-(((S)-1-cyclohexyl-2-(4-(5,6-difluoro-1-(14-hydroxy-3-methyl-2-oxo-6,9,12-trioxa-3-azatetradecyl)-1H-indole-2-carbonyl)piperazin-1-yl)-2-oxoethyl)amino)-1-oxopropan-2-yl)(methyl)carbamate (670 mg), triphenylphosphine (1.05 g) and toluene (8 mL) was added di-tert-butyl azodicarboxylate (553 mg), and the reaction mixture was stirred at room temperature for 1 h. The reaction mixture was concentrated under reduced pressure, and the residue was purified by silica gel column chromatography (C18, acetonitrile/5 mM aqueous ammonium acetate) to give the title compound (575 mg).

MS: $[M+H]^+$ 1150.4.

F) (S)—N—((S)-1-Cyclohexyl-2-(4-(5,6-difluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)-2-(methylamino)propanamide hydrochloride To a mixture of tert-butyl ((S)-1-(((S)-1-cyclohexyl-2-(4-(5,6-difluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)amino)-1-oxopropan-2-yl)(methyl)carbamate (575 mg) and ethyl acetate (1 mL) was added 4M hydrogen chloride/ethyl acetate solution (2 mL), and the reaction mixture was stirred at room temperature for 1 h. The reaction mixture was concentrated under reduced pressure to give the title compound (549 mg).

$^1$H NMR (400 MHz, DMSO-$d_6$, 100° C.) δ 0.95-1.32 (5H, m), 1.35-1.40 (3H, m), 1.57-1.78 (6H, m), 1.94-2.08 (2H, m), 2.18-2.27 (2H, m), 3.05-3.78 (32H, m), 3.84-3.95 (1H, m), 3.99-4.21 (2H, m), 4.28-4.33 (2H, m), 4.63-4.70 (1H, m), 4.93-5.03 (1H, m), 5.17-5.26 (2H, m), 6.32-6.40 (1H, m), 6.72 (1H, s), 7.07-7.17 (1H, m), 7.47-7.59 (3H, m), 8.08-8.13 (1H, m), 8.39-8.48 (1H, m), 8.53-8.62 (1H, m), 8.63-8.93 (2H, m).

Example 25

(S)—N—((S)-1-Cyclohexyl-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide hydrochloride A) (S)-3-(Pyrrolidin-2-ylmethoxy)-5-((4-(thieno[3,2-b]pyridin-7-yloxy)piperidin-1-yl)methyl)isoxazole To a mixture of 5-((4-(thieno[3,2-b]pyridin-7-yloxy)piperidin-1-yl)methyl)isoxazol-3-ol (398.8 mg), (9H-fluoren-9-yl)methyl (S)-2-(hydroxymethyl)pyrrolidine-1-carboxylate (389.2 mg), triphenylphosphine (378.8 mg) and toluene (5 mL) was added di-tert-butyl azodicarboxylate (332.5 mg). The reaction mixture was stirred at room temperature for 30 min and concentrated under reduced pressure. The residue was dissolved in DMF (4 mL) and tetrabutylammonium fluoride (6 mL). The reaction mixture was stirred at room temperature for 15 min and concentrated under reduced pressure, and TFA (5 mL) was added to the residue. The reaction mixture was stirred at room temperature for 5 min, diluted with water and washed with ethyl acetate. The aqueous layer was basified with aqueous 2M sodium hydroxide solution and extracted with ethyl acetate. The organic layer was washed with water and brine and dried over anhydrous magnesium sulfate, and the solvent was removed under reduced pressure. The residue was purified by silica gel column chromatography (NH, methanol/ethyl acetate) to give the title compound (199.4 mg).

MS: [M+H]$^+$ 415.2.

B) tert-Butyl ((S)-1-(((S)-1-cyclohexyl-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)amino)-1-oxopropan-2-yl)(methyl)carbamate To a mixture of 2-(2-(4-((S)-2-((S)-2-((tert-butoxycarbonyl)(methyl)amino)propanamido)-2-cyclohexylacetyl)piperazine-1-carbonyl)-5,6-difluoro-1H-indol-1-yl)acetic acid (199.8 mg), (S)-3-(pyrrolidin-2-ylmethoxy)-5-((4-(thieno[3,2-b]pyridin-7-yloxy)piperidin-1-yl)methyl)isoxazole (140.7 mg), DIEA (107 μL), 1-hydroxybenzotriazole (83.37 mg) and DMF (3 mL) was added 1-ethyl-3-(3-dimethylaminopropyl)carbodiimide hydrochloride (118.3 mg). The reaction mixture was stirred at room temperature for 2 h, water was added thereto, and the precipitates were collected by filtration and washed with water to give the title compound (320.8 mg).

MS: [M+H]$^+$ 1044.3.

C) (S)—N—((S)-1-Cyclohexyl-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide hydrochloride To a mixture of tert-butyl ((S)-1-(((S)-1-cyclohexyl-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)amino)-1-oxopropan-2-yl)(methyl)carbamate (380.2 mg) and ethyl acetate (1.5 mL) was added 4M hydrogen chloride/ethyl acetate solution (1 mL). The reaction mixture was stirred at room temperature for 1.5 h, and diisopropyl ether was added thereto. The precipitates were collected by filtration and washed with diisopropyl ether to give the title compound (280.3 mg).

MS: [M+H]$^+$ 944.2.

The title compound was neutralized with saturated aqueous sodium bicarbonate, and the precipitates were collected by filtration as free base, subjected to $^1$H NMR measurement.

$^1$H NMR (300 MHz, DMSO-$d_6$) δ 0.78-1.27 (7H, m), 1.45-2.21 (19H, m), 2.41 (3H, s), 2.58-2.78 (2H, m), 2.86-3.03 (1H, m), 3.18-3.85 (10H, m), 4.02-4.31 (3H, m), 4.53-4.87 (3H, m), 5.04-5.38 (2H, m), 6.10-6.39 (1H, m), 6.76 (1H, s), 7.05 (1H, dd, J=5.6, 2.7 Hz), 7.49 (1H, dd, J=5.5, 2.1 Hz), 7.62 (1H, dd, J=10.9, 8.0 Hz), 7.66-7.84 (1H, m), 7.93 (1H, d, J=8.6 Hz), 8.02 (1H, dd, J=5.4, 3.3 Hz), 8.49 (1H, d, J=5.4 Hz).

Example 26

(S)—N—((S)-1-Cyclohexyl-2-(4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide A) tert-Butyl ((S)-1-(((S)-1-cyclohexyl-2-(4-(5-fluoro-1H-indole-2-carbonyl)piperazin-1-yl)-2-oxoethyl)amino)-1-oxopropan-2-yl)(methyl)carbamate To a mixture of tert-butyl ((S)-1-(((S)-1-cyclohexyl-2-oxo-2-(piperazin-1-yl)ethyl)amino)-1-oxopropan-2-yl)(methyl)carbamate (7 g) and DMF (60 mL) were added 5-fluoro-1H-indole-2-carboxylic acid (3.36 g), 1-hydroxybenzotriazole (3.00 g), DIEA (11.9 mL) and 1-ethyl-3-(3-dimethylaminopropyl)carbodiimide hydrochloride (4.25 g). The reaction mixture was stirred at room temperature for 16 h, water was added thereto, and extracted with ethyl acetate. The organic layer was washed with water, saturated aqueous ammonium chloride, saturated aqueous sodium bicarbonate and brine sequentially and dried over anhydrous sodium sulfate. The solvent was removed under reduced pressure to give the title compound (9.5 g).

MS: $[M+H]^+$ 572.0.

B) Methyl 2-(2-(4-((S)-2-((S)-2-((tert-butoxycarbonyl)(methyl)amino)propanamido)-2-cyclohexylacetyl)piperazine-1-carbonyl)-5-fluoro-1H-indol-1-yl)acetate To a mixture of tert-butyl ((S)-1-(((S)-1-cyclohexyl-2-(4-(5-fluoro-1H-indole-2-carbonyl)piperazin-1-yl)-2-oxoethyl)amino)-1-oxopropan-2-yl)(methyl)carbamate (9.5 g) and DMF (50 mL) were added potassium carbonate (6.89 g) and methyl bromoacetate (4.59 mL) under ice-cooling, the reaction mixture was stirred at room temperature for 16 h, water was added thereto, and extracted with ethyl acetate. The organic layer was washed with water and brine sequentially and dried over anhydrous sodium sulfate, and the solvent was removed under reduced pressure. The residue was purified by silica gel column chromatography (ethyl acetate/hexane) to give the title compound (8.6 g).

MS: $[M+H]^+$ 644.1.

C) 2-(2-(4-((S)-2-((S)-2-((tert-Butoxycarbonyl)(methyl)amino)propanamido)-2-cyclohexylacetyl)piperazine-1-carbonyl)-5-fluoro-1H-indol-1-yl)acetic acid To a mixture of methyl 2-(2-(4-((S)-2-((S)-2-((tert-butoxycarbonyl)(methyl)amino)propanamido)-2-cyclohexylacetyl)piperazine-1-carbonyl)-5-fluoro-1H-indol-1-yl)acetate (8.6 g) and methanol (25 mL) was added aqueous 2M sodium hydroxide solution (13.4 mL), and the reaction mixture was stirred at room temperature for 20 min. The reaction mixture was diluted with water and washed with diethyl ether. The organic layer was extracted with aqueous 0.01 M sodium hydroxide solution. The aqueous layer was acidified with 6M hydrochloric acid and extracted with ethyl acetate. The organic layer was dried over anhydrous sodium sulfate, and the solvent was removed under reduced pressure to give the title compound (8.1 g).

MS: $[M+H]^+$ 630.2.

D) tert-Butyl ((S)-1-(((S)-1-cyclohexyl-2-(4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)amino)-1-oxopropan-2-yl)(methyl)carbamate To a mixture of 2-(2-(4-((S)-2-((S)-2-((tert-butoxycarbonyl)(methyl)amino)propanamido)-2-cyclohexylacetyl)piperazine-1-carbonyl)-5-fluoro-1H-indol-1-yl)acetic acid (700 mg) and DMF (10 mL) were added (S)-3-(pyrrolidin-2-ylmethoxy)-5-((4-(thieno[3,2-b]pyridin-7-yloxy)piperidin-1-yl)methyl)isoxazole (506.8 mg), DIEA (0.78 mL) and HATU (507.8 mg), and the reaction mixture was stirred at room temperature for 16 h. To the reaction mixture was added ice-cooling water, and the reaction mixture was extracted with ethyl acetate. The organic layer was washed with water and brine in sequentially and dried over anhydrous magnesium sulfate, and the solvent was removed under reduced pressure. The residue was purified by silica gel column chromatography (ethyl acetate/hexane) to give the title compound (950 mg).

MS: $[M+H]^+$ 1025.8.

E) (S)—N—((S)-1-Cyclohexyl-2-(4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide To a mixture of tert-butyl ((S)-1-(((S)-1-cyclohexyl-2-(4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)amino)-1-oxopropan-2-yl)(methyl)carbamate (60 mg) and ethyl acetate (0.2 mL) was added 4M hydrogen chloride/ethyl acetate solution (0.043 mL), and the reaction mixture was stirred at room temperature for 4 h. To a mixture of (S)—N—((S)-1-cyclohexyl-2-(4-(5-fluoro-1-(2-oxo-2-((S)-2-(((5-((4-(thieno[3,2-b]pyridin-7-yloxy)piperidin-1-yl)methyl)-1,2-oxazol-3-yl)oxy)methyl)pyrrolidin-1-yl)ethyl)-1H-indole-2-carbonyl)piperazin-1-yl)-2-oxoethyl)-2-(methylamino)propanamide hydrochloride obtained by filtration of precipitates and water (0.2 mL) was added saturated aqueous sodium bicarbonate (0.043 mL) at room temperature. The reaction mixture was stirred at room temperature for 30 min, and the precipitates were collected by filtration to give the title compound (46 mg).

$^1H$ NMR (400 MHz, DMSO-$d_6$, 100° C.) δ 1.07-1.25 (m, 6H), 1.55-1.76 (m, 6H), 1.76-1.88 (m, 2H), 1.88-2.12 (m, 7H), 2.24 (s, 3H), 2.32 (s, 2H), 2.70-2.79 (m, 2H), 2.95-3.05 (m, 2H), 3.57-3.72 (m, 12H), 4.09-4.40 (m, 3H), 4.65 (s, 1H), 4.79 (s, 1H), 5.17-5.23 (m, 2H), 5.99-6.29 (m, 1H), 6.70 (s, 1H), 6.98 (d, J=5.3 Hz, 1H), 7.01-7.06 (m, 1H), 7.12-7.21 (m, 1H), 7.20-7.29 (m, 1H), 7.34 (d, J=8.5 Hz, 1H), 7.42-7.55 (m, 2H), 7.67 (s, 1H), 7.95 (d, J=5.1 Hz, 1H), 8.49 (d, J=5.2 Hz, 1H).

Example 27

(S)—N—((S)-1-Cyclohexyl-2-((S)-4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide A) tert-Butyl (S)-4-(5,6-difluoro-1H-indole-2-carbonyl)-3-methylpiperazine-1-carboxylate To a mixture of tert-butyl (S)-3-methylpiperazine-1-carboxylate (1.12 g), 5,6-difluoro-1H-indole-2-carboxylic acid (1.00 g), DIEA (2.72 mL) and DMF (20 mL) was added HATU (2.89 g). The reaction mixture was stirred at room temperature for 1 h, diluted with water and ethyl acetate, and extracted with ethyl acetate. The organic layer was dried over anhydrous magnesium sulfate, and the solvent was removed under reduced pressure to give the title compound (1.61 g).

MS: $[M+H-tBu]^+$324.2.

B) Methyl 2-(2-((S)-4-((S)-2-((tert-butoxycarbonyl)amino)-2-cyclohexylacetyl)-2-methylpiperazine-1-carbonyl)-5,6-difluoro-1H-indol-1-yl)acetate A mixture of tert-butyl (S)-4-(5,6-difluoro-1H-indole-2-carbonyl)-3-methylpiperazine-1-carboxylate (1.61 g), potassium carbonate (762 mg), methyl 2-bromoacetate (0.629 mL) and DMF (15 mL) was stirred at room temperature for 16 h. To the reaction mixture were added water and ethyl acetate, and the reaction mixture was extracted with ethyl acetate. The organic layer was dried over anhydrous magnesium sulfate, and the solvent was removed under reduced pressure. The residue was purified by silica gel column chromatography (ethyl acetate/hexane). To a mixture of tert-butyl (S)-4-(5,6-difluoro-1-(2-methoxy-2-oxoethyl)-1H-indole-2-carbonyl)-3-methylpiperazine-1-carboxylate thus obtained and ethyl acetate (10 mL) was added 4M hydrogen chloride/ethyl acetate solution (21.2 mL). The reaction mixture was stirred at room temperature for 1 h, and the solvent was removed under reduced pressure. To a mixture of methyl (S)-2-(5,6-difluoro-2-(2-methylpiperazine-1-carbonyl)-1H-indol-1-yl)acetate hydrochloride thus obtained, (S)-2-((tert-butoxycarbonyl)amino)-2-cyclohexylacetic acid (1.20 g), DIEA (3.0 mL) and DMF (20 mL) was added HATU (3.22 g). The reaction mixture was stirred at room temperature for 1 h, water and ethyl acetate were added thereto, and the mixture was extracted with ethyl acetate. The organic layer was dried over anhydrous magnesium sulfate, and the solvent was removed under reduced pressure to give the title compound (639 mg).

MS: $[M+H]^+$ 591.5.

C) Methyl 2-(2-((S)-4-((S)-2-((S)-2-((tert-butoxycarbonyl)(methyl)amino)propanamido)-2-cyclohexylacetyl)-2-methylpiperazine-1-carbonyl)-5,6-difluoro-1H-indol-1-yl)acetate To a mixture of methyl 2-(2-((S)-4-((S)-2-((tert-butoxycarbonyl)amino)-2-cyclohexylacetyl)-2-methylpiperazine-1-carbonyl)-5,6-difluoro-1H-indol-1-yl)acetate (639 mg) and ethyl acetate (3 mL) was added 4M hydrogen chloride/ethyl acetate solution (5 mL). The reaction mixture was stirred at room temperature for 1 h, and the solvent was removed under reduced pressure. To a mixture of methyl 2-(2-((S)-4-((S)-2-amino-2-cyclohexylacetyl)-2-methylpiperazine-1-carbonyl)-5,6-difluoro-1H-indol-1-yl)acetate hydrochloride thus obtained, N-(tert-butoxycarbonyl)-N-methyl-L-alanine (329 mg), DIEA (0.85 mL) and DMF (5 mL) was added HATU (616 mg). The reaction mixture was stirred at room temperature for 1 h, water and ethyl acetate were added thereto, and was extracted with ethyl acetate. The organic layer was dried over anhydrous magnesium sulfate, and the solvent was removed under reduced pressure. The residue was purified by silica gel column chromatography (ethyl acetate/hexane) to give the title compound (450 mg).

MS: $[M+H]^+$ 676.5.

D) 2-(2-((S)-4-((S)-2-((S)-2-((tert-Butoxycarbonyl)(methyl)amino)propanamido)-2-cyclohexylacetyl)-2-methylpiperazine-1-carbonyl)-5,6-difluoro-1H-indol-1-yl)acetic acid To a mixture of methyl 2-(2-((S)-4-((S)-2-((S)-2-((tert-butoxycarbonyl)(methyl)amino)propanamido)-2-cyclohexylacetyl)-2-methylpiperazine-1-carbonyl)-5,6-difluoro-1H-indol-1-yl)acetate (225 mg) and methanol (1.6 mL) was added 2M aqueous sodium hydroxide (0.8 mL). The reaction mixture was stirred at room temperature for 1 h, acidified with 1M hydrochloric acid, and extracted with ethyl acetate. The organic layer was dried over anhydrous magnesium sulfate, and the solvent was removed under reduced pressure to give the title compound (221 mg).

MS: $[M+H]^+$ 662.4.

E) tert-Butyl ((S)-1-(((S)-1-cyclohexyl-2-((S)-4-(5,6-difluoro-1-(2-oxo-2-((S)-2-(((5-((4-(thieno[3,2-b]pyridin-7-yloxy)piperidin-1-yl)methyl) isoxazol-3-yl)oxy) methyl) pyrrolidin-1-yl) ethyl)-1H-indole-2-carbonyl)-3-methylpiperazin-1-yl)-2-oxoethyl) amino)-1-oxopropan-2-yl)(methyl)carbamate To a mixture of 2-(2-((S)-4-((S)-2-((S)-2-((tert-butoxycarbonyl) (methyl)amino) propanamido)-2-cyclohexylacetyl)-2-methylpiperazine-1-carbonyl)-5,6-difluoro-1H-indol-1-yl) acetic acid (336 mg), (S)-3-(pyrrolidin-2-ylmethoxy)-5-((4-(thieno[3,2-b]pyridin-7-yloxy)piperidin-1-yl)methyl)isoxazole trihydrochloride (319 mg), DIEA (0.53 mL) and DMF (3 mL) was added HATU (386 mg). The reaction mixture was stirred at room temperature for 2 h, water was added thereto, and the precipitates were collected by filtration and purified by silica gel column chromatography (C18, acetonitrile/5 mM aqueous ammonium acetate). To the product thus obtained were added ethyl acetate and saturated aqueous sodium bicarbonate, the organic layer was dried over anhydrous magnesium sulfate, and the solvent was removed under reduced pressure to give the title compound (320 mg).

MS: $[M+H]^+$ 1058.5.

F) (S)—N—((S)-1-Cyclohexyl-2-((S)-4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide To a mixture of tert-butyl ((S)-1-(((S)-1-cyclohexyl-2-((S)-4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)amino)-1-oxopropan-2-yl)(methyl)carbamate (320 mg) and ethyl acetate (2 mL) was added 4M hydrogen chloride/ethyl acetate solution (2 mL). The reaction mixture was stirred at room temperature for 1.5 h, and the solvent was removed under reduced pressure. To the residue was added saturated aqueous sodium bicarbonate, and the precipitates were collected by filtration to give the title compound (216 mg).

$^1H$ NMR (300 MHz, DMSO-$d_6$) δ 0.77-1.33 (10H, m), 1.40-2.24 (19H, m), 2.31-2.46 (2H, m), 2.58-3.49 (8H, m), 3.53-3.70 (3H, m), 3.82-4.86 (8H, m), 5.01-5.48 (2H, m), 6.07-6.39 (1H, m), 6.67-6.81 (1H, m), 7.05 (1H, dd, J=5.6, 1.9 Hz), 7.49 (1H, dd, J=5.6, 3.0 Hz), 7.62 (1H, dd, J=10.9, 8.1 Hz), 7.68-7.83 (1H, m), 7.89 (1H, t, J=9.4 Hz), 7.97-8.07 (1H, m), 8.49 (1H, d, J=5.7 Hz).

Example 28

(S)—N—((S)-1-Cyclohexyl-2-((S)-4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide A) Benzyl (S)-4-((S)-2-((tert-butoxycarbonyl)amino)-2-cyclohexylacetyl)-2-methylpiperazine-1-carboxylate To a mixture of (S)-2-((tert-butoxycarbonyl)amino)-2-cyclohexylacetic acid (5 g), benzyl (S)-2-methylpiperazine- 1-carboxylate hydrochloride (5.26 g), 1-hydroxybenzotriazole (3.4 g), DIEA (10.2 mL) and DMF (50 mL) was added 1-ethyl-3-(3-dimethylaminopropyl)carbodiimide hydrochloride (4.8 g). The reaction mixture was stirred at room temperature for 2 h, ice-cooling water was added thereto, and the aqueous layer was extracted with ethyl acetate. The organic layer was washed with water, saturated aqueous sodium bicarbonate and brine sequentially and dried over anhydrous sodium sulfate, and the solvent was removed under reduced pressure to give the title compound (6.7 g).

MS: $[M+H]^+$ 474.2.

B) Benzyl (S)-4-((S)-2-amino-2-cyclohexylacetyl)-2-methylpiperazine-1-carboxylate hydrochloride To a mixture of benzyl (S)-4-((S)-2-(((tert-butoxy)carbonyl)amino)-2-cyclohexylacetyl)-2-methylpiperazine-1-carboxylate (6.7 g) and DCM (60 mL) was added 4M hydrogen chloride/dioxane solution (30 mL). The reaction mixture was stirred at room temperature for 3 h, and the solvent was removed under reduced pressure. The residue was washed with DCM to give the title compound (6 g).

$^1$H NMR (400 MHz, DMSO-$d_6$) δ 1.01-1.25 (8H, m), 1.59-1.70 (6H, m), 2.85-3.18 (3H, m), 3.77-4.28 (5H, m), 5.10 (2H, s), 7.33-7.37 (5H, m), 8.06-8.04 (3H, m).

C) Benzyl (S)-4-((S)-2-((S)-2-((tert-butoxycarbonyl)(methyl)amino)propanamido)-2-cyclohexylacetyl)-2-methylpiperazine-1-carboxylate To a mixture of N-(tert-butoxycarbonyl)-N-methyl-L-alanine (3 g) and DMF (30 mL) were added benzyl (S)-4-((S)-2-amino-2-cyclohexylacetyl)-2-methylpiperazine-1-carboxylate hydrochloride (6 g), DIEA (10.3 mL) and HATU (7.3 g). The reaction mixture was stirred at room temperature for 16 h, ice-cooling water was added thereto, and the aqueous layer was extracted with ethyl acetate. The organic layer was washed with water, saturated aqueous sodium bicarbonate, and brine sequentially and dried over anhydrous sodium sulfate, and the solvent was removed under reduced pressure. The residue was purified by silica gel column chromatography (ethyl acetate/hexane) to give the title compound (6 g).

MS: $[M+H]^+$ 559.1.

D) tert-Butyl ((S)-1-(((S)-1-cyclohexyl-2-((S)-3-methylpiperazin-1-yl)-2-oxoethyl)amino)-1-oxopropan-2-yl)(methyl)carbamate To a mixture of benzyl (S)-4-((S)-2-((S)-2-((tert-butoxycarbonyl)(methyl)amino)propanamido)-2-cyclohexylacetyl)-2-methylpiperazine-1-carboxylate (3.8 g) and ethanol (50 mL) was added 10% palladium on carbon (1 g). The reaction mixture was stirred under the normal pressure hydrogen atmosphere at room temperature for 16 h and filtered with Celite®. The filtrate was concentrated under reduced pressure to give the title compound (2.3 g).

MS: $[M+H]^+$ 425.2.

E) Methyl 2-(2-((S)-4-((S)-2-((S)-2-((tert-butoxycarbonyl)(methyl)amino)propanamido)-2-cyclohexylacetyl)-2-methylpiperazine-1-carbonyl)-5-fluoro-1H-indol-1-yl)acetate To a mixture of tert-butyl ((S)-1-(((S)-1-cyclohexyl-2-((S)-3-methylpiperazin-1-yl)-2-oxoethyl)amino)-1-oxopropan-2-yl)(methyl)carbamate (901 mg), 5-fluoro-1H-indole-2-carboxylic acid (380 mg), DIEA (1.14 mL) and DMF (12 mL) was added HATU (1.21 g). The reaction mixture was stirred at room temperature for 1 h and poured into water, and the precipitates were collected by filtration and azeotroped with toluene. A mixture of tert-butyl ((S)-1-(((S)-1-cyclohexyl-2-((S)-4-(5-fluoro-1H-indole-2-carbonyl)-3-methylpiperazin-1-yl)-2-oxoethyl)amino)-1-oxopropan-2-yl)(methyl)carbamate thus obtained, potassium carbonate (322 mg), methyl 2-bromoacetate (356 mg) and DMF (12 mL) was stirred at room temperature for 16 h. The reaction mixture was diluted with water and ethyl acetate and extracted with ethyl acetate. The organic layer was dried over anhydrous magnesium sulfate, and the solvent was removed under reduced pressure. The residue was purified by silica gel column chromatography (ethyl acetate/hexane) to give the title compound (979 mg).

MS: $[M+H]^+$ 658.4.

F) 2-(2-((S)-4-((S)-2-((S)-2-((tert-Butoxycarbonyl)(methyl)amino)propanamido)-2-cyclohexylacetyl)-2-methylpiperazine-1-carbonyl)-5-fluoro-1H-indol-1-yl)acetic acid To a mixture of methyl 2-(2-((S)-4-((S)-2-((S)-2-((tert-butoxycarbonyl)(methyl)amino)propanamido)-2-cyclohexylacetyl)-2-methylpiperazine-1-carbonyl)-5-fluoro-1H-indol-1-yl)acetate (979 mg) and methanol (8 mL) was added 2M aqueous sodium hydroxide (3.72 mL). The reaction mixture was stirred at room temperature for 1 h, acidified with 1M hydrochloric acid, and extracted with ethyl acetate. The organic layer was dried over anhydrous magnesium sulfate, and the solvent was removed under reduced pressure to give the title compound (915 mg).

MS: $[M+H]^+$ 644.4.

G) tert-Butyl ((S)-1-(((S)-1-cyclohexyl-2-((S)-4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)amino)-1-oxopropan-2-yl)(methyl)carbamate To a mixture of 2-(2-((S)-4-((S)-2-((S)-2-((tert-butoxycarbonyl)(methyl)amino)propanamido)-2-cyclohexylacetyl)-2-methylpiperazine-1-carbonyl)-5-fluoro-1H-indol-1-yl)acetic acid (621 mg), (S)-3-(pyrrolidin-2-ylmethoxy)-5-((4-(thieno[3,2-b]pyridin-7-yloxy)piperidin-1-yl)methyl)isoxazole trihydrochloride (606 mg), DIEA (1.0 mL) and DMF (5 mL) was added HATU (734 mg). The reaction mixture was stirred at room temperature for 2 h, water was added thereto, and the precipitates were collected by filtration and purified by silica gel column chromatography (C18, acetonitrile/5 mM aqueous ammonium acetate). The compound thus obtained was diluted with ethyl acetate, and the organic layer was washed with saturated aqueous sodium bicarbonate. The organic layer was dried over anhydrous sodium sulfate, and the solvent was removed under reduced pressure to give the title compound (367 mg).

MS: $[M+H]^+$ 1040.5.

H) (S)—N—((S)-1-Cyclohexyl-2-((S)-4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide To a mixture of tert-butyl ((S)-1-(((S)-1-cyclohexyl-2-((S)-4-(5-fluoro-1-(2-oxo-2-((S)-2-(((5-((4-(thieno[3,2-b]

pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)amino)-1-oxopropan-2-yl)(methyl)carbamate (367 mg) and ethyl acetate (2 mL) was added 4M hydrogen chloride/ethyl acetate solution (3 mL). The reaction mixture was stirred at room temperature for 1.5 h, and the solvent was removed under reduced pressure. To the residue was added saturated aqueous sodium bicarbonate, and the precipitates were collected by filtration to give the title compound (249 mg).

$^1$H NMR (300 MHz, DMSO-$d_6$) δ 0.74-1.34 (10H, m), 1.38-2.25 (19H, m), 2.33-2.46 (2H, m), 2.60-3.50 (8H, m), 3.55-3.71 (3H, m), 3.79-4.94 (8H, m), 5.00-5.50 (2H, m), 6.03-6.43 (1H, m), 6.61-6.82 (1H, m), 6.98-7.19 (2H, m), 7.26-7.71 (3H, m), 7.89 (1H, t, J=9.7 Hz), 7.98-8.13 (1H, m), 8.49 (1H, d, J=5.5 Hz).

Example 48

(S)—N—((S)-2-(4-(5,6-Difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-1-(4,4-difluorocyclohexyl)-2-oxoethyl)-2-(methylamino)propanamide trifluoroacetate A) Benzyl (S)-4-(2-(tert-butoxycarbonyl)amino)-2-(4,4-difluorocyclohexyl)acetyl)piperazine-1-carboxylate To a mixture of (S)-2-((tert-butoxycarbonyl)amino)-2-(4,4-difluorocyclohexyl)acetic acid (230 mg) and DMF (10 ml) were added benzyl piperazine-1-carboxylate (172.7 mg), 1-hydroxybenzotriazole (137.7 mg), DIEA (0.41 mL) and 1-ethyl-3-(3-dimethylaminopropyl)carbodiimide hydrochloride (195.4 mg), and the reaction mixture was stirred at room temperature for 16 h. To the reaction mixture was added ice water, and the mixture was extracted with ethyl acetate. The organic layer was washed with water, saturated aqueous sodium bicarbonate and brine and dried over anhydrous sodium sulfate, and then the solvent was removed under reduced pressure. The residue was purified by silica gel column chromatography (ethyl acetate/hexane) to give the title compound (300 mg).

MS: [M+H]$^+$ 496.0.

B) Benzyl 4-((S)-2-((S)-2-((tert-butoxycarbonyl)(methyl)amino)propanamido)-2-(4,4-difluorocyclohexyl)acetyl)piperazine-1-carboxylate To a mixture of benzyl (S)-4-(2-((tert-butoxycarbonyl)amino)-2-(4,4-difluorocyclohexyl)acetyl)piperazine-1-carboxylate (300 mg) and DCM (20 mL) was added 4M hydrogen chloride/dioxane (5 mL), the reaction mixture was stirred at room temperature for 3 h, and then the solvent was removed under reduced pressure. To a mixture of benzyl (S)-4-(2-amino-2-(4,4-difluorocyclohexyl)acetyl)piperazine-1-carboxylate thus obtained and DMF (10 mL) were added N-(tert-butoxycarbonyl)-N-methyl-L-alanine (122.9 mg), DIEA (0.42 ml) and HATU (299.3 mg), and the reaction mixture was stirred at room temperature for 16 h. To the reaction mixture was added ice water, and the mixture was extracted with ethyl acetate. The organic layer was washed with water and brine and dried over anhydrous sodium sulfate, and then the solvent was removed under reduced pressure. The residue was purified by silica gel column chromatography (ethyl acetate/hexane) to give the title compound (300 mg).

MS: [M+H]$^+$ 580.9.

C) tert-Butyl ((S)-1-(((S)-1-(4,4-difluorocyclohexyl)-2-oxo-2-(piperazin-1-yl)ethyl)amino)-1-oxopropan-2-yl)(methyl)carbamate To a mixture of benzyl 4-((S)-2-((S)-2-((tert-butoxycarbonyl)(methyl)amino)propanamido)-2-(4,4-difluorocyclohexyl)acetyl)piperazine-1-carboxylate (300 mg) and ethanol (10 mL) was added 10% palladium on carbon (90 mg), and the mixture was stirred under the normal pressure hydrogen atmosphere at room temperature for 16 h. The reaction mixture was filtered with Celite®, and the filtrate was concentrated under reduced pressure to give the title compound (220 mg).

MS: [M+H]$^+$ 447.1.

D) tert-Butyl ((S)-1-(((S)-2-(4-(5,6-difluoro-1H-indole-2-carbonyl)piperazin-1-yl)-1-(4,4-difluorocyclohexyl)-2-oxoethyl)amino)-1-oxopropan-2-yl)(methyl)carbamate To a mixture of tert-butyl ((S)-1-(((S)-1-(4,4-difluorocyclohexyl)-2-oxo-2-(piperazin-1-yl)ethyl)amino)-1-oxopropan-2-yl)(methyl)carbamate (200 mg) and DMF (15 mL) were added 5,6-difluoro-1H-indole-2-carboxylic acid (88.3 mg), DIEA (0.31 mL) and HATU (221.4 mg), and the reaction mixture was stirred at room temperature for 16 h. To the reaction mixture was added ice water, and the mixture was extracted with ethyl acetate. The organic layer was washed with water and brine and dried over anhydrous sodium sulfate, and then the solvent was removed under reduced pressure. The residue was purified by silica gel column chromatography (ethyl acetate/hexane) to give the title compound (170 mg).

MS: [M+H]$^+$ 626.3.

E) Benzyl 2-(2-(4-((S)-2-((S)-2-((tert-butoxycarbonyl)(methyl)amino)propanamido)-2-(4,4-difluorocyclohexyl)acetyl)piperazine-1-carbonyl)-5,6-difluoro-1H-indol-1-yl)acetate To a mixture of tert-butyl ((S)-1-(((S)-2-(4-(5,6-difluoro-1H-indole-2-carbonyl)piperazin-1-yl)-1-(4,4-difluorocyclohexyl)-2-oxoethyl)amino)-1-oxopropan-2-yl)(methyl)carbamate (150 mg) and DMF (10 mL) were added benzyl 2-bromoacetate (0.076 mL) and cesium carbonate (194.8 mg), and the mixture was stirred at room temperature for 16 h. To the reaction mixture was added ice water, and the mixture was extracted with ethyl acetate. The organic layer was washed with water and brine and dried over anhydrous sodium sulfate, and then the solvent was removed under reduced pressure. The residue was purified by silica gel column chromatography (ethyl acetate) to give the title compound (150 mg).

MS: [M+H]$^+$ 773.9.

F) 2-(2-(4-((S)-2-((S)-2-((tert-butoxycarbonyl)(methyl)amino)propanamido)-2-(4,4-difluorocyclohexyl)acetyl)piperazine-1-carbonyl)-5,6-difluoro-1H-indol-1-yl)acetic acid A mixture of benzyl 2-(2-(4-((S)-2-((S)-2-((tert-butoxycarbonyl)(methyl)amino)propanamido)-2-(4,4-difluorocyclohexyl)acetyl)piperazine-1-carbonyl)-5,6-difluoro-1H-indol-1-yl)acetate (150 mg) and ethanol (10 mL) was substituted with nitrogen, 10% palladium on carbon (60 mg) was added thereto, and the mixture was stirred under the normal pressure hydrogen atmosphere at room temperature for 16 h. The reaction mixture was filtered with Celite®, and the filtrate was concentrated under reduced pressure to give the title compound (123 mg).

MS: $[M+H]^+$ 684.1.

G) tert-Butyl ((S)-1-(((S)-2-(4-(5,6-difluoro-1-(2-oxo-2-((S)-2-(((5-((4-(thieno[3,2-b]pyridin-7-yloxy) piperidin-1-yl)methyl)isoxazol-3-yl)oxy)methyl) pyrrolidin-1-yl)ethyl)-1H-indole-2-carbonyl) piperazin-1-yl)-1-(4,4-difluorocyclohexyl)-2-oxoethyl)amino)-1-oxopropan-2-yl)(methyl) carbamate To a mixture of 2-(2-(4-((S)-2-((S)-2-((tert-butoxycarbonyl)(methyl)amino)propanamido)-2-(4,4-difluorocyclohexyl)acetyl)piperazine-1-carbonyl)-5,6-difluoro-1H-indol-1-yl)acetic acid (50 mg) and DMF (5 mL) were added (S)-3-(pyrolidin-2-ylmethoxy)-5-((4-(thieno[3,2-b]pyridin-7-yloxy)piperidin-1-yl)methyl)isoxazole (30.3 mg), DIEA (0.051 ml) and HATU (36.1 mg), and the mixture was stirred at room temperature for 16 h. To the reaction mixture was added water, and the mixture was extracted with ethyl acetate. The organic layer was washed with water and brine and dried over anhydrous sodium sulfate, and then the solvent was removed under reduced pressure. The residue was purified by preparative thin layer chromatography (methanol/DCM) to give the title compound (52 mg).

MS: $[M+H]^+$ 1080.4.

H) (S)—N—((S)-2-(4-(5,6-Difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-1-(4,4-difluorocyclohexyl)-2-oxoethyl)-2-(methylamino)propanamide trifluoroacetate To a mixture of tert-butyl ((S)-1-(((S)-2-(4-(5,6-difluoro-1-(2-oxo-2-((S)-2-(((5-((4-(thieno[3,2-b]pyridin-7-yloxy) piperidin-1-yl)methyl)isoxazol-3-yl)oxy)methyl)pyrrolidin-1-yl)ethyl)-1H-indole-2-carbonyl)piperazin-1-yl)-1-(4,4-difluorocyclohexyl)-2-oxoethyl)amino)-1-oxopropan-2-yl) (methyl)carbamate (52 mg) and DCM (5 mL) was added TFA (0.037 mL), and the mixture was stirred at room temperature for 16 h. The reaction mixture was removed under reduced pressure to give the title compound (44 mg).

MS: $[M+H]^+$ 980.6.

Example 51

(S)—N—((S)-1-Cyclohexyl-2-(4-(5,6-difluoro-1-methyl-4-(2-(2-(2-(2-((5-((4-(thieno[3,2-b]pyridin-7-yloxy)piperidin-1-yl)methyl)isoxazol-3-yl)oxy) ethoxy)ethoxy)ethoxy)ethoxy)-1H-indole-2-carbonyl)piperazin-1-yl)-2-oxoethyl)-2-(methylamino)propanamide hydrochloride A) 2-(Benzyloxy)-3,4-difluorobenzaldehyde To a mixture of 3,4-difluoro-2-hydroxy-benzaldehyde (5 g) and acetonitrile (50 mL) were added potassium carbonate (6.56 g), benzyl bromide (4.51 mL) and sodium iodide (2.37 g). The reaction mixture was stirred at 60° C. for 6 h and filtered with Celite®, and the filtrate was concentrated under reduced pressure. The residue was purified by silica gel column chromatography (ethyl acetate/hexane) to give the title compound (7.0 g).

$^1H$ NMR (400 MHz, DMSO-$d_6$): δ 5.33 (2H, s), 7.30-7.42 (4H, m), 7.45-7.47 (2H, m), 7.55-7.59 (1H, m), 10.04 (1H, s).

B) Methyl (Z)-2-azido-3-(2-(benzyloxy)-3,4-difluorophenyl)acrylate

To a mixture of methyl azidoacetate (3.15 mL), 2-(benzyloxy)-3,4-difluorobenzaldehyde (2.0 g) and methanol (10 mL) was added a mixture of sodium methoxide (1.74 g) and methanol (10 mL) at −10° C. under argon atmosphere dropwise. The reaction mixture was stirred at the same temperature for 4 h and stirred at 4° C. for 16 h. Ice water was added thereto, and the precipitates were collected by filtration to give the title compound (2.1 g).

$^1H$ NMR (400 MHz, DMSO-$d_6$): δ 3.83 (3H, s), 5.14 (2H, s), 6.94 (1H, s), 7.26 (1H, m), 7.38-7.40 (5H, m), 7.97 (1H, t, J=6.9 Hz).

C) Methyl 4-(benzyloxy)-5,6-difluoro-1H-indole-2-carboxylate

A mixture of methyl (Z)-2-azido-3-(2-(benzyloxy)-3,4-difluorophenyl)acrylate (2.0 g) and xylene (30 mL) was stirred at 140° C. for 2 h. The reaction mixture was cooled, and the precipitates were collected by filtration to give the title compound (700 mg).

$^1H$ NMR (400 MHz, DMSO-$d_6$): δ 3.87 (3H, s), 5.41 (2H, s), 7.05 (1H, m), 7.26 (1H, s), 7.32-7.41 (3H, m), 7.47-7.49 (2H, m), 12.19 (1H, s).

D) Methyl 4-(benzyloxy)-5,6-difluoro-1-methyl-1H-indole-2-carboxylate

To a mixture of methyl 4-(benzyloxy)-5,6-difluoro-1H-indole-2-carboxylate (1.7 g) and DMF (20 mL) were added potassium carbonate (1.1 g) and iodomethane (0.4 mL). The reaction mixture was stirred at room temperature for 2 h, ice water was added thereto, and extracted with ethyl acetate. The organic layer was washed with water and brine and then dried over anhydrous sodium sulfate, and the solvent was removed under reduced pressure to give the title compound (1.5 g).

MS: $[M+H]^+$ 332.1.

E) 4-(Benzyloxy)-5,6-difluoro-1-methyl-1H-indole-2-carboxylic acid

To a mixture of methyl 4-(benzyloxy)-5,6-difluoro-1-methyl-1H-indole-2-carboxylate (1.5 g) and THF (30 mL) were added water (6.0 mL) and lithium hydroxide monohydrate (0.285 g). The reaction mixture was stirred at room temperature for 6 h, the solvent was removed under reduced pressure, and the residue was acidified with 1M hydrochloric acid and extracted with ethyl acetate. The organic layer was washed with water and brine and dried over anhydrous sodium sulfate, and the solvent was removed under reduced pressure to give the title compound (1.35 g).

MS: $[M+H]^+$ 318.1.

F) tert-Butyl ((S)-1-(((S)-2-(4-(4-(benzyloxy)-5,6-difluoro-1-methyl-1H-indole-2-carbonyl)piperazin-1-yl)-1-cyclohexyl-2-oxoethyl)amino)-1-oxopropan-2-yl)(methyl)carbamate To a mixture of 4-(benzyloxy)-5,6-difluoro-1-methyl-1H-indole-2-carboxylic acid (1.4 g) and DMF (20 mL) were added tert-butyl ((S)-1-(((S)-1-cyclohexyl-2-oxo-2-(piperazin-1-yl)ethyl)amino)-1-oxopropan-2-yl)(methyl)carbamate (1.81 g), HATU (2.52 g) and DIEA (1.9 mL). The reaction mixture was stirred at room temperature for 2 h, ice water was added thereto, and the mixture was extracted with ethyl acetate. The organic layer was washed with saturated aqueous sodium bicarbonate, water and brine sequentially and then dried over anhydrous sodium sulfate, and the solvent was removed under reduced pressure. The residue was purified by silica gel column chromatography (ethyl acetate/hexane) to give the title compound (2.1 g).

MS: $[M+H]^+$ 710.1.

G) tert-Butyl ((S)-1-(((S)-1-cyclohexyl-2-(4-(5,6-difluoro-4-hydroxy-1-methyl-1H-indole-2-carbonyl)piperazin-1-yl)-2-oxoethyl)amino)-1-oxopropan-2-yl)(methyl)carbamate To a mixture of tert-butyl ((S)-1-(((S)-2-(4-(4-(benzyloxy)-5,6-difluoro-1-methyl-1H-indole-2-carbonyl)piperazin-1-yl)-1-cyclohexyl-2-oxoethyl)amino)-1-oxopropan-2-yl)(methyl)carbamate (2.1 g) and ethanol (50 mL) was added palladium on carbon (400 mg), and the mixture was stirred under the normal pressure hydrogen atmosphere at room temperature for 2 h. The reaction mixture was filtered with Celite®, and the filtrate was concentrated under reduced pressure to give the title compound (1.7 g).

MS: $[M+H]^+$ 620.4.

H) 2-(2-(2-(2-(benzyloxy)ethoxy)ethoxy)ethoxy)ethyl 4-methylbenzenesulfonate

To a mixture of 2-(2-(2-(2-(benzyloxy)ethoxy)ethoxy)ethoxy)ethanol (15 g) and DCM (250 mL) were added TEA (11.03 mL), DMAP (3.22 g) and p-toluenesulfonyl chloride (12.07 g) under ice-cooling, and the reaction mixture was stirred at room temperature for 2 h. The reaction mixture was diluted with DCM and washed with water and brine. The organic layer was dried over anhydrous sodium sulfate, and the solvent was removed under reduced pressure. The residue was purified by silica gel column chromatography (ethyl acetate/hexane) to give the title compound (14 g).

MS: $[M+H]^+$ 439.2.

I) tert-Butyl ((S)-1-(((S)-1-cyclohexyl-2-(4-(5,6-difluoro-1-methyl-4-((1-phenyl-2,5,8,11-tetraoxatridecan-13-yl)oxy)-1H-indole-2-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(5,6-difluoro-4-hydroxy-1-methyl-1H-indole-2-carbonyl)piperazin-1-yl)-2-oxoethyl)amino)-1-oxopropan-2-yl)(methyl)carbamate (450 mg) and DMF (5 mL) were added cesium carbonate (591 mg) and 2-(2-(2-(2-(benzyloxy)ethoxy)ethoxy)ethoxy)ethyl 4-methylbenzenesulfonate (573 mg). The reaction mixture was stirred at room temperature for 16 h, ice water was added thereto, and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (490 mg).

MS: $[M+H]^+$ 886.4.

J) tert-Butyl ((S)-1-(((S)-1-cyclohexyl-2-(4-(5,6-difluoro-4-(2-(2-(2-(2-hydroxyethoxy)ethoxy)ethoxy)ethoxy)-1-methyl-1H-indole-2-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(5,6-difluoro-1-methyl-4-((1-phenyl-2,5,8,11-tetraoxatridecan-13-yl)oxy)-1H-indole-2-carbonyl)piperazin-1-yl)-2-oxoethyl)amino)-1-oxopropan-2-yl)(methyl)carbamate (490 mg) and ethanol (15 mL) was added palladium on carbon (100 mg). The reaction mixture was stirred under the normal pressure hydrogen atmosphere at room temperature for 16 h and filtered with Celite®, and the filtrate was concentrated under reduced pressure to give the title compound (360 mg).

MS: $[M+H]^+$ 796.2.

K) tert-Butyl ((S)-1-(((S)-1-cyclohexyl-2-(4-(5,6-difluoro-1-methyl-4-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)-1H-indole-2-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(5,6-difluoro-4-(2-(2-(2-(2-hydroxyethoxy)ethoxy)ethoxy)ethoxy)-1-methyl-1H-indole-2-carbonyl)piperazin-1-yl)-2-oxoethyl)amino)-1-oxopropan-2-yl)(methyl)carbamate (20 mg), 5-((4-(thieno[3,2-b]pyridin-7-yloxy)piperidin-1-yl)methyl)isoxazol-3-ol (12.4 mg), triphenylphosphine (32.9 mg) and toluene (2 mL) was added di-tert-butyl azodicarboxylate (17.3 mg). The reaction mixture was stirred at room temperature for 16 h, and the solvent was removed under reduced pressure. The residue was purified by preparative thin layer chromatography to give the title compound (25 mg).

MS: $[M+H]^+$ 1109.8.

L) (S)—N—((S)-1-Cyclohexyl-2-(4-(5,6-difluoro-1-methyl-4-(2-(2-(2-(2-((5-((4-(thieno[3,2-b]pyridin-7-yloxy)piperidin-1-yl)methyl) isoxazol-3-yl)oxy) ethoxy) ethoxy) ethoxy) ethoxy)-1H-indole-2-carbonyl) piperazin-1-yl)-2-oxoethyl)-2-(methylamino) propanamide hydrochloride To a mixture of tert-butyl ((S)-1-(((S)-1-cyclohexyl-2-(4-(5,6-difluoro-1-methyl-4-(2-(2-(2-(2-((5-((4-(thieno[3,2-b]pyridin-7-yloxy)piperidin-1-yl)methyl) isoxazol-3-yl)oxy) ethoxy) ethoxy) ethoxy) ethoxy)-1H-indole-2-carbonyl) piperazin-1-yl)-2-oxoethyl)amino)-1-oxopropan-2-yl) (methyl) carbamate (25 mg) and DCM (1 mL) was added 4M hydrogen chloride/dioxane solution (0.3 mL) at 0° C. The reaction mixture was stirred at room temperature for 1 h, the solvent was removed under reduced pressure, and the residue was washed with diethyl ether to give the title compound (17 mg).

$^1H$ NMR (400 MHz, DMSO-$d_6$) δ 0.83-1.34 (9H, m), 1.60-1.69 (5H, m), 2.07-2.18 (3H, m), 3.17 (3H, s), 3.44-3.74 (25H, m), 3.85-4.66 (9H, m), 5.01-5.27 (2H, m), 6.63 (1H, brs), 6.81 (1H, s), 7.36-7.44 (2H, m), 7.66 (1H, d, J=5.32 Hz), 8.35-8.36 (1H, m), 8.74-8.80 (2H, m), 9.10-9.11 (1H, m), 11.36 (1H, brs).

Example 53

(S)—N—((S)-1-Cyclohexyl-2-(4-(2-methyl-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-5-carbonyl)piperazin-1-yl)-2-oxoethyl)-2-(methylamino)propanamide A) tert-Butyl ((S)-1-(((S)-1-cyclohexyl-2-(4-(2-methyl-1H-indole-5-carbonyl)piperazin-1-yl)-2-oxoethyl)amino)-1-oxopropan-2-yl)(methyl)carbamate To a mixture of tert-butyl ((S)-1-(((S)-1-cyclohexyl-2-oxo-2-(piperazin-1-yl)ethyl)amino)-1-oxopropan-2-yl)(methyl)carbamate (4 g) and DMF (70 mL) were added 2-methyl-1H-indole-5-carboxylic acid (1.9 g), DIEA (6.8 mL) and HATU (4.45 g), and the reaction mixture was stirred at room temperature for 16 h. The reaction mixture was diluted with water, and the aqueous layer was extracted with ethyl acetate. The organic layer was washed with water and brine sequentially and then dried over anhydrous sodium sulfate, and the solvent was removed under reduced pressure. The residue was purified by silica gel column chromatography (ethyl acetate/hexane) to give the title compound (4 g).

MS: $[M+H]^+$ 568.3.

B) tert-Butyl ((S)-1-(((S)-1-cyclohexyl-2-(4-(2-methyl-1-(1-phenyl-2,5,8,11-tetraoxatridecan-13-yl)-1H-indole-5-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(2-methyl-1H-indole-5-carbonyl)piperazin-1-yl)-2-oxoethyl)amino)-1-oxopropan-2-yl)(methyl)carbamate (2 g) and DMF (30 mL) was added cesium carbonate (2.87 g), the resultant mixture was stirred at room temperature for 5 min, then 2-(2-(2-(2-(benzyloxy)ethoxy)ethoxy)ethoxy)ethyl 4-methylbenzensulfonate (2.78 g) was added thereto, and the reaction mixture was stirred at 80° C. for 16 h. The reaction mixture was diluted with water, and the aqueous layer was extracted with ethyl acetate. The organic layer was washed with water and brine and then dried over anhydrous sodium sulfate, and the solvent was removed under reduced pressure. The residue was purified by silica gel column chromatography (NH, ethyl acetate/hexane) to give the title compound (1.3 g).

MS: $[M+H]^+$ 834.4.

C) tert-Butyl ((S)-1-(((S)-1-cyclohexyl-2-(4-(1-(2-(2-(2-(2-hydroxyethoxy)ethoxy)ethoxy)ethyl)-2-methyl-1H-indole-5-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(2-methyl-1-(1-phenyl-2,5,8,11-tetraoxatridecan-13-yl)-1H-indole-5-carbonyl)piperazin-1-yl)-2-oxoethyl)amino)-1-oxopropan-2-yl)(methyl)carbamate (1.3 g) and ethanol (50 mL) was added 10% palladium on carbon (250 mg), and the reaction mixture was stirred under the normal pressure hydrogen atmosphere at 25° C. for 16 h. The reaction mixture was filtered with Celite®, and the filtrate was concentrated under reduced pressure to give the title compound (1.1 g).

MS: $[M+H]^+$ 744.3.

D) tert-Butyl ((S)-1-(((S)-1-cyclohexyl-2-(4-(2-methyl-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-5-carbonyl)piperazin-1-yl)-2-oxoethyl)amino)-1-oxopropan-2-yl)(methyl)carbamate To a mixture of tert-butyl ((S)-1-(((S)-1-cyclohexyl-2-(4-(1-(2-(2-(2-(2-hydroxyethoxy)ethoxy)ethoxy)ethyl)-2-methyl-1H-indole-5-carbonyl)piperazin-1-yl)-2-oxoethyl)amino)-1-oxopropan-2-yl)(methyl)carbamate (20 mg), 5-((4-(thieno[3,2-b]pyridin-7-yloxy)piperidin-1-yl)methyl)isoxazol-3-ol (10.6 mg), triphenylphosphine (32.5 mg) and toluene (2 mL) was added di-tert-butyl azodicarboxylate (24.7 mg), and the reaction mixture was stirred at 25° C. for 16 h. The reaction mixture was concentrated under reduced pressure, and the residue was purified by preparative thin layer chromatography to give the title compound (17 mg).

MS: $[M+H]^+$ 1057.3.

E) (S)—N—((S)-1-Cyclohexyl-2-(4-(2-methyl-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-5-carbonyl)piperazin-1-yl)-2-oxoethyl)-2-(methylamino)propanamide To a mixture of tert-butyl ((S)-1-(((S)-1-cyclohexyl-2-(4-(2-methyl-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-5-carbonyl)piperazin-1-yl)-2-oxoethyl)amino)-1-oxopropan-2-yl)(methyl)carbamate (17 mg) and DCM (1 mL) was added TFA (0.01 mL) at 0° C., and the reaction mixture was stirred at 25° C. for 1 h. The reaction mixture was concentrated under reduced pressure, and the residue was purified by preparative HPLC (C18, mobile phase: acetonitrile/20 mM aqueous ammonium bicarbonate) to give the title compound (4 mg).

MS: $[M+H]^+$ 957.8.

Example compounds produced according to the above-mentioned production methods or the methods shown in examples, or similar methods thereto are described below. For each compound, the compound name, structural formula, salt type and MS value (MS is the measured value) are shown.

Example Compound 1 (compound 1): 2-(4-((S)-2-cyclohexyl-2-((S)-2-(methylamino)propanamido)acetyl)piperazine-1-carbonyl)-5,6-difluoro-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

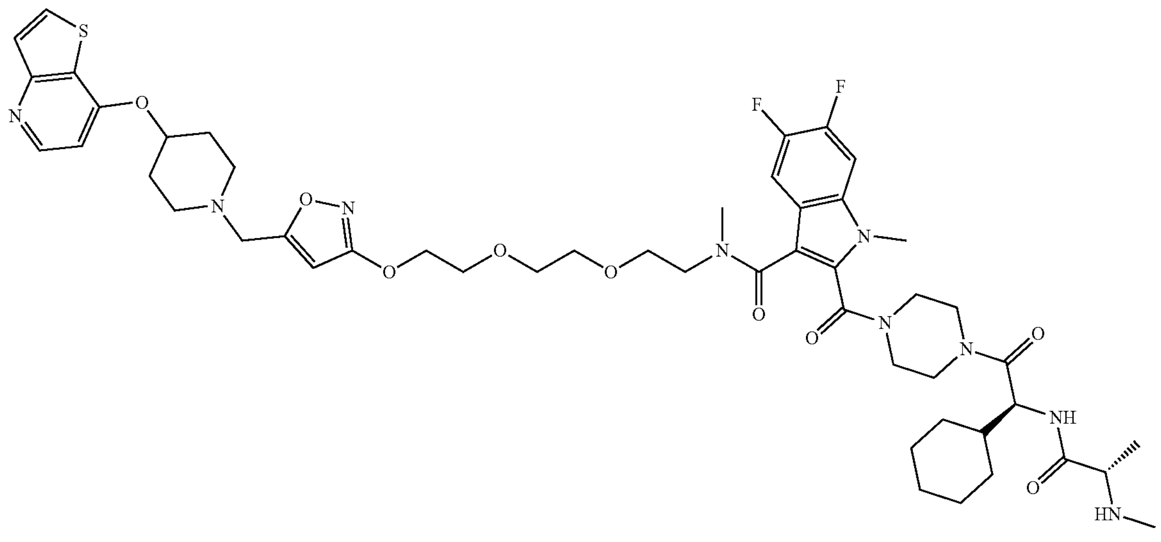 [SMILES: CN[C@@H](C)C(=O)N[C@H](C(=O)N1CCN(C(=O)c2c(C(=O)N(C)CCOCCOCCOc3cc(CN4CCC(Oc5ccnc6ccsc56)CC4)on3)c3cc(F)c(F)cc3n2C)CC1)C1CCCCC1]

Salt type: HCl; MS value: 1006.6

Example Compound 2 (compound 2): 2-(4-((S)-2-cyclohexyl-2-((S)-2-(methylamino)propanamido)acetyl)piperazine-1-carbonyl)-6-methoxy-1-methyl-N-(2-(2-(2-(4-((4-(thieno[3,2-d]pyrimidin-4-yloxy)piperidin-1-yl)sulfonyl)phenoxy)ethoxy)ethoxy)ethyl)-1H-indole-3-carboxamide

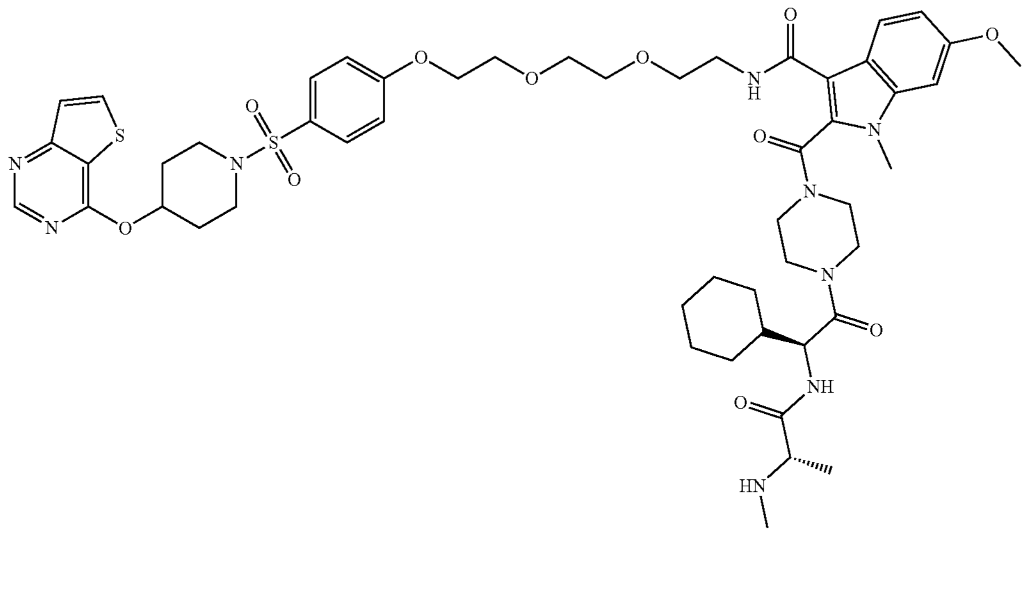 [SMILES: CN[C@@H](C)C(=O)N[C@H](C(=O)N1CCN(C(=O)c2c(C(=O)NCCOCCOCCOc3ccc(S(=O)(=O)N4CCC(Oc5ncnc6ccsc56)CC4)cc3)c3ccc(OC)cc3n2C)CC1)C1CCCCC1]

Salt type: HCl; MS value: 1046.5

Example Compound 3 (compound 3): 2-(4-((S)-2-cyclohexyl-2-((S)-2-(methylamino)propanamido)acetyl)piperazine-1-carbonyl)-5-fluoro-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide Salt type: -; MS value: 988.6

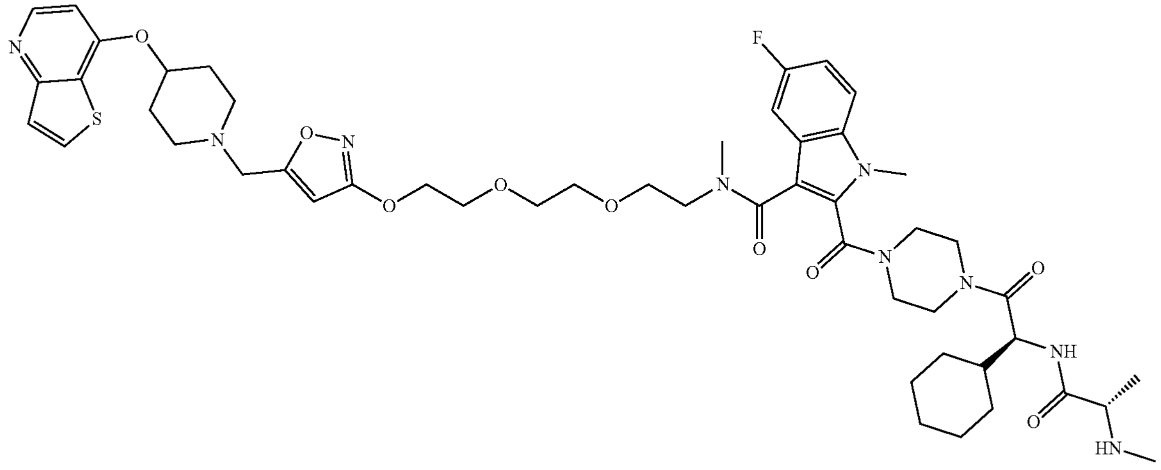 [SMILES: CN[C@@H](C)C(=O)N[C@H](C(=O)N1CCN(C(=O)c2c(C(=O)N(C)CCOCCOCCOc3cc(CN4CCC(Oc5ccnc6ccsc56)CC4)on3)c3cc(F)ccc3n2C)CC1)C1CCCCC1]

Example Compound 4 (compound 4): 2-(4-((S)-2-cyclohexyl-2-((S)-2-(methylamino)propanamido)acetyl)piperazine-1-carbonyl)-5,6-difluoro-1-methyl-N-(2-(2-((5-((4-(thieno[3,2-b]pyridin-7-yloxy)piperidin-1-yl)methyl)isoxazol-3-yl)oxy)ethoxy)ethyl)-1H-indole-3-carboxamide

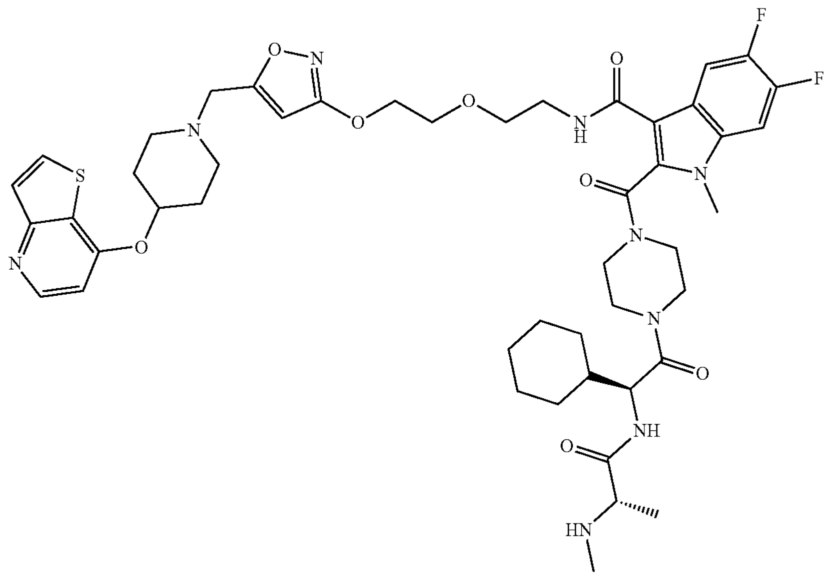 [SMILES: CN[C@@H](C)C(=O)N[C@H](C(=O)N1CCN(C(=O)c2c(C(=O)NCCOCCOc3cc(CN4CCC(Oc5ccnc6ccsc56)CC4)on3)c3cc(F)c(F)cc3n2C)CC1)C1CCCCC1]

Salt type: HCl; MS value: 948.7

Example Compound 5 (compound 5): 2-(4-((S)-2-cyclohexyl-2-((S)-2-(methylamino)propanamido)acetyl)piperazine-1-carbonyl)-5,6-difluoro-1-methyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

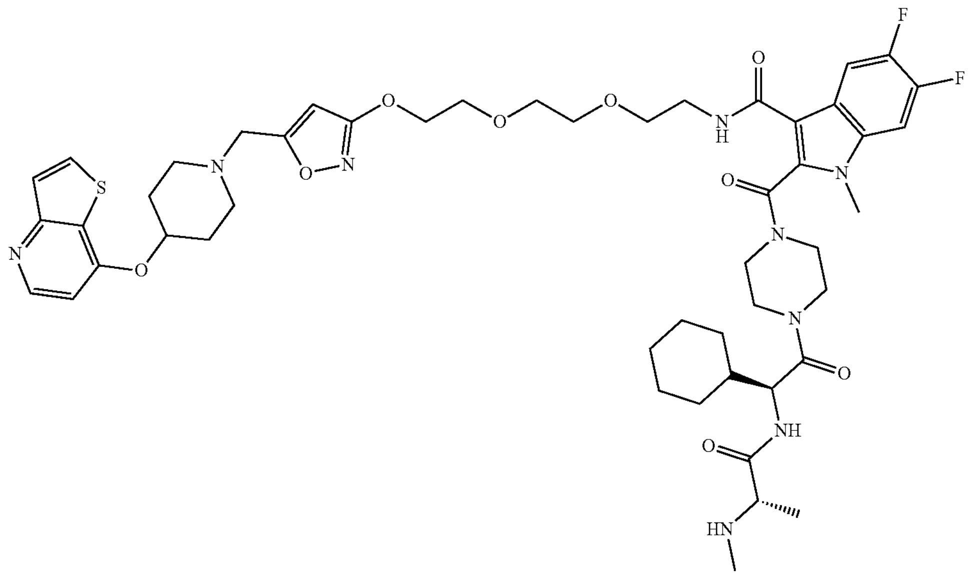 [SMILES: CN[C@@H](C)C(=O)N[C@H](C(=O)N1CCN(C(=O)c2c(C(=O)NCCOCCOCCOc3cc(CN4CCC(Oc5ccnc6ccsc56)CC4)on3)c3cc(F)c(F)cc3n2C)CC1)C1CCCCC1]

Salt type: HCl; MS value: 992.7

Example Compound 6 (compound 6): 2-(4-((S)-2-cyclohexyl-2-((S)-2-(methylamino)propanamido)acetyl)piperazine-1-carbonyl)-5,6-difluoro-1-methyl-N-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-3-carboxamide

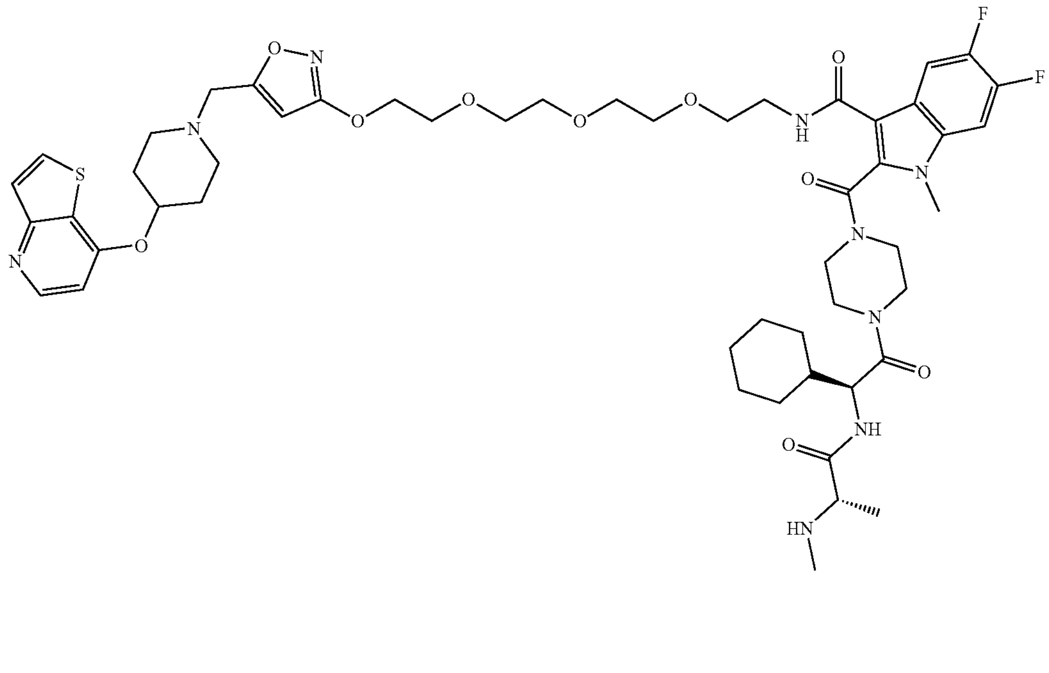 [SMILES: CN[C@@H](C)C(=O)N[C@H](C(=O)N1CCN(C(=O)c2c(C(=O)NCCOCCOCCOCCOc3cc(CN4CCC(Oc5ccnc6ccsc56)CC4)on3)c3cc(F)c(F)cc3n2C)CC1)C1CCCCC1]

Salt type: HCl; MS value: 1036.6

Example Compound 7 (compound 7): 2-(4-((S)-2-cyclohexyl-2-((S)-2-(methylamino)propanamido)acetyl)piperazine-1-carbonyl)-5,6-difluoro-1-methyl-N-(2-(2-(2-((1-methyl-5-((4-(thieno[3,2-b]pyridin-7-yloxy)piperidin-1-yl)methyl)-1H-pyrazol-3-yl)oxy)ethoxy)ethoxy)ethyl)-1H-indole-3-carboxamide

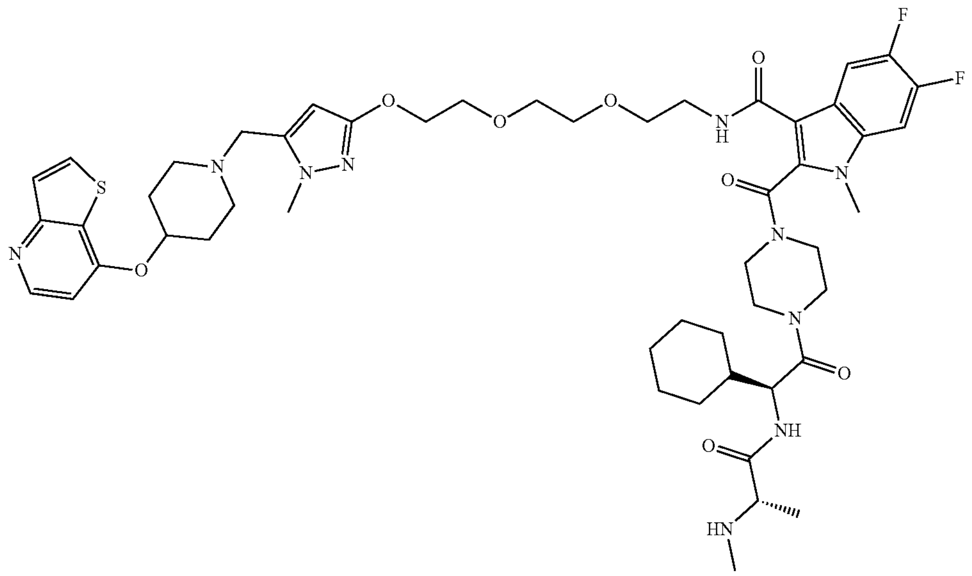 [SMILES: CN[C@@H](C)C(=O)N[C@H](C(=O)N1CCN(C(=O)c2c(C(=O)NCCOCCOCCOc3cc(CN4CCC(Oc5ccnc6ccsc56)CC4)n(C)n3)c3cc(F)c(F)cc3n2C)CC1)C1CCCCC1]

Salt type: HCl; MS value: 1005.6

Example Compound 8 (compound 8): 2-(4-((S)-2-cyclohexyl-2-((S)-2-(methylamino)propanamido)acetyl)piperazine-1-carbonyl)-5,6-difluoro-1-methyl-N-(2-(2-(2-((5-((4-((2-methylthieno[3,2-b]pyridin-7-yl)oxy)piperidin-1-yl)methyl)isoxazol-3-yl)oxy)ethoxy)ethoxy)ethyl)-1H-indole-3-carboxamide

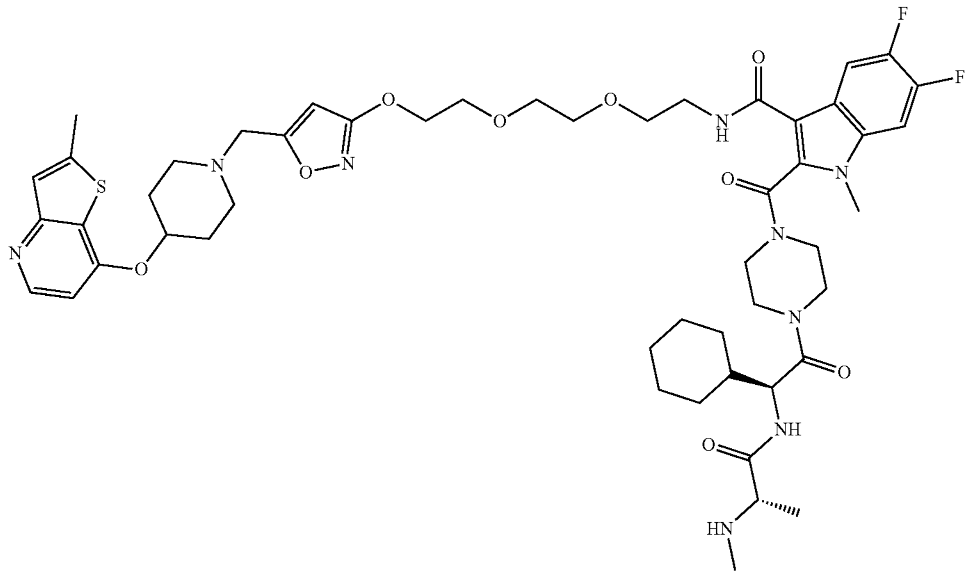 [SMILES: CN[C@@H](C)C(=O)N[C@H](C(=O)N1CCN(C(=O)c2c(C(=O)NCCOCCOCCOc3cc(CN4CCC(Oc5ccnc6cc(C)sc56)CC4)on3)c3cc(F)c(F)cc3n2C)CC1)C1CCCCC1]

Salt type: HCl; MS value: 1006.6

Example Compound 9 (compound 9): 2-(4-((S)-2-cyclohexyl-2-((S)-2-(methylamino)propanamido) acetyl)piperazine-1-carbonyl)-5,6-difluoro-1-methyl-N-(2-(2-(2-((5-(1-(4-((2-methylthieno[3,2-b]pyridin-7-yl)oxy)piperidin-1-yl)ethyl)isoxazol-3-yl)oxy) ethoxy)ethoxy)ethyl)-1H-indole-3-carboxamide

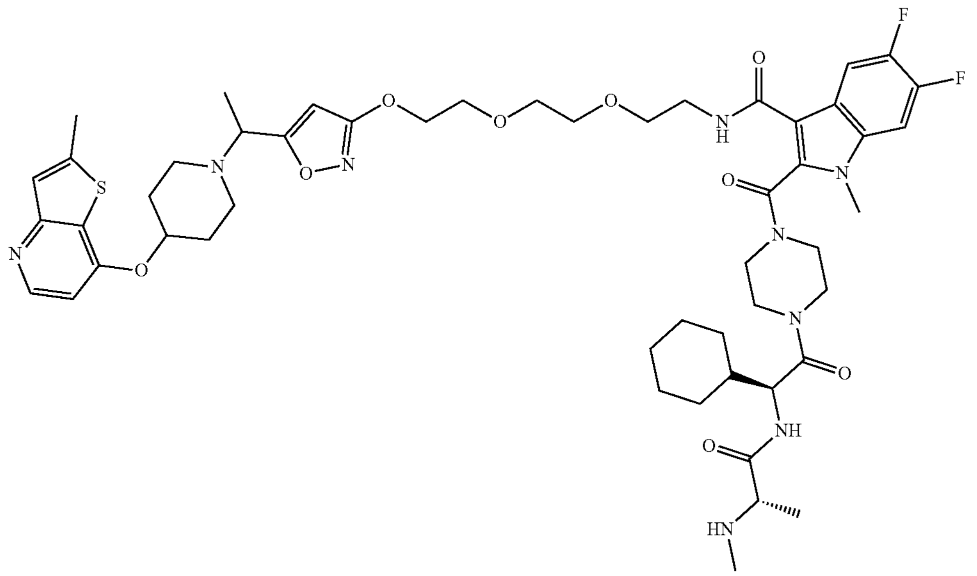 [SMILES: CN[C@@H](C)C(=O)N[C@H](C(=O)N1CCN(C(=O)c2c(C(=O)NCCOCCOCCOc3cc(C(C)N4CCC(Oc5ccnc6cc(C)sc56)CC4)on3)c3cc(F)c(F)cc3n2C)CC1)C1CCCCC1]

Salt type: HCl; MS value: 1020.6

Example Compound 10 (compound 10): 2-((R)-4-((S)-2-cyclohexyl-2-((S)-2-(methylamino)propanamido)acetyl)-3-methylpiperazine-1-carbonyl)-5,6-difluoro-1-methyl-N-(2-(2-(2-((5-((4-(thieno[3,2-b] pyridin-7-yloxy)piperidin-1-yl)methyl)isoxazol-3-yl) oxy)ethoxy)ethoxy)ethyl)-1H-indole-3-carboxamide

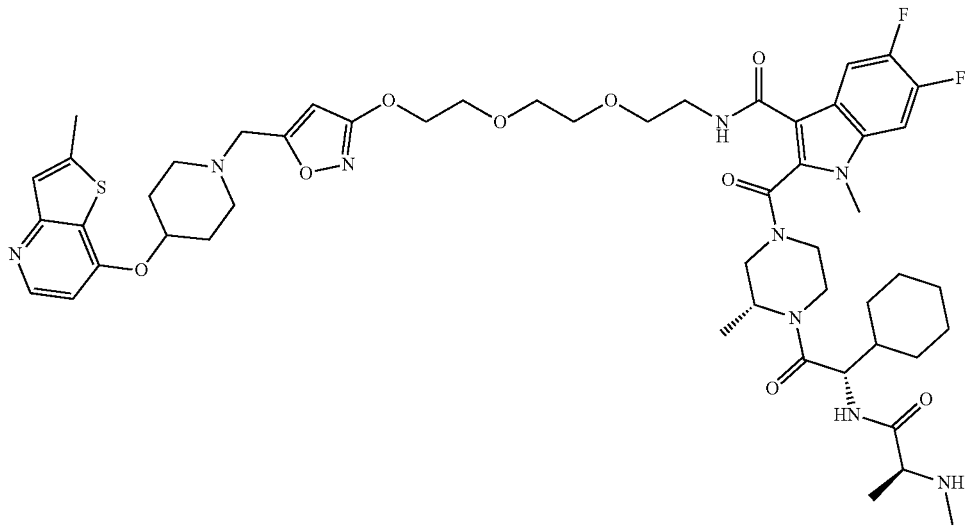 [SMILES: CN[C@@H](C)C(=O)N[C@H](C(=O)N1CCN(C(=O)c2c(C(=O)NCCOCCOCCOc3cc(CN4CCC(Oc5ccnc6cc(C)sc56)CC4)on3)c3cc(F)c(F)cc3n2C)C[C@H]1C)C1CCCCC1]

Salt type: HCl; MS value: 1006.7

Example Compound 11 (compound 11): 2-((R)-4-((S)-2-cyclohexyl-2-((S)-2-(methylamino)propanamido)acetyl)-3-methylpiperazine-1-carbonyl)-5,6-difluoro-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

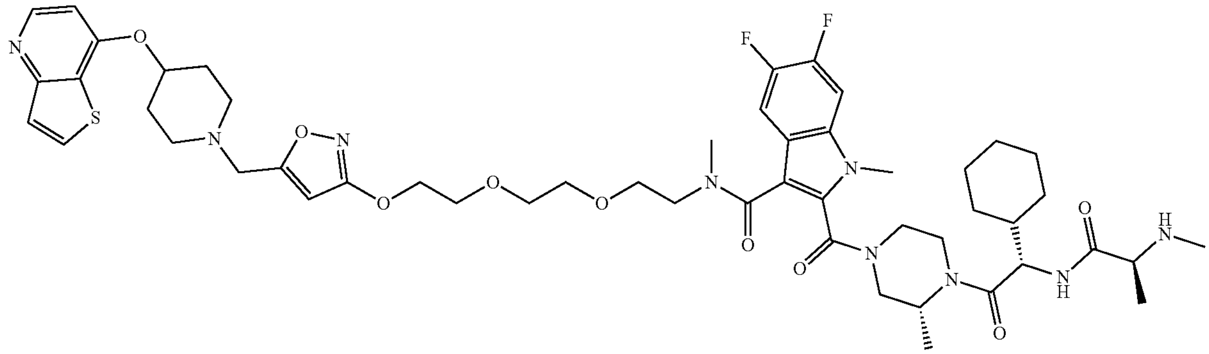 [SMILES: CN[C@@H](C)C(=O)N[C@H](C(=O)N1CCN(C(=O)c2c(C(=O)N(C)CCOCCOCCOc3cc(CN4CCC(Oc5ccnc6ccsc56)CC4)on3)c3cc(F)c(F)cc3n2C)C[C@H]1C)C1CCCCC1]

Salt type: HCl; MS value: 1020.7

Example Compound 12 (compound 12): 2-((S)-4-((S)-2-cyclohexyl-2-((S)-2-(methylamino)propanamido)acetyl)-2-methylpiperazine-1-carbonyl)-5,6-difluoro-1-methyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

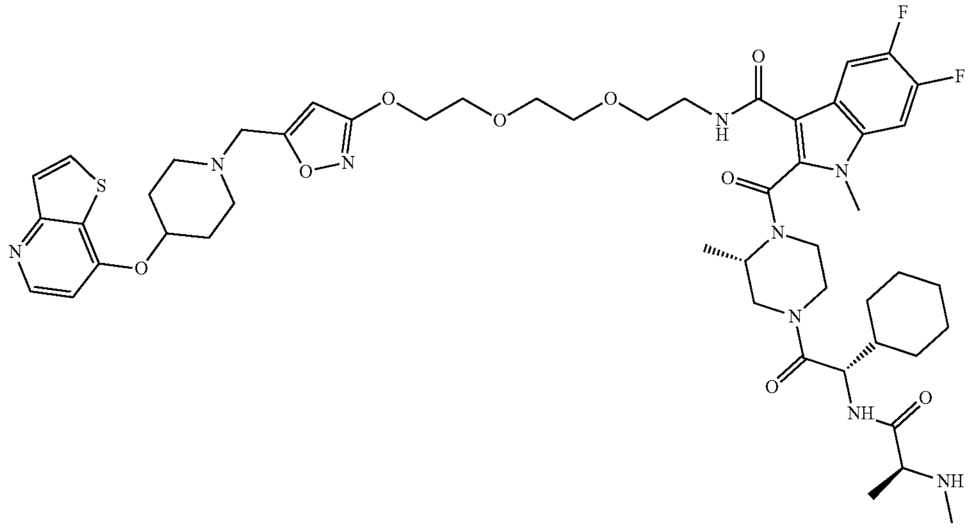 [SMILES: CN[C@@H](C)C(=O)N[C@H](C(=O)N1CCN(C(=O)c2c(C(=O)NCCOCCOCCOc3cc(CN4CCC(Oc5ccnc6ccsc56)CC4)on3)c3cc(F)c(F)cc3n2C)[C@@H](C)C1)C1CCCCC1]

Salt type: HCl; MS value: 1007.1

Example Compound 13 (compound 13): 2-(4-((S)-2-cyclohexyl-2-((S)-2-(methylamino)propanamido)acetyl)piperazine-1-carbonyl)-5-fluoro-6-methoxy-1-methyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

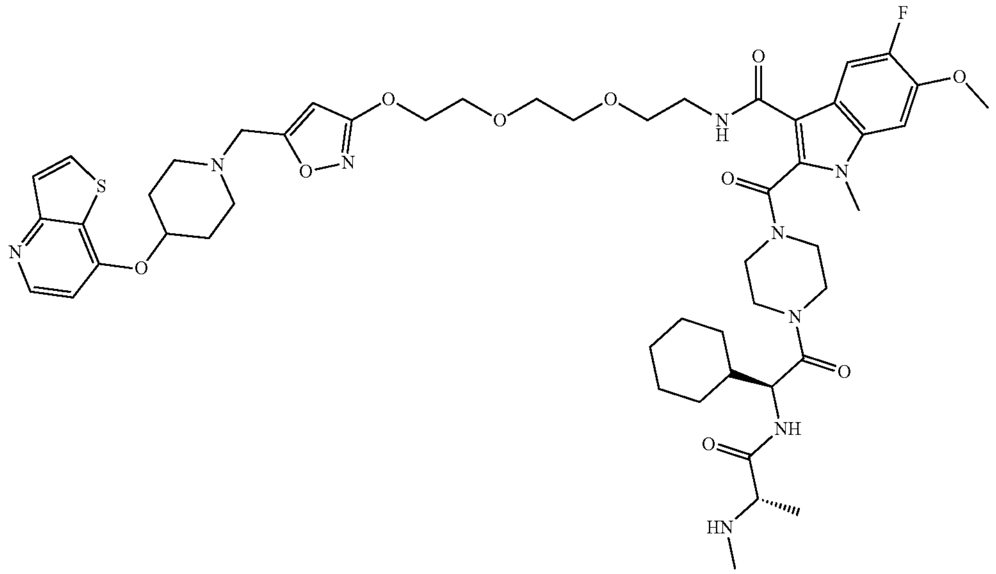 [SMILES: CN[C@@H](C)C(=O)N[C@H](C(=O)N1CCN(C(=O)c2c(C(=O)NCCOCCOCCOc3cc(CN4CCC(Oc5ccnc6ccsc56)CC4)on3)c3cc(F)c(OC)cc3n2C)CC1)C1CCCCC1]

Salt type: HCl; MS value: 1004.8

Example Compound 14 (compound 14): 5-fluoro-2-(4-((2S,3R)-3-hydroxy-4-methyl-2-((S)-2-(methylamino)propanamido)pentanoyl)piperazine-1-carbonyl)-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

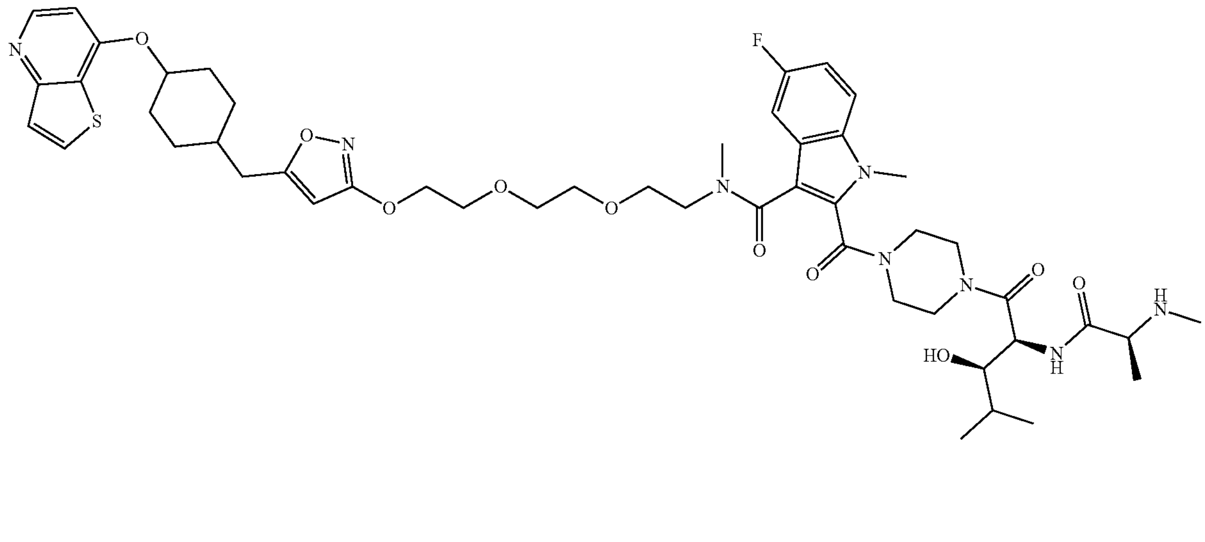 [SMILES: CN[C@@H](C)C(=O)N[C@H](C(=O)N1CCN(C(=O)c2c(C(=O)N(C)CCOCCOCCOc3cc(CC4CCC(Oc5ccnc6ccsc56)CC4)on3)c3cc(F)ccc3n2C)CC1)[C@H](O)C(C)C]

Salt type: HCl; MS value: 978.7

Example Compound 15 (compound 15): 5-fluoro-N,1-dimethyl-2-(4-((S)-2-((S)-2-(methylamino)propanamido)-3-(1H-pyrazol-1-yl)propanoyl)piperazine-1-carbonyl)-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

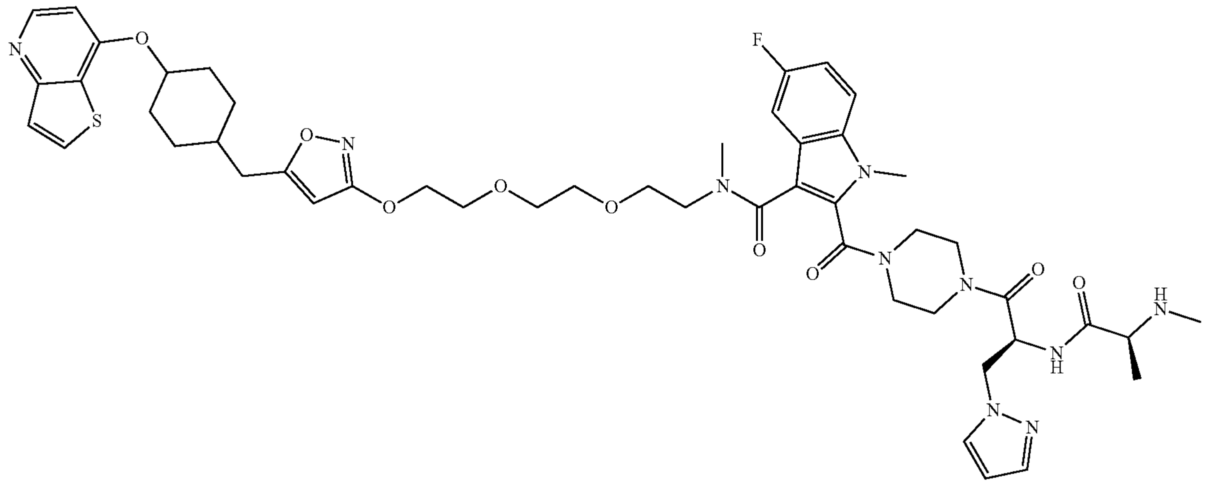 [SMILES: CN[C@@H](C)C(=O)N[C@@H](Cn1cccn1)C(=O)N1CCN(C(=O)c2c(C(=O)N(C)CCOCCOCCOc3cc(CC4CCC(Oc5ccnc6ccsc56)CC4)on3)c3cc(F)ccc3n2C)CC1]

Salt type: HCl; MS value: 986.8

Example Compound 16 (compound 16): 5-fluoro-2-(4-((S)-3-hydroxy-3-methyl-2-((S)-2-(methylamino)propanamido)butanoyl)piperazine-1-carbonyl)-N,1-dimethyl-N-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-3-carboxamide

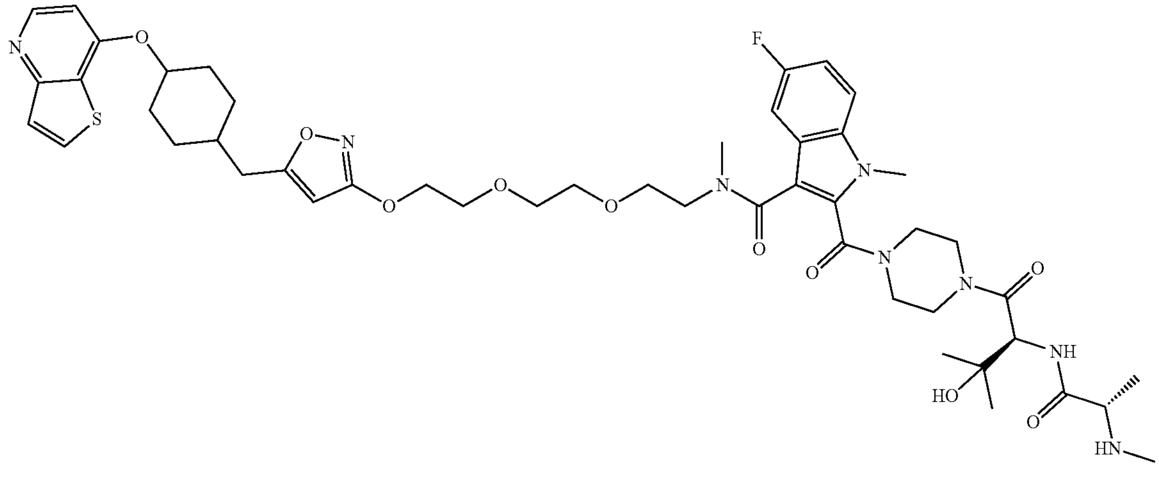 [SMILES: CN[C@@H](C)C(=O)N[C@H](C(=O)N1CCN(C(=O)c2c(C(=O)N(C)CCOCCOCCOc3cc(CC4CCC(Oc5ccnc6ccsc56)CC4)on3)c3cc(F)ccc3n2C)CC1)C(C)(C)O]

Salt type: HCl; MS value: 964.8

Example Compound 17 (compound 17): 1-((R)-4-(5,6-difluoro-1-methyl-1H-indole-2-carbonyl)-2-methylpiperazin-1-yl)-2-((2R,5R)-5-methyl-2-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazin-1-yl)ethan-1-one

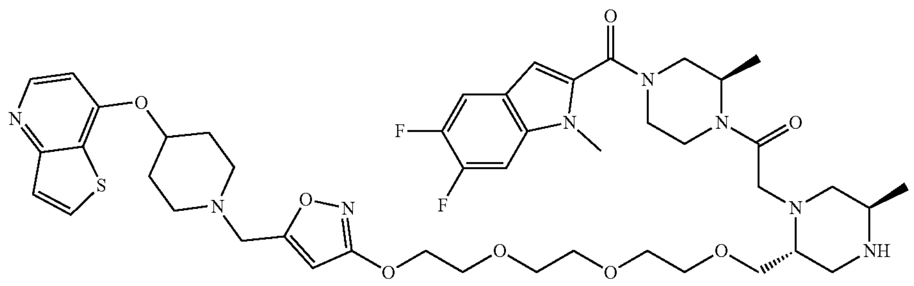 [SMILES: C[C@@H]1CN(CC(=O)N2CCN(C(=O)c3cc4cc(F)c(F)cc4n3C)C[C@H]2C)[C@@H](COCCOCCOCCOc2cc(CN3CCC(Oc4ccnc5ccsc45)CC3)on2)CN1]

Salt type: HCl; MS value: 909.7

Example Compound 18 (compound 18): 2-((2R,5R)-5-methyl-2-((2-(2-(2-((5-((4-(thieno[3,2-b]pyridin-7-yloxy)piperidin-1-yl)methyl)isoxazol-3-yl)oxy)ethoxy)ethoxy)ethoxy)methyl)piperazin-1-yl)-1-(4-(2-methylindolizine-6-carbonyl)piperazin-1-yl)ethan-1-one

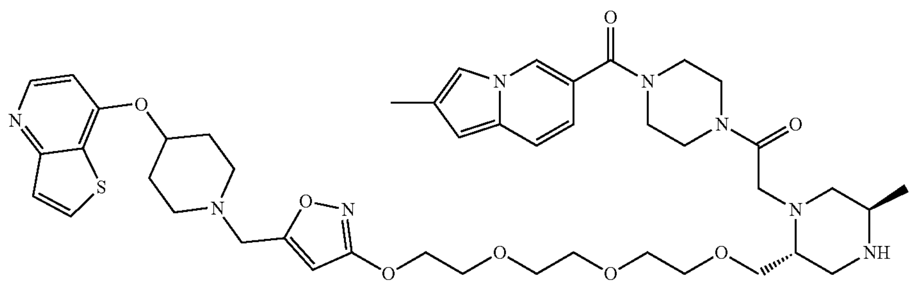 [SMILES: Cc1cc2ccc(C(=O)N3CCN(C(=O)CN4C[C@@H](C)NC[C@@H]4COCCOCCOCCOc4cc(CN5CCC(Oc6ccnc7ccsc67)CC5)on4)CC3)cn2c1]

Salt type: -; MS value: 859.5
Example Compound 19 (compound 19): 1-((R)-4-(5,6-difluoro-1-methyl-1H-indole-2-carbonyl)-2-methylpiperazin-1-yl)-2-((2R,5R)-5-methyl-2-(13-((5-((4-(thieno[3,2-b]pyridin-7-yloxy)piperidin-1-yl)methyl)isoxazol-3-yl)oxy)-2,5,8,11-tetraoxatridecyl)piperazin-1-yl)ethan-1-one
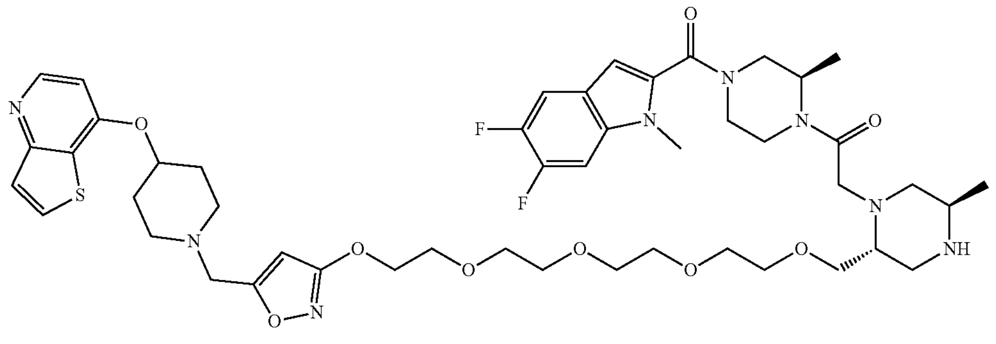 [SMILES: C[C@@H]1CN(CC(=O)N2CCN(C(=O)c3cc4cc(F)c(F)cc4n3C)C[C@H]2C)[C@@H](COCCOCCOCCOCCOc2cc(CN3CCC(Oc4ccnc5ccsc45)CC3)on2)CN1]

Salt type: HCl; MS value: 953.7

Example Compound 20 (compound 20): 1-((R)-4-(5,6-difluoro-1-methyl-1H-indole-2-carbonyl)-2-methylpiperazin-1-yl)-2-((2R,5R)-5-methyl-2-((2-(2-((5-((4-(thieno[3,2-b]pyridin-7-yloxy)piperidin-1-yl)methyl)isoxazol-3-yl)oxy)ethoxy)ethoxy)methyl)piperazin-1-yl)ethan-1-one

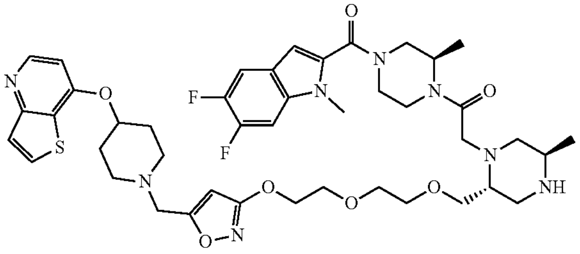 [SMILES: C[C@@H]1CN(CC(=O)N2CCN(C(=O)c3cc4cc(F)c(F)cc4n3C)C[C@H]2C)[C@@H](COCCOCCOc2cc(CN3CCC(Oc4ccnc5ccsc45)CC3)on2)CN1]

Salt type: -; MS value: 865.8

Example Compound 21 (compound 21): (S)—N—((S)-1-cyclohexyl-2-(4-(5,6-difluoro-1-methyl-3-(2-(2-(2-((5-((4-(thieno[3,2-b]pyridin-7-yloxy)piperidin-1-yl)methyl)isoxazol-3-yl)oxy)ethoxy)ethoxy)ethoxy)-1H-indole-2-carbonyl)piperazin-1-yl)-2-oxoethyl)-2-(methylamino)propanamide

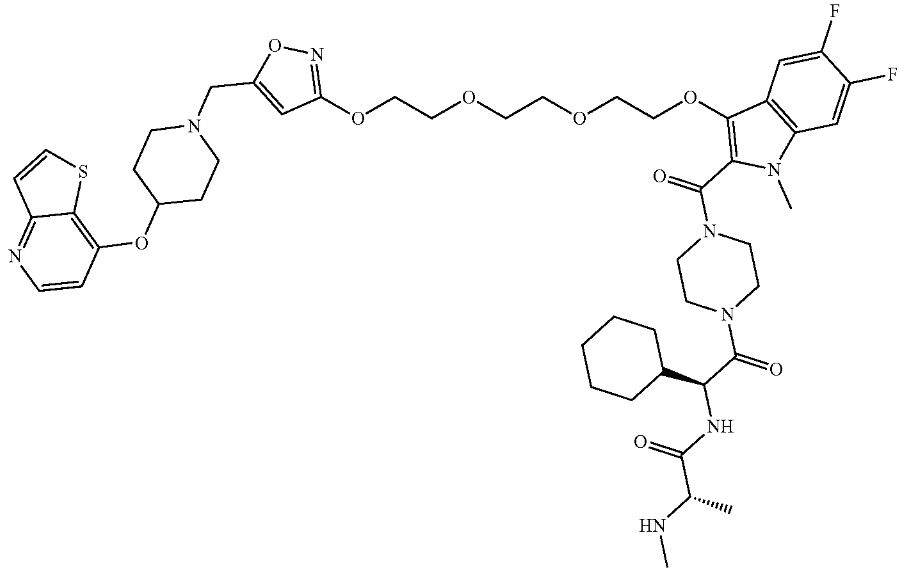 [SMILES: CN[C@@H](C)C(=O)N[C@H](C(=O)N1CCN(C(=O)c2c(OCCOCCOCCOc3cc(CN4CCC(Oc5ccnc6ccsc56)CC4)on3)c3cc(F)c(F)cc3n2C)CC1)C1CCCCC1]

Salt type: HCl; MS value: 966.4

Example Compound 22 (compound 22): (S)—N—((S)-1-cyclohexyl-2-(4-(5,6-difluoro-1-methyl-3-(2-(2-((5-((4-(thieno[3,2-b]pyridin-7-yloxy)piperidin-1-yl)methyl)isoxazol-3-yl)oxy)ethoxy)ethoxy)-1H-indole-2-carbonyl)piperazin-1-yl)-2-oxoethyl)-2-(methylamino)propanamide

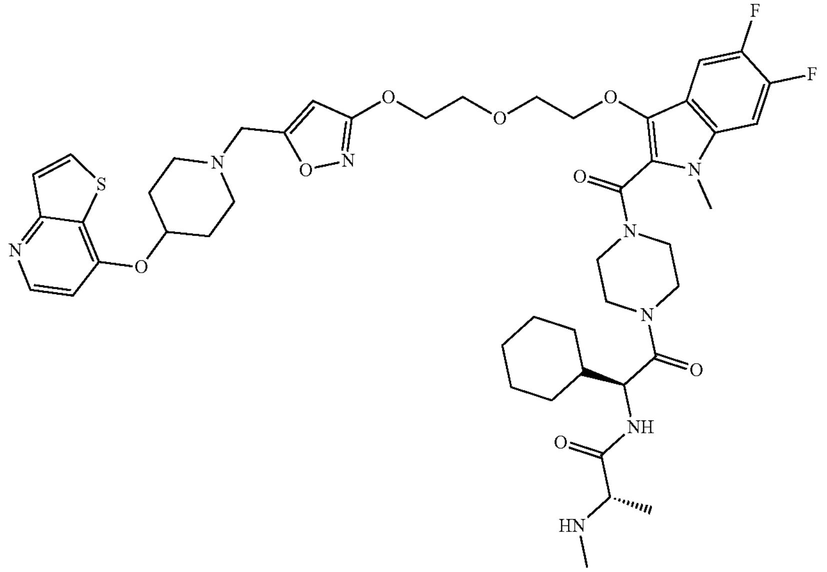 [SMILES: CN[C@@H](C)C(=O)N[C@H](C(=O)N1CCN(C(=O)c2c(OCCOCCOc3cc(CN4CCC(Oc5ccnc6ccsc56)CC4)on3)c3cc(F)c(F)cc3n2C)CC1)C1CCCCC1]

Salt type: -; MS value: 921.6

Example Compound 23 (compound 23): (S)—N—((S)-1-cyclohexyl-2-(4-(5,6-difluoro-1-methyl-3-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)-1H-indole-2-carbonyl)piperazin-1-yl)-2-oxoethyl)-2-(methylamino)propanamide

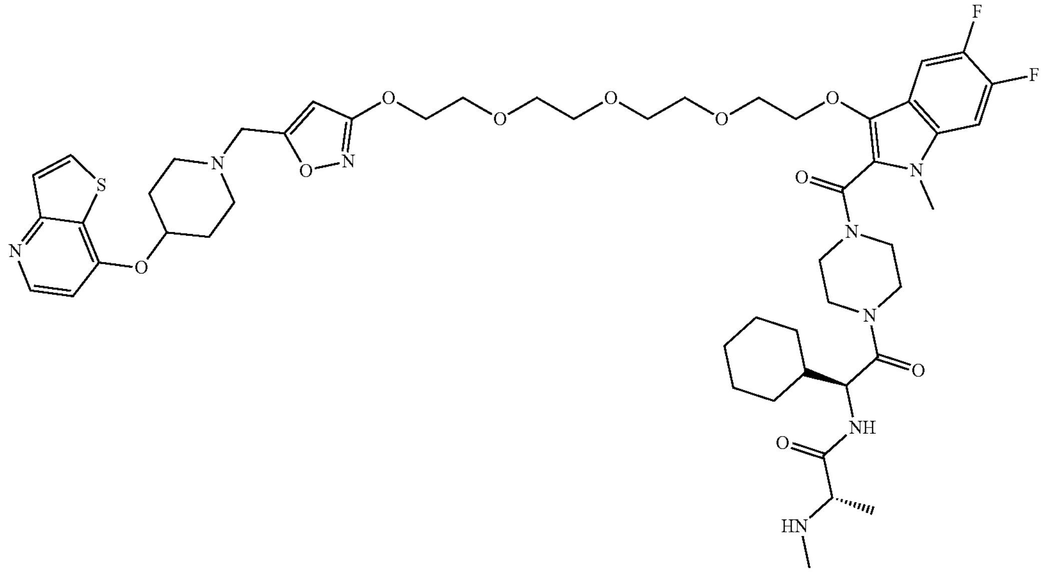 [SMILES: CN[C@@H](C)C(=O)N[C@H](C(=O)N1CCN(C(=O)c2c(OCCOCCOCCOCCOc3cc(CN4CCC(Oc5ccnc6ccsc56)CC4)on3)c3cc(F)c(F)cc3n2C)CC1)C1CCCCC1]

Salt type: -; MS value: 1009.5

Example Compound 24 (compound 24): (S)—N—((S)-1-cyclohexyl-2-(4-(5,6-difluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)-2-(methylamino)propanamide

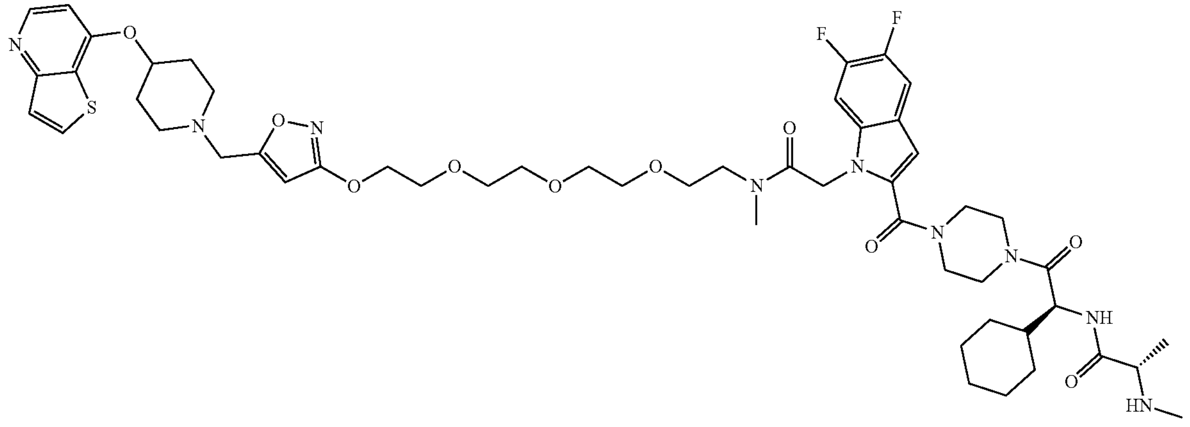 [SMILES: CN[C@@H](C)C(=O)N[C@H](C(=O)N1CCN(C(=O)c2cc3cc(F)c(F)cc3n2CC(=O)N(C)CCOCCOCCOCCOc2cc(CN3CCC(Oc4ccnc5ccsc45)CC3)on2)CC1)C1CCCCC1]

Salt type: HCl; MS value: 1050.3

Example Compound 25 (compound 25): (S)—N—((S)-1-cyclohexyl-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide

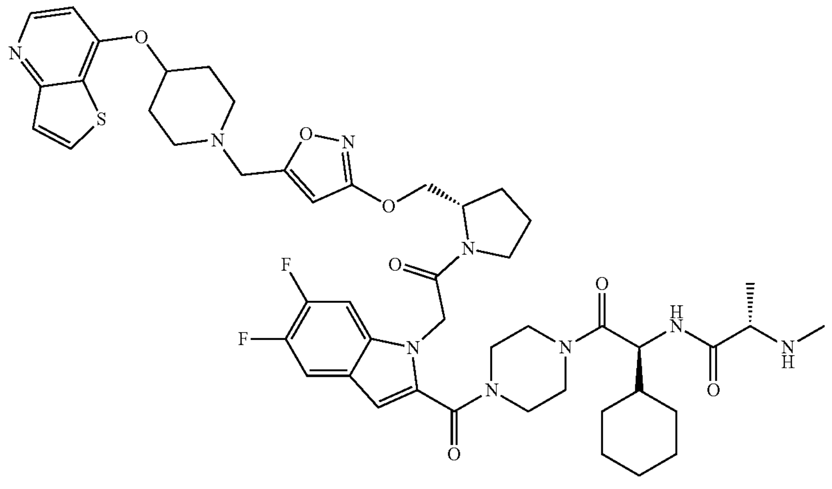 [SMILES: CN[C@@H](C)C(=O)N[C@H](C(=O)N1CCN(C(=O)c2cc3cc(F)c(F)cc3n2CC(=O)N2CCC[C@H]2COc2cc(CN3CCC(Oc4ccnc5ccsc45)CC3)on2)CC1)C1CCCCC1]

Salt type: -; MS value: 944.2

Example Compound 26 (compound 26): (S)—N—((S)-1-cyclohexyl-2-(4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-piperazin-1-yl)-2-oxoethyl)-2-(methylamino)propanamide

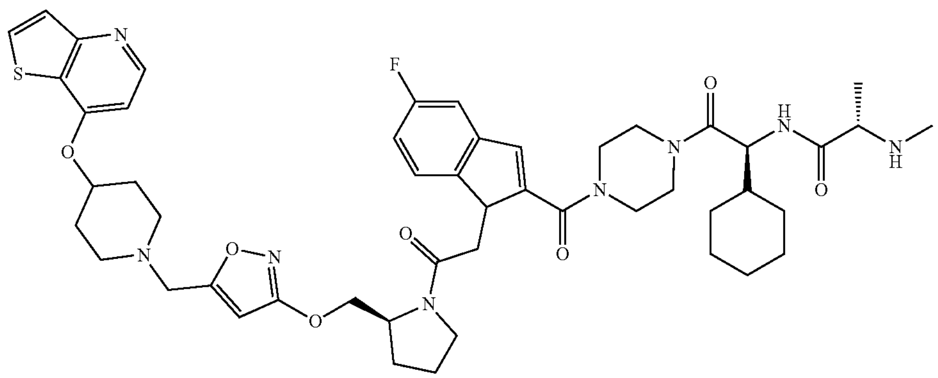 [SMILES: CN[C@@H](C)C(=O)N[C@H](C(=O)N1CCN(C(=O)C2=Cc3cc(F)ccc3C2CC(=O)N2CCC[C@H]2COc2cc(CN3CCC(Oc4ccnc5ccsc45)CC3)on2)CC1)C1CCCCC1]

Salt type: -; MS value: 926.1

Example Compound 27 (compound 27): (S)—N—((S)-1-cyclohexyl-2-((S)-4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide

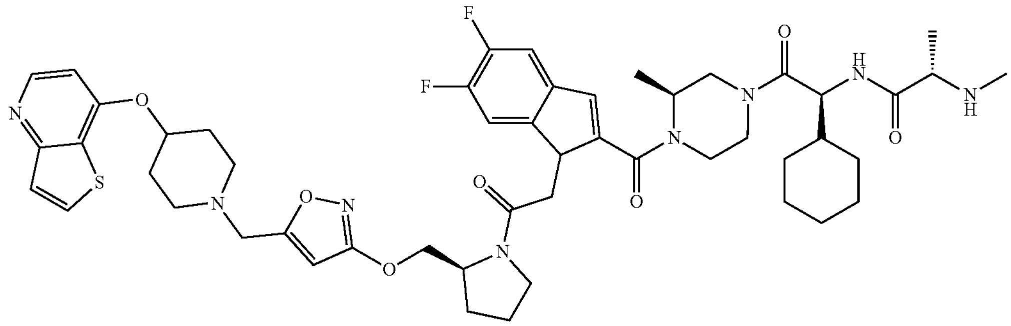 [SMILES: CN[C@@H](C)C(=O)N[C@H](C(=O)N1CCN(C(=O)C2=Cc3cc(F)c(F)cc3C2CC(=O)N2CCC[C@H]2COc2cc(CN3CCC(Oc4ccnc5ccsc45)CC3)on2)[C@@H](C)C1)C1CCCCC1]

Salt type: -; MS value: 958.4

Example Compound 28 (compound 28): (S)—N—((S)-1-cyclohexyl-2-((S)-4-(5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-2-oxoethyl)-2-(methylamino)propanamide

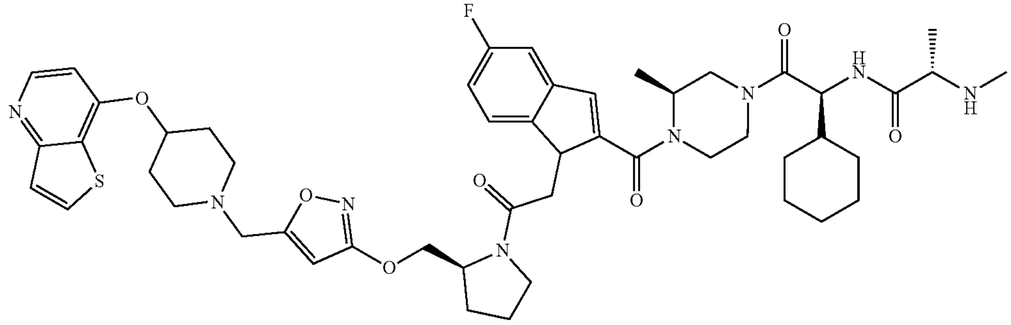 [SMILES: CN[C@@H](C)C(=O)N[C@H](C(=O)N1CCN(C(=O)C2=Cc3cc(F)ccc3C2CC(=O)N2CCC[C@H]2COc2cc(CN3CCC(Oc4ccnc5ccsc45)CC3)on2)[C@@H](C)C1)C1CCCCC1]

Salt type: -; MS value: 940.4

Example Compound 29 (compound 29): (S)—N—((S)-1-cyclohexyl-2-(4-(5,6-difluoro-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-2-carbonyl)piperazin-1-yl)-2-oxoethyl)-2-(methylamino)propanamide

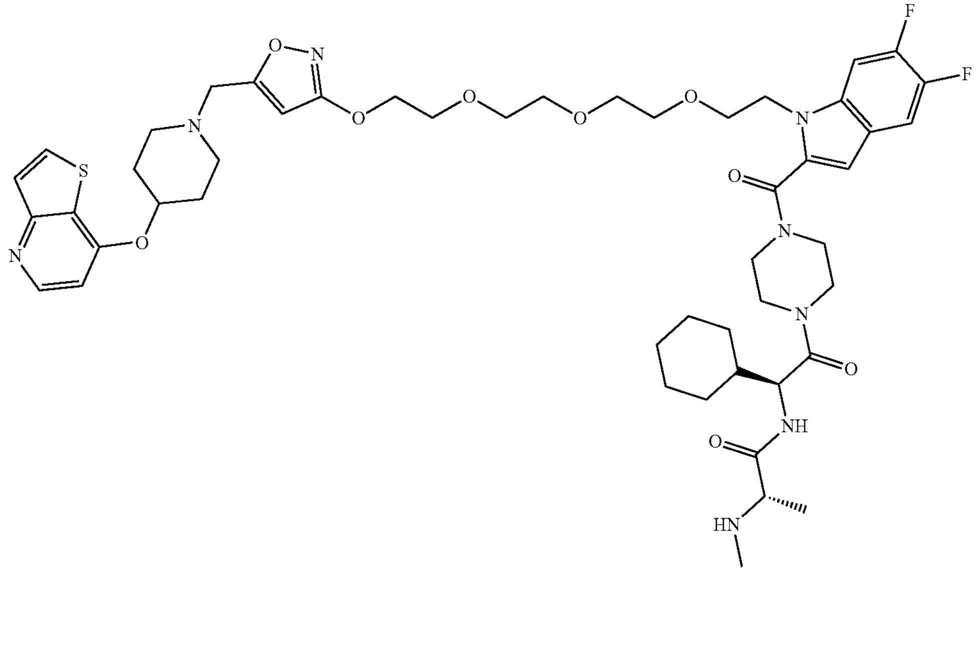 [SMILES: CN[C@@H](C)C(=O)N[C@H](C(=O)N1CCN(C(=O)c2cc3cc(F)c(F)cc3n2CCOCCOCCOCCOc2cc(CN3CCC(Oc4ccnc5ccsc45)CC3)on2)CC1)C1CCCCC1]

Salt type: -; MS value: 9/9.5

Example Compound 30 (compound 30): (S)—N—((S)-1-cyclohexyl-2-(4-(5,6-difluoro-1-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-2-carbonyl)piperazin-1-yl)-2-oxoethyl)-2-(methylamino)propanamide

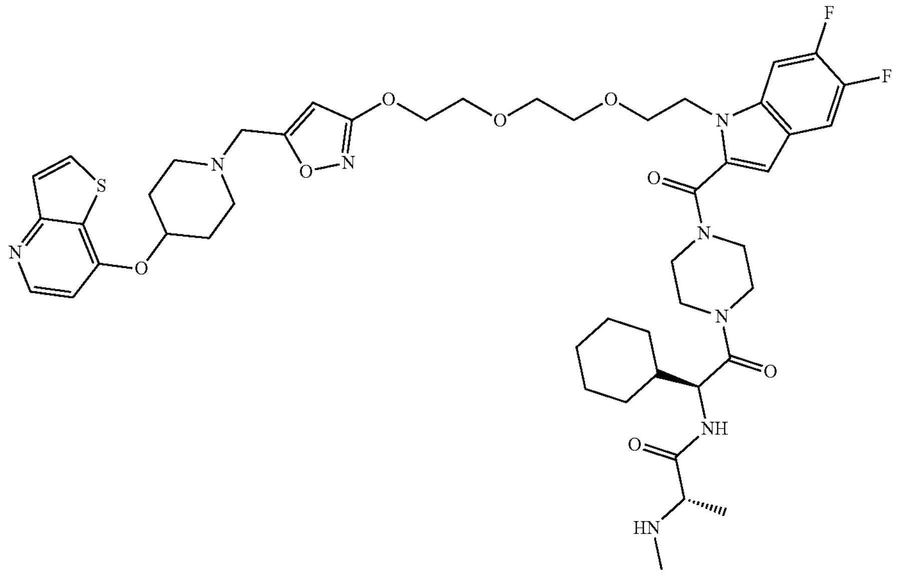 [SMILES: CN[C@@H](C)C(=O)N[C@H](C(=O)N1CCN(C(=O)c2cc3cc(F)c(F)cc3n2CCOCCOCCOc2cc(CN3CCC(Oc4ccnc5ccsc45)CC3)on2)CC1)C1CCCCC1]

Salt type: HCl; MS value: 935.5

Example Compound 31 (compound 31): (S)—N—((S)-1-cyclohexyl-2-(4-(5,6-difluoro-1-(2-oxo-2-((R)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide

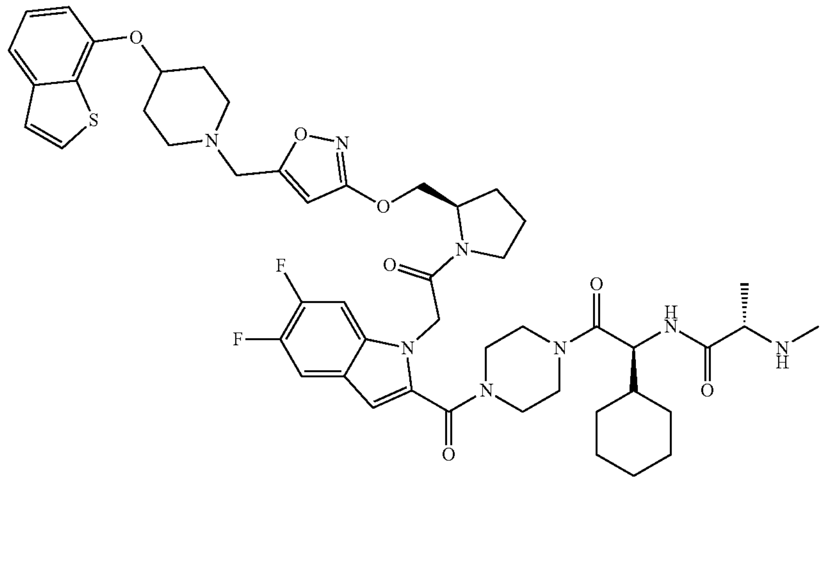

Salt type: HCl; MS value: 945.5

Example Compound 32 (compound 32): (S)—N—((S)-2-(4-(3-chloro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-1-cyclohexyl-2-oxoethyl)-2-(methylamino)propanamide

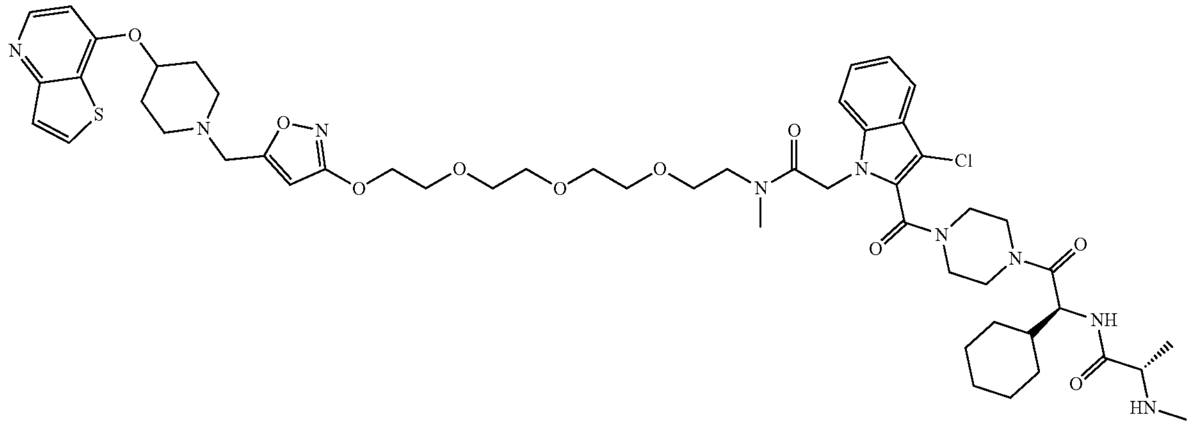 [SMILES: CN[C@@H](C)C(=O)N[C@H](C(=O)N1CCN(C(=O)c2c(Cl)c3ccccc3n2CC(=O)N(C)CCOCCOCCOCCOc2cc(CN3CCC(Oc4ccnc5ccsc45)CC3)on2)CC1)C1CCCCC1]

Salt type: HCl; MS value: 1048.9

Example Compound 33 (compound 33): (S)—N—((S)-1-cyclohexyl-2-(4-(5-fluoro-3-methyl-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)-2-(methylamino)propanamide

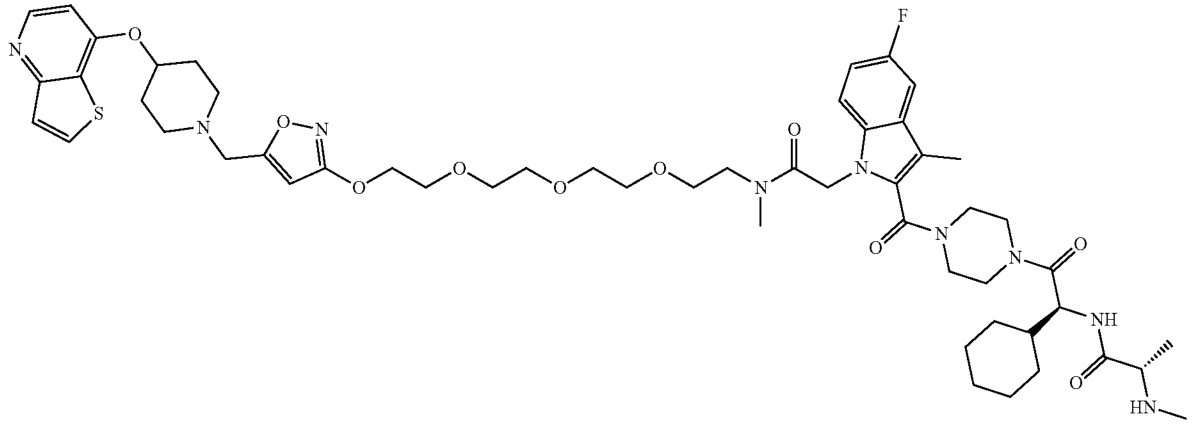 [SMILES: CN[C@@H](C)C(=O)N[C@H](C(=O)N1CCN(C(=O)c2c(C)c3cc(F)ccc3n2CC(=O)N(C)CCOCCOCCOCCOc2cc(CN3CCC(Oc4ccnc5ccsc45)CC3)on2)CC1)C1CCCCC1]

Salt type: HCl; MS value: 1047.0

Example Compound 34 (compound 34): (S)—N—((S)-2-(4-(3-chloro-5-fluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-1-cyclohexyl-2-oxoethyl)-2-(methylamino)propanamide

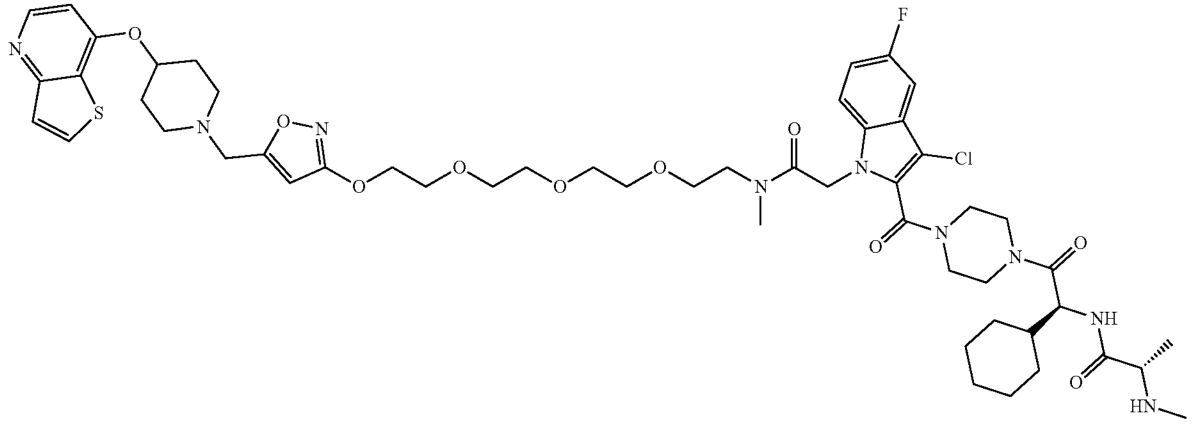 [SMILES: CN[C@@H](C)C(=O)N[C@H](C(=O)N1CCN(C(=O)c2c(Cl)c3cc(F)ccc3n2CC(=O)N(C)CCOCCOCCOCCOc2cc(CN3CCC(Oc4ccnc5ccsc45)CC3)on2)CC1)C1CCCCC1]

Salt type: HCl; MS value: 1066.9

Example Compound 35 (compound 35): (S)—N—((S)-1-cyclohexyl-2-(4-(3-methyl-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)-2-(methylamino)propanamide

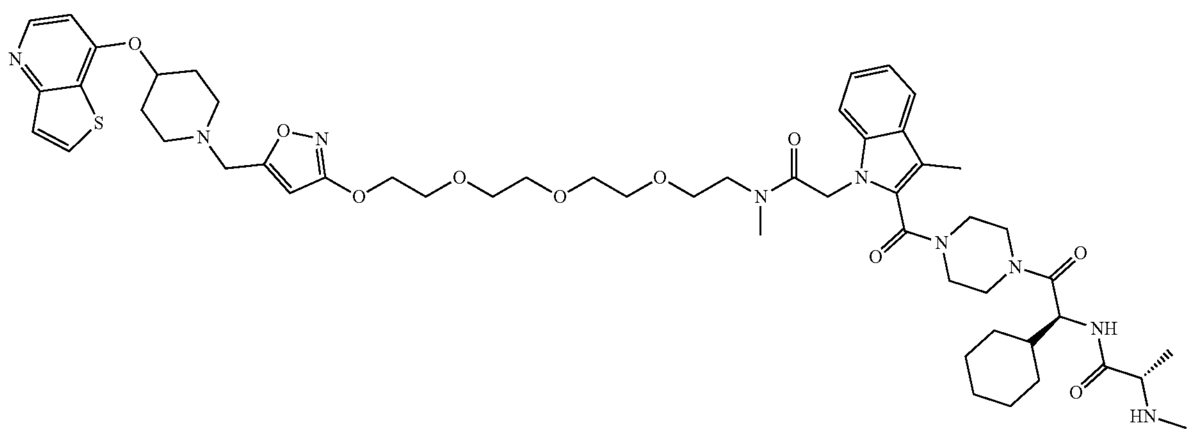 [SMILES: CN[C@@H](C)C(=O)N[C@H](C(=O)N1CCN(C(=O)c2c(C)c3ccccc3n2CC(=O)N(C)CCOCCOCCOCCOc2cc(CN3CCC(Oc4ccnc5ccsc45)CC3)on2)CC1)C1CCCCC1]

Salt type: HCl; MS value: 1028.7

Example Compound 36 (compound 36): (S)—N—((S)-1-cyclohexyl-2-(4-(3,5-difluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)-2-(methylamino)propanamide

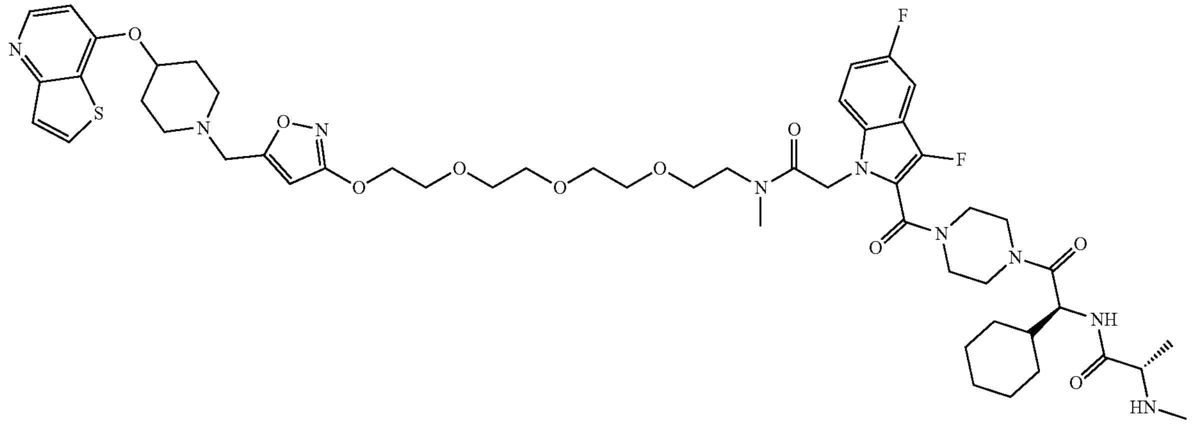

Salt type: HCl; MS value: 1050.7

Example Compound 37 (compound 37): (S)—N—((S)-1-cyclohexyl-2-(4-(3-fluoro-1-(3-methyl-2-oxo-14-((5-((4-(thieno[3,2-b]pyridin-7-yloxy)piperidin-1-yl)methyl)isoxazol-3-yl)oxy)-6,9,12-trioxa-3-azatetradecyl)-1H-indole-2-carbonyl)piperazin-1-yl)-2-oxoethyl)-2-(methylamino)propanamide

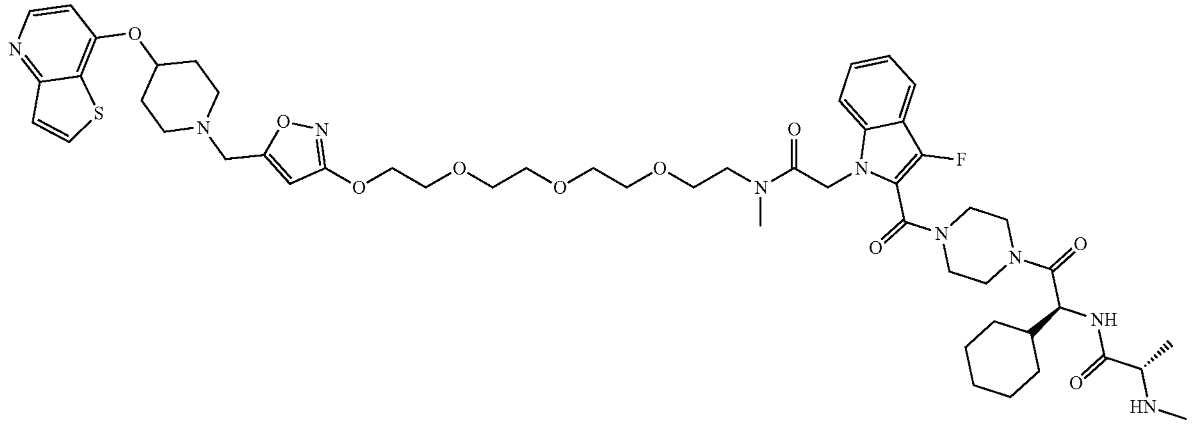

Salt type: -; MS value: 1033.0

Example Compound 38 (compound 38): (S)—N—((S)-2-(4-(3-chloro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-1-cyclohexyl-2-oxoethyl)-2-(methylamino)propanamide

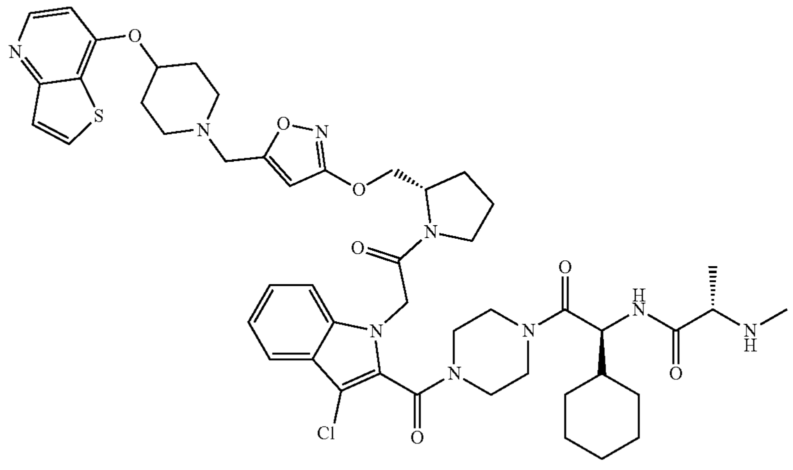 [SMILES: CN[C@@H](C)C(=O)N[C@H](C(=O)N1CCN(C(=O)c2c(Cl)c3ccccc3n2CC(=O)N2CCC[C@H]2COc2cc(CN3CCC(Oc4ccnc5ccsc45)CC3)on2)CC1)C1CCCCC1]

Salt type: HCl; MS value: 942.6

Example Compound 39 (compound 39): (S)—N—((S)-1-cyclohexyl-2-(4-(5-fluoro-3-methyl-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide

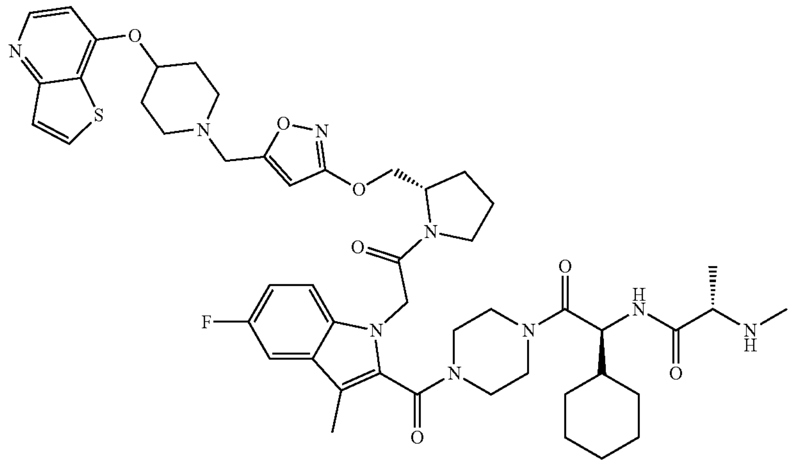 [SMILES: CN[C@@H](C)C(=O)N[C@H](C(=O)N1CCN(C(=O)c2c(C)c3cc(F)ccc3n2CC(=O)N2CCC[C@H]2COc2cc(CN3CCC(Oc4ccnc5ccsc45)CC3)on2)CC1)C1CCCCC1]

Salt type: HCl; MS value: 940.7

Example Compound 40 (compound 40): (S)—N—((S)-2-(4-(3-chloro-5-fluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-1-cyclohexyl-2-oxoethyl)-2-(methylamino)propanamide

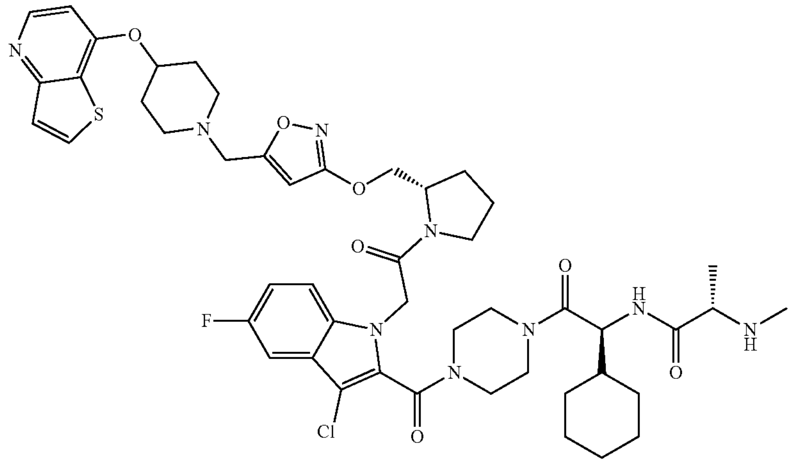

Salt type: HCl; MS value: 960.6

Example Compound 41 (compound 41): (S)—N—((S)-1-cyclohexyl-2-(4-(3,5-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-2-oxoethyl)-2-(methylamino)propanamide

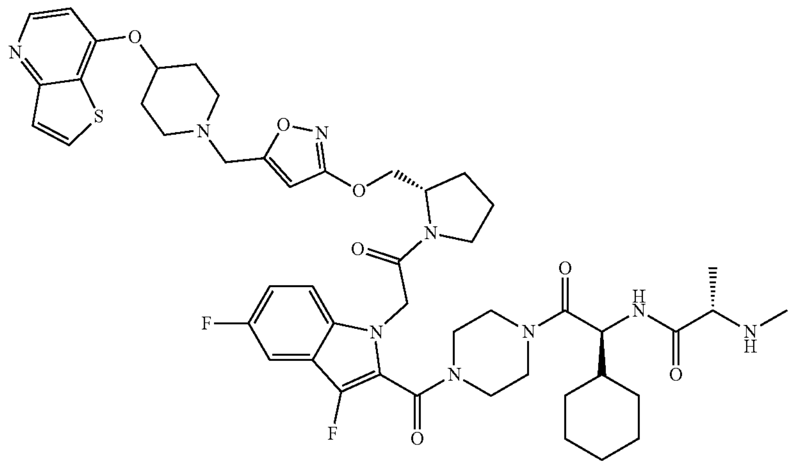

Salt type: HCl; MS value: 944.8

Example Compound 42 (compound 42): (S)—N—((S)-1-cyclohexyl-2-((S)-4-(5-fluoro-1-(2-((2S,4S)-4-hydroxy-2-(((5-((4-(thieno[3,2-b]pyridin-7-yloxy)piperidin-1-yl)methyl)isoxazol-3-yl)oxy)methyl)pyrrolidin-1-yl)-2-oxoethyl)-1H-indole-2-carbonyl)-3-methylpiperazin-1-yl)-2-oxoethyl)-2-(methylamino)propanamide

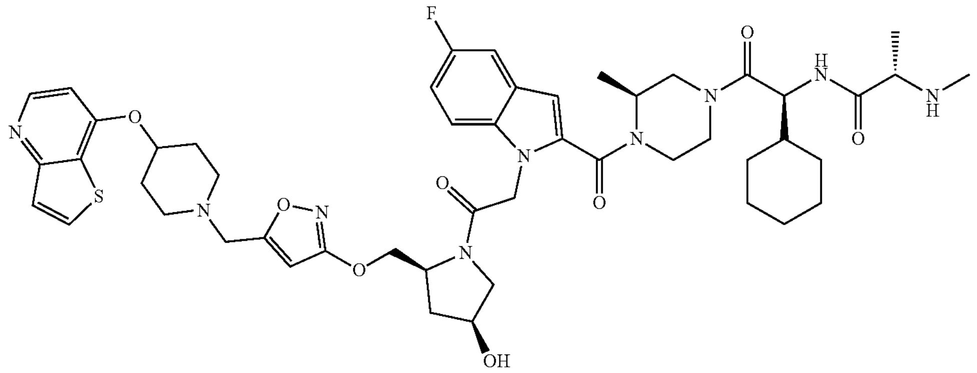 [SMILES: CN[C@@H](C)C(=O)N[C@H](C(=O)N1CCN(C(=O)c2cc3cc(F)ccc3n2CC(=O)N2C[C@@H](O)C[C@H]2COc2cc(CN3CCC(Oc4ccnc5ccsc45)CC3)on2)[C@@H](C)C1)C1CCCCC1]

Salt type: TFA; MS value: 956.8

Example Compound 43 (compound 43): (S)—N—((S)-1-cyclohexyl-2-((S)-4-(5-fluoro-1-(2-((2S,4S)-2-(hydroxymethyl)-4-((5-((4-(thieno[3,2-b]pyridin-7-yloxy)piperidin-1-yl)methyl)isoxazol-3-yl)oxy)pyrrolidin-1-yl)-2-oxoethyl)-1H-indole-2-carbonyl)-3-methylpiperazin-1-yl)-2-oxoethyl)-2-(methylamino)propanamide

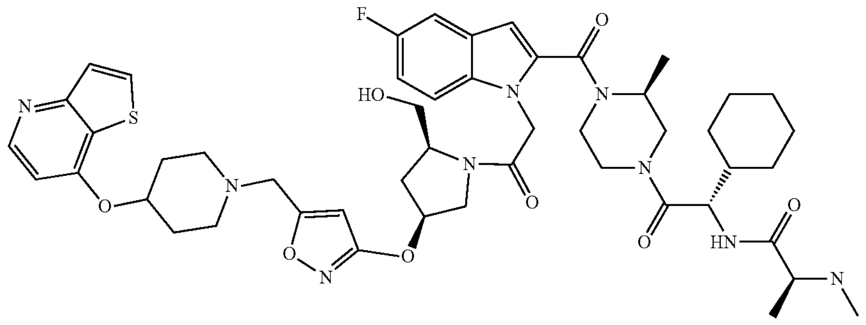 [SMILES: CN[C@@H](C)C(=O)N[C@H](C(=O)N1CCN(C(=O)c2cc3cc(F)ccc3n2CC(=O)N2C[C@@H](Oc3cc(CN4CCC(Oc5ccnc6ccsc56)CC4)on3)C[C@H]2CO)[C@@H](C)C1)C1CCCCC1]

Salt type: -; MS value: 956.8

Example Compound 44 (compound 44): (S)—N—((S)-1-cyclohexyl-2-(4-(5,6-difluoro-1-(2-oxo-2-((S)-3-(((5-((4-(thieno[3,2-b]pyridin-7-yloxy)piperidin-1-yl)methyl)isoxazol-3-yl)oxy)methyl)morpholino)ethyl)-1H-indole-2-carbonyl)piperazin-1-yl)-2-oxoethyl)-2-(methylamino)propanamide

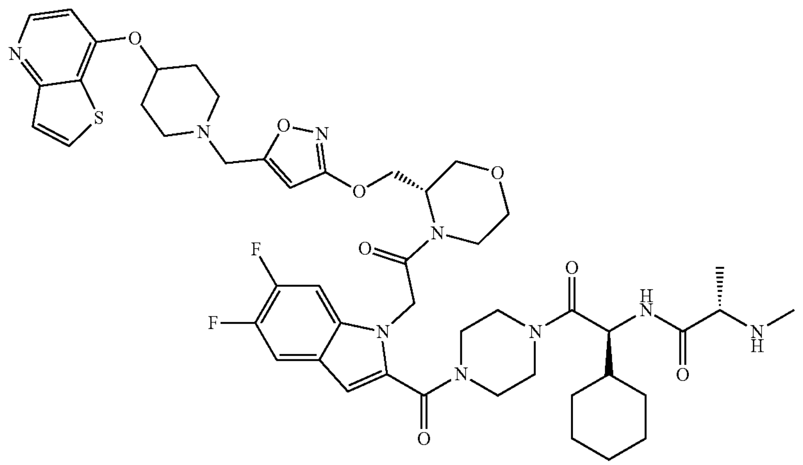 [SMILES: CN[C@@H](C)C(=O)N[C@H](C(=O)N1CCN(C(=O)c2cc3cc(F)c(F)cc3n2CC(=O)N2CCOC[C@H]2COc2cc(CN3CCC(Oc4ccnc5ccsc45)CC3)on2)CC1)C1CCCCC1]

Salt type: TFA; MS value: 960.7

Example Compound 45 (compound 45): (S)—N—((S)-1-cyclohexyl-2-(4-(5,6-difluoro-1-(2-oxo-2-((R)-3-(((5-((4-(thieno[3,2-b]pyridin-7-yloxy)piperidin-1-yl)methyl)isoxazol-3-yl)oxy)methyl)morpholino)ethyl)-1H-indole-2-carbonyl)piperazin-1-yl)-2-oxoethyl)-2-(methylamino)propanamide

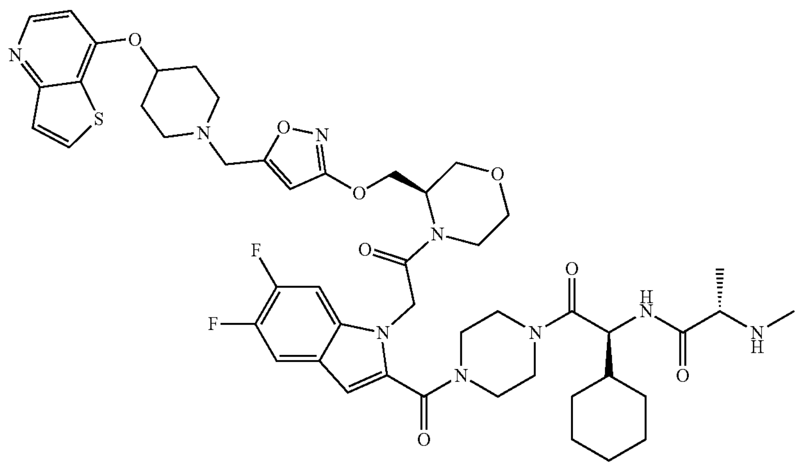 [SMILES: CN[C@@H](C)C(=O)N[C@H](C(=O)N1CCN(C(=O)c2cc3cc(F)c(F)cc3n2CC(=O)N2CCOC[C@@H]2COc2cc(CN3CCC(Oc4ccnc5ccsc45)CC3)on2)CC1)C1CCCCC1]

Salt type: TFA; MS value: 960.7

Example Compound 46 (compound 46): (S)—N—((S)-1-cyclohexyl-2-((S)-4-(5-fluoro-1-(2-oxo-2-((R)-3-(((5-((4-(thieno[3,2-b]pyridin-7-yloxy)piperidin-1-yl)methyl)isoxazol-3-yl)oxy)methyl)morpholino)ethyl)-1H-indole-2-carbonyl)-3-methylpiperazin-1-yl)-2-oxoethyl)-2-(methylamino)propanamide

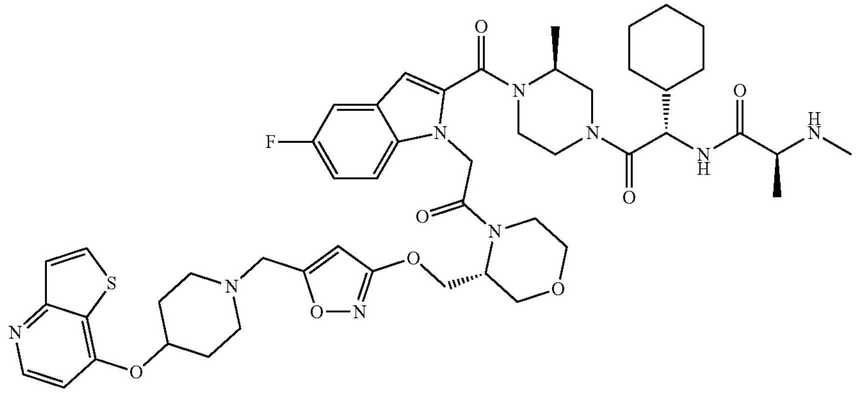 [SMILES: CN[C@@H](C)C(=O)N[C@H](C(=O)N1CCN(C(=O)c2cc3cc(F)ccc3n2CC(=O)N2CCOC[C@@H]2COc2cc(CN3CCC(Oc4ccnc5ccsc45)CC3)on2)[C@@H](C)C1)C1CCCCC1]

Salt type: TFA; MS value: 956.4

Example Compound 47 (compound 47): (S)—N—((S)-1-cyclohexyl-2-((S)-4-(5-fluoro-1-(2-oxo-2-((S)-3-(((5-((4-(thieno[3,2-b]pyridin-7-yloxy)piperidin-1-yl)methyl)isoxazol-3-yl)oxy)methyl)morpholino)ethyl)-1H-indole-2-carbonyl)-3-methylpiperazin-1-yl)-2-oxoethyl)-2-(methylamino)propanamide

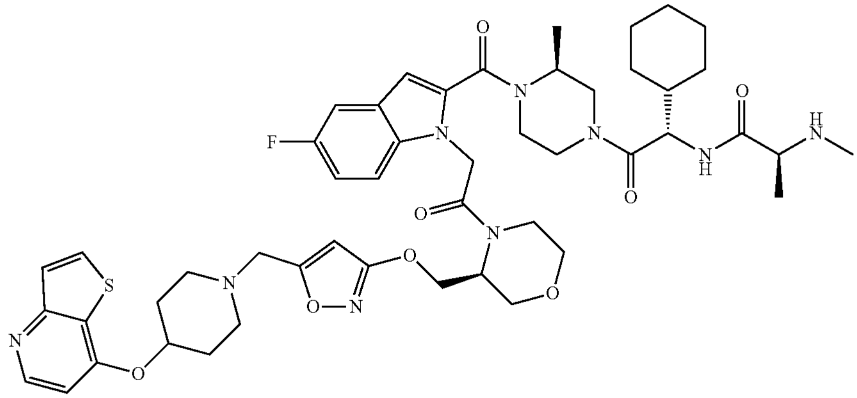 [SMILES: CN[C@@H](C)C(=O)N[C@H](C(=O)N1CCN(C(=O)c2cc3cc(F)ccc3n2CC(=O)N2CCOC[C@H]2COc2cc(CN3CCC(Oc4ccnc5ccsc45)CC3)on2)[C@@H](C)C1)C1CCCCC1]

Salt type: TFA; MS value: 956.2

Example Compound 48 (compound 48): (S)—N—((S)-2-(4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)piperazin-1-yl)-1-(4,4-difluorocyclohexyl)-2-oxoethyl)-2-(methylamino)propanamide

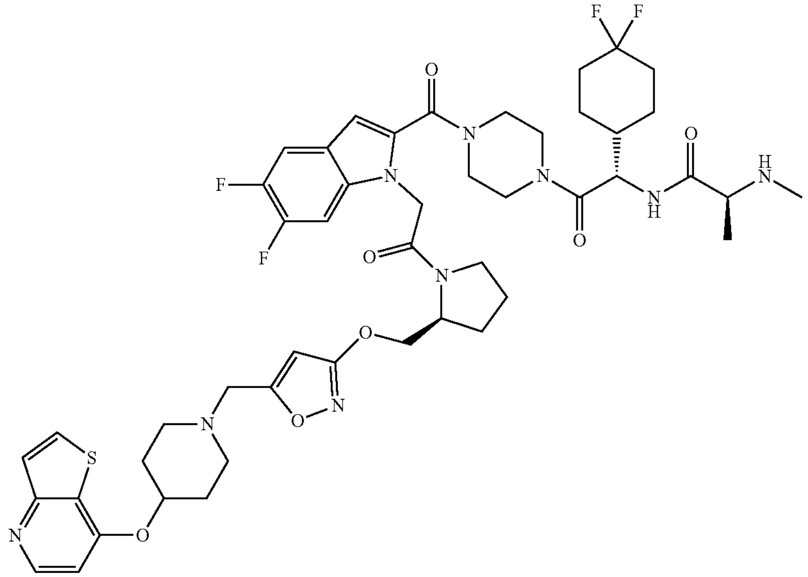 [SMILES: CN[C@@H](C)C(=O)N[C@H](C(=O)N1CCN(C(=O)c2cc3cc(F)c(F)cc3n2CC(=O)N2CCC[C@H]2COc2cc(CN3CCC(Oc4ccnc5ccsc45)CC3)on2)CC1)C1CCC(F)(F)CC1]

Salt type: TFA; MS value: 980.6

Example Compound 49 (compound 49): (S)—N—((S)-2-((S)-4-(5,6-difluoro-1-(2-oxo-2-((S)-2-(((5-((4-(thieno[3,2-b]pyridin-7-yloxy)piperidin-1-yl)methyl)isoxazol-3-yl)oxy)methyl)pyrrolidin-1-yl)ethyl)-1H-indole-2-carbonyl)-3-methylpiperazin-1-yl)-1-(4,4-difluorocyclohexyl)-2-oxoethyl)-2-(methylamino)propanamide

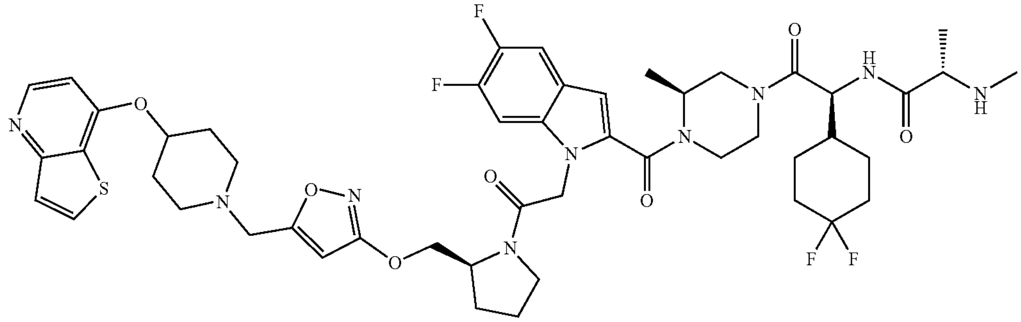 [SMILES: CN[C@@H](C)C(=O)N[C@H](C(=O)N1CCN(C(=O)c2cc3cc(F)c(F)cc3n2CC(=O)N2CCC[C@H]2COc2cc(CN3CCC(Oc4ccnc5ccsc45)CC3)on2)[C@@H](C)C1)C1CCC(F)(F)CC1]

Salt type: TFA; MS value: 994.7

Example Compound 50 (compound 50): (S)—N—((S)-1-cyclohexyl-2-((S)-4-(5-fluoro-1-(2-(methyl(2-((5-((4-(thieno[3,2-b]pyridin-7-yloxy)piperidin-1-yl)methyl)isoxazol-3-yl)oxy)ethyl)amino)-2-oxoethyl)-1H-indole-2-carbonyl)-3-methylpiperazin-1-yl)-2-oxoethyl)-2-(methylamino)propanamide

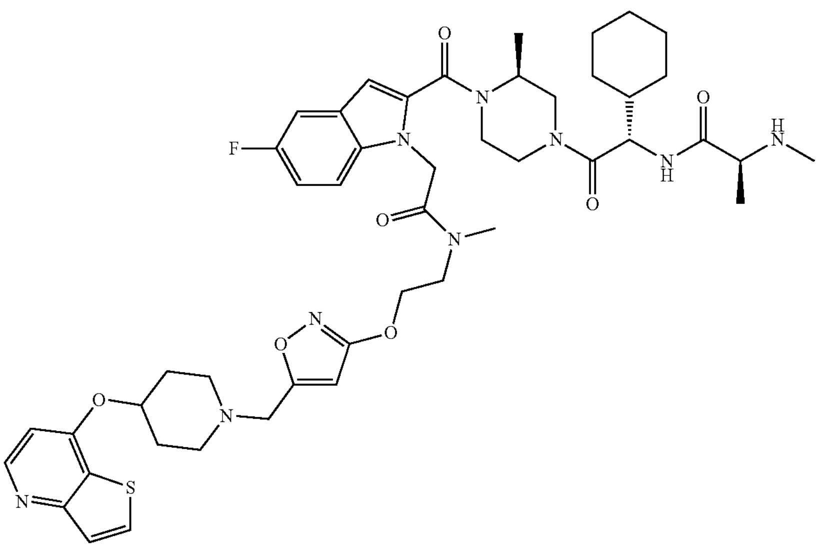 [SMILES: CN[C@@H](C)C(=O)N[C@H](C(=O)N1CCN(C(=O)c2cc3cc(F)ccc3n2CC(=O)N(C)CCOc2cc(CN3CCC(Oc4ccnc5ccsc45)CC3)on2)[C@@H](C)C1)C1CCCCC1]

Salt type: TFA; MS value: 914.7

Example Compound 51 (compound 51): (S)—N—((S)-1-cyclohexyl-2-(4-(5,6-difluoro-1-methyl-4-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)-1H-indole-2-carbonyl)piperazin-1-yl)-2-oxoethyl)-2-(methylamino)propanamide

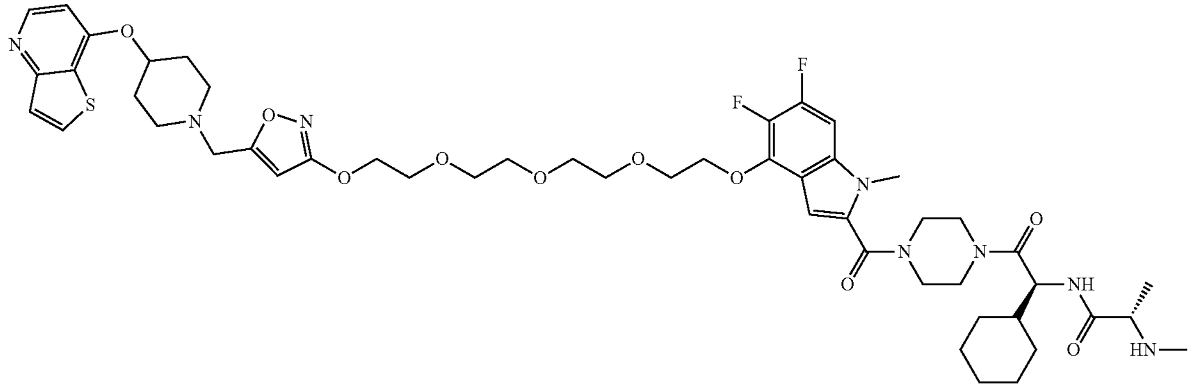 [SMILES: CN[C@@H](C)C(=O)N[C@H](C(=O)N1CCN(C(=O)c2cc3c(OCCOCCOCCOCCOc4cc(CN5CCC(Oc6ccnc7ccsc67)CC5)on4)c(F)c(F)cc3n2C)CC1)C1CCCCC1]

Salt type: HCl; MS value: 1009.7

Example Compound 52 (compound 52): (S)—N—((S)-1-cyclohexyl-2-(4-(5,6-difluoro-1-methyl-4-(2-(2-(2-((5-((4-(thieno[3,2-b]pyridin-7-yloxy)piperidin-1-yl)methyl)isoxazol-3-yl)oxy)ethoxy)ethoxy)ethoxy)-1H-indole-2-carbonyl)piperazin-1-yl)-2-oxoethyl)-2-(methylamino)propanamide

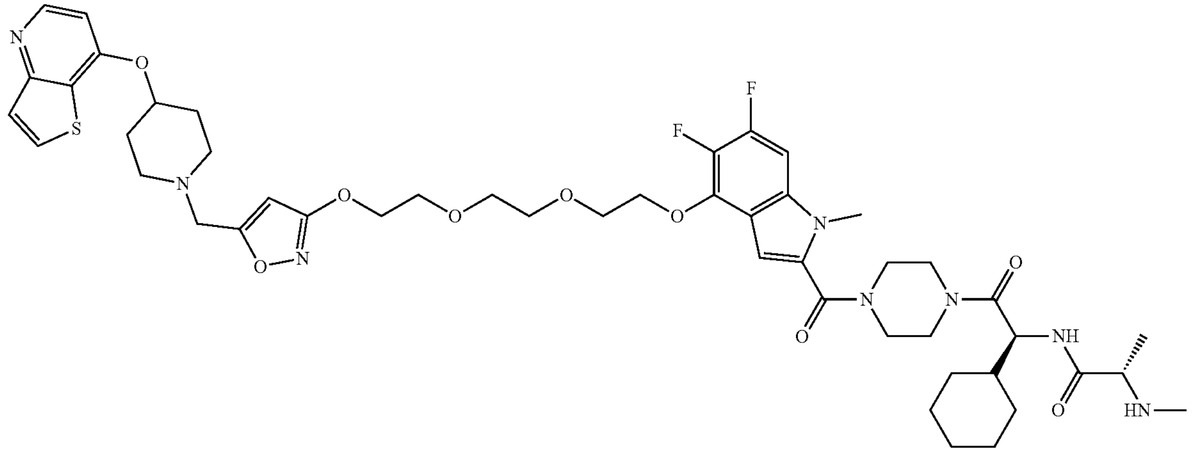 [SMILES: CN[C@@H](C)C(=O)N[C@H](C(=O)N1CCN(C(=O)c2cc3c(OCCOCCOCCOc4cc(CN5CCC(Oc6ccnc7ccsc67)CC5)on4)c(F)c(F)cc3n2C)CC1)C1CCCCC1]

Salt type: HCl; MS value: 965.7

Example Compound 53 (compound 53): (S)—N—((S)-1-cyclohexyl-2-(4-(2-methyl-1-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethyl)-1H-indole-5-carbonyl)piperazin-1-yl)-2-oxoethyl)-2-(methylamino)propanamide

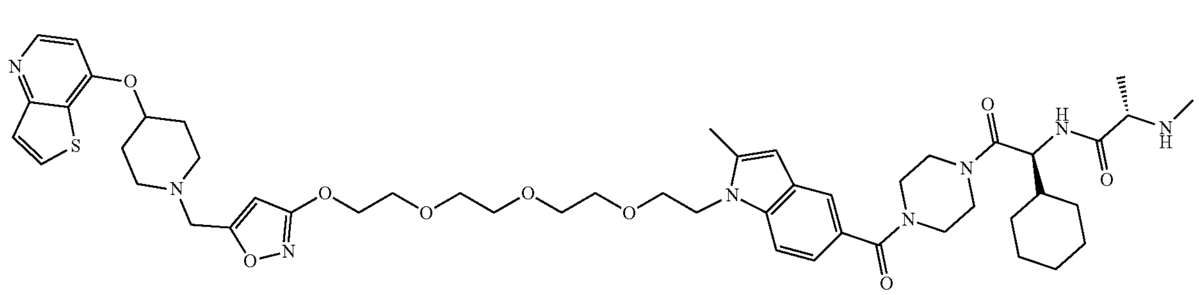 [SMILES: CN[C@@H](C)C(=O)N[C@H](C(=O)N1CCN(C(=O)c2ccc3c(c2)cc(C)n3CCOCCOCCOCCOc2cc(CN3CCC(Oc4ccnc5ccsc45)CC3)on2)CC1)C1CCCCC1]

Salt type: -; MS value: 957.8

Example Compound 54 (compound 54): (S)—N—((S)-1-cyclohexyl-2-(4-(2-methyl-1-(2-(2-((5-((4-(thieno[3,2-b]pyridin-7-yloxy)piperidin-1-yl)methyl)isoxazol-3-yl)oxy)ethoxy)ethyl)-1H-indole-5-carbonyl)piperazin-1-yl)-2-oxoethyl)-2-(methylamino)propanamide

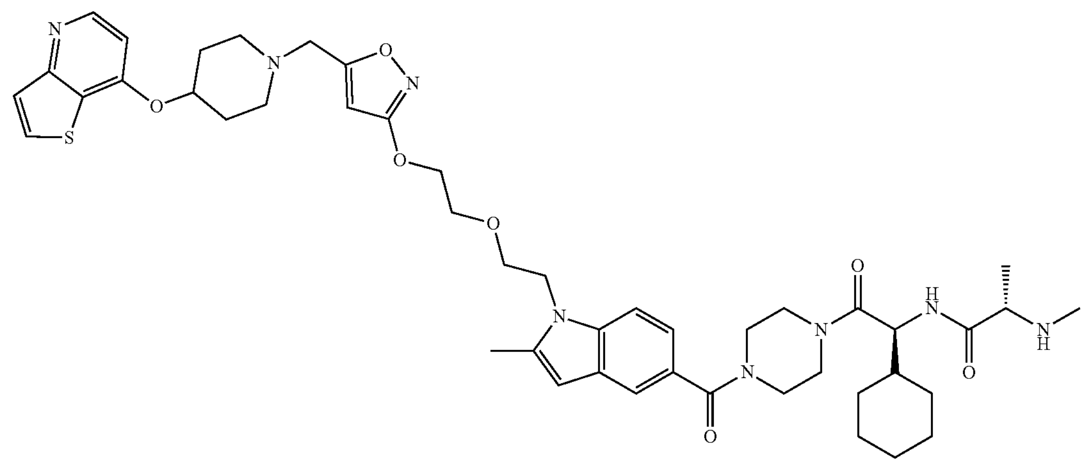 [SMILES: CN[C@@H](C)C(=O)N[C@H](C(=O)N1CCN(C(=O)c2ccc3c(c2)cc(C)n3CCOCCOc2cc(CN3CCC(Oc4ccnc5ccsc45)CC3)on2)CC1)C1CCCCC1]

Salt type: TFA; MS value: 869.7

Example Compound 55 (compound 55): (S)—N—((S)-1-cyclohexyl-2-(4-(2-methyl-1-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-5-carbonyl)piperazin-1-yl)-2-oxoethyl)-2-(methylamino)propanamide

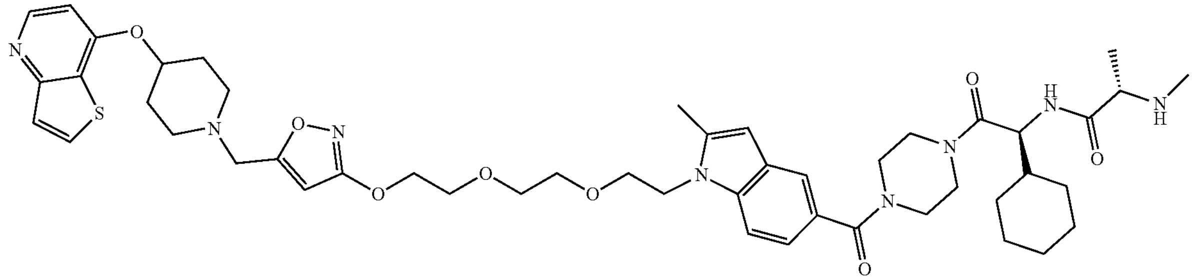 [SMILES: CN[C@@H](C)C(=O)N[C@H](C(=O)N1CCN(C(=O)c2ccc3c(c2)cc(C)n3CCOCCOCCOc2cc(CN3CCC(Oc4ccnc5ccsc45)CC3)on2)CC1)C1CCCCC1]

Salt type: -; MS value: 913.7

Example Compound 56 (compound 56): (S)—N—((S)-1-cyclohexyl-2-((R)-2-methyl-4-(2-methyl-1-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-5-carbonyl)piperazin-1-yl)-2-oxoethyl)-2-(methylamino)propanamide

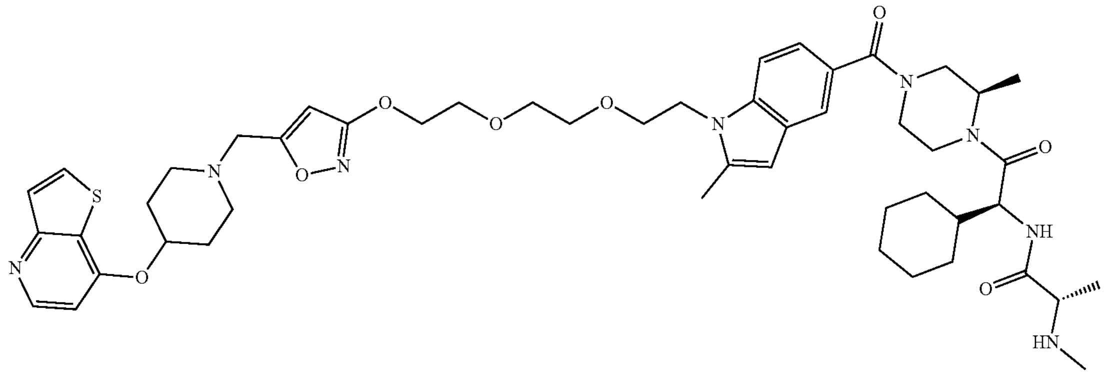 [SMILES: CN[C@@H](C)C(=O)N[C@H](C(=O)N1CCN(C(=O)c2ccc3c(c2)cc(C)n3CCOCCOCCOc2cc(CN3CCC(Oc4ccnc5ccsc45)CC3)on2)C[C@H]1C)C1CCCCC1]

Salt type: TFA; MS value: 927.7

Example Compound 57 (compound 57): (S)—N—((S)-1-cyclohexyl-2-(4-(3-fluoro-2-methyl-1-(2-(2-(2-((5-((4-(thieno[3,2-b]pyridin-7-yloxy)piperidin-1-yl)methyl)isoxazol-3-yl)oxy)ethoxy)ethoxy)ethyl)-1H-indole-5-carbonyl)piperazin-1-yl)-2-oxoethyl)-2-(methylamino)propanamide

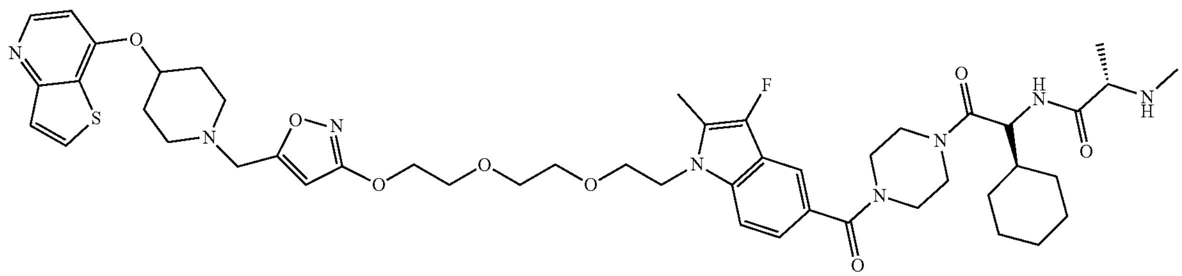

Salt type: -; MS value: 931.8

Example Compound 58 (compound 58): (S)—N—((S)-1-cyclohexyl-2-oxo-2-((S)-2-(4-(3-(2-(2-((5-((4-(thieno[3,2-b]pyridin-7-yloxy)piperidin-1-yl)methyl)isoxazol-3-yl)oxy)ethoxy)ethoxy)benzoyl)thiazol-2-yl)pyrrolidin-1-yl)ethyl)-2-(methylamino)propanamide

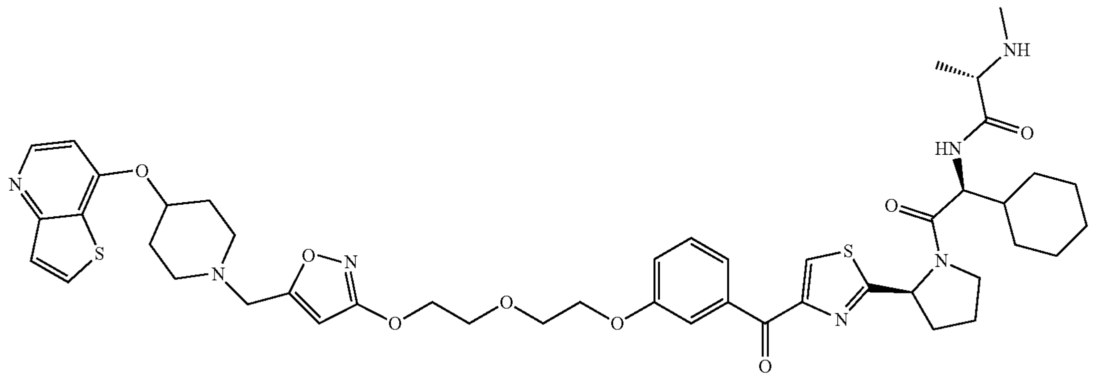 [SMILES: CN[C@@H](C)C(=O)N[C@H](C(=O)N1CCC[C@H]1c1nc(C(=O)c2cccc(OCCOCCOc3cc(CN4CCC(Oc5ccnc6ccsc56)CC4)on3)c2)cs1)C1CCCCC1]

Salt type: HCl; MS value: 900.5

Example Compound 59 (compound 59): (S)—N—((S)-1-cyclohexyl-2-oxo-2-((S)-2-(4-(3-(2-(2-(2-((5-((4-(thieno[3,2-b]pyridin-7-yloxy)piperidin-1-yl)methyl)isoxazol-3-yl)oxy)ethoxy)ethoxy)ethoxy)benzoyl)thiazol-2-yl)pyrrolidin-1-yl)ethyl)-2-(methylamino)propanamide

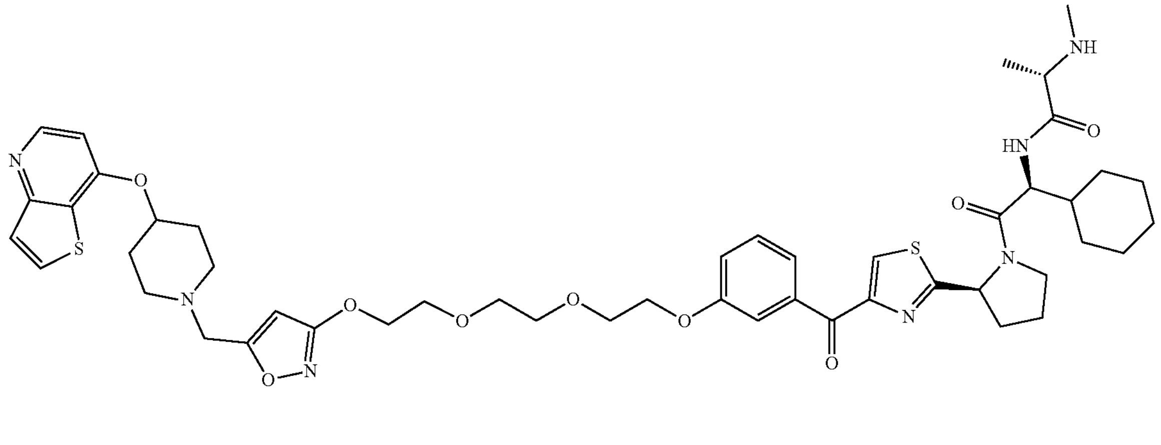 [SMILES: CN[C@@H](C)C(=O)N[C@H](C(=O)N1CCC[C@H]1c1nc(C(=O)c2cccc(OCCOCCOCCOc3cc(CN4CCC(Oc5ccnc6ccsc56)CC4)on3)c2)cs1)C1CCCCC1]

Salt type: HCl; MS value: 944.8

Example Compound 60 (compound 60): (S)—N—((S)-1-cyclohexyl-2-oxo-2-((S)-2-(4-(3-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)benzoyl)thiazol-2-yl)pyrrolidin-1-yl)ethyl)-2-(methylamino)propanamide

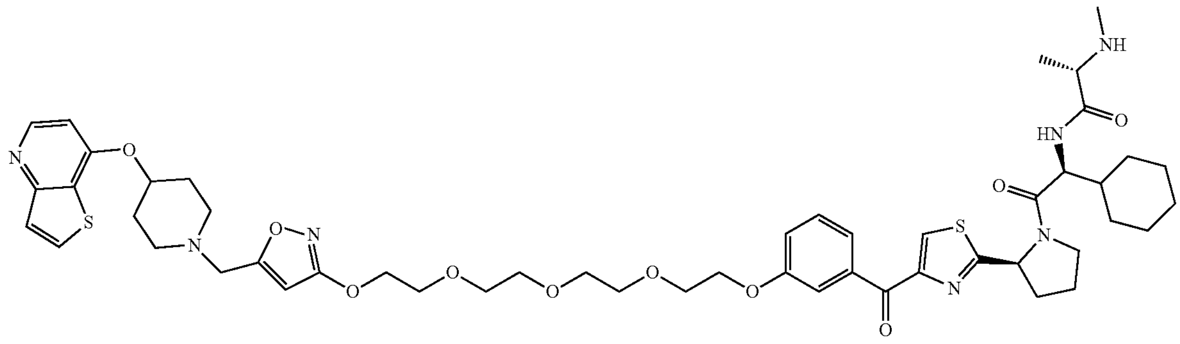 [SMILES: CN[C@@H](C)C(=O)N[C@H](C(=O)N1CCC[C@H]1c1nc(C(=O)c2cccc(OCCOCCOCCOCCOc3cc(CN4CCC(Oc5ccnc6ccsc56)CC4)on3)c2)cs1)C1CCCCC1]

Salt type: HCl; MS value: 988.8

Example Compound 61 (compound 61): (2S,4R)-1-((S)-2-(tert-butyl)-4-oxo-14-((5-((4-(thieno[3,2-b]pyridin-7-yloxy)piperidin-1-yl)methyl)isoxazol-3-yl)oxy)-6,9,12-trioxa-3-azatetradecanoyl)-4-hydroxy-N-(4-(4-methylthiazol-5-yl)benzyl)pyrrolidine-2-carboxamide

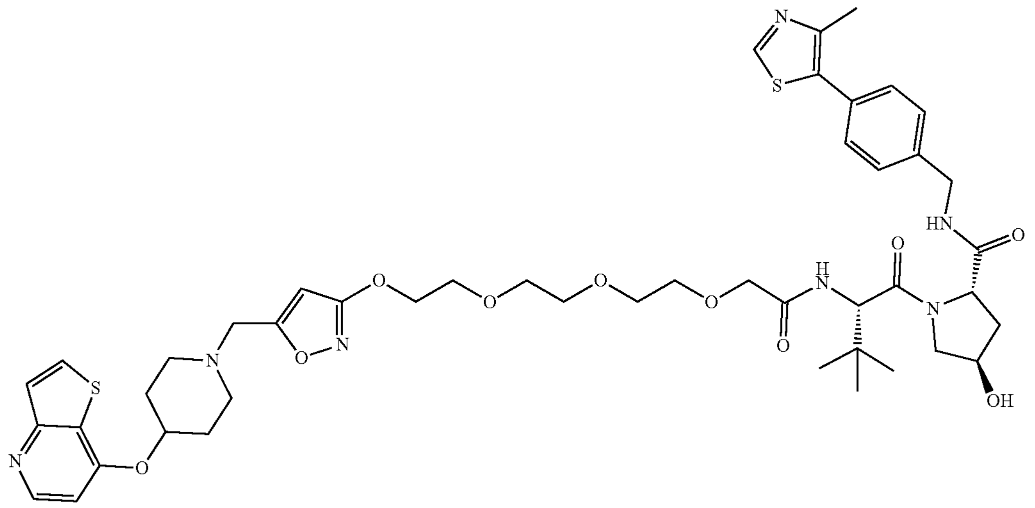 [SMILES: Cc1ncsc1-c1ccc(CNC(=O)[C@@H]2C[C@@H](O)CN2C(=O)[C@@H](NC(=O)COCCOCCOCCOc2cc(CN3CCC(Oc4ccnc5ccsc45)CC3)on2)C(C)(C)C)cc1]

Salt type: HCl; MS value: 934.6

Example Compound 62 (compound 62): (2S,4R)-4-hydroxy-1-((S)-3-methyl-2-(1-oxoisoindolin-2-yl)butanoyl)-N-(4-(4-methylthiazol-5-yl)-2-(2-(2-(2-((5-((4-(thieno[3,2-b]pyridin-7-yloxy)piperidin-1-yl)methyl)isoxazol-3-yl)oxy)ethoxy)ethoxy)ethoxy)benzyl)pyrrolidine-2-carboxamide

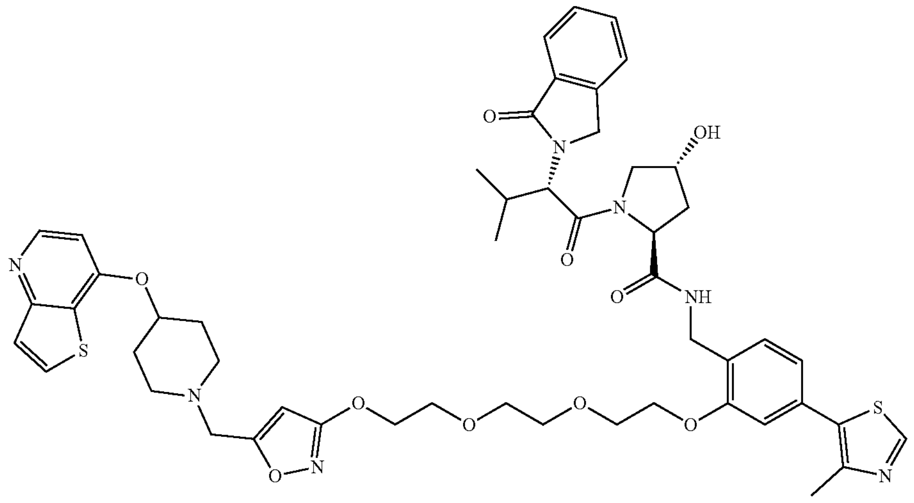 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOc2cc(CN3CCC(Oc4ccnc5ccsc45)CC3)on2)c1]

Salt type: -; MS value: 994.8

Example Compound 63 (compound 63): (2S,4R)-4-hydroxy-1-((S)-3-methyl-2-(1-oxoisoindolin-2-yl)butanoyl)-N-(4-(4-methylthiazol-5-yl)-2-(2-(2-((5-((4-(thieno[3,2-b]pyridin-7-yloxy)piperidin-1-yl)methyl)isoxazol-3-yl)oxy)ethoxy)ethoxy)benzyl)pyrrolidine-2-carboxamide

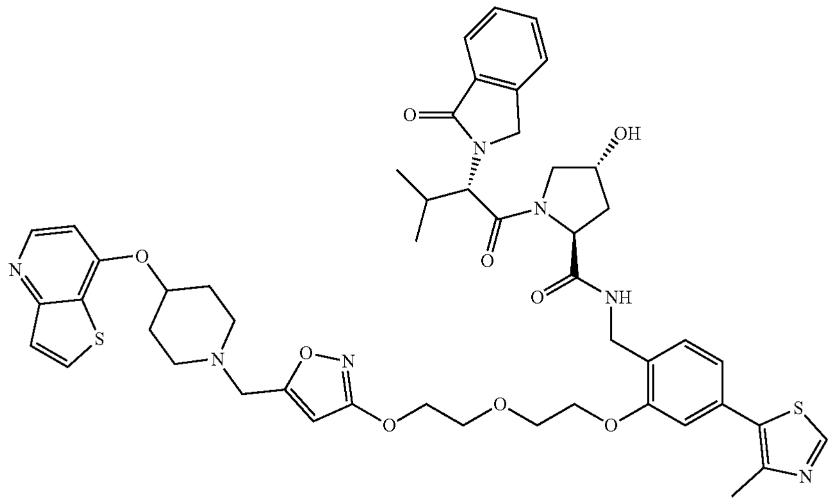 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOc2cc(CN3CCC(Oc4ccnc5ccsc45)CC3)on2)c1]

Salt type: -; MS value: 950.1

Example Compound 64 (compound 64): (2S,4R)-4-hydroxy-1-((S)-3-methyl-2-(1-oxoisoindolin-2-yl)butanoyl)-N-(4-(4-methylthiazol-5-yl)-2-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)benzyl)pyrrolidine-2-carboxamide

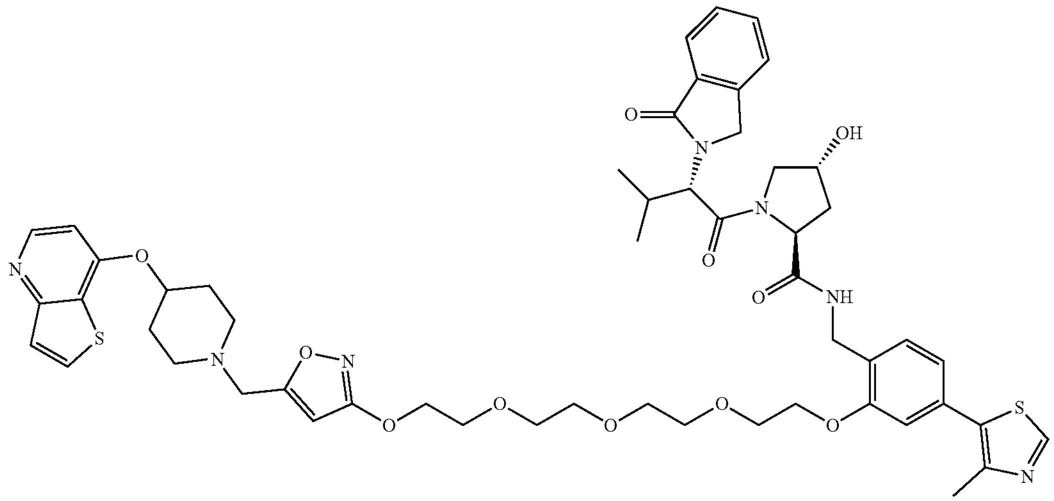 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOc2cc(CN3CCC(Oc4ccnc5ccsc45)CC3)on2)c1]

Salt type: -; MS value: 1038.8

Example Compound 65 (compound 65): 2-(2,6-dioxopiperidin-3-yl)-4-(2-(2-(2-((5-((4-(thieno[3,2-b]pyridin-7-yloxy)piperidin-1-yl)methyl)isoxazol-3-yl)oxy)ethoxy)ethoxy)ethoxy)isoindoline-1,3-dione

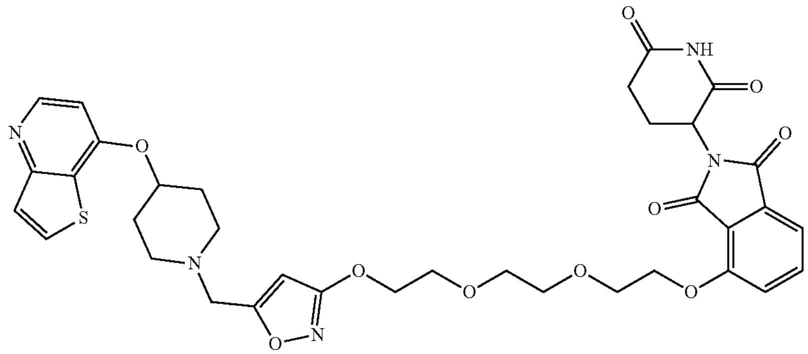 [SMILES: O=C1CCC(N2C(=O)c3cccc(OCCOCCOCCOc4cc(CN5CCC(Oc6ccnc7ccsc67)CC5)on4)c3C2=O)C(=O)N1]

Salt type: -; MS value: 720.4

Example Compound 66 (compound 66): 2-(2,6-dioxopiperidin-3-yl)-4-(2-(2-((5-((4-(thieno[3,2-b]pyridin-7-yloxy)piperidin-1-yl)methyl)isoxazol-3-yl)oxy)ethoxy)ethoxy)isoindoline-1,3-dione

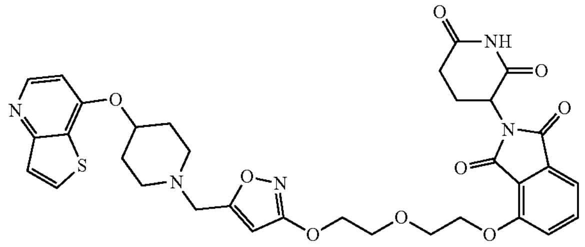 [SMILES: O=C1CCC(N2C(=O)c3cccc(OCCOCCOc4cc(CN5CCC(Oc6ccnc7ccsc67)CC5)on4)c3C2=O)C(=O)N1]

Salt type: -; MS value: 676.7

Example Compound 67 (compound 67): 2-(2,6-dioxopiperidin-3-yl)-4-(2-(2-(2-(2-((5-((4-(thieno[3,2-b]pyridin-7-yloxy)piperidin-1-yl)methyl)isoxazol-3-yl)oxy)ethoxy)ethoxy)ethoxy)ethoxy)isoindoline-1,3-dione

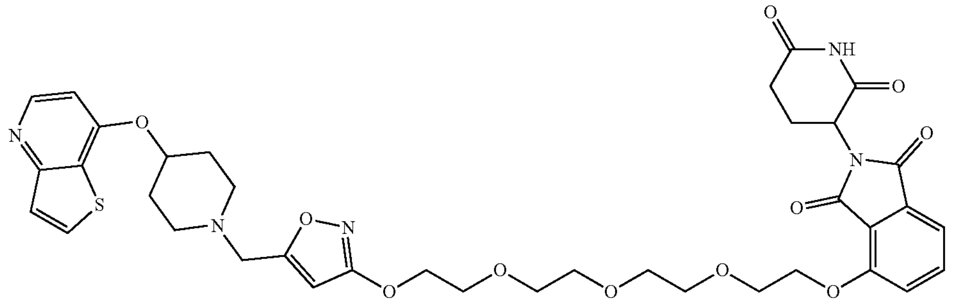 [SMILES: O=C1CCC(N2C(=O)c3cccc(OCCOCCOCCOCCOc4cc(CN5CCC(Oc6ccnc7ccsc67)CC5)on4)c3C2=O)C(=O)N1]

Salt type: -; MS value: 764.3

Example Compound 68 (compound 68): N-(4-(N-(3-cyano-4-methyl-1H-indol-7-yl)sulfamoyl)benzyl)-2-(2-(2-((5-((4-(thieno[3,2-b]pyridin-7-yloxy)piperidin-1-yl)methyl)isoxazol-3-yl)oxy)ethoxy)ethoxy)acetamide

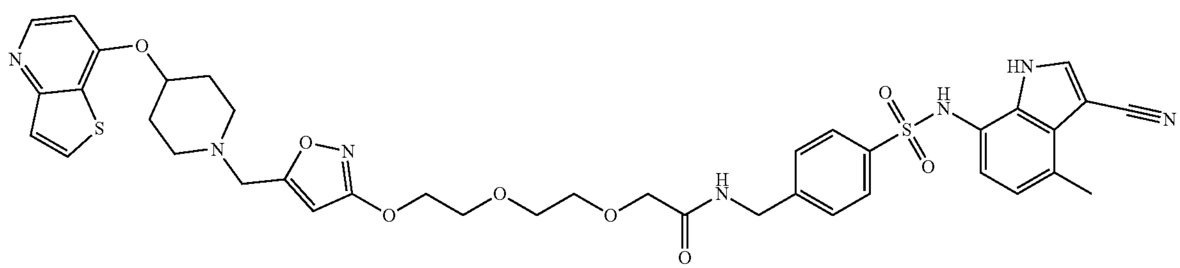 [SMILES: Cc1ccc(NS(=O)(=O)c2ccc(CNC(=O)COCCOCCOc3cc(CN4CCC(Oc5ccnc6ccsc56)CC4)on3)cc2)c2[nH]cc(C#N)c12]

Salt type: -; MS value: 800.6

Example Compound 69 (compound 69): N-(4-(N-(3-cyano-4-methyl-1H-indol-7-yl)sulfamoyl)benzyl)-2-(2-(2-(2-((5-((4-(thieno[3,2-b]pyridin-7-yloxy)piperidin-1-yl)methyl)isoxazol-3-yl)oxy)ethoxy)ethoxy)ethoxy)acetamide

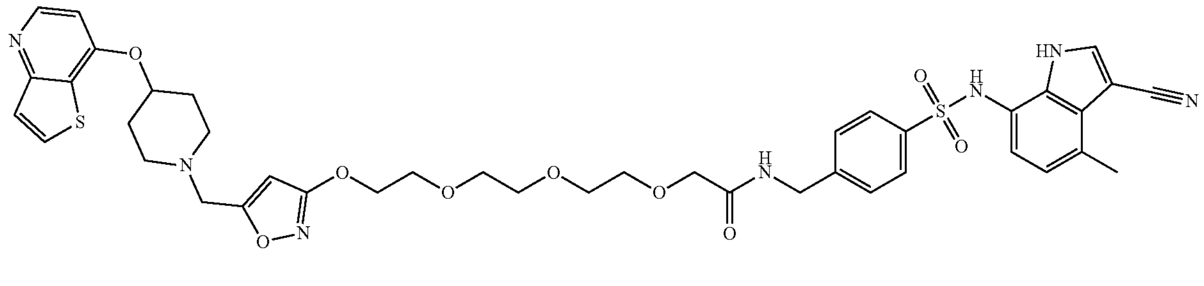 [SMILES: Cc1ccc(NS(=O)(=O)c2ccc(CNC(=O)COCCOCCOCCOc3cc(CN4CCC(Oc5ccnc6ccsc56)CC4)on3)cc2)c2[nH]cc(C#N)c12]

Salt type: -; MS value: 842.5, and

Example Compound 70 (compound 70): N-(4-(N-(3-cyano-4-methyl-1H-indol-7-yl)sulfamoyl)benzyl)-2-(2-((5-((4-(thieno[3,2-b]pyridin-7-yloxy)piperidin-1-yl)methyl)isoxazol-3-yl)oxy)ethoxy)acetamide

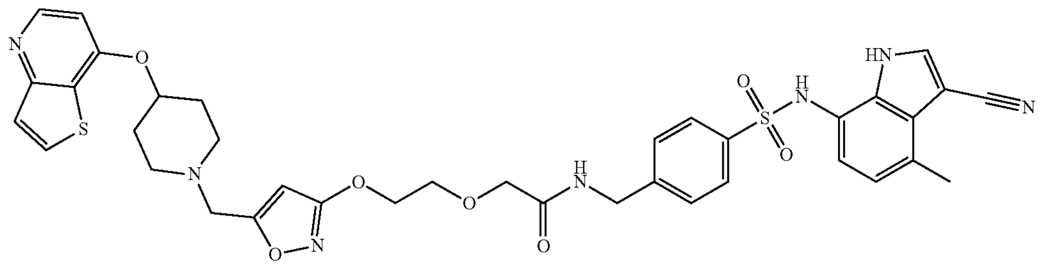 [SMILES: Cc1ccc(NS(=O)(=O)c2ccc(CNC(=O)COCCOc3cc(CN4CCC(Oc5ccnc6ccsc56)CC4)on3)cc2)c2[nH]cc(C#N)c12]

Salt type: -; MS value: 756.6

Experimental Example 1: Measurement of XIAP Binding Inhibitory Activity

Human XIAP binding inhibitory activity was measured by the Homogeneous Time Resolved Fluorescence (HTRF) method with using commercially available human XIAP-_BIR3 domain purified protein (R & D) and as a ligand a Smac N-terminal peptide (AVPIAQK (SEQ ID NO: 1)) (hereinafter referred to as "b-Smac"; Peptide Research Laboratories, Inc.) biotinylated at the C-terminus according to a conventional method.

The HTRF method will be described in detail below.

The test compound diluted with a reaction buffer (25 mM HEPES Buffer containing 100 mM NaCl, 0.1% BSA, and 0.1% triton X-100, pH 7.5) was added to a 384-well white shallow bottom plate (Greiner 784076) at 1 μL/well and flash centrifuged for 30 seconds. Subsequently, human XIAP_BIR3 domain purified protein was diluted with the reaction buffer to obtain a 90 nM sample diluent, and the resultant sample diluent was added to the above-mentioned white superficial plate at 4.5 μL/well and flash centrifuged for 30 seconds. Subsequently, b-Smac diluted to 90 nM with the reaction buffer was added to the above-mentioned white superficial plat at 4.5 μL/well and flash centrifuged for 30 seconds. A mixed solution of Anti-6 HIS-Cryptate ($Eu^{3+}$ Cryptate-conjugated mouse monoclonal antibody anti-6 Histidine; cisbio) and Streptavidin-$XL^{eat}$ (Highgrade XL665-conjugated streptavidin; cisbio) both diluted 100-fold with HTRF detection buffer (cisbio) at a volume ratio of 1:1 was added to the above white superficial plate at 10 μL/well. After flash centrifuging the white shallow bottom plate for 30 seconds, the white shallow bottom plate was left at room temperature for 4 hours or more in the dark. The white superficial plate after being left was subjected to fluorescence intensity measurement (excitation wavelength: 320 nm, fluorescence wavelength: 665 nm and 615 nm) by EnVision (Perkin Elmer). The binding inhibition rate (%) was calculated based on the HTRF ratio in the presence of the test compound to the HTRF ratio in the absence of the test compound (fluorescence intensity at 665 nm/fluorescence intensity at 615 nm).

The XIAP binding inhibition rate (%) of test compounds was evaluated. The XIAP binding inhibition ratio described as A≥75%, 75%>B≥50%, 50%>C≥25%, D>25% when the concentration of the test compound is 3 μM, or 50% inhibitory concentration (IC50 value) described as A<0.3 μM, 0.3 μM≤B<3 μM, 3 μM≤C<30 μM, is shown in the table below.

TABLE 1

| Compound | *Binding inhibition rate |
|---|---|
| Example 1 | -/B |
| Example 2 | -/B |
| Example 3 | -/B |
| Example 4 | -/B |
| Example 5 | -/B |
| Example 6 | -/B |
| Example 7 | -/B |
| Example 8 | -/B |
| Example 9 | -/B |
| Example 10 | -/B |
| Example 11 | -/C |
| Example 12 | -/B |
| Example 13 | -/A |
| Example 14 | -/C |
| Example 15 | -/B |
| Example 16 | -/B |
| Example 17 | -/A |
| Example 18 | -/A |
| Example 19 | -/B |
| Example 20 | -/B |
| Example 21 | C/- |
| Example 22 | C/- |
| Example 23 | C/- |
| Example 24 | -/C |
| Example 25 | -/C |
| Example 26 | -/C |
| Example 27 | -/C |
| Example 28 | -/C |
| Example 29 | -/C |
| Example 30 | D/- |
| Example 31 | C/- |
| Example 32 | -/C |
| Example 33 | -/C |
| Example 34 | -/C |
| Example 35 | -/C |
| Example 36 | -/C |
| Example 37 | -/C |
| Example 38 | -/C |
| Example 39 | -/C |
| Example 40 | -/C |
| Example 41 | -/C |
| Example 42 | D/- |
| Example 43 | -/C |
| Example 44 | -/C |
| Example 45 | -/C |
| Example 46 | D/- |
| Example 47 | D/- |
| Example 48 | -/C |
| Example 49 | -/C |
| Example 50 | -/C |
| Example 51 | -/B |
| Example 52 | -/B |
| Example 53 | -/B |
| Example 54 | -/A |
| Example 55 | -/B |
| Example 56 | -/B |
| Example 57 | -/B |
| Example 58 | -/A |
| Example 59 | -/A |
| Example 60 | -/A |

*Binding inhibition rate: binding inhibition rate when the concentration of the test compound is 3 μM/IC50 value From the above results, it was shown that the compounds of the present invention have an excellent IAP (in particular XIAP) binding (inhibition) activities.

Experimental Example 2: Measurement of Binding Inhibitory Activity of IRAK-M

IRAK-M binding inhibitory activity was evaluated using active site-dependent competitive assay KINOMEscan® provided by Eurofins Discover X (Goldstein, D. M. et al. High-throughput kinase profiling as a platform for drug discovery. Nat. Rev. Drug Discovery. 7, 391-397 (2008)). IRAK-M binding inhibitory activity of the test compound was evaluated. The "% Ctrl" when the concentration of the test compound is 1 μM described as A<25%, 50%>B≥25%, 75%>C≥50%, D≥75%, or IC50 value described as A<0.03 μM, 0.03 μM≤B<0.1 μM, 0.1 μM≤C<0.3 μM, 0.3 μM≤D<1 μM, 1 μM≤E<3 μM is shown in the table below. The "% Ctrl" is calculated by the following formula.

(test compound signal−positive control compound signal)/(negative control compound signal−positive control compound signal)×100

Negative control compound=DMSO (100 Ctrl)
Positive control compound=control compound (0%×Ctrl)

TABLE 2-1

| Compound | *Binding inhibition activity |
|---|---|
| Example 1 | -/D |
| Example 2 | -/D |
| Example 3 | -/C |
| Example 4 | -/D |
| Example 5 | -/D |
| Example 6 | -/C |
| Example 7 | B/- |
| Example 8 | -/B |
| Example 9 | -/B |
| Example 10 | B/- |
| Example 11 | A/- |
| Example 12 | A/- |
| Example 13 | A/- |
| Example 14 | A/- |
| Example 15 | B/- |
| Example 16 | B/- |
| Example 17 | -/D |
| Example 18 | -/D |
| Example 19 | -/D |
| Example 20 | B/- |
| Example 21 | B/- |
| Example 22 | B/- |
| Example 23 | B/- |
| Example 24 | A/- |
| Example 25 | A/- |
| Example 26 | -/D |
| Example 27 | -/D |
| Example 28 | -/D |
| Example 29 | A/- |
| Example 31 | B/- |
| Example 32 | A/- |
| Example 33 | A/- |
| Example 34 | B/- |
| Example 35 | B/- |
| Example 36 | B/- |
| Example 37 | D/- |
| Example 38 | B/- |
| Example 39 | B/- |
| Example 40 | B/- |
| Example 41 | B/- |
| Example 42 | -/C |
| Example 44 | B/- |
| Example 45 | B/- |
| Example 46 | -/C |
| Example 47 | -/E |
| Example 51 | A/- |
| Example 52 | A/- |
| Example 53 | A/- |
| Example 54 | B/- |
| Example 55 | B/- |
| Example 56 | C/- |
| Example 57 | B/- |
| Example 58 | A/- |
| Example 59 | A/- |
| Example 60 | A/- |
| Example 61 | -/D |
| Example 62 | C/- |
| Example 63 | A/- |

TABLE 2-1-continued

| Compound | *Binding inhibition activity |
|---|---|
| Example 64 | D/- |
| Example 65 | -/D |
| Example 66 | -/C |
| Example 67 | -/C |
| Example 68 | B/- |
| Example 69 | B/- |
| Example 70 | A/- |

*Binding inhibition activity: % Ctrl/IC50 value when the concentration of the test compound is 1 μM

TABLE 2-2

| Compound | *Binding inhibition activity |
|---|---|
| Ref. example 1 | D/- |
| Ref. example 2 | B/- |
| Ref. example 3 | -/C |
| Ref. example 4 | C/- |
| Ref. example 5 | -/B |
| Ref. example 6 | -/C |
| Ref. example 7 | A/- |
| Ref. example 8 | A/- |
| Ref. example 9 | A/- |
| Ref. example 10 | A/- |
| Ref. example 11 | C/- |
| Ref. example 12 | D/- |
| Ref. example 13 | D/- |
| Ref. example 14 | B/- |
| Ref. example 15 | B/- |
| Ref. example 16 | C/- |
| Ref. example 17 | D/- |
| Ref. example 18 | C/- |
| Ref. example 19 | C/- |
| Ref. example 20 | C/- |
| Ref. example 21 | A/- |
| Ref. example 22 | C/- |
| Ref. example 23 | B/- |
| Ref. example 24 | C/- |
| Ref. example 25 | B/- |
| Ref. example 26 | D/- |
| Ref. example 27 | C/- |
| Ref. example 28 | C/- |
| Ref. example 29 | B/- |
| Ref. example 30 | D/- |
| Ref. example 31 | D/- |
| Ref. example 32 | D/- |
| Ref. example 33 | D/- |
| Ref. example 34 | D/- |
| Ref. example 35 | D/- |
| Ref. example 36 | D/- |
| Ref. example 37 | D/- |
| Ref. example 38 | B/- |
| Ref. example 39 | C/- |
| Ref. example 40 | B/- |
| Ref. example 41 | B/- |
| Ref. example 42 | C/- |
| Ref. example 43 | C/- |
| Ref. example 44 | B/- |
| Ref. example 45 | A/- |
| Ref. example 46 | A/- |
| Ref. example 47 | A/- |
| Ref. example 48 | A/- |
| Ref. example 49 | B/- |
| Ref. example 50 | B/- |
| Ref. example 51 | B/- |
| Ref. example 52 | A/- |
| Ref. example 53 | B/- |
| Ref. example 54 | B/- |
| Ref. example 55 | B/- |
| Ref. example 56 | B/- |
| Ref. example 57 | B/- |
| Ref. example 58 | B/- |

TABLE 2-2-continued

| Compound | *Binding inhibition activity |
|---|---|
| Ref. example 59 | B/- |
| Ref. example 60 | B/- |
| Ref. example 61 | D/- |
| Ref. example 62 | B/- |
| Ref. example 63 | A/- |
| Ref. example 64 | A/- |
| Ref. example 65 | D/- |
| Ref. example 66 | C/- |
| Ref. example 67 | B/- |
| Ref. example 68 | B/- |
| Ref. example 69 | -/C |
| Ref. example 70 | -/C |
| Ref. example 71 | -/B |
| Ref. example 72 | -/B |
| Ref. example 73 | D/- |
| Ref. example 74 | C/- |
| Ref. example 75 | D/- |
| Ref. example 76 | C/- |
| Ref. example 77 | B/- |
| Ref. example 78 | B/- |
| Ref. example 79 | B/- |
| Ref. example 80 | B/- |
| Ref. example 81 | C/- |
| Ref. example 82 | C/- |
| Ref. example 83 | -/A |
| Ref. example 84 | B/- |
| Ref. example 85 | -/C |
| Ref. example 86 | -/C |
| Ref. example 87 | B/- |
| Ref. example 88 | B/- |

Experimental Example 3: Measurement of in vitro Degradation Activity of Target Protein In vitro degradation activities of target protein of the example compounds were evaluated using Enzyme-linked immuno-sorbent assay (ELISA) by the following assay steps. THP1 cells (ATCC, TIB-202) were cultured in RPMI-1640 supplemented with 10% FBS, lx sodium pyruvate, lx HEPES, D-(+)-glucose and 1% penicillin/streptomycin. THP1 cells were seeded at a density of $1\times10^6$ cells/well in 24-well plate and treated with DMSO control or test compound, and then incubated for 24 hours. The cells were collected and lysed on ice for 30 minutes in lysis buffer (PBS containing 0.1% Triton X-100) containing a protease inhibitor cocktail (Roche, Cat #11836170001). The lysates were sonicated for 30 sec ON/30 sec OFF for ten cycles and centrifuged for 10 minutes at 13 k rpm at 4° C. Protein concentrations were determined by the BCA assay (Sigma, Cat #QPBCA-1KT). The ELISA assay was performed using the Human IRAK3/IRAKM/IRAK-M ELISA Kit (LifeSpan BioSciences, Cat #LS-F35271), and the protein levels of IRAK-M were evaluated according to the kit protocol. As to the IRAK-M degradation rate of test compounds, protein degradation rate (%) when the concentration of the test compound is 1 M described as A≥75%, 50%≤B<75%, 25%≤C<50%, D<25%, or 50% degradation concentration (DC50 value) described as A<0.03 μM, 0.03 μM≤B<0.1 μM, 0.1 μM≤C<0.3 μM, 0.3 μM≤D<1 μM, is shown in the table below.

TABLE 3

| Compound | *Degradation rate |
|---|---|
| Example 1 | -/D |
| Example 2 | C/- |
| Example 3 | B/- |

TABLE 3-continued

| Compound | *Degradation rate |
|---|---|
| Example 4 | B/- |
| Example 5 | C/- |
| Example 6 | C/- |
| Example 7 | A/- |
| Example 8 | B/- |
| Example 9 | A/- |
| Example 10 | B/- |
| Example 11 | C/- |
| Example 12 | -/C |
| Example 13 | A/- |
| Example 14 | D/- |
| Example 15 | D/- |
| Example 16 | D/- |
| Example 17 | C/- |
| Example 18 | C/- |
| Example 19 | B/- |
| Example 20 | B/- |
| Example 21 | A/- |
| Example 22 | A/- |
| Example 23 | A/- |
| Example 24 | -/D |
| Example 25 | -/B |
| Example 26 | -/A |
| Example 27 | -/A |
| Example 28 | -/A |
| Example 29 | -/D |
| Example 30 | A/- |
| Example 31 | A/- |
| Example 32 | -/D |
| Example 33 | -/D |
| Example 34 | -/D |
| Example 35 | -/D |
| Example 36 | -/D |
| Example 37 | -/D |
| Example 38 | -/D |
| Example 39 | -/C |
| Example 40 | -/D |
| Example 41 | -/C |
| Example 42 | B/- |
| Example 43 | A/- |
| Example 44 | -/D |
| Example 45 | B/- |
| Example 46 | A/- |
| Example 47 | B/- |
| Example 48 | -/C |
| Example 49 | -/B |
| Example 50 | B/- |
| Example 51 | -/C |
| Example 52 | A/- |
| Example 53 | A/- |
| Example 54 | A/- |
| Example 55 | C/- |
| Example 56 | D/- |
| Example 57 | A/- |
| Example 58 | B/- |
| Example 59 | -/D |
| Example 60 | A/- |
| Example 68 | D/- |

*Degradation rate: protein degradation rate when the concentration of the test compound is 1 μM/DC50 value

Experimental Example 4: Antitumor Effect in a Mouse Lewis Lung Cancer Cell Inoculation Model C57B3L/6 mice (Charles River Laboratories Japan, male, 7-8W) were subcutaneously inoculated with $2\times10^4$ cells/mouse of mouse Lewis lung carcinoma LL/2 (Lewis lung carcinoma, LLC) (ATCC, CRL-1642) along with Matrigel on the flank of the mouse. Tumor size was measured by electronic calipers 7 days after inoculation, and the groups were divided so that each group had an equivalent size, and administration of the compound was started 8 days later. Tumor size was calculated by the formula, major diameter of the tumor×minor diameter×minor diameter/2.

The test compound was suspended in 0.5% methylcellulose or dissolved in saline and administered subcutaneously every 3 days for 3 times. Tumor size was measured periodically until 16-18 days after the start of the study, and a two-tailed test was performed for tumor size in the test compound-treated group and the solvent-treated group on the last day of the study.

Daily changes of tumor size in each group of example compounds 1, 25, 26, 27, 28 and 38, are shown in FIG. 1. Each compound was used with the salt shown in the FIGURE. FIGURE shows the mean±standard error.

From the above results, it was shown that these compounds have suppressive effects on tumor growth.

Formulation Example 1

A medicament containing the compound of the present invention as an active ingredient can be produced, for example, by the following composition.

1. Capsule

| | |
|---|---|
| (1) Compound obtained in Example 1 | 40 mg |
| (2) Lactose | 70 mg |
| (3) Microcrystalline cellulose | 9 mg |
| (4) Magnesium stearate | 1 mg |
| 1 capsule | 120 mg |

After mixing (1), (2), (3) and 1/2 volume of (4), the mixture is granulated. The remaining (4) is added to this, and then the whole is encapsulated in a gelatin capsule.

2. Tablet

| | |
|---|---|
| (1) Compound obtained in Example 1 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 tablet | 120 mg |

After mixing (1), (2), (3) and 2/3 volume of (4) and 1/2 volume of (5), the mixture is granulated.

Then, the remaining (4) and (5) are added to the granules and pressed-molded into tablets.

Formulation Example 2

After dissolving 50 mg of the compound obtained in Example 1 in 50 mL of distilled water for injection (Japanese Pharmacopoeia grade), the distilled water for injection is added to make 100 mL. The solution is filtered under sterile conditions, then, 1 mL each of this solution is taken, filled under sterile conditions into vials for injection, lyophilized and sealed.

The foregoing merely illustrates objects and subjects of the present invention, and it is not intended to be limiting the accompanying Claims. Without departing from the accompanying Claims, various modifications and alterations to the described embodiments will be apparent to those skilled in the art in view of the teachings herein.

INDUSTRIAL APPLICABILITY

The compounds of the present invention are capable of degrading IRAK-M protein as a target.

Therefore, it is expected to provide effective drugs for the prevention or treatment of cancer and other IRAK-M associated diseases.

The invention claimed is:

1. A compound represented by the following formula (I):

I

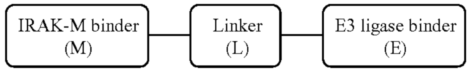

, or a pharmaceutically acceptable salt thereof, wherein the IRAK-M binder (M) is represented by the following formula (III):

III

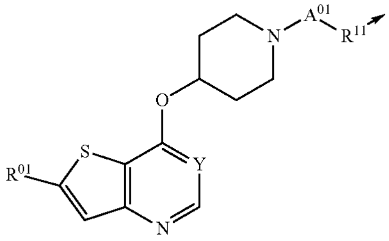

where

Y represents CH or N, $R^{01}$ represents a hydrogen atom or a C1-6 alkyl group, $A^{01}$ is *—$SO_2$—*, or a group represented by the following structural formula:

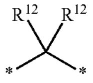

where each $R^{12}$ independently represents a hydrogen atom or a C1-6 alkyl group, and $R^{11}$ is a group represented by any one of the following structural formulae:

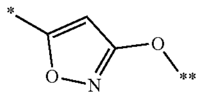

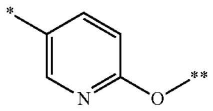

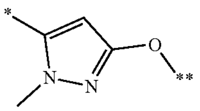

where * represents the binding position to $A^{01}$, and ** represents the binding position to the Linker (L), the Linker (L) represents a group represented by any one of the following formulae:

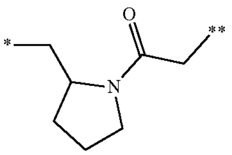

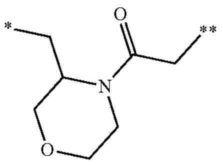

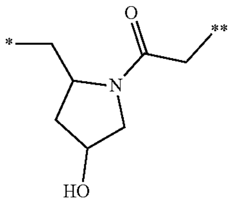

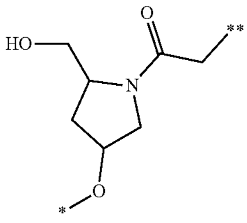

where * represents the binding to the IRAK-M binder (M), or *—$(CH_2CH_2O)n(CH_2)m(NRCO)s(CH_2)t$-* with n being an integer from 0 to 4, m being 0, 1, or 2, s being 0 or 1, t being 0 or 1, and R representing a hydrogen atom or a C1-6 alkyl group, and ** represents the binding to the E3 ligase binder (E), and the E3 ligase binder (E) is represented by the following formula (IV):

(IV)

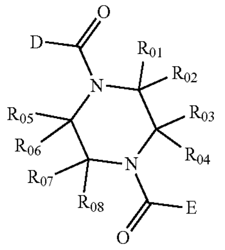

where $R_{01}$, $R_{02}$, $R_{03}$, $R_{04}$, $R_{05}$, $R_{06}$, $R_{07}$ and $R_{08}$ each independently represent a hydrogen atom or a C1-6 alkyl group, D represents the following formula (V):

(V)

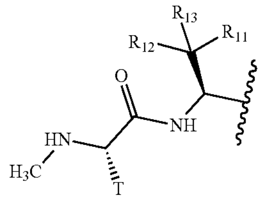

where $R_{11}$ represents a hydrogen atom or a hydroxyl group, and $R_{12}$ and $R_{13}$ each independently represent a hydrogen atom, a C1-6 alkyl group, a pyrazole group, or a cyclohexyl group optionally substituted with a fluorine atom, and T represents a C1-3 alkyl group, or the following formula (VI):

(VI)

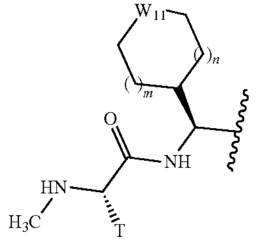

where m is 1, n is 1, $W_{11}$ represents a methylene group, and T represents a C1-3 alkyl group, or the following formula (VII):

(VII)

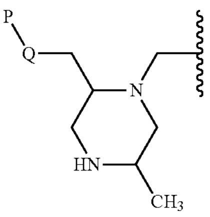

where Q represents a bond, and P represents the binding to the Linker (L) when D is bonded to the Linker (L), and E is represented by any one of the following formulae:

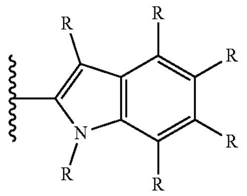

,

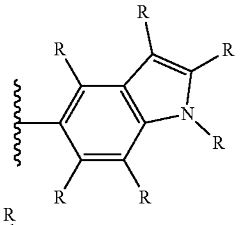

,

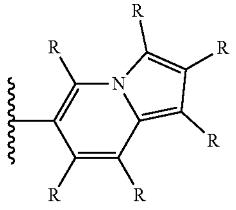

, where R bonded to N each independently represent a hydrogen atom, or a C1-6 alkyl group, and other Rs each independently represent a hydrogen atom, a halogen atom, a C1-6 alkyl group, or a C1-6 alkoxy group, wherein when E is bonded to the Linker (L), E is bonded to the Linker (L) at any one position indicted by R in the above formulae, and either D or E binds to the Linker (L).

2. The compound according to claim 1, wherein the IRAK-M binder (M) is a monovalent group derived from a compound selected from the group consisting of N-(3-(methylsulfonyl)phenyl)thieno[3,2-d]pyrimidin-4-amine, 4-((4-(thieno[3,2-d]pyrimidin-4-yloxy)piperidin-1-yl)sulfonyl)phenol, 3-(allyloxy)-5-((4-(thieno[3,2-b]pyridin-7-yloxy)piperidin-1-yl)methyl)isoxazole, 5-((4-(thieno[3,2-b]pyridin-7-yloxy)piperidin-1-yl)methyl) isoxazol-3-ol, 3-(allyloxy)-5-(1-(4-(thieno[3,2-b]pyridin-7-yloxy)piperidin-1-yl) ethyl) isoxazole, 3-(allyloxy)-5-(1-(4-((2-methylthieno[3,2-b]pyridin-7-yl)oxy)piperidin-1-yl) ethyl) isoxazole, (S)-3-(pyrrolidin-2-ylmethoxy)-5-((4-(thieno[3,2-b]pyridin-7-yloxy)piperidin-1-yl)methyl)isoxazole, 3-((tetrahydrofuran-3-yl)oxy)-4-(thieno[3,2-d]pyrimidin-4-ylamino)benzamide, N,6-diphenylthieno[3,2-d]pyrimidin-4-amine, N-(2-methoxyphenyl)-6-phenylthieno[3,2-d]pyrimidin-4-amine, N-(cyclopropylmethyl)-6-phenylthieno[3,2-d]pyrimidin-4-amine, 6-phenyl-N-(pyridin-2-yl) thieno[3,2-d]pyrimidin-4-amine, 6-phenyl-N-(pyridin-3-ylmethyl) thieno[3,2-d]pyrimidin-4-amine, N-phenethyl-6-phenylthieno[3,2-d]pyrimidin-4-amine, 4-(thieno[3,2-d]pyrimidin-4-ylamino)benzamide, N-(2-((tetrahydrofuran-3-yl)oxy)phenyl)thieno[3,2-d]pyrimidin-4-amine, 3-(thieno[3,2-d]pyrimidin-4-ylamino)benzamide, N-(pyridin-4-yl) thieno[3,2-d]pyrimidin-4-amine, N-(2-(trifluoromethyl) pyridin-4-yl) thieno[3,2-d]pyrimidin-4-amine, N-(2-methoxypyridin-4-yl) thieno[3,2-d]pyrimidin-4-amine, N-(2-(trifluoromethyl) pyridin-3-yl) thieno[3,2-d]pyrimidin-4-amine, N-(3-methyl-1-(pyridin-2-yl)-1H-pyrazol-5-yl) thieno[3,2-d]pyrimidin-4-amine, N-(1H-benzo[d]imidazol-5-yl) thieno[3,2-d]pyrimidin-4-amine, 5-(thieno[3,2-d]pyrimidin-4-ylamino) isoindoline-1,3-dione, N-(1H-indazol-6-yl) thieno[3,2-d]pyrimidin-4-amine, 5-(thieno[3,2-d]pyrimidin-4-ylamino) isobenzofuran-1 (3H)-one, methyl 4-((cyclopropylmethyl) amino) thieno[3,2-d]pyrimidine-6-carboxylate, 6-(1-methyl-1H-pyrazol-4-yl)-4-((1-methylpiperidin-4-yl)oxy) thieno[3,2-d]pyrimidine, 6-ethynyl-4-((1-methylpiperidin-4-yl)oxy)thieno[3,2-d]pyrimidine, 4-((2-chlorothieno[3,2-d]

pyrimidin-4-yl)amino)benzamide, 6-iodo-4-((tetrahydro-2H-pyran-4-yl)oxy)thieno[3,2-d]pyrimidine, 6-iodo-4-((tetrahydro-2H-thiopyran-4-yl)oxy)thieno[3,2-d]pyrimidine, 6-iodo-4-((1-methylpiperidin-4-yl)oxy)thieno[3,2-d]pyrimidine, 4-((6-iodothieno[3,2-d]pyrimidin-4-yl)oxy) tetrahydro-2H-thiopyran 1,1-dioxide, 4-((1-((2,6-difluorophenyl)sulfonyl)piperidin-4-yl)oxy)thieno[3,2-d]pyrimidine, 4-((1-(methylsulfonyl)piperidin-4-yl)oxy)thieno[3,2-d]pyrimidine, 4-((1-((2-methoxyethyl)sulfonyl)piperidin-4-yl)oxy)thieno[3,2-d]pyrimidine, 4-((1-(benzylsulfonyl)piperidin-4-yl)oxy)thieno[3,2-d]pyrimidine, tert-butyl 4-(((4-(thieno[3,2-d]pyrimidin-4-yloxy)piperidin-1-yl)sulfonyl)methyl)piperidine-1-carboxylate, ethyl 3-((4-(thieno[3,2-d]pyrimidin-4-yloxy)piperidin-1-yl)sulfonyl) propanoate, 4-((1-(cyclopropylsulfonyl)piperidin-4-yl)oxy)thieno[3,2-d]pyrimidine, 4-((1-((2-chlorophenyl)sulfonyl)piperidin-4-yl)oxy)thieno[3,2-d]pyrimidine, 4-((1-((2-methoxyphenyl)sulfonyl)piperidin-4-yl)oxy)thieno[3,2-d]pyrimidine, 4-((1-(o-tolylsulfonyl)piperidin-4-yl)oxy)thieno[3,2-d]pyrimidine, 4-((1-((2-(4-fluorophenoxy)phenyl)sulfonyl)piperidin-4-yl)oxy)thieno[3,2-d]pyrimidine, 4-((1-((2-fluorophenyl)sulfonyl)piperidin-4-yl)oxy)thieno[3,2-d]pyrimidine, 4-((1-((2-(trifluoromethoxy)phenyl)sulfonyl)piperidin-4-yl)oxy)thieno[3,2-d]pyrimidine, 4-((1-((4-methoxyphenyl)sulfonyl)piperidin-4-yl)oxy)thieno[3,2-d]pyrimidine, 4-((1-((4-chlorophenyl)sulfonyl)piperidin-4-yl)oxy)thieno[3,2-d]pyrimidine, 4-((1-((4-fluorophenyl)sulfonyl)piperidin-4-yl)oxy)thieno[3,2-d]pyrimidine, 4-((1-((3-methoxyphenyl)sulfonyl)piperidin-4-yl)oxy)thieno[3,2-d]pyrimidine, 4-((1-(4-methylbenzenesulfonyl)piperidin-4-yl)oxy)thieno[3,2-d]pyrimidine, 4-((1-((3-fluorophenyl)sulfonyl)piperidin-4-yl)oxy)thieno[3,2-d]pyrimidine, 4-((1-((3-chlorophenyl)sulfonyl)piperidin-4-yl)oxy)thieno[3,2-d]pyrimidine, 4-((1-(pyridin-3-ylsulfonyl)piperidin-4-yl)oxy)thieno[3,2-d]pyrimidine, 4-((1-((1-benzyl-1H-pyrazol-4-yl)sulfonyl)piperidin-4-yl)oxy)thieno[3,2-d]pyrimidine, 4-((1-((6-methoxypyridin-3-yl)sulfonyl)piperidin-4-yl)oxy)thieno[3,2-d]pyrimidine, 4-((1-((1,4-dimethyl-1H-pyrazol-5-yl)sulfonyl)piperidin-4-yl)oxy)thieno[3,2-d]pyrimidine, 4-((1-(isobutylsulfonyl)piperidin-4-yl)oxy)thieno[3,2-d]pyrimidine, 4-((1-(phenethylsulfonyl)piperidin-4-yl)oxy)thieno[3,2-d]pyrimidine, 4-((1-((3-phenoxyphenyl)sulfonyl)piperidin-4-yl)oxy)thieno[3,2-d]pyrimidine, N-(4-ethoxyphenyl) thieno[3,2-d]pyrimidin-4-amine, N-(3,4-dimethoxyphenyl)-2,6-dimethylthieno[3,2-d]pyrimidin-4-amine, 7-((1-(prop-2-yn-1-yl)piperidin-4-yl)oxy)thieno[3,2-b]pyridine, 1-methyl-5-((4-(thieno[3,2-b]pyridin-7-yloxy)piperidin-1-yl)methyl)-1H-pyrazol-3-ol, 7-((1-((3-(allyloxy)-1-methyl-1H-pyrazol-5-yl)methyl)piperidin-4-yl)oxy)thieno[3,2-b]pyridine, 3-(allyloxy)-5-((4-(thieno[3,2-d]pyrimidin-4-yloxy)piperidin-1-yl)methyl)isoxazole, 3-(prop-2-yn-1-yloxy)-5-((4-(thieno[3,2-b]pyridin-7-yloxy)piperidin-1-yl)methyl)isoxazole, 3-(allyloxy)-5-((4-((2-methylthieno[3,2-b]pyridin-7-yl)oxy)piperidin-1-yl)methyl)isoxazole, 7-((1-((1-methyl-1H-pyrazol-4-yl)methyl)piperidin-4-yl)oxy)thieno[3,2-b]pyridine, 7-((1-((1,3-dimethyl-1H-pyrazol-4-yl)methyl)piperidin-4-yl)oxy)thieno[3,2-b]pyridine, 7-((1-((1,3,5-trimethyl-1H-pyrazol-4-yl)methyl)piperidin-4-yl)oxy)thieno[3,2-b]pyridine, 7-((1-((1,5-dimethyl-1H-pyrazol-4-yl)methyl)piperidin-4-yl)oxy)thieno[3,2-b]pyridine, 7-((1-((1-methyl-1H-pyrazol-5-yl)methyl)piperidin-4-yl)oxy)thieno[3,2-b]pyridine, 3,5-dimethyl-4-((4-(thieno[3,2-b]pyridin-7-yloxy)piperidin-1-yl)methyl)isoxazole, 7-((1-(thiazol-2-ylmethyl)piperidin-4-yl)oxy)thieno[3,2-b]pyridine, 7-((1-((2-methylthiazol-5-yl)methyl)piperidin-4-yl)oxy)thieno[3,2-b]pyridine, 2-(1H-pyrazol-1-yl)-1-(4-(thieno[3,2-b]pyridin-7-yloxy)piperidin-1-yl) ethan-1-one, 1-(4-(thieno[3,2-b]pyridin-7-yloxy)piperidin-1-yl)-2-(2H-1,2,3-triazol-2-yl) ethan-1-one, 2-allyl-5-((4-(thieno[3,2-b]pyridin-7-yloxy)piperidin-1-yl)methyl) isoxazol-3 (2H)-one, 3-(2-methoxyethoxy)-5-((4-(thieno[3,2-b]pyridin-7-yloxy)piperidin-1-yl)methyl)isoxazole, 7-((1-((3-(allyloxy) isoxazol-5-yl)methyl)piperidin-4-yl)oxy)thieno[3,2-b]pyridine-2-carbonitrile, 5-((4-((2-methylthieno[3,2-b]pyridin-7-yl)oxy)piperidin-1-yl)methyl) isoxazol-3-ol and 5-(1-(4-((2-methylthieno[3,2-b]pyridin-7-yl)oxy)piperidin-1-yl) ethyl) isoxazol-3-ol, or a pharmaceutically acceptable salt thereof.

3. The compound according to claim 2, wherein the IRAK-M binder (M) is a monovalent group derived from the compound selected from the group consisting of 5-((4-(thieno[3,2-b]pyridin-7-yloxy)piperidin-1-yl)methyl) isoxazol-3-ol, 5-((4-((2-methylthieno[3,2-b]pyridin-7-yl)oxy)piperidin-1-yl)methyl) isoxazol-3-ol, 1-methyl-5-((4-(thieno[3,2-b]pyridin-7-yloxy)piperidin-1-yl)methyl)-1H-pyrazol-3-ol and (4-((4-(thieno[3,2-d]pyrimidin-4-yloxy)piperidin-1-yl)sulfonyl)phenol, or a pharmaceutically acceptable salt thereof.

4. The compound according to claim 1, wherein the Linker (L) represents a group represented by any one of the following formulae:

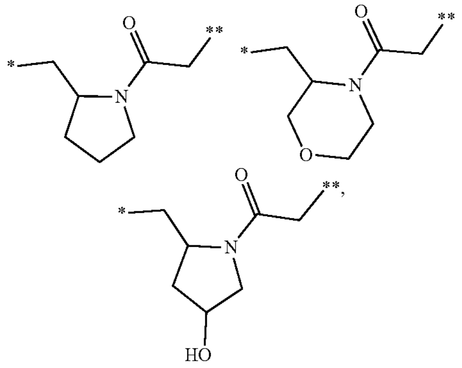

or a pharmaceutically acceptable salt thereof.

5. The compound according to claim 1, wherein E represents the following formula (VIII):

VIII

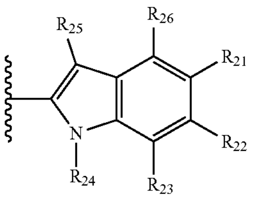

wherein $R_{21}$, $R_{22}$, and $R_{23}$ each independently represent a hydrogen atom, a halogen atom, a C1-6 alkyl group, or a C1-6 alkoxy group, $R_{25}$ and $R_{26}$ each independently represent a hydrogen atom, a halogen atom, a C1-6 alkyl group, or the binding to the Linker (L), $R_{24}$ represents a methyl group, or the binding to the Linker (L), provided that the binding to the Linker (L) is any one of $R_{24}$, $R_{25}$, or $R_{26}$, or a pharmaceutically acceptable salt thereof.

6. The compound according to claim 1, wherein E represents the following formula (X):

X

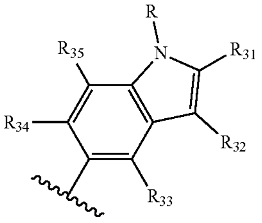

wherein $R_{31}$, $R_{32}$, $R_{33}$, $R_{34}$, and $R_{35}$ each independently represent a hydrogen atom, a halogen atom, or a C1-6 alkyl group, and R represents a hydrogen atom, or the binding to the Linker (L), or a pharmaceutically acceptable salt thereof.

7. The compound according to claim 1, which is a compound selected from the group consisting of 2-(4-((S)-2-cyclohexyl-2-((S)-2-(methylamino) propanamido) acetyl) piperazine-1-carbonyl)-5,6-difluoro-N, 1-dimethyl-N-(2-(2-(2-((5-((4-(thieno[3,2-b]pyridin-7-yloxy)piperidin-1-yl) methyl) isoxazol-3-yl)oxy) ethoxy) ethoxy) ethyl)-1H-indole-3-carboxamide, 2-(4-((S)-2-cyclohexyl-2-((S)-2-(methylamino) propanamido) acetyl) piperazine-1-carbonyl)-6-methoxy-1-methyl-N-(2-(2-(2-(4-((4-(thieno[3,2-d]pyrimidin-4-yloxy)piperidin-1-yl)sulfonyl) phenoxy) ethoxy) ethoxy) ethyl)-1H-indole-3-carboxamide, 1-((R)-4-(5,6-difluoro-1-methyl-1H-indole-2-carbonyl)-2-methylpiperazin-1-yl)-2-((2R,5R)-5-methyl-2-((2-(2-(2-((5-((4-(thieno[3,2-b]pyridin-7-yloxy)piperidin-1-yl)methyl) isoxazol-3-yl)oxy) ethoxy) ethoxy) ethoxy) methyl) piperazin-1-yl) ethan-1-one, (S)—N—((S)-1-cyclohexyl-2-(4-(5,6-difluoro-1-methyl-3-(2-(2-(2-((5-((4-(thieno[3,2-b]pyridin-7-yloxy)piperidin-1-yl)methyl) isoxazol-3-yl)oxy) ethoxy) ethoxy) ethoxy)-1H-indole-2-carbonyl) piperazin-1-yl)-2-oxoethyl)-2-(methylamino) propanamide, (S)—N—((S)-1-cyclohexyl-2-(4-(5,6-difluoro-1-(3-methyl-2-oxo-14-((5-((4-(thieno[3,2-b]pyridin-7-yloxy)piperidin-1-yl) methyl) isoxazol-3-yl)oxy)-6,9, 12-trioxa-3-azatetradecyl)-1H-indole-2-carbonyl) piperazin-1-yl)-2-oxoethyl)-2-(methylamino) propanamide, (S)—N—((S)-1-cyclohexyl-2-(4-(5,6-difluoro-1-(2-oxo-2-((S)-2-(((5-((4-(thieno[3,2-b]pyridin-7-yloxy)piperidin-1-yl)methyl) isoxazol-3-yl)oxy) methyl) pyrrolidin-1-yl) ethyl)-1H-indole-2-carbonyl) piperazin-1-yl)-2-oxoethyl)-2-(methylamino) propanamide, (S)—N—((S)-1-cyclohexyl-2-(4-(5-fluoro-1-(2-oxo-2-((S)-2-(((5-((4-(thieno[3,2-b]pyridin-7-yloxy)piperidin-1-yl) methyl) isoxazol-3-yl)oxy) methyl) pyrrolidin-1-yl) ethyl)-1H-indole-2-carbonyl) piperazin-1-yl)-2-oxoethyl)-2-(methylamino) propanamide, (S)—N—((S)-1-cyclohexyl-2-((S)-4-(5,6-difluoro-1-(2-oxo-2-((S)-2-(((5-((4-(thieno[3,2-b]pyridin-7-yloxy)piperidin-1-yl)methyl) isoxazol-3-yl) oxy) methyl) pyrrolidin-1-yl) ethyl)-1H-indole-2-carbonyl)-3-methylpiperazin-1-yl)-2-oxoethyl)-2-(methylamino) propanamide, (S)—N—((S)-1-cyclohexyl-2-((S)-4-(5-fluoro-1-(2-oxo-2-((S)-2-(((5-((4-(thieno[3,2-b]pyridin-7-yloxy)piperidin-1-yl)methyl) isoxazol-3-yl)oxy) methyl) pyrrolidin-1-yl) ethyl)-1H-indole-2-carbonyl)-3-methylpiperazin-1-yl)-2-oxoethyl)-2-(methylamino) propanamide, (S)—N—((S)-2-(4-(5,6-difluoro-1-(2-oxo-2-((S)-2-(((5-((4-(thieno[3,2-b]pyridin-7-yloxy)piperidin-1-yl)methyl) isoxazol-3-yl)oxy) methyl) pyrrolidin-1-yl) ethyl)-1H-indole-2-carbonyl) piperazin-1-yl)-1-(4,4-difluorocyclohexyl)-2-oxoethyl)-2-(methylamino) propanamide, (S)—N—((S)-1-cyclohexyl-2-(4-(5,6-difluoro-1-methyl-4-(2-(2-(2-(2-((5-((4-(thieno[3,2-b]pyridin-7-yloxy)piperidin-1-yl) methyl) isoxazol-3-yl)oxy) ethoxy) ethoxy) ethoxy) ethoxy)-1H-indole-2-carbonyl) piperazin-1-yl)-2-oxoethyl)-2-(methylamino) propanamide and(S)—N—((S)-1-cyclohexyl-2-(4-(2-methyl-1-(2-(2-(2-(2-((5-((4-(thieno[3,2-b] pyridin-7-yloxy)piperidin-1-yl)methyl) isoxazol-3-yl)oxy) ethoxy) ethoxy) ethoxy) ethyl)-1H-indole-5-carbonyl) piperazin-1-yl)-2-oxoethyl)-2-(methylamino) propanamide, or a pharmaceutically acceptable salt thereof.

8. A medicament containing the compound according to claim 1, or a pharmaceutically acceptable salt thereof.

9. The medicament according to claim 8, which is a therapeutic agent for cancers.

10. A method for inducing IRAK-M protein degradation, the method comprising administering to a patient in need thereof an effective amount of the compound or pharmacologically acceptable salt thereof according to claim 1.

11. A method for treatment of cancers, the method comprising administering to a patient in need thereof an effective amount of the compound or pharmacologically acceptable salt thereof according to claim 1.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: a partial sequence of Smac peptide

<400> SEQUENCE: 1

Ala Val Pro Ile Ala Gln Lys
1               5


<210> SEQ ID NO 2
<211> LENGTH: 4
<212> TYPE: PRT
<213> ORGANISM: Artificial Sequence
<220> FEATURE:
<223> OTHER INFORMATION: a partial sequence of Smac peptide

<400> SEQUENCE: 2

Ala Val Pro Ile
1
```